US008252903B2

(12) United States Patent
Scanlan et al.

(10) Patent No.: US 8,252,903 B2
(45) Date of Patent: Aug. 28, 2012

(54) HUMAN SARCOMA-ASSOCIATED ANTIGENS

(75) Inventors: Matthew J. Scanlan, Princeton Junction, NJ (US); Cynthia H. Scanlan, legal representative, Princeton Junction, NJ (US); Sang-Yull Lee, New York, NY (US); Lloyd J. Old, New York, NY (US)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 12/683,374

(22) Filed: Jan. 6, 2010

(65) Prior Publication Data

US 2010/0172910 A1 Jul. 8, 2010

Related U.S. Application Data

(60) Division of application No. 10/529,655, filed as application No. PCT/US03/30870 on Sep. 30, 2003, now Pat. No. 7,662,917, which is a continuation-in-part of application No. 10/260,708, filed on Sep. 30, 2002, now Pat. No. 7,560,537.

(51) Int. Cl.
*C07K 16/00* (2006.01)
*G01N 33/53* (2006.01)
(52) U.S. Cl. .................................... 530/387.1; 435/7.1
(58) Field of Classification Search .................. None
See application file for complete search history.

(56) References Cited

U.S. PATENT DOCUMENTS

| 6,392,019 | B1 | 5/2002 | Ford et al. | |
|---|---|---|---|---|
| 6,783,961 | B1 * | 8/2004 | Edwards et al. | 435/91.1 |
| 6,835,556 | B2 | 12/2004 | Attersand | |
| 7,560,537 | B2 | 7/2009 | Scanlan et al. | |
| 2008/0089888 | A1 | 4/2008 | Scanlan et al. | |

FOREIGN PATENT DOCUMENTS

| CA | 2422114 A1 | 3/2002 |
|---|---|---|
| EP | 1033401 A1 | 7/2001 |
| EP | 1179589 A1 | 2/2002 |
| WO | WO-01/40466 A2 | 6/2001 |
| WO | WO-01/53312 | 7/2001 |
| WO | WO-2004/031354 A2 | 4/2004 |

OTHER PUBLICATIONS

[No Author Listed] 1997/1998 Stratagene Catalog.
Aho et al., Isolation, expression, and chromosomal localization of the human mitochondrial capsule selenoprotein gene (MCSP). Genomics. Mar. 1, 1996;32(2):184-90.
Altman et al., Phenotypic analysis of antigen-specific T lymphocytes. Science. Oct. 4, 1996;274(5284):94-6.
Antonescu et al., MAGE antigen expression in monophasic and biphasic synovial sarcoma. Hum Pathol. Feb. 2002;33(2):225-9.
Ayyoub et al., Proteasome-assisted identification of a SSX-2-derived epitope recognized by tumor-reactive CTL infiltrating metastatic melanoma. J Immunol. Feb. 15, 2002;168(4):1717-22.
Boel et al., BAGE: a new gene encoding an antigen recognized on human melanomas by cytolytic T lymphocytes. Immunity. Feb. 1995;2(2):167-75.
Cancer Immunome Database. SEREX-Sequence Information. Serex ID: 2356. Sequence Name: NY-SAR-36. Last updated Sep. 12, 2002. www2.licr.org/CancerImmunomeDB/SEREX_ShowSequence. php?SerexId=2356.
Cancer Immunome Database. SEREX-Sequence Information. Serex ID: 2368. Sequence Name: NY-SAR-48. Last updated Sep. 12, 2002. www2.licr.org/CancerImmunomeDB/SEREX_ShowSequence. php?SerexId=2368.
Chen et al., A testicular antigen aberrantly expressed in human cancers detected by autologous antibody screening. Proc Natl Acad Sci U S A. Mar. 4, 1997;94(5):1914-8.
Chen et al., Identification of human tumor antigens by serological expression cloning. In: Principles and Practice of Biologic Therapy of Cancer. S.A. Rosenberg, ed. Philadelphia: Lippincott Williams & Wilkins. 2000:557-70.
Chen et al., Identification of multiple cancer/testis antigens by allogeneic antibody screening of a melanoma cell line library. Proc Natl Acad Sci U S A. Jun. 9, 1998;95(12):6919-23.
Conrad et al., Differential expression of transforming growth factor beta 1 and interleukin 10 in progressing and regressing areas of primary melanoma. J Exp Clin Cancer Res. Jun. 1999;18(2):225-32.
Cox et al., Identification of a peptide recognized by five melanoma-specific human cytotoxic T cell lines. Science. Apr. 29, 1994;264(5159):716-9.
Domenjoud et al., Sequence of human protamine 2 cDNA. Nucleic Acids Res. Aug. 11, 1988;16(15):7733.
Garrido et al., MHC antigens and tumor escape from immune surveillance. Adv Cancer Res. 2001;83:117-58.
Gaugler et al., Human gene MAGE-3 codes for an antigen recognized on a melanoma by autologous cytolytic T lymphocytes. J Exp Med. Mar. 1, 1994;179(3):921-30.
GenBank Submission; NIH/NCBI, Accession No. AA906131. Last updated May 19, 1998.
GenBank Submission; NIH/NCBI, Accession No. AA909915. Last updated May 19, 1998.
GenBank Submission; NIH/NCBI, Accession No. AK098602. Oshima et al. Sep. 14, 2006.
GenBank Submission; NIH/NCBI, Accession No. AW893050. Last updated Sep. 28, 2004.
GenBank Submission; NIH/NCBI, Accession No. AY211909. Lee et al. Mar. 23, 2003.
GenBank Submission; NIH/NCBI, Accession No. AY211910. Lee et al. Mar. 23, 2003.
GenBank Submission; NIH/NCBI, Accession No. AY211911. Lee et al. Mar. 23, 2003.
GenBank Submission; NIH/NCBI, Accession No. AY211912. Lee et al. Mar. 23, 2003.
GenBank Submission; NIH/NCBI, Accession No. AY211913. Lee et al. Mar. 23, 2003.
GenBank Submission; NIH/NCBI, Accession No. AY211914. Lee et al. Mar. 23, 2003.
GenBank Submission; NIH/NCBI, Accession No. AY211915. Lee et al. Mar. 23, 2003.

(Continued)

*Primary Examiner* — Sean Aeder
(74) *Attorney, Agent, or Firm* — Wolf, Greenfield & Sacks, P.C.

(57) ABSTRACT

The invention relates to sarcoma-associated antigens and the nucleic acid molecules that encode them. The invention further relates to the use of the nucleic acid molecules, polypeptides and fragments thereof associated with sarcoma in methods and compositions for the diagnosis and treatment of diseases, such as cancer. More specifically, the invention relates to the discovery of a novel cancer/testis (CT) antigen, NY-SAR-35.

24 Claims, 4 Drawing Sheets

OTHER PUBLICATIONS

GenBank Submission; NIH/NCBI, Accession No. AY211916. Lee et al. Mar. 23, 2003.
GenBank Submission; NIH/NCBI, Accession No. AY211917. Lee et al. Mar. 23, 2003.
GenBank Submission; NIH/NCBI, Accession No. AY211918. Lee et al. Mar. 23, 2003.
GenBank Submission; NIH/NCBI, Accession No. AY211919. Lee et al. Mar. 23, 2003.
GenBank Submission; NIH/NCBI, Accession No. AY211920. Lee et al. Mar. 23, 2003.
GenBank Submission; NIH/NCBI, Accession No. AY211921. Lee et al. Mar. 23, 2003.
GenBank Submission; NIH/NCBI, Accession No. AY211922. Lee et al. Mar. 23, 2003.
GenBank Submission; NIH/NCBI, Accession No. AY211923. Lee et al. Mar. 23, 2003.
GenBank Submission; NIH/NCBI, Accession No. AY211924. Lee et al. Mar. 23, 2003.
GenBank Submission; NIH/NCBI, Accession No. AY211925. Lee et al. Mar. 23, 2003.
GenBank Submission; NIH/NCBI, Accession No. AY211926. Lee et al. Mar. 23, 2003.
GenBank Submission; NIH/NCBI, Accession No. AY211927. Lee et al. Mar. 23, 2003.
GenBank Submission; NIH/NCBI, Accession No. AY211928. Lee et al. Mar. 23, 2003.
GenBank Submission; NIH/NCBI, Accession No. AY211929. Lee et al. Mar. 23, 2003.
GenBank Submission; NIH/NCBI, Accession No. AY211930. Lee et al. Mar. 23, 2003.
GenBank Submission; NIH/NCBI, Accession No. AY211931. Lee et al. Mar. 23, 2003.
GenBank Submission; NIH/NCBI, Accession No. AY214130. Lee et al. Mar. 11, 2003.
GenBank Submission; NIH/NCBI, Accession No. BC034320. Strausberg et al. Jul. 17, 2006.
GenBank Submission; NIH/NCBI, Accession No. BG771667. Last updated May 15, 2001.
GenBank Submission; NIH/NCBI, Accession No. BI465380. Last updated Aug. 21, 2006.
GenBank Submission; NIH/NCBI, Accession No. BP370444. Last updated Apr. 24, 2006.
GenBank Submission; NIH/NCBI, Accession No. BX098898. Last updated Feb. 6, 2003.
GenBank Submission; NIH/NCBI, Accession No. CV024823. Last updated Aug. 20, 2004.
GenBank Submission; NIH/NCBI, Accession No. DB450405. Last updated Apr. 13, 2006.
GenBank Submission; NIH/NCBI, Accession No. DB482835. Last updated Mar. 30, 2006.
GenBank Submission; NIH/NCBI, Accession No. DB551686. Last updated Jul. 10, 2006.
GenBank Submission; NIH/NCBI, Accession No. NM_152578. Lee et al. Nov. 17, 2006.
GenBank Submission; NIH/NCBI, Accession No. NW_042622. Waterston et al. Apr. 28, 2006.
GenBank Submission; NIH/NCBI, Accession No. XM_098959. Aug. 1, 2002.
GenBank Submission; NIH/NCBI, Accession No. XP_150408. Feb. 24, 2003.
GenBank Submission; NIH/NCBI; Accession No. AW593050.
GenBank Submission; NIH/NCBI; Accession No. AX463882 (PAT Jul. 16, 2002).
Guillaudeux et al., Expression of HLA class I genes in meiotic and post-meiotic human spermatogenic cells. Biol Reprod. Jul. 1996;55(1):99-110.
Gure et al., SSX: a multigene family with several members transcribed in normal testis and human cancer. Int J Cancer. Sep. 17, 1997;72(6):965-71.

Hoffmann et al., The P-domain or trefoil motif: a role in renewal and pathology of mucous epithelia? Trends Biochem. Jul. 1993;18(7):239-43.
Jager et al., Identification of a tissue-specific putative transcription factor in breast tissue by serological screening of a breast cancer library. Cancer Res. Mar. 1, 2001;61(5):2055-61.
Jager et al., Serological cloning of a melanocyte rab guanosine 5'-triphosphate-binding protein and a chromosome condensation protein from a melanoma complementary DNA library. Cancer Res. Jul. 1, 2000;60(13):3584-91.
Jungbluth et al., Expression of MAGE-antigens in normal tissues and cancer. Int J Cancer. Feb. 15, 2000;85(4):460-5.
Jungbluth et al., Immunohistochemical analysis of NY-ESO-1 antigen expression in normal and malignant human tissues. Int J Cancer. Jun. 15, 2001;92(6):856-60.
Jungbluth et al., Monophasic and biphasic synovial sarcomas abundantly express cancer/testis antigen NY-ESO-1 but not MAGE-A1 or CT7. Int J Cancer. Oct. 15, 2001;94(2):252-6.
Kawakami et al., Cloning of the gene coding for a shared human melanoma antigen recognized by autologous T cells infiltrating into tumor. Proc Natl Acad Sci U S A. Apr. 26, 1994;91(9):3515-9.
Kiuru et al., Few FH mutations in sporadic counterparts of tumor types observed in hereditary leiomyomatosis and renal cell cancer families. Cancer Res. Aug. 15, 2002;62(16):4554-7.
Laprevotte et al., Nucleotide sequence of the gag gene and gag-pol junction of feline leukemia virus. J Virol. Jun. 1984;50(3):884-94.
Le Naour et al., Proteomics-based identification of RS/DJ-1 as a novel circulating tumor antigen in breast cancer. Clin Cancer Res. Nov. 2001;7(11):3328-35.
Lee et al., Immunomic analysis of human sarcoma. Proc Natl Acad Sci U S A. Mar. 4, 2003;100(5):2651-6.
Lethe et al., LAGE-1, a new gene with tumor specificity. Int J Cancer. Jun. 10, 1998;76(6):903-8.
Li et al., Molecular cloning of a novel tissue-specific gene from human nasopharyngeal epithelium. Gene. Sep. 3, 1999;237(1):235-40.
Martelange et al., Identification on a human sarcoma of two new genes with tumor-specific expression. Cancer Res. Jul. 15, 2000;60(14):3848-55.
Naka et al., Expression of SSX genes in human osteosarcomas. Int J Cancer. Apr. 1, 2002;98(4):640-2.
Ono et al., Serological analysis of BALB/C methylcholanthrene sarcoma Meth A by SEREX: identification of a cancer/testis antigen. Int J Cancer. Dec. 15, 2000;88(6):845-51.
Pascolo et al., A MAGE-A1 HLA-A A*0201 epitope identified by mass spectrometry. Cancer Res. May 15, 2001;61(10):4072-7.
Preuss et al., Analysis of the B-cell repertoire against antigens expressed by human neoplasms. Immunol Rev. Oct. 2002;188:43-50. Review.
Rosenberg et al., Progress in human tumour immunology and immunotherapy. Nature. May 17, 2001;411(6835):380-4. Review.
Sahin et al., Expression of multiple cancer/testis (CT) antigens in breast cancer and melanoma: basis for polyvalent CT vaccine strategies. Int J Cancer. Oct. 29, 1998;78(3):387-9.
Sahin et al., Human neoplasms elicit multiple specific immune responses in the autologous host. Proc Natl Acad Sci U S A. Dec. 5, 1995;92(25):11810-3.
Scanlan et al., Antigens recognized by autologous antibody in patients with renal-cell carcinoma. Int J Cancer. Nov. 12, 1999;83(4):456-64.
Scanlan et al., Cancer-related serological recognition of human colon cancer: identification of potential diagnostic and immunotherapeutic targets. Cancer Res. Jul. 15, 2002;62(14):4041-7.
Scanlan et al., Cancer/testis antigens: an expanding family of targets for cancer immunotherapy. Immunol Rev. Oct. 2002;188:22-32. Review.
Scanlan et al., Characterization of human colon cancer antigens recognized by autologous antibodies. Int J Cancer. May 29, 1998;76(5):652-8.
Scanlan et al., Expression of cancer-testis antigens in lung cancer: definition of bromodomain testis-specific gene (BRDT) as a new CT gene, CT9. Cancer Lett. Mar. 31, 2000;150(2):155-64.

Scanlan et al., Humoral immunity to human breast cancer: antigen definition and quantitative analysis of mRNA expression. Cancer Immun. Mar. 30, 2001;1:4.

Sequence Comparison cited in U.S. Appl. No. 10/260,708.

Skipper et al., An HLA-A2-restricted tyrosinase antigen on melanoma cells results from posttranslational modification and suggests a novel pathway for processing of membrane proteins. J Exp Med. Feb. 1, 1996;183(2):527-34.

Stockert et al., A survey of the humoral immune response of cancer patients to a panel of human tumor antigens. J Exp Med. Apr. 20, 1998;187(8):1349-54.

Tockman et al., Considerations in bringing a cancer biomarker to clinical application. Cancer Res. May 1, 1992;52(9 Suppl):2711s-2718s.

Tomlinson et al., Germline mutations in FH predispose to dominantly inherited uterine fibroids, skin leiomyomata and papillary renal cell cancer. Nat Genet. Apr. 2002;30(4):406-10.

Tureci et al., Expression of SSX genes in human tumors. Int J Cancer. Jul. 3, 1998;77(1):19-23.

UniGene Submission; NIH/NCBI; Accession No. HS.128580.

UniGene Submission; NIH/NCBI; Accession No. HS.375082.

Van Den Eynde et al., A new family of genes coding for an antigen recognized by autologous cytolytic T lymphocytes on a human melanoma. J Exp Med. Sep. 1, 1995;182(3):689-98.

Van Den Eynde et al., T cell defined tumor antigens. Curr Opin Immunol. Oct. 1997;9(5):684-93.

Van Der Bruggen et al., A gene encoding an antigen recognized by cytolytic T lymphocytes on a human melanoma. Science. Dec. 13, 1991;254(5038):1643-7.

Van Der Bruggen et al., Tumor-specific shared antigenic peptides recognized by human T cells. Immunol Rev. Oct. 2002;188:51-64. Review.

Westerhuis et al., Human mesangial cells in culture and in kidney sections fail to express Fc alpha receptor (CD89). J Am Soc Nephrol. Apr. 1999;10(4):770-8.

Wildner et al., Enzyme prodrug gene therapy: synergistic use of the herpes simplex virus-cellular thymidine kinase/ganciclovir system and thymidylate synthase inhibitors for the treatment of colon cancer. Cancer Res. Oct. 15, 1999;59(20):5233-8.

Yang et al., CML66, a broadly immunogenic tumor antigen, elicits a humoral immune response associated with remission of chronic myelogenous leukemia. Proc Natl Acad Sci U S A. Jun. 19, 2001;98(13):7492-7.

* cited by examiner

```
                              ggcttccatcctaatacgactcgctatagggctcgagcggccg
cccgggcaaaagtctgggccacggactgccggaccgttgggctgtgaggcagcgtctcagcgaggcggcacccggagcc
atg tct tca cat agg agg aaa gcg aag ggg agg aat agg aga agt cac cgt gcc atg cgt   180
 M   S   S   H   R   R   K   A   K   G   R   N   R   R   S   H   R   A   M   R    20
gtg gct cac tta gag ctg gca act tat gag ttg gcg gca act gag tcg aat ccc gag agc   240
 V   A   H   L   E   L   A   T   Y   E   L   A   A   T   E   S   N   P   E   S    40
agc cat cct gga tac gag gcc gcc atg gct gac agg cct cag cca gga tag cgg gaa tct   300
 S   H   P   G   Y   E   A   A   M   A   D   R   P   Q   P   G   W   R   E   S    60
cat aag atg cgg gtc agc aaa ccc ttt ggg atg ctc atg ctc tcc att tgg atc ctg ctg   360
 L   K   M   R   V   S   K   P   F   G   M   L   M   L   S   I   W   I   L   L    80
ttc gtg tgc tac tac ctg tcc tac tac ctg tgc tcc ggg tcc tca tat ttt gtg ctt gca   420
 F   V   C   Y   Y   L   S   Y   Y   L   C   S   G   S   S   Y   F   V   L   A   100
aat gga cat atc ctg ccc aac agt gaa aat gct cat ggc caa tct ctg gaa gaa gat tcc   480
 N   G   H   I   L   P   N   S   E   N   A   H   G   Q   S   L   E   E   D   S   120
gca ttg gaa gct ttg ctg aat ttt ttc ttt cca aca act tgc aat ctg agg gaa aat cag   540
 A   L   E   A   L   N   F   F   F   P   T   T   C   N   L   R   E   N   Q   140
gtg gca aag cct tgt aat gag ctg caa gat ctt agt gag agt gaa tgt ttg aga cac aaa   600
 V   A   K   P   C   N   E   L   Q   D   L   S   E   S   E   C   L   R   H   K   160
tgc tgt ttt tca tca tcg ggg acc acg agc ttc aaa tgt ttt gct cca ttt aga gat gtg   660
 C   C   F   S   S   S   G   T   T   S   F   K   C   F   A   P   F   R   D   V   180
cct aaa cag atg atg caa atg ttt ggg ctt ggt gcg atc agc ctt atc ctg gta tgt ctg   720
 P   K   Q   M   M   Q   M   F   G   L   G   A   I   S   L   I   L   V   C   L   200
ccc att tat tgc cgc tct ctt ttc tgg agg agc gaa ccg gcc gat gat tta caa agg cag   780
 P   I   Y   C   R   S   L   F   W   R   S   E   P   A   D   D   L   Q   R   Q   220
gac aac aga gtt gta acg ggt ttg aag aaa caa aga agg aag cga aag agg aag tct gaa   840
 D   N   R   V   V   T   G   L   K   K   Q   R   R   K   R   K   R   K   S   E   240
atg tta cag aaa gca gca aga gga cgt gag gaa cat ggt gac gag tga caagagaccaaa     900
 M   L   Q   K   A   A   R   G   R   E   E   H   G   D   E   *                   255
gcattattttcccctcaagacaacagaaaccattcagagcagaggggactgtctcagccatgcaaacctcatggag
catttggaaagttaaaattgattcttattttgtcatgtttactttcaaacatgaaataaaattgagttctgttt
tcatgcatcaaaaaaaaaaaaaaaaaaaaa    1082
```

Fig. 2

HUMAN SARCOMA-ASSOCIATED ANTIGENS

RELATED APPLICATIONS

This application is a divisional of U.S. Non-Provisional patent application Ser. No. 10/529,655, filed Nov. 28, 2006, issued on Feb. 16, 2010 as U.S. Pat. No. 7,662,917, which is a national stage filing under 35 U.S.C. §371 of PCT International application PCT/US03/30870, filed Sep. 30, 2003, which was published under PCT Article 21(2) in English, which is a continuation-in-part of U.S. application Ser. No. 10/260,708, filed on Sep. 30, 2002, and issued on Jul. 14, 2009 as U.S. Pat. No. 7,560,537, the entire disclosure of each of which is incorporated herein by reference.

FIELD OF THE INVENTION

The invention relates to sarcoma-associated antigens and the nucleic acid molecules that encode them. The invention further relates to the use of the nucleic acid molecules, polypeptides and fragments thereof associated with sarcoma in methods and compositions for the diagnosis and treatment of diseases, such as cancer. More specifically, the invention relates to the discovery of a novel cancer/testis (CT) antigen, NY-SAR-35.

BACKGROUND OF THE INVENTION

The identification of human tumor antigens recognized by the autologous host is yielding new and promising target molecules for immunotherapy, diagnosis and monitoring of human cancer (van der Bruggen P, et al. 1991. A gene encoding an antigen recognized by cytolytic T lymphocytes on a human melanoma. Science 254:1643-47; Gaugler, B., et al. Human gene MAGE-3 codes for an antigen recognized on a melanoma by autologous cytolytic T lymphocytes. *J. Exp. Med.* 1994; 179: 921-30; Kawakami, Y., et al. Cloning of the gene for a shared human melanoma antigen recognized by autologous T cells infiltrating into tumor. *Proc. Natl. Acad. Sci. USA.* 1994; 91: 3515-19 and Chen, Y.-T., et al. A testicular antigen aberrantly expressed in human cancers detected by autologous antibody screening. *Proc. Natl. Acad. Sci. USA.* 1997; 94: 1914-18). Studies of the cellular and humoral immune response to cancer have revealed an extensive repertoire of tumor antigens recognized by the immune system, collectively termed the cancer immunome (Jager D, et al. Identification of a tissue-specific putative transcription factor in breast tissue by serological screening of a breast cancer library. Cancer Res 2001 Mar. 1; 61(5):2055-61).

The immunome is composed largely of antigens defined by T-cell epitope cloning (van der Bruggen P, et al. 1991. A gene encoding an antigen recognized by cytolytic T lymphocytes on a human melanoma. Science 254:1643-47; Gaugler, B., et al. Human gene MAGE-3 codes for an antigen recognized on a melanoma by autologous cytolytic T lymphocytes. *J. Exp. Med.* 1994; 179: 921-30; Kawakami, et al. Cloning of the gene for a shared human melanoma antigen recognized by autologous T cells infiltrating into tumor. *Proc. Natl. Acad. Sci. USA.* 1994; 91: 3515-19; Boel, P., et al. BAGE: a new gene encoding an antigen recognized on human melanomas by cytolytic T lymphocytes. *Immunity* 1995; 2: 167-75. (PMID: 7895173); Van den Eynde, B., et al. A new family of genes coding for an antigen recognized by autologous cytolytic T lymphocytes on a human melanoma. *J. Exp. Med.* 1995; 182: 689-98. (PMID: 7544395)), MHC peptide elution (Skipper J C, et al. An HLA-A2-restricted tyrosinase antigen on melanoma cells results from posttranslational modification and suggests a novel pathway for processing of membrane proteins. J Exp Med 1996 Feb. 1; 183(2):527-34; Cox A L, et al. Identification of a peptide recognized by five melanoma-specific human cytotoxic T cell lines. Science 1994 Apr. 29; 264(5159):716-9; Pascolo S, et al. A MAGE-A1 HLA-A A*0201 epitope identified by mass spectrometry. Cancer Res 2001 May 15; 61(10):4072-7), and serological expression cloning (SEREX, Chen, Y.-T., et al. A testicular antigen aberrantly expressed in human cancers detected by autologous antibody screening. *Proc. Natl. Acad. Sci. USA.* 1997; 94: 1914-18; Jager D, et al. Identification of a tissue-specific putative transcription factor in breast tissue by serological screening of a breast cancer library. Cancer Res 2001 Mar. 1; 61(5):2055-61; Sahin, U., et al. Human neoplasms elicit multiple specific immune responses in the autologous host. *Proc. Natl. Acad. Sci. USA* 1995; 92: 11810-13; Scanlan, M. J., et al. Characterization of human colon cancer antigens recognized by autologous antibodies. *Int. J. Cancer* 1998; 76: 652-8; Scanlan, M. J., et al. Antigens recognized by autologous antibody in patients with renal-cell carcinoma. *Int. J. Cancer* 1999; 83: 456-64; Scanlan M J, et al. Humoral immunity to human breast cancer: antigen definition and quantitative analysis of mRNA expression. Cancer Immunity 1:4 [epub]), and is catalogued in three databases: the peptide database of T-cell defined tumor antigens (authored by members of the Ludwig Institute for Cancer Research (LICR) that is available on the website of Cancer Immunity, Journal of the Academy of Cancer Immunology, cancerimmunity.org/peptidedatabase/Tcellepitopes); the SYFPEITHI database of MHC ligands and peptide motifs (available on the website of Biomedical Informatics-Heidelberg, bmi-heidelberg.com/syfpeithi/) and the cancer immunome database available on the website of the LICR (licr.org/CancerImmunomeDB, formerly licr.org/SEREX.html).

SEREX is a method of immunoscreening tumor-derived cDNA expression libraries with cancer patient sera in order to identify molecules recognized by high titered IgG antibodies (Sahin, U., et al. Human neoplasms elicit multiple specific immune responses in the autologous host. *Proc. Natl. Acad. Sci. USA* 1995; 92: 11810-13) Approximately 1000 distinct antigens have been defined by SEREX analysis, including a number of etiologically and therapeutically significant cancer antigens, such as mutational antigens (e.g. p53, LKB1, BUB1; Scanlan, M. J., et al. Characterization of human colon cancer antigens recognized by autologous antibodies. *Int. J. Cancer* 1998; 76: 652-8; Scanlan, M. J., et al. Antigens recognized by autologous antibody in patients with renal-cell carcinoma. *Int. J. Cancer* 1999; 83: 456-64; Scanlan M J, et al. Humoral immunity to human breast cancer: antigen definition and quantitative analysis of mRNA expression. Cancer Immunity 1:4 [epub]), differentiation antigens (e.g. tyrosinase, NY-BR-1, rab 38; Jager D, et al. Identification of a tissue-specific putative transcription factor in breast tissue by serological screening of a breast cancer library. Cancer Res 2001 Mar. 1; 61(5):2055-61; Sahin, U., et al. Human neoplasms elicit multiple specific immune responses in the autologous host. *Proc. Natl. Acad. Sci. USA* 1995; 92: 11810-13; Jager D, et al. Serological cloning of a melanocyte rab guanosine 5'-triphosphate-binding protein and a chromosome condensation protein from a melanoma complementary DNA library. Cancer Res 2000 Jul. 1; 60(13):3584-91), overexpressed gene products (e.g. Her2neu, TPD52, eIF4-gamma; Scanlan M J, et al. Humoral immunity to human breast cancer: antigen definition and quantitative analysis of mRNA expression. Cancer Immunity 1:4 [epub]; Chen, Y.-T., et al. Identification of human tumor antigens by serological expression cloning. In: S. A. Rosenberg (ed.). Principles and Practice of Biologic Therapy of Cancer, pp. 557-570. Philadelphia: Lippincott Williams & Wilkins, 2000) and cancer/testis (CT) antigens (e.g. MAGE-1, NY-ESO-1, SSX-2; Chen, Y.-T., et al. A testicular antigen aberrantly expressed in human cancers detected by autologous antibody screening. *Proc. Natl. Acad. Sci. USA.* 1997; 94: 1914-18; Sahin, U., et al. Human neoplasms elicit multiple specific immune responses in the autologous host. *Proc. Natl. Acad. Sci. USA* 1995; 92: 11810-13).

CT antigens represent a group of shared, tumor-specific antigens expressed exclusively in developing germ cells of the testis and fetal ovary, as well as in placental trophoblast, and most notably, in a proportion of human cancers of diverse origins (Chen, Y.-T., et al. Identification of human tumor antigens by serological expression cloning. In: S. A. Rosenberg (ed.). Principles and Practice of Biologic Therapy of Cancer, pp. 557-570. Philadelphia: Lippincott Williams & Wilkins, 2000). These antigens elicit spontaneous cellular (Van den Eynde, B. J. and van der Bruggen, P. (1997) Curr. Opin. Immunol. 9,684-693) and humoral immune responses (Stockert, E., et al. (1998) J. Exp. Med. 187, 1349-1354) in some cancer patients. On the basis of tissue-restricted expression and immunogenicity, CT antigens are attractive targets for vaccine-based immunotherapies. In general, CT antigens are expressed in 20-40% of specimens from a given tumor type (Sahin U, et al. 1998. Expression of multiple cancer/testis antigens in breast cancer and melanoma: basis for polyvalent CT vaccine strategies. Int J Cancer 78:387-89; Scanlan M J et al. 2000. Expression of cancer-testis antigens in lung cancer: definition of bromodomain testis-specific gene (BRDT) as a new CT gene, CT9. Cancer Lett. 150:155-64; Van den Eynde B J and van der Bruggen P. 1997. T cell defined tumor antigens. Curr Opin Immunol 9:684-693). One exception to this is synovial sarcoma, in which 80% of specimens express NY-ESO-1 (Jungbluth A A, et al. 2001. Monophasic and biphasic synovial sarcomas abundantly express cancer/testis antigen NY-ESO-1 but not MAGE-A1 or CT7. Int J Cancer 94:252-6) and MAGE antigens (Antonescu C R, et al. MAGE antigen expression in monophasic and biphasic synovial sarcoma. Hum Pathol 2002 February; 33(2):225-9); the expression of which are often homogeneous throughout the tumor. Thus, identification of additional CT antigens and other genes having a tumor-associated expression profile is needed for the development of additional therapeutics and diagnostics to permit effective treatment and diagnosis of a broader group of cancer patients.

SUMMARY OF THE INVENTION

The humoral immune response of sarcoma patients to CT antigens was examined using the SEREX method. Sera from patients which showed a humoral immune response to CT antigens were subsequently used to screen cDNA libraries derived from CT-rich synovial sarcoma cell lines as well as normal testis. Although there was little overlap in the identity of clones isolated with different sarcoma sera, more than 30% of the isolated clones were previously identified during SEREX analysis of other tumor types. Approximately 60% of these antigens also reacted with sera from normal individuals. This is in conformity with other findings (Scanlan, M. J., et al. Antigens recognized by autologous antibody in patients with renal-cell carcinoma. *Int. J. Cancer* 1999; 83: 456-64 and Scanlan M J, et al. Humoral immunity to human breast cancer: antigen definition and quantitative analysis of mRNA expression. Cancer Immunity 20001; 1:4 [epub]). Thus, only a fraction of the serologically-defined immunome is associated with a cancer-related immune response. The studies described herein have led to the identification of antigens, which include antigens not before associated with cancer along with several novel gene products associated with a sarcoma-related immune response. One such novel CT antigen is NY-SAR-35, which appears to be a cell surface/secreted molecule.

According to one aspect of the invention, isolated nucleic acid molecules are provided. The isolated nucleic acid molecules are selected from the group consisting of (a) nucleic acid molecules which hybridize under high stringency conditions to a nucleic acid molecule comprising a nucleotide sequence selected from the group consisting of nucleotide sequences set forth as SEQ ID NOs: 1-14 and 97-107 and which code for a sarcoma-associated antigen, (b) nucleic acid molecules that differ from the nucleic acid molecules of (a) in codon sequence due to the degeneracy of the genetic code, and (c) complements of (a) or (b).

In some embodiments, the isolated nucleic acid molecule includes a nucleotide sequence selected from the group consisting of nucleotide sequences set forth as SEQ ID NOs: 1-14 and 97-107. In some embodiments the isolated nucleic acid molecule comprises a nucleotide sequence selected from the group consisting of nucleotide sequences set forth as SEQ ID NOs: 10, 11, 99, 102 and 104. In other embodiments the nucleic acid molecule comprises a nucleotide sequence set forth as SEQ ID NO: 10. In yet other embodiments the nucleic acid molecule comprises a nucleotide sequence set forth as SEQ ID NO: 11. In still other embodiments the nucleic acid molecule comprises a nucleotide sequence set forth as SEQ ID NO: 102. In still further embodiments the nucleic acid molecule comprises a nucleotide sequence set forth as SEQ ID NO: 104.

In some embodiments the nucleic acid molecule comprises a nucleotide sequence set forth as SEQ ID NOs: 121, 123, 125, 127, 129 or 131. In some embodiments the nucleic acid molecule comprises a nucleotide sequence set forth as SEQ ID NO: 121. In other embodiments the nucleic acid molecule comprises a nucleotide sequence set forth as SEQ ID NO: 123. In still other embodiments the nucleic acid molecule comprises a nucleotide sequence set forth as SEQ ID NO: 125. In yet other embodiments the nucleic acid molecule comprises a nucleotide sequence set forth as SEQ ID NO: 131.

According to another aspect of the invention, additional isolated nucleic acid molecules are provided. The isolated nucleic acid molecules are selected from the group consisting of: (a) unique fragments of a nucleotide sequence selected from the group consisting of nucleotide sequences set forth as SEQ ID NOs: 10, 11, 99, 102 and 104, which encodes an immunogenic peptide and (b) complements of (a). In some embodiments the isolated nucleic acid molecules are selected from the group consisting of: (a) unique fragments of a nucleotide sequence set forth as SEQ ID NO: 10, which encodes an immunogenic peptide and (b) complements of (a). In other embodiments the isolated nucleic acid molecules are selected from the group consisting of: (a) unique fragments of a nucleotide sequence set forth as SEQ ID NO: 11, which encodes an immunogenic peptide and (b) complements of (a). In yet other embodiments the isolated nucleic acid molecules are selected from the group consisting of: (a) unique fragments of a nucleotide sequence set forth as SEQ ID NO: 102, which encodes an immunogenic peptide and (b) complements of (a). In still other embodiments the isolated nucleic acid molecules are selected from the group consisting of: (a) unique fragments of a nucleotide sequence set forth as SEQ ID NO: 104, which encodes an immunogenic peptide and (b) complements of (a). In some embodiments the nucleic acid molecule comprises a nucleotide sequence set forth as SEQ ID NO: 121. In other embodiments the nucleic acid molecule comprises a nucleotide sequence set forth as SEQ ID NO: 123. In still other embodiments the nucleic acid molecule comprises a nucleotide sequence set forth as SEQ ID NO: 125. In yet other embodiments the nucleic acid molecule comprises a nucleotide sequence set forth as SEQ ID NO: 131.

In certain embodiments, the isolated nucleic acid molecule includes a nucleotide sequence that is at least about 90% identical to a nucleotide sequence selected from the group consisting of SEQ ID NOs: 1-14 and 97-107; preferably the nucleotide sequence is at least about 95% identical, more preferably the nucleotide sequence is at least about 97% identical, still more preferably the nucleotide sequence is at least about 98% identical, and yet more preferably the nucleotide sequence is at least about 99% identical.

According to further aspects of the invention, expression vectors that include any of the foregoing isolated nucleic acid molecules operably linked to a promoter are provided, as are host cells transformed or transfected with these expression vectors. In certain embodiments, the host cell expresses a MHC molecule, and in some of these embodiments the MHC molecule is expressed recombinantly.

According to another aspect of the invention, isolated polypeptides are provided that are encoded by the isolated nucleic acid molecules described herein. In certain embodiments, the isolated polypeptide includes an amino acid sequence as set forth in SEQ ID NOs: 46-60, 109-120 or a fragment thereof that is at least eight amino acids in length. In certain embodiments, the isolated polypeptides are antigenic polypeptides that are capable of eliciting antibodies to a sarcoma-associated antigen. In some embodiments the isolated polypeptide includes an amino acid sequence as set forth in SEQ ID NO: 55 or a fragment thereof that is at least eight amino acids in length. In other embodiments the isolated polypeptide includes an amino acid sequence as set forth in SEQ ID NO: 56 or a fragment thereof that is at least eight amino acids in length. In yet other embodiments the isolated polypeptide includes an amino acid sequence as set forth in SEQ ID NO: 111 or a fragment thereof that is at least eight amino acids in length. In still other embodiments the isolated polypeptide includes an amino acid sequence as set forth in SEQ ID NO: 114 or a fragment thereof that is at least eight amino acids in length. In yet other embodiments the isolated polypeptide includes an amino acid sequence as set forth in SEQ ID NO: 116 or a fragment thereof that is at least eight amino acids in length. In still other embodiments the isolated polypeptide includes an amino acid sequence as set forth in SEQ ID NO: 122. In yet other embodiments the isolated polypeptide includes an amino acid sequence as set forth in SEQ ID NO: 124. In still further embodiments the isolated polypeptide includes an amino acid sequence as set forth in SEQ ID NO: 126. In yet other embodiments the polypeptide includes the amino acid sequence set forth as SEQ ID NOs: 128, 130 or 132.

Another aspect of the invention provides binding polypeptides that selectively bind to the foregoing isolated polypeptides. In some embodiments these binding polypeptides are isolated also. In other embodiments, the binding polypeptides are antibodies or antigen-binding fragments thereof.

According to another aspect of the invention, methods of diagnosing cancer in a subject are provided. The methods include obtaining a biological sample from the subject, and determining the presence of an antibody in the biological sample that binds specifically to one or more sarcoma-associated antigens encoded by a nucleotide sequence selected from the group consisting of SEQ ID NOs: 3, 5-8, 10-45, 99, 102, 104 and 108. The presence of such antibodies indicates that the subject has cancer. In some embodiments the one or more sarcoma-associated antigens is/are encoded by a nucleotide sequence selected from the group consisting of SEQ ID NOs: 5-7, 10-13, 15-45, 102, 104 and 108. In still other embodiments the one or more sarcoma-associated antigens is/are encoded by a nucleotide sequence selected from the group consisting of SEQ ID NOs: 10, 11, 15, 102, 104 and 108. In some embodiments the sarcoma-associated antigens is encoded by a nucleotide sequence set forth as SEQ ID NO: 10.

In some embodiments, the step of determining the presence of an antibody includes contacting the biological sample with one or more sarcoma-associated antigens that are specifically bound by the antibody and are encoded by a nucleic acid molecule comprising a nucleotide sequence selected from the group consisting of (1) nucleotide sequences set forth as SEQ ID NOs: 3, 5-8, 10-45, 99, 102, 104 and 108 and (2) nucleotide sequences that are at least 90% identical to the nucleotide sequences of (1), and then determining the binding of the antibody to the sarcoma-associated antigen. In other embodiments, the step of determining the presence of an antibody includes contacting the biological sample with one or more sarcoma-associated antigens that are specifically bound by the antibody and are encoded by a nucleic acid molecule comprising a nucleotide sequence selected from the group consisting of (1) nucleotide sequences set forth as SEQ ID NOs: 5-7, 10-13, 15-45, 102, 104 and 108 and (2) nucleotide sequences that are at least 90% identical to the nucleotide sequences of (1), and then determining the binding of the antibody to the sarcoma-associated antigen.

In some embodiments, the nucleic acid molecule comprises a nucleotide sequence selected from the group consisting of nucleotide sequences set forth as SEQ ID NOs: 10, 11, 15, 102, 104 and 108, and in other embodiments the nucleic acid molecule includes the nucleotide sequence set forth as SEQ ID NO: 10. In other embodiments the nucleic acid molecule includes the nucleotide sequence set forth as SEQ ID NO: 121. In still other embodiments the nucleic acid molecule includes the nucleotide sequence set forth in SEQ ID NO: 123. In other embodiments the nucleic acid molecule includes the nucleotide sequence set forth in SEQ ID NO: 125. In yet other embodiments the nucleic acid molecule includes the nucleotide sequence set forth in SEQ ID NOs: 127, 129 or 131.

In other embodiments, the sarcoma-associated antigen is a polypeptide that includes the amino acid sequence of any of SEQ ID NOs: 48, 50-53, 55-90, 111, 114, 116 and 120 or a fragment thereof that is at least eight amino acids in length. In still other embodiments, the sarcoma-associated antigen is a polypeptide that includes the amino acid sequence of any of SEQ ID NOs: 50-52, 55-58, 60-90, 114, 116, 120 or a fragment thereof that is at least eight amino acids in length. In still other embodiments, the sarcoma-associated antigen is a polypeptide that includes the amino acid sequence of any of SEQ ID NOs: 55, 56, 60, 114, 116 and 120 or a fragment thereof that is at least eight amino acids in length.

In some embodiments, the sarcoma-associated antigen includes the amino acid sequence set forth as SEQ ID NO: 55 or a fragment thereof that is at least eight amino acids in length. In certain embodiments the sarcoma-associated antigen includes the amino acid sequence set forth as SEQ ID NO: 122. In still other embodiments the sarcoma-associated antigen includes the amino acid sequence set forth as SEQ ID NO: 124. In yet other embodiments the sarcoma-associated antigen includes the amino acid sequence set forth as SEQ ID NO: 126. In still other embodiments the sarcoma-associated antigen includes the amino acid sequence set forth as SEQ ID NO: 128, 130 or 132.

In certain embodiments, the biological sample is serum. In other embodiments, the one or more sarcoma-associated antigens are produced recombinantly, and/or the one or more sarcoma-associated antigens are bound to a substrate. In some embodiments, the step of determining the binding of the antibody with the one or more sarcoma-associated antigens is performed with an ELISA-based method. In still other embodiments a serum antibody detection assay (SADA) is used.

According to still another aspect of the invention, methods for diagnosing cancer in a subject are provided. The methods include obtaining a biological sample from a subject, and determining the expression of a sarcoma-associated antigen or a nucleic acid molecule that encodes it. The nucleic acid molecule includes a nucleotide sequence selected from the group consisting of SEQ ID NOs: 3, 5-8, 10-45, 99, 102, 104 and 108 in the biological sample. The nucleic acid molecule is some embodiments includes a nucleotide sequence selected from the group consisting of SEQ ID NOs: 5-7, 10-13, 15-45, 102, 104 and 108 in the biological sample. The expression of the sarcoma-associated antigen or the nucleic acid molecule that encodes it in the sample is diagnostic for cancer in the subject.

In certain embodiments, the sarcoma-associated nucleic acid molecule comprises the nucleotide sequence selected from the group consisting of SEQ ID NOs: 10, 11, 15, 102, 104 and 108. In some embodiments the sarcoma-associated nucleic acid molecule includes the nucleotide sequence set forth as SEQ ID NO: 10. In other embodiments the nucleic acid molecule includes the nucleotide sequence set forth as SEQ ID NO: 121. In still other embodiments the nucleic acid molecule includes the nucleotide sequence set forth in SEQ ID NO: 123. In yet other embodiments the nucleic acid molecule includes the nucleotide sequence set forth in SEQ ID NO: 125. In yet other embodiments the nucleic acid molecule includes the nucleotide sequence set forth in SEQ ID NOs: 127, 129 or 131.

In other embodiments, the sarcoma-associated antigen comprises an amino acid sequence selected from the group consisting of SEQ ID NOs: 48, 50-53, 55-90, 111, 114, 116 and 120 or a fragment thereof that is at least eight amino acids in length. In yet other embodiments, the sarcoma-associated antigen comprises an amino acid sequence selected from the group consisting of SEQ ID NOs: 50-52, 55-58, 60-90, 114, 116 and 120 or a fragment thereof that is at least eight amino acids in length. The sarcoma-associated antigen in some embodiments includes an amino acid sequence selected from the group consisting of SEQ ID NOs: 55, 56, 60, 114, 116 and 120. In some embodiments the sarcoma-associated antigen includes an amino acid sequence set forth as SEQ ID NO: 55 or a fragment thereof that is at least eight amino acids in length. In certain embodiments the sarcoma-associated antigen includes the amino acid sequence set forth as SEQ ID NO: 122. In still other embodiments the sarcoma-associated antigen includes the amino acid sequence set forth as SEQ ID NO: 124. In yet other embodiments the sarcoma-associated antigen includes the amino acid sequence set forth as SEQ ID NO: 126. In still further embodiments the sarcoma-associated antigen includes the amino acid sequence set forth as SEQ ID NOs: 128, 130 or 132.

According to yet another aspect of the invention, methods for determining onset, progression, or regression of cancer in a subject are provided. The methods include obtaining from a subject a first biological sample, determining the expression of a sarcoma-associated antigen or the nucleic acid molecule that encodes it in the first sample, obtaining from the subject a second biological sample, determining the expression of the sarcoma-associated antigen or the nucleic acid molecule that encodes it in the second sample, and comparing the expression in the first sample to the expression in the second sample as a determination of the onset, progression, or regression of the cancer. The nucleic acid molecule comprises a nucleotide sequence selected from the group consisting of (1) nucleotide sequences set forth as SEQ ID NOs: 3, 5-8, 10-45, 99, 102, 104 and 108 and (2) nucleotide sequences that are at least 90% identical to the nucleotide sequences of (1). In some embodiments the nucleic acid molecule comprises a nucleotide sequence selected from the group consisting of (1) nucleotide sequences set forth as SEQ ID NOs: 5-7, 10-13, 15-45, 102, 104 and 108 and (2) nucleotide sequences that are at least 90% identical to the nucleotide sequences of (1).

In some embodiments, the nucleic acid molecule that encodes the sarcoma-associated antigen includes a nucleotide sequence selected from the group consisting of SEQ ID NOs: 10, 11, 15, 102, 104 and 108. In other embodiments the nucleic acid molecule includes the nucleotide sequence of SEQ ID NO: 10. In yet other embodiments the nucleic acid molecule includes the nucleotide sequence set forth as SEQ ID NO: 121. In still other embodiments the nucleic acid molecule includes the nucleotide sequence set forth in SEQ ID NO: 123. In yet other embodiments the nucleic acid molecule includes the nucleotide sequence set forth in SEQ ID NO: 125. In still other embodiments the nucleic acid molecule includes the nucleotide sequence set forth in SEQ ID NOs: 127, 129 or 131. In other embodiments, the sarcoma-associated antigen includes a polypeptide sequence selected from the group consisting of polypeptide sequences set forth as SEQ ID NOs: 48, 50-53, 55-90, 111, 114, 116 and 120 or a fragment thereof that is at least eight amino acids in length. In still other embodiments, the sarcoma-associated antigen includes a polypeptide sequence selected from the group consisting of polypeptide sequences set forth as SEQ ID NOs: 50-52, 55-58, 60-90, 114, 116 and 120 or a fragment thereof that is at least eight amino acids in length. In yet other embodiments, the sarcoma-associated antigen includes a polypeptide sequence selected from the group consisting of polypeptide sequences set forth as SEQ ID NOs: 55, 56, 60, 114, 116 and 120 or a fragment thereof that is at least eight amino acids in length. In some embodiments the sarcoma-associated antigen includes the amino acid sequence of SEQ ID NO: 55 or a fragment thereof that is at least eight amino acids in length. In certain embodiments the sarcoma-associated antigen includes the amino acid sequence set forth as SEQ ID NO: 122. In still other embodiments the sarcoma-associated antigen includes the amino acid sequence set forth as SEQ ID NO: 124. In yet other embodiments the sarcoma-associated antigen includes the amino acid sequence set forth as SEQ ID NO: 126. In still other embodiments the sarcoma-associated antigen includes the amino acid sequence set forth as SEQ ID NOs: 128, 130 or 132.

In some embodiments of the foregoing methods, the step of determining the expression of the sarcoma-associated antigen or the nucleic acid molecule that encodes it includes contacting the biological sample with an agent that selectively binds to the sarcoma-associated antigen or the nucleic acid molecule that encodes it. For methods in which the agent that selectively binds is a nucleic acid molecule, it is preferred that the expression of the sarcoma-associated nucleic acid molecule is determined by nucleic acid hybridization or nucleic acid amplification; some embodiments of the methods utilize real-time RT-PCR or RT-PCR as methods of nucleic acid amplification, or use a nucleic acid microarray as a method for nucleic acid hybridization. For methods in which the agent that selectively binds is a polypeptide, the polypeptide preferably is an antibody or antigen-binding fragment thereof. More preferably, the antibody is a monoclonal antibody, particularly a chimeric, human, or humanized antibody, a single chain antibody, or the antigen-binding fragment is a F(ab')$_2$, Fab, Fd, or Fv fragment. In certain embodiments, the antibody or antigen-binding fragment is labeled with a detectable label, preferably a fluorescent or radioactive label.

In certain embodiments of the foregoing methods, the sample is selected from the group consisting of tissue, cells, and blood. In some embodiments, the cancer is a sarcoma.

In another aspect of the invention, kits for detecting antibodies reactive to a sarcoma-associated antigen in a biological sample are provided. The kits include one or more sarcoma-associated antigens encoded by a nucleic acid molecule comprising a nucleotide sequence selected from the group consisting of nucleotide sequences set forth as SEQ ID NOs: 3, 5-8, 10-45, 99, 102, 104 and 108, and instructions for the use of the sarcoma-associated antigens in the detection of antibodies in the biological sample. In some embodiments the one or more sarcoma-associated antigens is/are encoded by a nucleic acid molecule comprising a nucleotide sequence selected from the group consisting of nucleotide sequences set forth as SEQ ID NOs: 5-7, 10-13, 15-45, 102, 104 and 108. In some embodiments, the sarcoma-associated nucleic acid molecule comprises the nucleotide sequence set forth as SEQ ID NO: 10, 11, 15, 102, 104 or 108. In other embodiments, the sarcoma-associated nucleic acid molecule comprises the nucleotide sequence set forth as SEQ ID NO: 10. In other embodiments the nucleic acid molecule includes the nucleotide sequence set forth as SEQ ID NO: 121. In still other embodiments the nucleic acid molecule includes the nucleotide sequence set forth in SEQ ID NO: 123. In yet other embodiments the nucleic acid molecule includes the nucleotide sequence set forth in SEQ ID NO: 125. In still further embodiments the nucleic acid molecule includes the nucleotide sequence set forth in SEQ ID NOs: 127, 129 or 131. In other embodiments, the sarcoma-associated antigens are bound to a substrate. In further embodiments, the kit also includes a labeling reagent and labeling reagent substrate, and/or a blocking reagent. Additional kit embodiments include secondary antibodies for detection of the antibody bound to the antigen.

In a further aspect of the invention, other kits for the diagnosis of cancer in a subject are provided. The kits include one or more binding agents that specifically bind to a sarcoma-associated antigen or the nucleic acid molecule that encodes it. In this aspect, the nucleic acid molecule includes a nucleotide sequence selected from the group consisting of SEQ ID NOs: 3, 5-8, 10-45, 99, 102, 104 and 108. In some embodiments the nucleic acid molecule includes a nucleotide sequence selected from the group consisting of SEQ ID NOs: 5-7, 10-13, 15-45, 102, 104 and 108. The kit also includes instructions for the use of the binding agents in the diagnosis of cancer. The one or more binding agents are nucleic acid molecules or polypeptides. If the latter, the polypeptides preferably are antibodies or antigen-binding fragments thereof. In other embodiments, the one or more agents are bound to a substrate. Further embodiments of the kits include one or more agents that bind specifically to a cancer-associated antigen other than those encoded by a nucleic acid molecule comprising a nucleotide sequence selected from the group consisting of SEQ ID NOs: 10, 11, 15, 102, 104 and 108. In some embodiments, the kit is configured for diagnosis of sarcomas.

According to another aspect of the invention, methods for treating a subject with a disorder characterized by the aberrant expression of a sarcoma-associated antigen or the nucleic acid molecule that encodes it are provided. The methods include administering to a subject an effective amount of an antibody or antigen-binding fragment thereof that specifically binds to the sarcoma-associated antigen. In this aspect, the antigen includes an amino acid sequence selected from the group consisting of SEQ ID NOs: 48, 50-53, 55-90, 111, 114, 116 and 120 or a fragment thereof that is eight or more amino acids in length. In some embodiments the antigen includes an amino acid sequence selected from the group consisting of SEQ ID NOs: 50-52, 55-58, 60-90, 114, 116 and 120 or a fragment thereof that is eight or more amino acids in length. In other embodiments the antigen includes an amino acid sequence selected from the group consisting of SEQ ID NOs: 55, 56, 60, 114, 116 and 120 or a fragment thereof that is eight or more amino acids in length. In some embodiments, the antibody or antigen-binding fragment thereof specifically binds to the extracellular domain of a sarcoma-associated antigen that includes the amino acid sequence of SEQ ID NO: 55 or a fragment thereof that is eight or more amino acids in length. In certain embodiments the sarcoma-associated antigen includes the amino acid sequence set forth as SEQ ID NO: 122. In still other embodiments the sarcoma-associated antigen includes the amino acid sequence set forth as SEQ ID NO: 124. In yet other embodiments the sarcoma-associated antigen includes the amino acid sequence set forth as SEQ ID NO: 126. In still other embodiments the sarcoma-associated antigen includes the amino acid sequence set forth as SEQ ID NO: 128, 130 or 132. In yet other embodiments the sarcoma-associated antigen includes the amino acid sequence set forth as SEQ ID NO: 134 or a fragment thereof that is eight or more amino acids in length.

In certain embodiments, the disorder is cancer, preferably sarcoma. In other embodiments, the antibody used in the methods is a monoclonal antibody, preferably a chimeric, human, or humanized antibody; a single chain antibody; or the antigen-binding fragment is a F(ab')$_2$, Fab, Fd, or Fv fragment.

In other embodiments, the antibody or antigen-binding fragment thereof is bound to a cytotoxic agent. Preferred cytotoxic agents include: calicheamicin, esperamicin, methotrexate, doxorubicin, melphalan, chlorambucil, ARA-C, vindesine, mitomycin C, cisplatinum, etopside, bleomycin and 5-fluorouracil. Other cytotoxic agents include radioisotopes, including those that emit $\alpha$, $\beta$, and/or $\gamma$ radiation. Preferred radioisotopes include: $^{225}$Ac, $^{211}$At, $^{212}$Bi, $^{213}$Bi, $^{186}$Rh, $^{188}$Rh, $^{177}$Lu, $^{90}$Y, $^{131}$I, $^{67}$Cu, $^{125}$I, $^{123}$I, $^{77}$Br, $^{153}$Sm, $^{166}$Bo, $^{64}$Cu, $^{212}$Pb, $^{224}$Ra and $^{223}$Ra.

According to another aspect of the invention, methods for treating a subject with a disorder characterized by the aberrant expression of a sarcoma-associated antigen or a nucleic acid molecule that encodes it are provided. The methods include administering an amount of an agent that selectively binds to the sarcoma-associated antigen or the nucleic acid molecule that encodes it effective to treat the disorder. The nucleic acid molecule comprises a nucleotide sequence selected from the group consisting of (a) an isolated nucleic acid molecule comprising a nucleotide sequence that is at least 90% identical to the nucleotide sequence selected from the group consisting of SEQ ID NOs: 3, 5-8, 10-45, 99, 102, 104 and 108, and (b) nucleic acid molecules that differ from the nucleic acid molecules of (a) in codon sequence due to the degeneracy of the genetic code. In some embodiments the nucleic acid molecule comprises a nucleotide sequence selected from the group consisting of (a) an isolated nucleic acid molecule comprising a nucleotide sequence that is at least 90% identical to the nucleotide sequence selected from the group consisting of SEQ ID NOs: 5-7, 10-13, 15-45, 102, 104 and 108, and (b) nucleic acid molecules that differ from the nucleic acid molecules of (a) in codon sequence due to the degeneracy of the genetic code. In certain embodiments the disorder is cancer, preferably sarcoma. In yet other embodiments the sarcoma-associated nucleic acid molecule comprises the nucleotide sequence selected from the group consisting of nucleotide sequences set forth as SEQ ID NOs: 10, 11, 15, 102, 104 and 108. In some embodiments the sarcoma-associated nucleic acid molecule comprises the nucleotide sequence set forth as SEQ ID NO: 10.

In other embodiments the sarcoma-associated nucleic acid molecule codes for a sarcoma-associated antigen which comprises the polypeptide sequence selected from the group consisting of polypeptide sequences set forth as SEQ ID NOs: 48, 50-53, 55-90, 111, 114, 116 and 120 or a fragment thereof that is at least eight amino acids in length. In still other embodiments the sarcoma-associated nucleic acid molecule codes for a sarcoma-associated antigen which comprises the polypeptide sequence selected from the group consisting of polypeptide sequences set forth as SEQ ID NOs: 50-52, 55-58, 60-90, 114, 116 and 120 or a fragment thereof that is at least eight amino acids in length. In some embodiments the sarcoma-associated nucleic acid molecule codes for a sarcoma-associated antigen which comprises the polypeptide sequence set forth as SEQ ID NO: 55, 56, 60, 114, 116 or 120 or a fragment thereof that is at least eight amino acids in length. In another embodiment the sarcoma-associated nucleic acid molecule codes for a sarcoma-associated antigen which comprises the polypeptide sequence set forth as SEQ ID NO: 55 or a fragment thereof that is at least eight amino acids in length. In certain embodiments the sarcoma-associated antigen includes the amino acid sequence set forth as SEQ ID NO: 122. In still other embodiments the sarcoma-associated antigen includes the amino acid sequence set forth as SEQ ID NO: 124. In yet other embodiments the sarcoma-associated antigen includes the amino acid sequence set forth as SEQ ID NO: 126. In still other embodiments the sarcoma-associated antigen includes the amino acid sequence set forth as SEQ ID NOs: 128, 130 or 132.

In certain embodiments, the binding agent is an antisense or RNAi molecule. In other embodiments, the binding agent is a polypeptide, preferably an antibody or antigen-binding fragment thereof. Preferred antibodies include monoclonal antibodies, including chimeric, human, or humanized antibodies, and single chain antibodies; preferred antigen-binding fragments include F(ab')$_2$, Fab, Fd, or Fv fragments. In other embodiments, the antibody or antigen-binding fragment is bound to a cytotoxic agent.

According to yet another aspect of the invention, methods for treating a subject with a disorder characterized by the aberrant expression of a sarcoma-associated antigen or the nucleic acid molecule that encodes it are provided. The methods include administering to the subject an amount of an agent effective to stimulate an immune response to a sarcoma-associated antigen encoded by a nucleic acid molecule comprising a nucleotide sequence that is at least 90% identical to the nucleotide sequence selected from the group consisting of SEQ ID NOs: 3, 5-8, 10-45, 99, 102, 104 and 108. In some embodiments the sarcoma-associated antigen is encoded by a nucleic acid molecule comprising a nucleotide sequence that is at least 90% identical to the nucleotide sequence selected from the group consisting of SEQ ID NOs: 5-7, 10-13, 15-45, 102, 104 and 108. In some embodiments, the disorder is cancer, particularly sarcoma. In other embodiments the sarcoma-associated nucleic acid molecule comprises the nucleotide sequence selected from the group consisting of nucleotide sequences set forth as SEQ ID NOs: 10, 11, 15, 102, 104 and 108. In some embodiments the sarcoma-associated nucleic acid molecule comprises the nucleotide sequence set forth as SEQ ID NO: 10. In other embodiments the sarcoma-associated antigen is encoded by a nucleic acid molecule comprising a nucleotide sequence set forth as SEQ ID NO: 133.

In yet other embodiments the sarcoma-associated antigen includes an amino acid sequence selected from the group consisting of SEQ ID NOs: 48, 50-53, 55-90, 111, 114, 116 and 120, or a fragment thereof that is at least eight amino acids in length. In still other embodiments the sarcoma-associated antigen includes an amino acid sequence selected from the group consisting of SEQ ID NOs: 50-52, 55-58, 60-90, 114, 116 and 120, or a fragment thereof that is at least eight amino acids in length. In some embodiments the sarcoma-associated antigen includes the amino acid sequence set forth as SEQ ID NO: 55, or a fragment thereof that is at least eight amino acids in length. In certain embodiments the sarcoma-associated antigen includes the amino acid sequence set forth as SEQ ID NO: 122. In still other embodiments the sarcoma-associated antigen includes the amino acid sequence set forth as SEQ ID NO: 124. In yet other embodiments the sarcoma-associated antigen includes the amino acid sequence set forth as SEQ ID NO: 126. In still other embodiments the sarcoma-associated antigen includes the amino acid sequence set forth as SEQ ID NOs: 128, 130 or 132. In still further embodiments the sarcoma-associated antigen includes the amino acid sequence set forth as SEQ ID NO: 134, or a fragment thereof that is at least eight amino acids in length.

In some embodiments, the agent that stimulates an immune response is a nucleic acid that encodes a sarcoma-associated antigen operably linked to a promoter for expressing the sarcoma-associated antigen; a polypeptide comprising the sarcoma-associated antigen; or a host cell that expresses the sarcoma-associated antigen, particularly a host cell that also expresses a MHC molecule. In some embodiments, the agent which stimulates an immune response is a peptide fragment of the sarcoma-associated antigen, or is a complex of a peptide fragment of the sarcoma-associated antigen and a MHC molecule. In other embodiments, the agent also includes an adjuvant or cytokine.

In another aspect of the invention, kits for diagnosing a disorder associated with the aberrant expression of a sarcoma-associated antigen or a nucleic acid molecule that encodes it are provided. The kits include one or more nucleic acid molecules that hybridize to the nucleic acid molecule that encodes the sarcoma-associated antigen comprising a nucleotide sequence selected from the group consisting of nucleotide sequences set forth as SEQ ID NOs: 3, 5-8, 10-45, 99, 102, 104 and 108 under high stringency conditions, and instructions for the use of the nucleic acid molecules in the diagnosis of a disorder associated with aberrant expression of the sarcoma-associated antigen or the nucleic acid molecule that encodes it. In some embodiments the one or more nucleic acid molecules that hybridize to the nucleic acid molecule that encodes the sarcoma-associated antigen comprises a nucleotide sequence selected from the group consisting of nucleotide sequences set forth as SEQ ID NOs: 5-7, 10-13, 15-45, 102, 104 and 108. In some embodiments, the one or more nucleic acid molecules are detectably labeled. In some embodiments the nucleic acid molecule that encodes the sarcoma-associated antigen comprises the nucleotide sequence set forth as SEQ ID NO: 10, 11, 15, 102, 104 or 108. In other embodiments the nucleic acid molecule that encodes the sarcoma-associated antigen comprises the nucleotide sequence set forth as SEQ ID NO: 10. In other embodiments the nucleic acid molecule includes the nucleotide sequence set forth as SEQ ID NO: 121. In still other embodiments the nucleic acid molecule includes the nucleotide sequence set forth in SEQ ID NO: 123. In yet other embodiments the nucleic acid molecule includes the nucleotide sequence set forth in SEQ ID NO: 125. In still other embodiments the nucleic acid molecule includes the nucleotide sequence set forth in SEQ ID NOs: 127, 129 or 131.

In certain embodiments, the one or more nucleic acid molecules consist of a first primer and a second primer, wherein the first primer and the second primer are constructed and arranged to selectively amplify at least a portion of a nucleic acid molecule that encodes the sarcoma-associated antigen and comprises a nucleotide sequence selected from the group consisting of SEQ ID NOs: 10, 11, 15, 102, 104 and 108. In other embodiments, the nucleic acids in the kit are bound to a substrate.

In still another aspect of the invention, methods for identifying a cancer-associated antigen are provided. The methods include obtaining a biological sample from one or more subjects, determining the reactivity of the biological sample to one or more known cancer-associated antigens, using the reactive biological sample to screen an expression library to determine the presence of cancer-associated antigens reactive with the biological sample, and isolating a clone that encodes the cancer-associated antigen from the expression library. In certain embodiments the biological sample is serum. In some embodiments the expression library is derived from a tumor, preferably from a tumor cell line.

In still other embodiments, the methods also include determining the identity of the cancer-associated antigen encoded by the isolated clone, preferably by DNA sequencing.

The invention in a further aspect provides a composition including an agent that stimulates an immune response to a sarcoma-associated antigen. In some embodiments sarcoma-associated antigens are those encoded by a nucleic acid molecule selected from the group consisting of an isolated nucleic acid molecule comprising a nucleotide sequence that is at least 90% identical to the nucleotide sequence selected from the group consisting of SEQ ID NOs: 3, 5-8, 10-45, 99, 102, 104 and 108, and nucleic acid molecules that differ from the nucleic acid molecules of (a) in codon sequence due to the degeneracy of the genetic code. In some embodiments the sarcoma-associated antigens are those encoded by a nucleic acid molecule selected from the group consisting of an isolated nucleic acid molecule comprising a nucleotide sequence that is at least 90% identical to the nucleotide sequence selected from the group consisting of SEQ ID NOs: 5-7, 10-13, 15-45, 102, 104 and 108, and nucleic acid molecules that differ from the nucleic acid molecules of (a) in codon sequence due to the degeneracy of the genetic code. In particular embodiments, the nucleic acid molecule includes a nucleotide sequence selected from the group consisting of SEQ ID NOs: 10, 11, 15, 102, 104 and 108. In some embodiments the nucleic acid molecule includes the nucleotide sequence set forth as SEQ ID NO: 10. In other embodiments the nucleic acid molecule includes the nucleotide sequence set forth as SEQ ID NO: 133.

In some embodiments, sarcoma-associated antigen comprises a polypeptide sequence selected from the group consisting of SEQ ID NOs: 48, 50-53, 55-90, 111, 114, 116 and 120 or a fragment thereof that is at least eight amino acids in length. In other embodiments, sarcoma-associated antigen comprises a polypeptide sequence selected from the group consisting of SEQ ID NOs: 50-52, 55-58, 60-90, 114, 116 and 120 or a fragment thereof that is at least eight amino acids in length. In some embodiments the sarcoma-associated antigen includes the amino acid sequence of SEQ ID NO: 55, 56, 60, 114, 116 or 120 or a fragment thereof that is at least eight amino acids in length. In other embodiments the sarcoma-associated antigen includes the amino acid sequence of SEQ ID NO: 55 or a fragment thereof that is at least eight amino acids in length. In certain embodiments the sarcoma-associated antigen includes the amino acid sequence set forth as SEQ ID NO: 122. In still other embodiments the sarcoma-associated antigen includes the amino acid sequence set forth as SEQ ID NO: 124. In yet other embodiments the sarcoma-associated antigen includes the amino acid sequence set forth as SEQ ID NO: 126. In still other embodiments the sarcoma-associated antigen includes the amino acid sequence set forth as SEQ ID NOs: 128, 130 or 132. In yet other embodiments the sarcoma-associated antigen includes the amino acid sequence set forth as SEQ ID NO: 134.

The agent, in some embodiments, is a nucleic acid that encodes a sarcoma-associated antigen operably linked to a promoter for expressing the sarcoma-associated antigen. In other embodiments, the agent is a polypeptide comprising the sarcoma-associated antigen. In still other embodiments, the agent is a host cell that expresses the sarcoma-associated antigen; preferably the host cell also expresses a MHC molecule. In yet other embodiments, the agent is a complex of a peptide derived from the sarcoma-associated antigen and a MHC molecule.

The composition also includes, in certain embodiments, an adjuvant or cytokine and/or one or more cytotoxic or chemotherapeutic agents. The compositions optionally includes a pharmaceutically acceptable carrier.

In another aspect of the invention, compositions are provided that include an agent that selectively binds to a sarcoma-associated antigen or a nucleic acid molecule that encodes it. The nucleic acid molecule includes a nucleotide sequence selected from the group consisting of: (a) an isolated nucleic acid molecule comprising a nucleotide sequence that is at least 90% identical to the nucleotide sequence selected from the group consisting of SEQ ID NOs: 3, 5-8, 10-13, 99, 102 and 104 and (b) nucleic acid molecules that differ from the nucleic acid molecules of (a) in codon sequence due to the degeneracy of the genetic code. In some embodiments the nucleic acid molecule includes a nucleotide sequence selected from the group consisting of: (a) an isolated nucleic acid molecule comprising a nucleotide sequence that is at least 90% identical to the nucleotide sequence selected from the group consisting of SEQ ID NOs: 5-7, 10-13, 102 and 104 and (b) nucleic acid molecules that differ from the nucleic acid molecules of (a) in codon sequence due to the degeneracy of the genetic code. In some embodiments the nucleic acid molecule includes a nucleotide sequence selected from the group consisting of SEQ ID NOs: 10, 11, 102 and 104; in other embodiments the nucleic acid molecule includes the nucleotide sequence set forth as SEQ ID NO: 10. In other embodiments the nucleic acid molecule includes the nucleotide sequence set forth as SEQ ID NO: 121. In still other embodiments the nucleic acid molecule includes the nucleotide sequence set forth in SEQ ID NO: 123. In yet other embodiments the nucleic acid molecule includes the nucleotide sequence set forth in SEQ ID NO: 125. In still other embodiments the nucleic acid molecule includes the nucleotide sequence set forth in SEQ ID NOs: 127, 129 or 131. In other embodiments, the sarcoma-associated antigen includes the amino acid sequence set forth as SEQ ID NO: 55, 56, 114 or 116 or a fragment thereof that is at least eight amino acids in length. In some embodiments the sarcoma-associated antigen includes the amino acid sequence set forth as SEQ ID NO: 55. In certain embodiments the sarcoma-associated antigen includes the amino acid sequence set forth as SEQ ID NO: 122. In still other embodiments the sarcoma-associated antigen includes the amino acid sequence set forth as SEQ ID NO: 124. In yet other embodiments the sarcoma-associated antigen includes the amino acid sequence set forth as SEQ ID NO: 126. In still other embodiments the sarcoma-associated antigen includes the amino acid sequence set forth as SEQ ID NOs: 128, 130 or 132. The agents in this aspect of the invention include nucleic acids and polypeptides, preferably antibodies or antigen-binding fragments thereof. Preferred antibodies include monoclonal antibodies (particularly chimeric, human, or humanized antibodies), and single chain antibodies; preferred antibody fragments include F(ab')$_2$, Fab, Fd, or Fv fragments.

In certain embodiments, the antibody or antigen-binding fragment is conjugated to cytotoxic or chemotherapeutic agent. In other embodiments, the composition includes one or more cytotoxic or chemotherapeutic agent. In still other embodiments, the composition includes a pharmaceutically acceptable carrier.

The use of the nucleotide and amino acid sequence as set forth as SEQ ID NOs: 133 and 134, respectively, in any of the compositions and methods described herein are also provided.

The invention also involves the use of the genes, gene products, fragments thereof, agents which bind thereto, and other compositions and molecules described herein in the preparation of medicaments. A particular medicament is for treating cancer.

These and other aspects of the invention will be described in further detail in connection with the detailed description of the invention.

BRIEF DESCRIPTION OF THE DRAWING

FIG. 1 provides the mRNA expression patterns of serologically defined sarcoma antigens.

FIG. 2 provides the nucleotide and predicted amino acid sequence of NY-SAR-35 from each of the four ATG codons. The underlined letters indicate the signal peptide and the italicized letters indicate the transmembrane domain. The letters shown in gray represent the trefoil domain, while the letters that are underlined and italicized represent the other hydrophilic turn.

DETAILED DESCRIPTION OF THE INVENTION

Figure 1A:
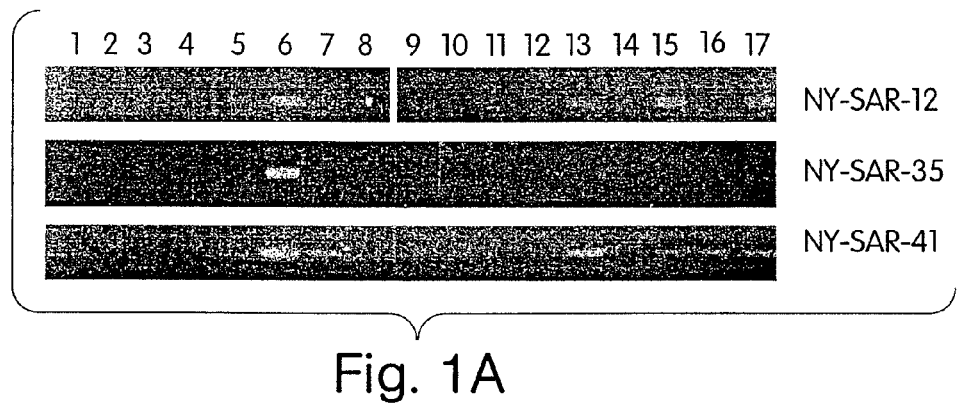
FIG. 1A shows the results of the RT-PCR analysis of NY-SAR-12, -35, and -41 in a panel of 17 normal tissues (Lanes 1, brain; 2, kidney; 3, liver; 4, pancreas; 5, placenta; 6, testis; 7, fetal brain; 8, small intestine; 9, heart; 10, prostate; 11, adrenal gland; 12, spleen; 13, colon; 14, stomach; 15, lung; 16, bladder; and 17, ovary).

The screening of cDNA expression libraries derived from human tumors with autologous antibody (SEREX) has proven to be a powerful method for defining the structure of tumor antigens recognized by the humoral immune system, and has led to the identification of new targets for cancer immunotherapy. The current study examined the humoral immune response of sarcoma patients to CT antigens. Sera from patients which showed a humoral immune response to CT antigens were subsequently used to screen cDNA libraries derived from CT-rich sarcoma cell lines, leading to the identification of antigens not before associated with cancer along with several novel antigens associated with a sarcoma-related immune response, including a novel CT antigen, NY-SAR-35.

Sarcoma-associated antigens were identified with an optimized SEREX analysis method. Cell lines that were rich in CT antigen expression were chosen as the source of cDNA. Additionally, sera was obtained from a group of patients that were actively mounting a humoral immune response to a panel of known CT antigens. This optimized SEREX analysis led to the identification of 113 antigens reactive with serum IgG of sarcoma patients. The antigens identified were further evaluated for cancer-restricted expression and the frequency of eliciting antibody responses in normal individuals as well as cancer patients.

In the first round of immunoscreenings, twenty-four of 72 antigens (33%) were found to have a serological profile that was not restricted to cancer patients, as evidenced by their reactivity with normal sera, while 48 antigens had a cancer-related serological profile, reacting only with sera from cancer patients. Notable antigens belonging to this latter category include the CT antigens, NY-SAR-36/SSX-1, NY-SAR-43/SSX-4 and NY-SAR-35. Although the antibody response in these studies to NY-SAR-4/FH was most frequent, occurring in 5/39 (13%) sarcoma patients, no individual antigen was serodominant. NY-SAR-4 is equivalent to fumarate hydratase (FH), an enzyme of the tricarboxylic acid cycle. This serological response to NY-SAR-4/FH may be of interest given the recent finding that germ line mutations in the FH gene are associated with a predisposition to uterine and cutaneous leiomyomata, and also renal cell carcinoma (Tomlinson I P, et al. Germline mutations in FH predispose to dominantly inherited uterine fibroids, skin leiomyomata and papillary renal cell cancer. Nat Genet 2002 April; 30(4):406-10).

In addition, 6 tissue-restricted antigens, LAGE-1/NY-SAR-17, SSX1/NY-SAR-36, SSX4/NY-SAR-43, NESG1/NY-SAR-12, NY-SAR-35, and NY-SAR-41 were identified. Two of these antigens, NY-SAR-35, and NY-SAR-41 are novel gene products, and a third, NESG1/NY-SAR-12 (Li Z, Yao K, Cao Y. Molecular cloning of a novel tissue-specific gene from human nasopharyngeal epithelium. Gene 1999

Sep. 3; 237(1):235-40), has not been previously studied in relation to cancer. NY-SAR-35 further represents a newly defined CT antigen expressed exclusively in normal testis, melanoma, sarcoma, lung cancer and breast cancer.

The second round of immunoscreenings performed led to the identification of 41 additional SEREX-defined sarcoma antigens, 11 of which are novel gene products (NY-SAR-77, -79, -80, -84, -88, -92, -95, -97, -104, 105 and -113). Within this group of 41 sarcoma antigens are three known testis-restricted antigens (NY-SAR-78/TSP-NY, NY-SAR-89/SSX2 and NY-SAR-99/SSX3), two differentially expressed antigens that are novel gene products (NY-SAR-92 and NY-SAR-97) and a tissue-restricted antigen that has not been previously studied in relation to cancer (NY-SAR-96/MCSP).

Table 1, below, provides a list of the sarcoma-associated antigens and their corresponding sequence identification numbers. The antigens listed include those that were found to be uncharacterized gene products as well as those sarcoma-associated antigens that exhibited cancer-restricted expression and were not found in the SEREX Database.

TABLE 1

Sarcoma-Associated Antigens (Uncharacterized Gene Products and Cancer-Related Antigens not Found in the SEREX Database)

| NY-SAR-Antigen | Sequence Identification Number (nucleotide and amino acid sequence, respectively) |
|---|---|
| 3 | SEQ ID NOs: 1 and 46 |
| 10 | SEQ ID NOs: 2 and 47 |
| 16 | SEQ ID NOs: 3 and 48 |
| 22 | SEQ ID NOs: 4 and 49 |
| 23 | SEQ ID NOs: 5 and 50 |
| 24 | SEQ ID NOs: 6 and 51 |
| 27 | SEQ ID NOs: 7 and 52 |
| 28 | SEQ ID NOs: 8 and 53 |
| 29 | SEQ ID NOs: 9 and 54 |
| 35 | SEQ ID NOs: 10 and 55 |
| 41 | SEQ ID NOs: 11 and 56 |
| 48 | SEQ ID NOs: 12 and 57 |
| 62 | SEQ ID NOs: 13 and 58 |
| 71 | SEQ ID NOs: 14 and 59 |
| 12 | SEQ ID NOs: 15 and 60 |
| 4 | SEQ ID NOs: 16 and 61 |
| 5 | SEQ ID NOs: 17 and 62 |
| 8 | SEQ ID NOs: 18 and 63 |
| 9 | SEQ ID NOs: 19 and 64 |
| 20 | SEQ ID NOs: 20 and 65 |
| 21 | SEQ ID NOs: 21 and 66 |
| 25 | SEQ ID NOs: 22 and 67 |
| 26 | SEQ ID NOs: 23 and 68 |
| 30 | SEQ ID NOs: 24 and 69 |
| 34 | SEQ ID NOs: 25 and 70 |
| 36 | SEQ ID NOs: 26 and 71 |
| 37 | SEQ ID NOs: 27 and 72 |
| 38 | SEQ ID NOs: 28 and 73 |
| 39 | SEQ ID NOs: 29 and 74 |
| 40 | SEQ ID NOs: 30 and 75 |
| 42 | SEQ ID NOs: 31 and 76 |
| 43 | SEQ ID NOs: 32 and 77 |
| 46 | SEQ ID NOs: 33 and 78 |
| 49 | SEQ ID NOs: 34 and 79 |
| 50 | SEQ ID NOs: 35 and 80 |
| 51 | SEQ ID NOs: 36 and 81 |
| 52 | SEQ ID NOs: 37 and 82 |
| 56 | SEQ ID NOs: 38 and 83 |
| 57 | SEQ ID NOs: 39 and 84 |
| 59 | SEQ ID NOs: 40 and 85 |
| 60 | SEQ ID NOs: 41 and 86 |
| 63 | SEQ ID NOs: 42 and 87 |
| 67 | SEQ ID NOs: 43 and 88 |
| 69 | SEQ ID NOs: 44 and 89 |
| 70 | SEQ ID NOs: 45 and 90 |

TABLE 1-continued

Sarcoma-Associated Antigens (Uncharacterized Gene Products and Cancer-Related Antigens not Found in the SEREX Database)

| NY-SAR-Antigen | Sequence Identification Number (nucleotide and amino acid sequence, respectively) |
|---|---|
| 77 | SEQ ID NOs: 97 and 109 |
| 79 | SEQ ID NOs: 98 and 110 |
| 80 | SEQ ID NOs: 99 and 111 |
| 84 | SEQ ID NOs: 100 and 112 |
| 88 | SEQ ID NOs: 101 and 113 |
| 92 | SEQ ID NOs: 102 and 114 |
| 95 | SEQ ID NOs: 103 and 115 |
| 97 | SEQ ID NOs: 104 and 116 |
| 104 | SEQ ID NOs: 105 and 117 |
| 105 | SEQ ID NOs: 106 and 118 |
| 113 | SEQ ID NOs: 107 and 119 |
| 96 | SEQ ID NOs: 108 and 120 |

The invention relates, in part, to the sarcoma-associated antigens defined herein and the nucleic acid molecules that encode them. The invention further relates to the use of the nucleic acid molecules, polypeptides and fragments thereof associated with sarcoma in methods and compositions for the diagnosis and treatment of diseases, such as cancer.

As used herein, the term "sarcoma-associated antigens" means polypeptides that elicit specific immune responses to the polypeptide when expressed by a tumor cell and thus, include sarcoma-associated polypeptides (including proteins) and fragments of sarcoma-associated polypeptides, that are recognized by the immune system (e.g., by antibodies and/or T lymphocytes). In part, the invention relates to sarcoma-associated antigens as well as the nucleic acid molecules that encode the sarcoma-associated antigens. As used herein, the "nucleic acid molecules that encode" means the nucleic acid molecules that code for the immunogenic sarcoma-associated polypeptides or immunogenic fragments thereof. These nucleic acid molecules may be DNA or may be RNA (e.g. mRNA). The sarcoma-associated nucleic acid molecules of the invention also encompass variants of the nucleic acid molecules described herein. These variants may be splice variants or allelic variants of certain sequences provided. Variants of the nucleic acid molecules of the invention are intended to include homologs and alleles which are described further below. Further, as used herein, the term "sarcoma-associated molecules" includes sarcoma-associated antigens (polypeptides and fragments thereof) as well as sarcoma-associated nucleic acids. In all embodiments, human sarcoma-associated antigens and the encoding nucleic acid molecules thereof, are preferred.

In one aspect, the invention provides isolated nucleic acid molecules that encode the sarcoma-associated antigens defined herein. The isolated nucleic acid molecules of this aspect of the invention comprise: (a) nucleotide sequences selected from the group consisting of nucleotide sequences set forth as SEQ ID NOs: 1-14 and 97-107 (b) isolated nucleic acid molecules which hybridize under highly stringent conditions to the nucleic acid molecules of (a) and which code for a sarcoma-associated antigen, (c) nucleic acid molecules that differ from (a) or (b) due to the degeneracy of the genetic code, and (d) complements of (a), (b) or (c).

As used herein the term "isolated nucleic acid molecule" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

The sarcoma-associated nucleic acid molecules of the invention also intended to encompass homologs and alleles which can be identified by conventional techniques. Identification of human and other organism homologs of sarcoma-associated polypeptides will be familiar to those of skill in the art. In general, nucleic acid hybridization is a suitable method for identification of homologous sequences of another species (e.g., human, cow, sheep), which correspond to a known sequence. Standard nucleic acid hybridization procedures can be used to identify related nucleic acid sequences of selected percent identity. For example, one can construct a library of cDNAs reverse transcribed from the mRNA of a selected tissue and use the nucleic acids that encode sarcoma-associated antigens identified herein to screen the library for related nucleotide sequences. The screening preferably is performed using high-stringency conditions to identify those sequences that are closely related by sequence identity. Nucleic acids so identified can be translated into polypeptides and the polypeptides can be tested for activity.

The term "high stringency" as used herein refers to parameters with which the art is familiar. Nucleic acid hybridization parameters may be found in references that compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. More specifically, high-stringency conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM NaH2PO4(pH7), 0.5% SDS, 2 mM EDTA). SSC is 0.15M sodium chloride/0.15M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5× SSC/0.1×SDS at temperatures up to 68° C.

There are other conditions, reagents, and so forth that can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of the sarcoma-associated nucleic acids of the invention (e.g., by using lower stringency conditions). The skilled artisan also is familiar with the methodology for screening cells and libraries for expression of such molecules, which then are routinely isolated, followed by isolation of the pertinent nucleic acid molecule and sequencing.

In general, homologs and alleles typically will share at least 90% nucleotide identity and/or at least 95% amino acid identity to the sequences of sarcoma-associated nucleic acids and polypeptides, respectively, in some instances will share at least 95% nucleotide identity and/or at least 97% amino acid identity, in other instances will share at least 97% nucleotide identity and/or at least 98% amino acid identity, in other instances will share at least 99% nucleotide identity and/or at least 99% amino acid identity, and in other instances will share at least 99.5% nucleotide identity and/or at least 99.5% amino acid identity. The homology can be calculated using various, publicly available software tools developed by NCBI (Bethesda, Md.) that can be obtained through the internet. Exemplary tools include the BLAST system available from the website of the National Center for Biotechnology Information (NCBI) at the National Institutes of Health. Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

In another aspect of the invention, unique fragments are provided which include unique fragments of the nucleotide sequences of the invention and complements thereof. The invention, in a preferred embodiment, provides unique fragments of SEQ ID NO: 10, 11, 15, 102, 104 or 108 and complements thereof. In another preferred embodiment, provides unique fragments of SEQ ID NO: 10 and complements thereof. In other embodiments the unique fragment includes the nucleotide sequence set forth as SEQ ID NO: 121. In still other embodiments the unique fragments includes the sequence set forth as SEQ ID NO: 123, 125, 127, 129 or 131. A unique fragment is one that is a 'signature' for the larger nucleic acid. It, for example, is long enough to assure that its precise sequence is not found in molecules outside of the nucleic acid molecules that encode the sarcoma-associated antigens defined above. Those of ordinary skill in the art may apply no more than routine procedures to determine if a fragment is unique within the human genome. In some instances the unique fragment is at least about 5, 6, 7, 8, 9, 10, 11, 12, 13, 14, 15, 16, 17, 18, 19, 20, 25, 30, 35, 40, 45, 50, 75, or 100 amino acids in length.

Unique fragments can be used as probes in Southern blot assays to identify such nucleic acid molecules, or can be used as probes in amplification assays such as those employing the polymerase chain reaction (PCR), including, but not limited to RT-PCR and RT-real-time PCR. As known to those skilled in the art, large probes such as 200 nucleotides or more are preferred for certain uses such as Southern blots, while smaller fragments will be preferred for uses such as PCR. Unique fragments also can be used to produce fusion proteins for generating antibodies or determining binding of the polypeptide fragments, or for generating immunoassay components. Likewise, unique fragments can be employed to produce nonfused fragments of the sarcoma-associated polypeptides useful, for example, in the preparation of antibodies and in immunoassays.

In screening for sarcoma-associated antigen genes, a Southern blot may be performed using the foregoing conditions, together with a detectably labeled probe (e.g. radioactive or chemiluminescent probes). After washing the membrane to which the DNA is finally transferred, the membrane can be placed against X-ray film or analyzed using a phosphorimager device to detect the radioactive or chemiluminescent signal. In screening for the expression of sarcoma-associated antigen nucleic acids, Northern blot hybridizations using the foregoing conditions can be performed on samples taken from cancer patients or subjects suspected of having a condition characterized by abnormal cell proliferation or neoplasia. Amplification protocols such as polymerase chain reaction using primers that hybridize to the sequences presented also can be used for detection of the sarcoma-associated antigen genes or expression thereof.

Identification of related sequences can also be achieved using polymerase chain reaction (PCR) and other amplification techniques suitable for cloning related nucleic acid sequences. Preferably, PCR primers are selected to amplify portions of a nucleic acid sequence believed to be conserved (e.g., a catalytic domain, a DNA-binding domain, etc.). Again, nucleic acids are preferably amplified from a tissue-specific library (e.g., testis). One also can use expression cloning utilizing the antisera described herein to identify nucleic acids that encode related antigenic proteins in humans or other species using the SEREX procedure to screen the appropriate expression libraries. (See: Sahin et al. Proc. Natl. Acad. Sci. USA 92:11810-11813, 1995).

The invention also includes degenerate nucleic acids that include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating sarcoma-associated polypeptide. Similarly, nucleotide sequence triplets which encode other amino acid residues include, but are not limited to: CCA, CCC, CCG, and CCT (proline codons); CGA, CGC, CGG, CGT, AGA, and AGG (arginine codons); ACA, ACC, ACG, and ACT (threonine codons); AAC and AAT (asparagine codons); and ATA, ATC, and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides modified nucleic acid molecules, which include additions, substitutions and deletions of one or more nucleotides (preferably 1-20 nucleotides). In preferred embodiments, these modified nucleic acid molecules and/or the polypeptides they encode retain at least one activity or function of the unmodified nucleic acid molecule and/or the polypeptides, such as antigenicity, receptor binding, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules that encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules that encode polypeptides having two amino acid changes can be prepared which have, e.g., 2-6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of activity or structural relation to the nucleic acids and/or polypeptides disclosed herein. As used herein the terms: "deletion", "addition", and "substitution" mean deletion, addition, and substitution changes to about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more nucleic acids of a sequence of the invention.

According to yet another aspect of the invention, an expression vector comprising any of the isolated nucleic acid molecules of the invention, preferably operably linked to a promoter is provided. In a related aspect, host cells transformed or transfected with such expression vectors also are provided. As used herein, a "vector" may be any of a number of nucleic acid molecules into which a desired sequence may be inserted by restriction and ligation for transport between different genetic environments or for expression in a host cell. Vectors are typically composed of DNA although RNA vectors are also available. Vectors include, but are not limited to, plasmids, phagemids, and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art, e.g., -galactosidase or alkaline phosphatase, and genes which visibly affect the phenotype of transformed or transfected cells, hosts, colonies or plaques, e.g., green fluorescent protein. Preferred vectors are those capable of autonomous replication and expression of the structural gene products present in the DNA segments to which they are operably joined.

As used herein, a coding sequence and regulatory sequences are said to be "operably joined" when they are covalently linked in such a way as to place the expression or transcription of the coding sequence under the influence or control of the regulatory sequences. As used herein, "operably joined" and "operably linked" are used interchangeably and should be construed to have the same meaning. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frameshift mutation, (2) interfere with the ability of the promoter region to direct the transcription of the coding sequences, or (3) interfere with the ability of the corresponding RNA transcript to be translated into a protein. Thus, a promoter region is operably joined to a coding sequence if the promoter region is capable of effecting transcription of that DNA sequence such that the resulting transcript can be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Often, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

It will also be recognized that the invention embraces the use of the sarcoma-associated nucleic acid molecules and genomic sequences in expression vectors, as well as to transfect host cells and cell lines, be these prokaryotic, e.g., *E. coli*, or eukaryotic, e.g., CHO cells, COS cells, yeast expression systems, and recombinant baculovirus expression in insect cells. Especially useful are mammalian cells such as human, mouse, hamster, pig, goat, primate, etc. They may be of a wide variety of tissue types, including mast cells, fibroblasts, oocytes, and lymphocytes, and may be primary cells and cell lines. Specific examples include dendritic cells, peripheral blood leukocytes, bone marrow stem cells and embryonic stem cells. The expression vectors require that the pertinent sequence, i.e., those nucleic acids described supra, be operably linked to a promoter.

The invention, in one aspect, also permits the construction of sarcoma-associated antigen gene "knock-outs" and "knock-ins" in cells and in animals, providing materials for studying certain aspects of cancer and immune system responses to cancer.

Expression vectors containing all the necessary elements for expression are commercially available and known to those skilled in the art. See, e.g., Sambrook et al., Molecular Cloning: A Laboratory Manual, Second Edition, Cold Spring Harbor Laboratory Press, 1989. Cells are genetically engineered by the introduction into the cells of heterologous DNA or RNA encoding a sarcoma-associated antigen, a mutant sarcoma-associated antigen, fragments, or variants thereof. The heterologous DNA or RNA is placed under operable control of transcriptional elements to permit the expression of the heterologous DNA in the host cell.

Preferred systems for mRNA expression in mammalian cells are those such as pcDNA1.1 and pCDM8 (Invitrogen) that contain a selectable marker (which facilitates the selection of stably transfected cell lines) and contain the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1, which stimulates efficiently transcription in vitro. The plasmid is described by Mizushima and Nagata (Nuc. Acids Res. 18:5322, 1990), and its use in transfection experiments is disclosed by, for example, Demoulin (Mol. Cell. Biol. 16:4710-4716, 1996). Still another preferred expression vector is an adenovirus, described by Stratford-Perricaudet, which is defective for E1 and E3 proteins (J. Clin. Invest. 90:626-630, 1992). The use of the adenovirus as an Adeno.P1A recombinant is described by Warnier et al., in intradermal injection in mice for immunization against P1A (Int. J. Cancer, 67:303-310, 1996).

The invention also embraces kits termed expression kits, which allow the artisan to prepare a desired expression vector or vectors. Such expression kits include at least separate portions of each of the previously discussed coding sequences. Other components may be added, as desired, as long as the previously mentioned sequences, which are required, are included.

The invention also includes kits for amplification of a sarcoma-associated antigen nucleic acid, including at least one pair of amplification primers which hybridize to a sarcoma-associated nucleic acid. The primers preferably are about 12, 13, 14, 15, 16, 17, 18, 19, 20, 21, 22, 23, 24, 25, 26, 27, 28, 29, 30, 31 or 32 nucleotides in length and are non-overlapping to prevent formation of "primer-dimers". One of the primers will hybridize to one strand of the sarcoma-associated nucleic acid and the second primer will hybridize to the complementary strand of the sarcoma-associated nucleic acid, in an arrangement which permits amplification of the sarcoma-associated nucleic acid. Selection of appropriate primer pairs is standard in the art. For example, the selection can be made with assistance of a computer program designed for such a purpose, optionally followed by testing the primers for amplification specificity and efficiency.

The invention, in another aspect provides isolated polypeptides (including whole proteins and partial proteins) encoded by the foregoing sarcoma-associated nucleic acids. Examples of the amino acid sequences encoded by the foregoing sarcoma-associated nucleic acids are set forth as SEQ ID NOs: 46-90 and 109-120. The amino acids of the invention are also intended to encompass amino acid sequences that result from the translation of the nucleic acid sequences provided herein in a different reading frame. In one preferred embodiment of the invention a polypeptide is provided which comprises the polypeptide sequence set forth as SEQ ID NO: 55, 56, 60, 114, 116 or 120. In another preferred embodiment a polypeptide is provided which comprises the polypeptide sequence set forth as SEQ ID NO: 122. In still another preferred embodiment a polypeptide is provided which comprises the polypeptide sequence set forth as SEQ ID NO: 124. In still other embodiments polypeptides are provided which comprise the polypeptide sequence set forth as SEQ ID NO: 126, 128, 130 or 132. Such polypeptides are useful, for example, alone or as fusion proteins to generate antibodies, and as components of an immunoassay or diagnostic assay. Immunogenic sarcoma-associated polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Fragments of the immunogenic sarcoma-associated polypeptides (including immunogenic peptides) also can be synthesized chemically using well-established methods of peptide synthesis. Thus, fragments of the disclosed polypeptides are useful for eliciting an immune response. In one embodiment fragments of a polypeptide which comprises SEQ ID NO: 55, 56, 60, 114, 116 or 120 that are at least eight amino acids in length and exhibit immunogenicity are provided. In one embodiment fragments of a polypeptide which comprises SEQ ID NO: 55 that are at least eight amino acids in length and exhibit immunogenicity are provided. In another embodiment a polypeptide is provided which comprises the polypeptide sequence set forth as SEQ ID NO: 122. In still another preferred embodiments a polypeptide is provided which comprises the polypeptide sequence set forth as SEQ ID NO: 124. In still other embodiments polypeptides are provided which comprise the polypeptide sequence set forth as SEQ ID NO: 126, 128, 130 or 132.

Fragments of a polypeptide preferably are those fragments that retain a distinct functional capability of the polypeptide. Functional capabilities that can be retained in a fragment of a polypeptide include interaction with antibodies or MHC molecules (e.g. immunogenic fragments), interaction with other polypeptides or fragments thereof, selective binding of nucleic acids or proteins, and enzymatic activity. One important activity is the ability to provoke in a subject an immune response. As will be recognized by those skilled in the art, the size of the fragment that can be used for inducing an immune response will depend upon factors such as whether the epitope recognized by an antibody is a linear epitope or a conformational epitope or the particular MHC molecule that binds to and presents the fragment (e.g. HLA class I or II). Thus, some immunogenic fragments of sarcoma-associated polypeptides will consist of longer segments while others will consist of shorter segments, (e.g. about 5, 6, 7, 8, 9, 10, 11 or 12 or more amino acids long, including each integer up to the full length of the sarcoma-associated polypeptide). Those skilled in the art are well versed in methods for selecting immunogenic fragments of polypeptides.

The invention embraces variants of the sarcoma-associated polypeptides described above. As used herein, a "variant" of a sarcoma-associated antigen polypeptide is a polypeptide which contains one or more modifications to the primary amino acid sequence of a sarcoma-associated polypeptide. Modifications which create a sarcoma-associated antigen variant can be made to a sarcoma-associated polypeptide 1) to reduce or eliminate an activity of a sarcoma-associated polypeptide; 2) to enhance a property of a sarcoma-associated polypeptide, such as protein stability in an expression system or the stability of protein-protein binding; 3) to provide a novel activity or property to a sarcoma-associated polypeptide, such as addition of an antigenic epitope or addition of a detectable moiety; or 4) to provide equivalent or better binding to a MHC molecule.

Modifications to a sarcoma-associated polypeptide are typically made to the nucleic acid which encodes the sarcoma-associated polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the sarcoma-associated antigen amino acid sequence. One of skill in the art will be familiar with methods for predicting the effect on protein conformation of a change in protein sequence, and can thus "design" a variant sarcoma-associated polypeptide according to known methods. One example of such a method is described by Dahiyat and Mayo in *Science* 278:82-87, 1997, whereby proteins can be designed de novo. The method can be applied to a known protein to vary a only a portion of the polypeptide sequence. By applying the computational methods of Dahiyat and Mayo, specific variants of a sarcoma-associated polypeptide can be proposed and tested to determine whether the variant retains a desired conformation.

In general, variants include sarcoma-associated polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of a sarcoma-associated polypeptide by eliminating proteolysis by proteases in an expression system (e.g., dibasic amino acid residues in yeast expression systems in which KEX2 protease activity is present).

Mutations of a nucleic acid which encode a sarcoma-associated polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant sarcoma-associated polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a sarcoma-associated antigen gene or cDNA clone to enhance expression of the polypeptide. The activity of variants of sarcoma-associated polypeptides can be tested by cloning the gene encoding the variant sarcoma-associated polypeptide into a bacterial or mammalian expression vector, introducing the vector into an appropriate host cell, expressing the variant sarcoma-associated polypeptide, and testing for a functional capability of the sarcoma-associated polypeptides as disclosed herein. For example, the variant sarcoma-associated polypeptide can be tested for reaction with autologous or allogeneic sera as described in the Examples. Preparation of other variant polypeptides may favor testing of other activities, as will be known to one of ordinary skill in the art.

The skilled artisan will also realize that conservative amino acid substitutions may be made in immunogenic sarcoma-associated polypeptides to provide functionally equivalent variants, or homologs of the foregoing polypeptides, i.e., the variants retain the functional capabilities of the immunogenic sarcoma-associated polypeptides. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Exemplary functionally equivalent variants or homologs of the sarcoma-associated polypeptides include conservative amino acid substitutions of in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the sarcoma-associated antigens disclosed herein and retain the specific antibody-binding characteristics of the antigens.

Likewise, upon determining that a peptide derived from a sarcoma-associated polypeptide is presented by an MHC molecule and recognized by antibodies or T lymphocytes (e.g., helper T cells or CTLs), one can make conservative amino acid substitutions to the amino acid sequence of the peptide, particularly at residues which are thought not to be direct contact points with the MHC molecule. For example, methods for identifying functional variants of HLA class II binding peptides are provided in a published PCT application of Strominger and Wucherpfennig (PCT/US96/03182). Peptides bearing one or more amino acid substitutions also can be tested for concordance with known HLA/MHC motifs prior to synthesis using, e.g. the computer program described by D'Amaro and Drijfhout (D'Amaro et al., Human Immunol. 43:13-18, 1995; Drijfhout et al., Human Immunol. 43:1-12, 1995). The substituted peptides can then be tested for binding to the MHC molecule and recognition by antibodies or T lymphocytes when bound to MHC. These variants can be tested for improved stability and are useful, inter alia, in vaccine compositions.

Conservative amino-acid substitutions in the amino acid sequence of sarcoma-associated polypeptides to produce functionally equivalent variants of sarcoma-associated polypeptides typically are made by alteration of a nucleic acid encoding a sarcoma-associated polypeptide. Such substitutions can be made by a variety of methods known to one of ordinary skill in the art. For example, amino acid substitutions may be made by PCR-directed mutation, site-directed mutagenesis according to the method of Kunkel (Kunkel, Proc. Nat. Acad. Sci. U.S.A. 82: 488-492, 1985), or by chemical synthesis of a gene encoding a sarcoma-associated polypeptide. Where amino acid substitutions are made to a small unique fragment of a sarcoma-associated polypeptide, such as an antigenic epitope recognized by autologous or allogeneic sera or T lymphocytes, the substitutions can be made by directly synthesizing the peptide. The activity of functionally equivalent variants of sarcoma-associated polypeptides can be tested by cloning the gene encoding the altered sarcoma-associated polypeptide into a bacterial or mammalian expression vector, introducing the vector into an appropriate host cell, expressing the altered polypeptide, and testing for a functional capability of the sarcoma-associated polypeptides as disclosed herein. Peptides that are chemically synthesized can be tested directly for function, e.g., for binding to antisera recognizing associated antigens.

The invention as described herein has a number of uses, some of which are described elsewhere herein. In one aspect of the invention a method of identifying cancer-associated antigens is provided. Novel cancer-associated antigens can be identified by obtaining a biological sample from a subject, determining the reactivity of the biological sample with one or more known cancer-associated antigens, and subsequently using the reactive biological sample to screen an expression library to identify novel cancer-associated antigens as well as proteins previously known but not previously associated with cancer.

As used herein, a "subject" is preferably a human, non-human primate, cow, horse, pig, sheep, goat, dog, cat or rodent. In all embodiments, human subjects are preferred. In some embodiments, the subject is suspected of having cancer or has been diagnosed with cancer. Cancers in which the sarcoma-associated nucleic acid or polypeptide are differentially expressed include sarcoma.

As used herein, a biological sample includes, but is not limited to: tissue, cells, or body fluid (e.g. serum, blood, lymph node fluid, etc.). The fluid sample may include cells and/or fluid. The tissue and cells may be obtained from a subject or may be grown in culture (e.g. from a cell line). As used herein, a biological sample is body fluid, tissue or cells obtained from a subject using methods well-known to those of ordinary skill in the related medical arts.

The invention in another aspect permits the isolation of the cancer-associated antigens described herein. A variety of methodologies well-known to the skilled practitioner can be utilized to obtain isolated cancer-associated antigens. The proteins may be purified from cells which naturally produce the protein by chromatographic means or immunological recognition. Alternatively, an expression vector may be introduced into cells to cause production of the protein. In another method, mRNA transcripts may be microinjected or otherwise introduced into cells to cause production of the encoded protein. Translation of mRNA in cell-free extracts such as the reticulocyte lysate system also may be used to produce the protein. Those skilled in the art also can readily follow known methods for isolating cancer-associated antigens. These include, but are not limited to, chromatographic techniques such as immunochromatography, HPLC, size-exclusion chromatography, ion-exchange chromatography, and immune-affinity chromatography.

The invention also involves diagnosing or monitoring cancer in subjects by determining the presence of an immune response to one or more sarcoma-associated antigens of the invention. In preferred embodiments, this determination is performed by assaying a bodily fluid obtained from the subject, preferably serum, blood, or lymph node fluid for the presence of antibodies against the sarcoma-associated antigens described herein. This determination may also be performed by assaying a tissue or cells from the subject for the presence of one or more sarcoma-associated antigens (or nucleic acid molecules that encode these antigens) described herein. In another embodiment, the presence of antibodies against at least one additional cancer antigen is determined for diagnosis of cancer. The additional antigen may be a sarcoma-associated antigen as described herein or may be some other cancer-associated antigen. This determination may also be performed by assaying a tissue or cells from the subject for the presence of the sarcoma-associated antigens described herein.

Measurement of the immune response against one of the sarcoma-associated antigens over time by sequential determinations permits monitoring of the disease and/or the effects of a course of treatment. For example, a sample, such as serum, blood, or lymph node fluid, may be obtained from a subject, tested for an immune response to one of the sarcoma-associated antigens, and at a second, subsequent time, another sample, may be obtained from the subject and similarly tested. The results of the first and second (or subsequent) tests can be compared as a measure of the onset, regression or progression of cancer, or, if cancer treatment was undertaken during the interval between obtaining the samples, the effectiveness of the treatment may be evaluated by comparing the results of the two tests. In preferred embodiments the sarcoma-associated antigens are bound to a substrate. In other preferred embodiments the immune response of the biological sample to the sarcoma-associated antigens is determined with ELISA. Other methods will be apparent to one of skill in the art.

Diagnostic methods of the invention also involve determining the aberrant expression of one or more of the sarcoma-associated antigens described herein or the nucleic acid molecules that encode them. Such determinations can be carried out via any standard nucleic acid assay, including the polymerase chain reaction or assaying with hybridization probes, which may be labeled, or by assaying biological samples with binding partners (e.g., antibodies) for sarcoma-associated antigens.

The diagnostic methods of the invention can be used to detect the presence of a disorder associated with aberrant expression of a sarcoma-associated molecule, as well as to assess the progression and/or regression of the disorder such as in response to treatment (e.g., chemotherapy, radiation). According to this aspect of the invention, the method for diagnosing a disorder characterized by aberrant expression of a sarcoma-associated molecule involve: detecting expression of a sarcoma-associated molecule in a first biological sample obtained from a subject, wherein differential expression of the sarcoma-associated molecule compared to a control sample indicates that the subject has a disorder characterized by aberrant expression of a sarcoma-associated molecule, such as cancer.

As used herein, "aberrant expression" of a sarcoma-associated antigen is intended to include any expression that is statistically significant from the expected amount of expression. For example, expression of a sarcoma-associated molecule (i.e., the sarcoma-associated antigen or the nucleic acid molecules that encode it) in a tissue that is not expected to express the sarcoma-associated molecule would be included in the definition of "aberrant expression". Likewise, expression of the sarcoma-associated molecule that is determined to be expressed at a significantly higher or lower level than expected is also included. Therefore, a determination of the level of expression of one or more of the sarcoma-associated antigens and/or the nucleic acids that encode them is diagnostic of cancer if the level of expression is above a baseline level determined for that tissue type. The baseline level of expression can be determined using standard methods known to those of skill in the art. Such methods include, for example, assaying a number of histologically normal tissue samples from subjects that are clinically normal (i.e. do not have clinical signs of cancer in that tissue type) and determining the mean level of expression for the samples.

The level of expression of the nucleic acid molecules of the invention or the antigens they encode can indicate cancer in the tissue when the level of expression is significantly more in the tissue than in a control sample. In some embodiments, a level of expression in the tissues that is at least about 5%, 10%, 20%, 30%, 40%, 50%, 60%, 70%, 80%, 90%, 100%, 150%, 200%, 250%, 300%, 400%, or 500% more than the level of expression in the control tissue indicates cancer in the tissue.

As used herein the term "control" means predetermined values, and also means samples of materials tested in parallel with the experimental materials. Examples include samples from control populations or control samples generated through manufacture to be tested in parallel with the experimental samples.

As used herein the term "control" includes positive and negative controls which may be a predetermined value that can take a variety of forms. The control(s) can be a single cut-off value, such as a median or mean, or can be established based upon comparative groups, such as in groups having normal amounts of sarcoma-associated molecules of the invention and groups having abnormal amounts of sarcoma-associated molecules of the invention. Another example of a comparative group is a group having a particular disease, condition and/or symptoms and a group without the disease, condition and/or symptoms. Another comparative group is a group with a family history of a particular disease and a group without such a family history of the particular disease. The predetermined control value can be arranged, for example, where a tested population is divided equally (or unequally) into groups, such as a low-risk group, a medium-risk group and a high-risk group or into quadrants or quintiles, the lowest quadrant or quintile being individuals with the lowest risk or lowest expression levels of a sarcoma-associated molecule of the invention that is up-regulated in cancer and the highest quadrant or quintile being individuals with the highest risk or highest expression levels of a sarcoma-associated molecule of the invention that is up-regulated in cancer.

The predetermined value of a control will depend upon the particular population selected. For example, an apparently healthy population will have a different "normal" sarcoma-associated molecule expression level range than will a population which is known to have a condition characterized by aberrant expression of the sarcoma-associated molecule. Accordingly, the predetermined value selected may take into account the category in which an individual falls. Appropriate ranges and categories can be selected with no more than routine experimentation by those of ordinary skill in the art. Typically the control will be based on apparently healthy individuals in an appropriate age bracket. As used herein, the term "increased expression" means a higher level of expression relative to a selected control.

The invention involves in some aspects diagnosing or monitoring cancer by determining the level of expression of one or more sarcoma-associated nucleic acid molecules and/or determining the level of expression of one or more sarcoma-associated polypeptides they encode. In some important embodiments, this determination is performed by assaying a tissue sample from a subject for the level of expression of one or more sarcoma-associated nucleic acid molecules or for the level of expression of one or more sarcoma-associated polypeptides encoded by the nucleic acid molecules of the invention.

The expression of the molecules of the invention may be determined using routine methods known to those of ordinary skill in the art. These methods include, but are not limited to: direct RNA amplification, reverse transcription of RNA to cDNA, real-time RT-PCR, amplification of cDNA, hybridization, and immunologically based assay methods, which include, but are not limited to immunohistochemistry, antibody sandwich capture assay, ELISA, and enzyme-linked immunospot assay (EliSpot assay). For example, the determination of the presence of level of nucleic acid molecules of the invention in a subject or tissue can be carried out via any standard nucleic acid determination assay, including the polymerase chain reaction, or assaying with labeled hybridization probes. Such hybridization methods include, but are not limited to microarray techniques.

These methods of determining the presence and/or level of the molecules of the invention in cells and tissues may include use of labels to monitor the presence of the molecules of the invention. Such labels may include, but are not limited to radiolabels or chemiluminescent labels, which may be utilized to determine whether a molecule of the invention is expressed in a cell or tissue, and to determine the level of expression in the cell or tissue. For example, a fluorescently labeled or radiolabeled antibody that selectively binds to a polypeptide of the invention may be contacted with a tissue or cell to visualize the polypeptide in vitro or in vivo. These and other in vitro and in vivo imaging methods for determining the presence of the nucleic acid and polypeptide molecules of the invention are well known to those of ordinary skill in the art.

The invention, therefore, also involves the use of agents such as polypeptides that bind to sarcoma-associated antigens. Such agents can be used in methods of the invention including the diagnosis and/or treatment of cancer. Such binding agents can be used, for example, in screening assays to detect the presence or absence of sarcoma-associated antigens and can be used in quantitative binding assays to determine levels of expression in biological samples and cells. Such agents also may be used to inhibit the native activity of the sarcoma-associated polypeptides, for example, by binding to such polypeptides.

According to this aspect, the binding polypeptides bind to an isolated nucleic acid or protein of the invention, including unique fragments thereof. Preferably, the binding polypeptides bind to a sarcoma-associated polypeptide, or a unique fragment thereof.

In preferred embodiments, the binding polypeptide is an antibody or antibody fragment, more preferably, an Fab or F(ab)$_2$ fragment of an antibody. Typically, the fragment includes a CDR3 region that is selective for the sarcoma-associated antigen. Any of the various types of antibodies can be used for this purpose, including polyclonal antibodies, monoclonal antibodies, humanized antibodies, and chimeric antibodies.

Thus, the invention provides agents which bind to sarcoma-associated antigens encoded by sarcoma-associated nucleic acid molecules of the invention, and in certain embodiments preferably to unique fragments of the sarcoma-associated polypeptides. Such binding partners can be used in screening assays to detect the presence or absence of a sarcoma-associated antigen and in purification protocols to isolate such sarcoma-associated antigens. Likewise, such binding partners can be used to selectively target drugs, toxins or other molecules (including detectable diagnostic molecules) to cells which express sarcoma-associated antigens. In this manner, for example, cells present in solid or non-solid tumors which express sarcoma-associated proteins can be treated with cytotoxic compounds that are selective for the sarcoma-associated molecules (nucleic acids and/or antigens). Such binding agents also can be used to inhibit the native activity of the sarcoma-associated antigen, for example, to further characterize the functions of these molecules.

The antibodies of the present invention thus are prepared by any of a variety of methods, including administering a protein, fragments of a protein, cells expressing the protein or fragments thereof and the like to an animal to induce polyclonal antibodies. The present invention also provides methods of producing monoclonal antibodies to the sarcoma-associated molecules of the invention described herein. The production of monoclonal antibodies is according to techniques well known in the art. As detailed herein, such antibodies may be used for example to identify tissues expressing protein or to purify protein. Antibodies also may be coupled to specific labeling agents or imaging agents, including, but not limited to a molecule preferably selected from the group consisting of fluorescent, enzyme, radioactive, metallic, biotin, chemiluminescent, bioluminescent, chromophore, or colored, etc. In some aspects of the invention, a label may be a combination of the foregoing molecule types.

Significantly, as is well-known in the art, only a small portion of an antibody molecule, the paratope, is involved in the binding of the antibody to its epitope (see, in general, Clark, W. R. (1986) The Experimental Foundations of Modem Immunology Wiley & Sons, Inc., New York; Roitt, I. (1991) Essential Immunology, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of nonspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762, and 5,859,205.

Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for F(ab')2, Fab, Fv, and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to sarcoma-associated antigens. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptides and non-peptide synthetic moieties.

The sarcoma-associated antigens of the invention can be used to screen peptide libraries, including phage display libraries, to identify and select peptide binding partners of the sarcoma-associated antigens of the invention. Such molecules can be used, as described, for screening assays, for diagnostic assays, for purification protocols or for targeting drugs, toxins and/or labeling agents (e.g., radioisotopes, fluorescent molecules, etc.) to cells which express sarcoma-associated molecules such as cancer cells which have aberrant sarcoma-associated expression.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the sarcoma-associated antigen. This process can be repeated through several cycles of reselection of phage that bind to the sarcoma-associated polypeptide. Repeated rounds lead to enrichment of phage bearing particular sequences. DNA sequence analysis can be conducted to identify the sequences of the expressed polypeptides. The minimal linear portion of the sequence that binds to the sarcoma-associated polypeptide can be determined One can repeat the procedure using a biased library containing inserts containing part or all of the minimal linear portion plus one or more additional degenerate residues upstream or downstream thereof. Yeast two-hybrid screening methods also may be used to identify polypeptides that bind to the sarcoma-associated antigens.

As detailed herein, the foregoing antibodies and other binding molecules may be used to identify tissues with normal or aberrant expression of a sarcoma-associated antigen. Antibodies also may be coupled to specific diagnostic labeling agents for imaging of cells and tissues with normal or aberrant sarcoma-associated antigen expression or to therapeutically useful agents according to standard coupling procedures. As used herein, "therapeutically useful agents" include any therapeutic molecule which desirably is targeted selectively to a cell or tissue selectively with an aberrant sarcoma-associated expression.

Diagnostic agents for in vivo use include, but are not limited to, barium sulfate, iocetamic acid, iopanoic acid, ipodate calcium, diatrizoate sodium, diatrizoate meglumine, metrizamide, tyropanoate sodium and radiodiagnostics including positron emitters such as fluorine-18 and carbon-11, gamma emitters such as iodine-123, technitium-99, iodine-131 and indium-111, and nuclides for nuclear magnetic resonance such as fluorine and gadolinium. Other diagnostic agents useful in the invention will be apparent to one of ordinary skill in the art.

The antibodies of the present invention can also be used to therapeutically target sarcoma-associated antigens. In a preferred embodiment, antibodies can be used to target antigens expressed on the cell surface, such as NY-SAR-35. These antibodies can be linked not only to a detectable marker but also an antitumor agent or an immunomodulator. Antitumor agents can include cytotoxic agents and agents that act on tumor neovasculature. Detectable markers include, for example, radioactive or fluorescent markers. Cytotoxic agents include cytotoxic radionuclides, chemical toxins and protein toxins.

The cytotoxic radionuclide or radiotherapeutic isotope preferably is an alpha-emitting isotope such as $^{225}$Ac, $^{211}$At, $^{212}$Bi, $^{213}$Bi, $^{212}$Pb, $^{224}$Ra or $^{223}$Ra. Alternatively, the cytotoxic radionuclide may a beta-emitting isotope such as $^{186}$Rh, $^{188}$Rh, $^{177}$Lu, $^{90}$Y, $^{131}$I, $^{67}$Cu, $^{64}$Cu, $^{153}$Sm or $^{166}$Ho. Further, the cytotoxic radionuclide may emit Auger and low energy electrons and include the isotopes $^{125}$I, $^{123}$I or $^{77}$Br.

Suitable chemical toxins or chemotherapeutic agents include members of the enediyne family of molecules, such as calicheamicin and esperamicin. Chemical toxins can also be taken from the group consisting of methotrexate, doxorubicin, melphalan, chlorambucil, ARA-C, vindesine, mitomycin C, cis-platinum, etoposide, bleomycin and 5-fluorouracil. Other antineoplastic agents that may be conjugated to the anti-PSMA antibodies of the present invention include dolastatins (U.S. Pat. Nos. 6,034,065 and 6,239,104) and derivatives thereof. Of particular interest is dolastatin 10 (dolavaline-valine-dolaisoleuine-dolaproine-dolaphenine) and the derivatives auristatin PHE (dolavaline-valine-dolaisoleuine-dolaproine-phenylalanine-methyl ester) (Pettit, G. R. et al., *Anticancer Drug Des.* 13(4):243-277, 1998; Woyke, T. et al., *Antimicrob. Agents Chemother.* 45(12):3580-3584, 2001), and aurastatin E and the like. Toxins that are less preferred in the compositions and methods of the invention include poisonous lectins, plant toxins such as ricin, abrin, modeccin, botulina and diphtheria toxins. Of course, combinations of the various toxins could also be coupled to one antibody molecule thereby accommodating variable cytotoxicity. Other chemotherapeutic agents are known to those skilled in the art.

Agents that act on the tumor vasculature can include tubulin-binding agents such as combrestatin A4 (Griggs et al., *Lancet Oncol.* 2:82, 2001), angiostatin and endostatin (reviewed in Rosen, *Oncologist* 5:20, 2000, incorporated by reference herein) and interferon inducible protein 10 (U.S. Pat. No. 5,994,292). A number of antiangiogenic agents currently in clinical trials are also contemplated. Agents currently in clinical trials include: 2ME2, Angiostatin, Angiozyme, Anti-VEGF RhuMAb, Apra (CT-2584), Avicine, Benefin, BMS275291, Carboxyamidotriazole, CC4047, CC5013, CC7085, CDC801, CGP-41251 (PKC 412), CM101, Combretastatin A-4 Prodrug, EMD 121974, Endostatin, Flavopiridol, Genistein (GCP), Green Tea Extract, IM-862, ImmTher, Interferon alpha, Interleukin-12, Iressa (ZD1839), Marimastat, Metastat (Col-3), Neovastat, Octreotide, Paclitaxel, Penicillamine, Photofrin, Photopoint, PI-88, Prinomastat (AG-3340), PTK787 (ZK22584), R0317453, Solimastat, Squalamine, SU 101, SU 5416, SU-6668, Suradista (FCE 26644), Suramin (Metaret), Tetrathiomolybdate, Thalidomide, TNP-470 and Vitaxin, additional antiangiogenic agents are described by Kerbel, J. Clin. Oncol. 19(18s):45s-51s, 2001, which is incorporated by reference herein Immunomodulators suitable for conjugation to the antibodies include α-interferon, γ-interferon, and tumor necrosis factor alpha (TNFα).

The coupling of one or more toxin molecules to the antibody is envisioned to include many chemical mechanisms, for instance covalent binding, affinity binding, intercalation, coordinate binding, and complexation. The toxic compounds used to prepare the immunotoxins are attached to the antibodies or antigen-binding fragments thereof by standard protocols known in the art.

In other aspects of the invention, the sarcoma-associated molecules and the antibodies and other binding molecules, as described herein, can be used for the treatment of disorders. When "disorder" is used herein, it refers to any pathological condition where the sarcoma-associated antigens are aberrantly expressed. An example of such a disorder is cancer, with sarcoma as a particular example. For human cancers, additional particular examples include synovial sarcoma, liposarcoma, neurosarcoma, chondrosarcoma, fibrosarcoma, Ewing sarcoma, leimyosarcoma, osteosarcoma, rhabdomyosarcoma, malignant fibrous histocytoma, DFSP, leukemia, lymphoma, gastric cancer, glioma, bladder cancer, breast cancer, ovarian cancer, renal cancer, lung cancer, colon cancer, prostate cancer, esophageal cancer, melanoma and hepatoma.

Conventional treatment for cancer may include, but is not limited to: surgical intervention, chemotherapy, radiotherapy, and adjuvant systemic therapies. In one aspect of the invention, treatment may include administering binding polypeptides such as antibodies that specifically bind to the sarcoma-associated antigen. These binding polypeptides can be optionally linked to one or more detectable markers, antitumor agents or immunomodulators as described above.

Cancer treatment, in another aspect of the invention may include administering an antisense molecules or RNAi molecules to reduce expression level and/or function level of sarcoma-associated polypeptides of the invention in the subject in cancers where a sarcoma-associated molecule is up-regulated. The use of RNA interference or "RNAi" involves the use of double-stranded RNA (dsRNA) to block gene expression. (see: Sui, G, et al, Proc Natl. Acad. Sci U.S.A. 99:5515-5520, 2002). Methods of applying RNAi strategies in embodiments of the invention would be understood by one of ordinary skill in the art.

Sarcoma-associated polypeptides as described herein, can also be used in one aspect of the invention to induce or enhance an immune response. Some therapeutic approaches based upon the disclosure are premised on a response by a subject's immune system, leading to lysis of antigen presenting cells, such as cancer cells which present one or more sarcoma-associated antigens of the invention. One such approach is the administration of autologous CTLs specific to a sarcoma-associated antigen/MHC complex to a subject with abnormal cells of the phenotype at issue. It is within the ability of one of ordinary skill in the art to develop such CTLs in vitro. An example of a method for T cell differentiation is presented in International Application number PCT/US96/05607. Generally, a sample of cells taken from a subject, such as blood cells, are contacted with a cell presenting the complex and capable of provoking CTLs to proliferate. The target cell can be a transfectant, such as a COS cell. These transfectants present the desired complex of their surface and, when combined with a CTL of interest, stimulate its proliferation. COS cells are widely available, as are other suitable host cells. Specific production of CTL clones is well known in the art. The clonally expanded autologous CTLs then are administered to the subject.

Another method for selecting antigen-specific CTL clones has recently been described (Altman et al., Science 274:94-96, 1996; Dunbar et al., Curr. Biol. 8:413-416, 1998), in which fluorogenic tetramers of MHC class I molecule/peptide complexes are used to detect specific CTL clones. Briefly, soluble MHC class I molecules are folded in vitro in the presence of $\beta_2$-microglobulin and a peptide antigen which binds the class I molecule. After purification, the MHC/peptide complex is purified and labeled with biotin. Tetramers are formed by mixing the biotinylated peptide-MHC complex with labeled avidin (e.g. phycoerythrin) at a molar ratio or 4:1. Tetramers are then contacted with a source of CTLs such as peripheral blood or lymph node. The tetramers bind CTLs which recognize the peptide antigen/MHC class I complex. Cells bound by the tetramers can be sorted by fluorescence activated cell sorting to isolate the reactive CTLs. The isolated CTLs then can be expanded in vitro for use as described herein.

To detail a therapeutic methodology, referred to as adoptive transfer (Greenberg, J. Immunol. 136(5): 1917, 1986; Riddel et al., Science 257: 238, 1992; Lynch et al, Eur. J. Immunol. 21: 1403-1410, 1991; Kast et al., Cell 59: 603-614, 1989), cells presenting the desired complex (e.g., dendritic cells) are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the relevant HLA/cancer associated antigen complex. This can be determined very easily, as the art is very familiar with methods for identifying cells which present a particular HLA molecule, as well as how to identify cells expressing DNA of the pertinent sequences, in this case a sarcoma-associated antigen sequence. Once cells presenting the relevant complex are identified via the foregoing screening methodology, they can be combined with a sample from a patient, where the sample contains CTLs. If the complex presenting cells are lysed by the mixed CTL sample, then it can be assumed that a sarcoma-associated antigen is being presented, and the subject is an appropriate candidate for the therapeutic approaches set forth supra.

Adoptive transfer is not the only form of therapy that is available in accordance with the invention. CTLs can also be provoked in vivo, using a number of approaches. One approach is the use of non-proliferative cells expressing the complex. The cells used in this approach may be those that normally express the complex, such as irradiated tumor cells or cells transfected with one or both of the genes necessary for presentation of the complex (i.e. the antigenic peptide and the presenting MHC molecule). Chen et al. (Proc. Natl. Acad. Sci. USA 88: 110-114, 1991) exemplifies this approach, showing the use of transfected cells expressing HPV E7 peptides in a therapeutic regime. Various cell types may be used. Similarly, vectors carrying one or both of the genes of interest may be used. Viral or bacterial vectors are especially preferred. For example, nucleic acids which encode a sarcoma-associated polypeptide may be operably linked to promoter and enhancer sequences which direct expression of the sarcoma-associated antigen polypeptide in certain tissues or cell types. The nucleic acid may be incorporated into an expression vector.

Expression vectors may be unmodified extrachromosomal nucleic acids, plasmids or viral genomes constructed or modified to enable insertion of exogenous nucleic acids, such as those encoding sarcoma-associated antigen, as described elsewhere herein. Nucleic acids encoding a sarcoma-associated antigen also may be inserted into a retroviral genome, thereby facilitating integration of the nucleic acid into the genome of the target tissue or cell type. In these systems, the gene of interest is carried by a microorganism, e.g., a Vaccinia virus, pox virus, herpes simplex virus, retrovirus or adenovirus, and the materials de facto "infect" host cells. The cells which result present the complex of interest, and are recognized by autologous CTLs, which then proliferate.

A similar effect can be achieved by combining the sarcoma-associated polypeptide or a stimulatory fragment thereof with an adjuvant to facilitate incorporation into antigen presenting cells in vivo. The sarcoma-associated polypeptide is processed to yield the peptide partner of the MHC molecule while a sarcoma-associated fragment may be presented without the need for further processing. Generally, subjects can receive an intradermal injection of an effective amount of the sarcoma-associated antigen. Initial doses can be followed by booster doses, following immunization protocols standard in the art. Preferred sarcoma-associated antigens include those found to react with allogeneic cancer antisera, shown in the examples below.

The invention involves the use of various materials disclosed herein to "immunize" subjects or as "vaccines". As used herein, "immunization" or "vaccination" means increasing or activating an immune response against an antigen. It does not require elimination or eradication of a condition but rather contemplates the clinically favorable enhancement of an immune response toward an antigen. Generally accepted animal models, can be used for testing of immunization against cancer using a sarcoma-associated nucleic acid. For example, human cancer cells can be introduced into a mouse to create a tumor, and one or more sarcoma-associated nucleic acids can be delivered by the methods described herein. The effect on the cancer cells (e.g., reduction of tumor size) can be assessed as a measure of the effectiveness of the sarcoma-associated nucleic acid immunization. Of course, testing of the foregoing animal model using more conventional methods for immunization include the administration of one or more sarcoma-associated polypeptides or fragments derived therefrom, optionally combined with one or more adjuvants and/or cytokines to boost the immune response.

Methods for immunization, including formulation of a vaccine composition and selection of doses, route of administration and the schedule of administration (e.g. primary and one or more booster doses), are well known in the art. The tests also can be performed in humans, where the end point is to test for the presence of enhanced levels of circulating CTLs against cells bearing the antigen, to test for levels of circulating antibodies against the antigen, to test for the presence of cells expressing the antigen and so forth.

As part of the immunization compositions, one or more sarcoma-associated polypeptides or immunogenic fragments thereof are administered with one or more adjuvants to induce an immune response or to increase an immune response. An adjuvant is a substance incorporated into or administered with antigen which potentiates the immune response. Adjuvants may enhance the immunological response by providing a reservoir of antigen (extracellularly or within macrophages), activating macrophages and stimulating specific sets of lymphocytes. Adjuvants of many kinds are well known in the art. Specific examples of adjuvants include monophosphoryl lipid A (MPL, SmithKline Beecham), a congener obtained after purification and acid hydrolysis of *Salmonella* minnesota Re 595 lipopolysaccharide; saponins including QS21 (SmithKline Beecham), a pure QA-21 saponin purified from *Quillja saponaria* extract; DQS21, described in PCT application WO96/33739 (SmithKline Beecham); QS-7, QS-17, QS-18, and QS-L1 (So et al., Mol. Cells 7:178-186, 1997); incomplete Freund's adjuvant; complete Freund's adjuvant; montanide; alum; CpG oligonucleotides (see e.g. Kreig et al., Nature 374:546-9, 1995); and various water-in-oil emulsions prepared from biodegradable oils such as squalene and/or tocopherol. Preferably, the antigens are administered mixed with a combination of DQS21/MPL. The ratio of DQS21 to MPL typically will be about 1:10 to 10:1, preferably about 1:5 to 5:1 and more preferably about 1:1. Typically for human administration, DQS21 and MPL will be present in a vaccine formulation in the range of about 1 μg to about 100 μg. Other adjuvants are known in the art and can be used in the invention (see, e.g. Goding, Monoclonal Antibodies: Principles and Practice, 2nd Ed., 1986). Methods for the preparation of mixtures or emulsions of polypeptide and adjuvant are well known to those of skill in the art of vaccination.

Other agents which stimulate the immune response of the subject can also be administered to the subject. For example, other cytokines are also useful in vaccination protocols as a result of their lymphocyte regulatory properties. Many other cytokines useful for such purposes will be known to one of ordinary skill in the art, including interleukin-12 (IL-12) which has been shown to enhance the protective effects of vaccines (see, e.g., Science 268: 1432-1434, 1995), GM-CSF and IL-18. Thus cytokines can be administered in conjunction with antigens and adjuvants to increase the immune response to the antigens.

There are a number of immune response potentiating compounds that can be used in vaccination protocols. These include costimulatory molecules provided in either protein or nucleic acid form. Such costimulatory molecules include the B7-1 and B7-2 (CD80 and CD86 respectively) molecules which are expressed on dendritic cells (DC) and interact with the CD28 molecule expressed on the T cell. This interaction provides costimulation (signal 2) to an antigen/MHC/TCR stimulated (signal 1) T cell, increasing T cell proliferation and effector function. B7 also interacts with CTLA4 (CD152) on T cells and studies involving CTLA4 and B7 ligands indicate that the B7-CTLA4 interaction can enhance antitumor immunity and CTL proliferation (Zheng P., et al. Proc. Natl. Acad. Sci. USA 95 (11):6284-6289 (1998)).

B7 typically is not expressed on tumor cells so they are not efficient antigen presenting cells (APCs) for T cells. Induction of B7 expression would enable the tumor cells to stimulate more efficiently CTL proliferation and effector function. A combination of B7/IL-6/IL-12 costimulation has been shown to induce IFN-gamma and a Th1 cytokine profile in the T cell population leading to further enhanced T cell activity (Gajewski et al., J. Immunol, 154:5637-5648 (1995)). Tumor cell transfection with B7 has been discussed in relation to in vitro CTL expansion for adoptive transfer immunotherapy by Wang et al., (J. Immunol., 19:1-8 (1986)). Other delivery mechanisms for the B7 molecule would include nucleic acid (naked DNA) immunization (Kim J., et al. Nat. Biotechnol., 15:7:641-646 (1997)) and recombinant viruses such as adeno and pox (Wendtner et al., Gene Ther., 4:7:726-735 (1997)). These systems are all amenable to the construction and use of expression cassettes for the coexpression of B7 with other molecules of choice such as the antigens or fragment(s) of antigens discussed herein (including polytopes) or cytokines. These delivery systems can be used for induction of the appropriate molecules in vitro and for in vivo vaccination situations. The use of anti-CD28 antibodies to directly stimulate T cells in vitro and in vivo could also be considered. Similarly, the inducible co-stimulatory molecule ICOS which induces T cell responses to foreign antigen could be modulated, for example, by use of anti-ICOS antibodies (Hutloff et al., Nature 397:263-266, 1999).

Lymphocyte function associated antigen-3 (LFA-3) is expressed on APCs and some tumor cells and interacts with CD2 expressed on T cells. This interaction induces T cell IL-2 and IFN-gamma production and can thus complement but not substitute, the B7/CD28 costimulatory interaction (Parra et al., J. Immunol., 158:637-642 (1997), Fenton et al., J. Immunother., 21:2:95-108 (1998)).

Lymphocyte function associated antigen-1 (LFA-1) is expressed on leukocytes and interacts with ICAM-1 expressed on APCs and some tumor cells. This interaction induces T cell IL-2 and IFN-gamma production and can thus complement but not substitute, the B7/CD28 costimulatory interaction (Fenton et al., J. Immunother., 21:2:95-108

(1998)). LFA-1 is thus a further example of a costimulatory molecule that could be provided in a vaccination protocol in the various ways discussed above for B7.

Complete CTL activation and effector function requires Th cell help through the interaction between the Th cell CD40L (CD40 ligand) molecule and the CD40 molecule expressed by DCs (Ridge et al., Nature, 393:474 (1998), Bennett et al., Nature, 393:478 (1998), Schoenberger et al., Nature, 393:480 (1998)). This mechanism of this costimulatory signal is likely to involve upregulation of B7 and associated IL-6/IL-12 production by the DC (APC). The CD40-CD40L interaction thus complements the signal 1 (antigen/MHC-TCR) and signal 2 (B7-CD28) interactions.

The use of anti-CD40 antibodies to stimulate DC cells directly, would be expected to enhance a response to tumor antigens which are normally encountered outside of an inflammatory context or are presented by non-professional APCs (tumor cells). In these situations Th help and B7 costimulation signals are not provided.

The invention contemplates delivery of nucleic acids, polypeptides or fragments thereof for vaccination. Delivery of polypeptides and fragments thereof can be accomplished according to standard vaccination protocols which are well known in the art. In another embodiment, the delivery of nucleic acid is accomplished by ex vivo methods, i.e. by removing a cell from a subject, genetically engineering the cell to include a sarcoma-associated polypeptide, and reintroducing the engineered cell into the subject. One example of such a procedure is outlined in U.S. Pat. No. 5,399,346 and in exhibits submitted in the file history of that patent, all of which are publicly available documents. In general, it involves introduction in vitro of a functional copy of a gene into a cell(s) of a subject, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo nucleic acid delivery using vectors such as viruses and targeted liposomes also is contemplated according to the invention.

A virus vector for delivering a nucleic acid encoding a sarcoma-associated polypeptide is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses (e.g., Xiang et al., Virology 219:220-227, 1996; Eloit et al., J. Virol. 7:5375-5381, 1997; Chengalvala et al., Vaccine 15:335-339, 1997), a modified retrovirus (Townsend et al., J. Virol. 71:3365-3374, 1997), a nonreplicating retrovirus (Irwin et al., J. Virol. 68:5036-5044, 1994), a replication defective Semliki Forest virus (Zhao et al., Proc. Natl. Acad. Sci. USA 92:3009-3013, 1995), canarypox virus and highly attenuated vaccinia virus derivative (Paoletti, Proc. Natl. Acad. Sci. USA 93:11349-11353, 1996), non-replicative vaccinia virus (Moss, Proc. Natl. Acad. Sci. USA 93:11341-11348, 1996), replicative vaccinia virus (Moss, Dev. Biol. Stand. 82:55-63, 1994), Venzuelan equine encephalitis virus (Davis et al., J. Virol. 70:3781-3787, 1996), Sindbis virus (Pugachev et al., Virology 212:587-594, 1995), and Ty virus-like particle (Allsopp et al., Eur. J. Immunol 26:1951-1959, 1996). A preferred virus vector is an adenovirus.

Preferably the foregoing nucleic acid delivery vectors: (1) contain exogenous genetic material that can be transcribed and translated in a mammalian cell and that can induce an immune response in a host, and (2) contain on a surface a ligand that selectively binds to a receptor on the surface of a target cell, such as a mammalian cell, and thereby gains entry to the target cell.

Various techniques may be employed for introducing nucleic acids of the invention into cells, depending on whether the nucleic acids are introduced in vitro or in vivo in a host. Such techniques include transfection of nucleic acid-$CaPO_4$ precipitates, transfection of nucleic acids associated with DEAE, transfection or infection with the foregoing viruses including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. Preferred antibodies include antibodies which selectively bind a sarcoma-associated antigen, alone or as a complex with a MHC molecule. Especially preferred are monoclonal antibodies. Where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

According to a further aspect of the invention, compositions containing the nucleic acid molecules, proteins, and binding polypeptides of the invention are provided. The compositions contain any of the foregoing therapeutic agents in an optional pharmaceutically acceptable carrier. Thus, in a related aspect, the invention provides a method for forming a medicament that involves placing a therapeutically effective amount of the therapeutic agent in the pharmaceutically acceptable carrier to form one or more doses. The effectiveness of treatment or prevention methods of the invention can be determined using standard diagnostic methods described herein.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines, and optionally other therapeutic agents.

As used herein, the term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The therapeutics of the invention can be administered by any conventional route, including injection or by gradual infusion over time. The administration may, for example, be oral, intravenous, intratumoral, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in Remington's Pharmaceutical Sciences, 18th edition, 1990, pp 1694-1712). Those of skill in the art can readily determine the various parameters and conditions for producing antibody aerosols without undue experimentation. When using antisense preparations of the invention, slow intravenous administration is preferred.

The compositions of the invention are administered in effective amounts. An "effective amount" is that amount of a sarcoma-associated polypeptide composition that alone, or together with further doses, produces the desired response, e.g. increases an immune response to the sarcoma-associated polypeptide. In the case of treating a particular disease or condition characterized by expression of one or more sarcoma-associated polypeptides, such as cancer, the desired response is inhibiting the progression of the disease. This may involve only slowing the progression of the disease temporarily, although more preferably, it involves halting the progression of the disease permanently. This can be monitored by routine methods or can be monitored according to diagnostic methods of the invention discussed herein. The desired response to treatment of the disease or condition also can be delaying the onset or even preventing the onset of the disease or condition.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of sarcoma-associated polypeptide or nucleic acid encoding sarcoma-associated polypeptide for producing the desired response in a unit of weight or volume suitable for administration to a patient. The response can, for example, be measured by determining the immune response following administration of the sarcoma-associated polypeptide composition via a reporter system by measuring downstream effects such as gene expression, or by measuring the physiological effects of the sarcoma-associated polypeptide composition, such as regression of a tumor or decrease of disease symptoms. Other assays will be known to one of ordinary skill in the art and can be employed for measuring the level of the response.

The doses of sarcoma-associated polypeptide compositions (e.g., polypeptide, peptide, antibody, cell or nucleic acid) administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In general, for treatments for eliciting or increasing an immune response, doses of sarcoma-associated antigen are formulated and administered in doses between 1 ng and 1 mg, and preferably between 10 ng and 100 µg, according to any standard procedure in the art. Where nucleic acids encoding sarcoma-associated polypeptides or variants thereof are employed, doses of between 1 ng and 0.1 mg generally will be formulated and administered according to standard procedures. Other protocols for the administration of sarcoma-associated polypeptide compositions will be known to one of ordinary skill in the art, in which the dose amount, schedule of injections, sites of injections, mode of administration (e.g., intra-tumoral) and the like vary from the foregoing. Administration of sarcoma-associated polypeptide compositions to mammals other than humans, e.g. for testing purposes or veterinary therapeutic purposes, is carried out under substantially the same conditions as described above.

Where sarcoma-associated polypeptides are used for vaccination, modes of administration which effectively deliver the sarcoma-associated polypeptide and adjuvant, such that an immune response to the polypeptide is increased, can be used. For administration of a sarcoma-associated polypeptide in adjuvant, preferred methods include intradermal, intravenous, intramuscular and subcutaneous administration. Although these are preferred embodiments, the invention is not limited by the particular modes of administration disclosed herein. Standard references in the art (e.g., Remington's Pharmaceutical Sciences, 18th edition, 1990) provide modes of administration and formulations for delivery of immunogens with adjuvant or in a non-adjuvant carrier.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, and lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases, and the like.

The pharmaceutical agents of the invention may be administered alone, in combination with each other, and/or in combination with other anti-cancer drug therapies and/or treatments. These therapies and/or treatments may include, but are not limited to: surgical intervention, chemotherapy, radiotherapy, and adjuvant systemic therapies.

The invention also provides a pharmaceutical kit comprising one or more containers comprising one or more of the pharmaceutical compounds or agents of the invention. Additional materials may be included in any or all kits of the invention, and such materials may include, but are not limited to buffers, water, enzymes, tubes, control molecules, etc. The kit may also include instructions for the use of the one or more pharmaceutical compounds or agents of the invention for the treatment of cancer.

The invention includes kits for assaying the presence of sarcoma-associated antigens and/or antibodies that specifically bind to sarcoma-associated polypeptides. An example of such a kit may include the above-mentioned polypeptides bound to a substrate, for example a dipstick, which is dipped into a blood or body fluid sample of a subject. The surface of the substrate may then be processed using procedures well known to those of skill in the art, to assess whether specific binding occurred between the polypeptides and agents (e.g. antibodies) in the subject's sample. For example, procedures may include, but are not limited to, contact with a secondary antibody, or other method that indicates the presence of specific binding.

Another example of a kit may include an antibody or antigen-binding fragment thereof, that binds specifically to a sarcoma-associated antigen. The antibody or antigen-binding fragment thereof, may be applied to a tissue or cell sample from a patient with cancer and the sample then processed to assess whether specific binding occurs between the antibody and an antigen or other component of the sample. In addition, the antibody or antigen-binding fragment thereof, may be applied to a body fluid sample, such as serum, from a subject, either suspected of having cancer, diagnosed with cancer, or believed to be free of cancer. As will be understood by one of skill in the art, such binding assays may also be performed with a sample or object contacted with an antibody and/or sarcoma-associated antigen that is in solution, for example in a 96-well plate or applied directly to an object surface.

Another example of a kit of the invention is a kit that provides components necessary to determine the level of expression of one or more sarcoma-associated nucleic acid molecules of the invention. Such components may include primers useful for amplification of one or more sarcoma-associated nucleic acid molecules and/or other chemicals for PCR amplification.

Another example of a kit of the invention is a kit that provides components necessary to determine the level of expression of one or more sarcoma-associated nucleic acid molecules of the invention using a method of hybridization.

The foregoing kits can include instructions or other printed material on how to use the various components of the kits for diagnostic purposes.

The invention further includes nucleic acid or protein microarrays (including antibody arrays) for the analysis of expression of sarcoma-associated antigens or nucleic acids encoding such antigens. In this aspect of the invention, standard techniques of microarray technology are utilized to assess expression of the sarcoma-associated antigens and/or identify biological constituents that bind such antigens. The constituents of biological samples include antibodies, lymphocytes (particularly T lymphocytes), and the like. Microarray substrates include but are not limited to glass, silica, aluminosilicates, borosilicates, metal oxides such as alumina and nickel oxide, various clays, nitrocellulose, or nylon. The microarray substrates may be coated with a compound to enhance synthesis of a probe (peptide or nucleic acid) on the substrate. Coupling agents or groups on the substrate can be used to covalently link the first nucleotide or amino acid to the substrate. A variety of coupling agents or groups are known to those of skill in the art. Peptide or nucleic acid probes thus can be synthesized directly on the substrate in a predetermined grid. Alternatively, peptide or nucleic acid probes can be spotted on the substrate, and in such cases the substrate may be coated with a compound to enhance binding of the probe to the substrate. In these embodiments, presynthesized probes are applied to the substrate in a precise, predetermined volume and grid pattern, preferably utilizing a computer-controlled robot to apply probe to the substrate in a contact-printing manner or in a non-contact manner such as ink jet or piezo-electric delivery. Probes may be covalently linked to the substrate. Nucleic acid probes preferably are linked using UV irradiation or heat.

Protein microarray technology, which is also known by other names including protein chip technology and solid-phase protein array technology, is well known to those of ordinary skill in the art and is based on, but not limited to, obtaining an array of identified peptides or proteins on a fixed substrate, binding target molecules or biological constituents to the peptides, and evaluating such binding. See, e.g., G. MacBeath and S. L. Schreiber, "Printing Proteins as Microarrays for High-Throughput Function Determination," *Science* 289(5485):1760-1763, 2000.

Targets are peptides or proteins and may be natural or synthetic. The tissue may be obtained from a subject or may be grown in culture (e.g. from a cell line).

In some embodiments of the invention, one or more control peptide or protein molecules are attached to the substrate. Preferably, control peptide or protein molecules allow determination of factors such as peptide or protein quality and binding characteristics, reagent quality and effectiveness, hybridization success, and analysis thresholds and success.

Nucleic acid arrays, particularly arrays that bind sarcoma-associated antigens, also can be used for diagnostic applications, such as for identifying subjects that have a condition characterized by aberrant sarcoma-associated antigen expression. Nucleic acid microarray technology, which is also known by other names including: DNA chip technology, gene chip technology, and solid-phase nucleic acid array technology, is well known to those of ordinary skill in the art and is based on, but not limited to, obtaining an array of identified nucleic acid probes on a fixed substrate, labeling target molecules with reporter molecules (e.g., radioactive, chemiluminescent, or fluorescent tags such as fluorescein, Cye3-dUTP, or Cye5-dUTP), hybridizing target nucleic acids to the probes, and evaluating target-probe hybridization. A probe with a nucleic acid sequence that perfectly matches the target sequence will, in general, result in detection of a stronger reporter-molecule signal than will probes with less perfect matches. Many components and techniques utilized in nucleic acid microarray technology are presented in *The Chipping Forecast, Nature Genetics*, Vol. 21, January 1999, the entire contents of which is incorporated by reference herein.

According to the invention, probes are selected from the group of nucleic acids including, but not limited to: DNA, genomic DNA, cDNA, and oligonucleotides; and may be natural or synthetic. Oligonucleotide probes preferably are 20 to 25-mer oligonucleotides and DNA/cDNA probes preferably are 500 to 5000 bases in length, although other lengths may be used. Appropriate probe length may be determined by one of ordinary skill in the art by following art-known procedures. In one embodiment, preferred probes are sets of one or more of the sarcoma-associated nucleic acid molecules as described herein. Probes may be purified to remove contaminants using standard methods known to those of ordinary skill in the art such as gel filtration or precipitation.

In one embodiment, the microarray substrate may be coated with a compound to enhance synthesis of the probe on the substrate. Such compounds include, but are not limited to, oligoethylene glycols. In another embodiment, coupling agents or groups on the substrate can be used to covalently link the first nucleotide or oligonucleotide to the substrate. These agents or groups may include, for example, amino, hydroxy, bromo, and carboxy groups. These reactive groups are preferably attached to the substrate through a hydrocarbyl radical such as an alkylene or phenylene divalent radical, one valence position occupied by the chain bonding and the remaining attached to the reactive groups. These hydrocarbyl groups may contain up to about ten carbon atoms, preferably up to about six carbon atoms. Alkylene radicals are usually preferred containing two to four carbon atoms in the principal chain. These and additional details of the process are disclosed, for example, in U.S. Pat. No. 4,458,066, which is incorporated by reference in its entirety.

In one embodiment, nucleic acid probes are synthesized directly on the substrate in a predetermined grid pattern using methods such as light-directed chemical synthesis, photochemical deprotection, or delivery of nucleotide precursors to the substrate and subsequent probe production.

Targets for microarrays are nucleic acids selected from the group, including but not limited to: DNA, genomic DNA, cDNA, RNA, mRNA and may be natural or synthetic. In all embodiments, nucleic acid target molecules from human tissue are preferred. The tissue may be obtained from a subject or may be grown in culture (e.g. from a cell line).

In embodiments of the invention one or more control nucleic acid molecules are attached to the substrate. Preferably, control nucleic acid molecules allow determination of factors such as nucleic acid quality and binding characteristics, reagent quality and effectiveness, hybridization success, and analysis thresholds and success. Control nucleic acids may include but are not limited to expression products of genes such as housekeeping genes or fragments thereof.

EXAMPLES

Materials and Methods
Cell Lines, Tissues, Sera and RNA
SW1045, SW982, and Fuji synovial sarcoma cell lines were obtained from the cell repository of the Ludwig Institute for Cancer Research (LICR), New York Branch at the Memorial Sloan-Kettering Cancer Center. Tumor tissues and sera were obtained from Memorial Sloan-Kettering Cancer Center, Weill Medical College of Cornell University and Aichi Cancer Center Research Center, Nagoya Japan. Normal tissue RNA preparations were purchased from Clontech laboratories Incorporated (Palo Alto, Calif.) and Ambion Incorporated (Austin, Tex.). Total RNA from tumor tissues was prepared by the guanidinium thiocyanate method.

SEREX Analysis of cDNA Expression Libraries
Poly(A)+ RNA from two sarcoma cell lines, SW1045 and SW982, was prepared using the Fast Track mRNA Purification Kit (Invitrogen, Life Technologies, Carlsbad, Calif.). Poly(A)+ RNA from normal testis was purchased from CLONTECH. Separate cDNA libraries were constructed for each of these in the ZAP Express vector (Stratagene, La Jolla, Calif.) according to the manufacturer's instructions using 5 μg polyA+ mRNA. Libraries containing $1-2\times10^6$ primary recombinants were obtained and were not amplified before immunoscreening.

To remove serum antibodies reactive with vector-related antigens, sera was absorbed against *E. coli*/bacteriophage lysates prepared in the following manner. Wild-type lambda ZAP Express bacteriophage at a concentration of 5,000 pfu (plaque-forming units) per 15 cm plate were amplified in *E. coli* XL1 Blue MRF' overnight in 100 ml NZY/0.7% agarose. 10 ml of binding buffer (0.1M NaHCO3, pH 8.3) was then added to the plates, and the plates were gently agitated at 4° C. for 15 hours. The resultant supernatants were collected and residual *E. coli* were lysed by sonication. The lysates were then coupled to CNBr-Sepharose 4B (Amersham Pharmacia Biotech, Piscataway, N.J.) according to the manufacturer's instructions. Patient sera (1:10 dilution) were absorbed by batch absorption with an equal volume of Sepharose 4B coupled *E. coli*/phage lysates at 4° C. for 6 hours. This procedure was repeated a total of three times and was followed by a 15 hour incubation with nitrocellulose filters precoated with proteins derived from *E. coli* and *E. coli*/phage lysates. Library screenings were performed as previously described (Scanlan, M. J., et al. Characterization of human colon cancer antigens recognized by autologous antibodies. *Int. J. Cancer* 1998; 76: 652-8. Scanlan, M. J., et al. Antigens recognized by autologous antibody in patients with renal-cell carcinoma. *Int. J. Cancer* 1999; 83: 456-64.) A total of five independent SEREX immunoscreenings of the cDNA libraries were undertaken. Sera from 2 sarcoma patients were used independently, at a dilution of 1:200, to immunoscreen the cDNA libraries. A total of $2.5$-$5.0\times10^5$ or $1.75\times10^6$ recombinants were screened per serum/cDNA library combination. Serum reactive phage clones were converted to plasmid forms and subjected to DNA sequencing (Cornell University DNA Services, Ithaca, N.Y.).

Determination of Serum Antibody Reactivity
Two assays were used to determine serological reactivity, an ELISA-based method and a bacteriophage expression method. With regard to CT antigens, serum antibody reactivity was determined by ELISA as previously described (Stockert E, et al. 1998. A survey of the humoral immune response of cancer patients to a panel of human tumor antigens. J Exp Med 187:1349-54.) Briefly, recombinant proteins (NY-ESO-1, SSX-2, MAGE-A1, MAGE-A3, MAGE-A4, MAGE-A10, CT7 and CT10) were produced in *E. coli* by transfection with pQE30 expression vectors (Qiagen, Chatsworth, Calif.) according to the manufacturer's protocol. 10 ng of recombinant protein (1 μg/ml) was absorbed to TC microwell plates (Nalge Nunc International Corp., Naperville, Ill.) for 15 hours at 4° C. After washing with PBS, plates were then blocked with 2% BSA and incubated with diluted (1:100-1:

25,000) patient sera for 2 hours at room temperature. Following a PBS wash step, 10 µl of a 1:5000 dilution of alkaline phosphatase-conjugated goat anti-human IgG secondary antibody (Southern Biotechnology, Birmingham, Ala.) was added to each well and incubated for 1 hour at room temperature. Following a PBS wash step, plates were incubated with 10 ul/well Attophose substrate (JBL Scientific, San Louis Obispo, Calif.) for 25 min, and the fluorescence was then read by a Cyto-Fluor 2350 (Millipore, Bedford, Mass.).

In the case of SEREX-defined sarcoma antigens, a previously described serum antibody detection array (SADA or spot immunoassay (Scanlan M J, et al. Humoral immunity to human breast cancer: antigen definition and quantitative analysis of mRNA expression. Cancer Immunity 1:4 [epub]; Scanlan M J. et al. 2002. Cancer-Related Serological Recognition of Human Colon Cancer: Identification of Potential Diagnostic and Immunotherapeutic Targets. Cancer Res. 2002 Jul. 15; 16 (14): 4041-7.) was used to determine serological reactivity.

Preabsorbed serum samples from 39 sarcoma patients and 33 healthy blood donors were evaluated for the presence of IgG antibody reactive to a panel of SEREX-defined sarcoma antigens, identified herein, in the following manner. Precut nitrocellulose membranes (80×120 mm) were precoated with a layer (approximately 0.2 mm) of growth media (NZY/0.7% Agarose/2.5 mM isopropyl-β-D-thiogalactopyranoside) and placed on a reservoir layer of NZY/0.7% Agarose in a 86×128 mm Omni Tray (Nalge Nunc). $5.0 \times 10^3$ pfu per µl of bacteriophage encoding individual SEREX-defined tumor antigens were mixed with an equal volume of exponentially growing E. coli XL-1 Blue MRF' and spotted (0.7 µl aliquots) on the precoated nitrocellulose membranes using a 96 pin replicator (Nalge Nunc). Membranes were incubated for 15 hours at 37° C. and then processed as per the standard SEREX protocol (Scanlan, et al., Int. J. Cancer 1998; 76: 652-8; Scanlan, et al., Int. J. Cancer 1999; 83: 456-64). Briefly, plates were blocked in 0.5% non-fat dried milk; incubated in 10 ml of a 1:200 dilution of sera at room temperature for 15 hours; and then incubated in a 1:3000 dilution of alkaline phosphatase conjugated, Fc fragment specific, goat anti-human IgG (Jackson Immunoresearch laboratories Inc., West Grove Pa.). Serum IgG reactivity was detected with the alkaline phosphatase substrate, 4-nitro blue tetrazolium chloride/5-bromo-4-chloro-3-indolyl-phosphate.

Reverse Transcriptase-PCR (RT-PCR) Analysis

The cDNA preparations used as templates in the RT-PCR reactions were prepared using the Superscript first strand synthesis kit (Invitrogen Life Technologies, Carlsbad, Calif.) according to the manufacturer's instructions using 2.5 µg of total RNA. For evaluation of CT antigens expression in sarcoma cell lines, PCR primers specific for NY-ESO-1, LAGE-1, MAGE-1, MAGE-3, MAGE-4, MAGE-10, SCP-1, BAGE, CT7, SSX-1, SSX-2, and SSX-4 were synthesized commercially (Invitrogen Life Technologies) using published primer sequences (van der Bruggen P, et al. 1991. A gene encoding an antigen recognized by cytolytic T lymphocytes on a human melanoma. Science 254:1643-47, Gaugler, B., et al. Human gene MAGE-3 codes for an antigen recognized on a melanoma by autologous cytolytic T lymphocytes. *J. Exp. Med.* 1994; 179: 921-30, Chen, Y.-T., et al. A testicular antigen aberrantly expressed in human cancers detected by autologous antibody screening. *Proc. Natl. Acad. Sci. USA.* 1997; 94: 1914-18; Boel, P., et al., and van der Bruggen, P. BAGE: a new gene encoding an antigen recognized on human melanomas by cytolytic T lymphocytes. *Immunity* 1995; 2: 167-75. (PMID: 7895173); Sahin U, et al. 1998. Expression of multiple cancer/testis antigens in breast cancer and melanoma: basis for polyvalent CT vaccine strategies. Int J Cancer 78:387-89, Lethe B, et al. 1998. LAGE-1, a new gene with tumor specificity. Int. J. Cancer 76:903-8, Türeci Ö, et al. 1998. Expression of SSX genes in human tumors. Int J Cancer 77:19-23, Gure A O, et al. 1997. SSX: a multigene family with several members transcribed in normal testis and human cancer. Int J Cancer 72:965-971). PCR primers specific for SEREX-defined antigens were also synthesized commercially (Invitrogen Life Technologies) and their sequences are as follows: NY-SAR-12 forward, TggCgCAgAAAggAAAAggAAAAT (SEQ ID NO: 91); NY-SAR-12 reverse, AgAggTAgCTggCAggATgTTAg (SEQ ID NO: 92); NY-SAR-35 forward, CTTggTgCgATCAgCCTTAT (SEQ ID NO: 93); NY-SAR-35 reverse, TTgATgCATgAAAACAgAACTC (SEQ ID NO: 94); NY-SAR-41 forward, AgAATTggCAgAggCTCgTCATCA (SEQ ID NO: 95); NY-SAR-41 reverse, TTCCAATTTTgCCTTCTCTAACTg (SEQ ID NO: 96); NY-SAR-73 forward, CCCggAgCACgTCgAggTCTAC (SEQ ID NO: 135); NY-SAR-73 reverse, ggTgAggggCCAggAAgC (SEQ ID NO: 136); NY-SAR-78 forward, CACAATgTATCCTgTTgAAAg (SEQ ID NO: 137); NY-SAR-78 reverse, gAgATgATACATTCTTCCAg (SEQ ID NO: 138); NY-SAR-92 forward, CTTCCgCCAACTCCTCCTACC (SEQ ID NO: 139); NY-SAR-92 reverse, gATgCCCgTgTCTTgTCCTT (SEQ ID NO: 140); NY-SAR-96 forward, CACTAggCTgCTgAggAAgAT (SEQ ID NO: 141); NY-SAR-96 reverse, gTTTTggTgggCAgCATTgAg (SEQ ID NO: 142); NY-SAR-97 forward, ggACCACCCCAAATAgAA (SEQ ID NO: 143); NY-SAR-97 reverse, CCACCAgCTCAggAAgA (SEQ ID NO: 144); NY-SAR-110 forward, TCTgATggAgCggTgggATgC (SEQ ID NO: 145); NY-SAR-110 reverse, gTgTgCCTCggCTTCTTTCTTC (SEQ ID NO: 146).

RT-PCR was performed in the following manner. Twenty-five µl PCR reaction mixtures, consisting of 2 µl cDNA, 0.2 mM dNTP, 1.5 mM $MgCl_2$, 0.25 µM gene specific forward and reverse primers, and 2.5 U Platinum Taq DNA polymerase (Invitrogen Life Technologies), were heated to 94° C. for 2 min., followed by 35 thermal cycles of 94° C. for 30 seconds, 55° C. for 30 seconds and 72° C. for 1 min., and a final cycle of 94° C. for 30 seconds, 55° C. for 30 seconds and 72° C. for 5 min. Thermal cycling was performed using a GeneAmp PCR System 9700 (Applied Biosystems, Foster City, Calif.). Resultant PCR products were analyzed in 2% Agarose/Tris-Acetate-EDTA gels.

Real-Time Quantitative Reverse Transcription (RT)-PCR

The concentration of NY-SAR-35 mRNA transcripts in normal tissues was measured by real-time RT-PCR using cDNA preparations derived from lung cancer specimens and 16 different normal tissues that had been normalized for 6 housekeeping genes (Clontech). Gene-specific TaqMan probes and PCR primers were designed using Primer Express software (PE Biosystems, Foster City, Calif.). PCR reactions were prepared using 2.5 µl of cDNA diluted in TaqMan PCR Master Mix (PE Biosystems) supplemented with 200 nM 6-carboxy-fluorescein labeled gene-specific TaqMan probe, and a predetermined, optimum concentration of gene specific forward and reverse primers (300-900 nM). Triplicate PCR reactions were prepared for each cDNA sample. PCR consisted of 40 cycles of 95° C. denaturation (15 seconds) and 60° C. annealing/extension (60 seconds). Thermal cycling and fluorescent monitoring were performed using an ABI 7700 sequence analyzer (PE Biosystems). The point at which the PCR product is first detected above a fixed threshold, termed cycle threshold (Ct), was determined for each sample. The abundance of gene-specific transcripts in normal tissues was determined by comparison with a standard curve generated from the Ct values of known concentrations of plasmid DNA template encoding NY-SAR-35.

TaqMan primers were as follow: NY-SAR-35 forward, TggTgCgATCAgCCTTATCC (SEQ ID NO: 147); NY-SAR-35 reverse, CggTTCgCTCCTCCAgAA (SEQ ID NO: 148). TaqMan probe: NY-SAR-35, TgTCTgCCCATTTATTgC-CgCTCTCT (SEQ ID NO: 149).

Northern Blot Analysis.

A Northern blot containing poly A+ RNA (2 μg/lane) from various normal tissues was obtained commercially (Clontech). An NY-SAR-35 cDNA probe (bp 263-1029) was labeled using the Bright Star Psoralen-Biotin Kit (Ambion Inc., Austin, Tex.) and hybridized to the membrane for 15 hours at 68° C. After washing, the hybridization signal was developed using the Bright Star Bio-Detect Kit, according to the manufacturer's instructions (Ambion).

Southern Blot Analysis

Genomic DNA was extracted from normal human testis, and samples (10 μg) were independently digested with EcoRI, HindIII, and BamHI at 37° C. overnight. The DNA was then separated on 0.7% agarose gel and blotted onto a nylon transfer membrane. An NY-SAR-35 cDNA probe (bp 252-1029) was radiolabeled with $^{32}$P-dCTP using a random-primer DNA labeling kit (Roche Molecular Biochemicals, Indianapolis, Ind.). The blot was hybridized to a $^{32}$P labeled probe at 68° C. After 15 hours of hybridization, the membrane was washed under high stringency conditions (0.1×SSC, 0.5% SDS at 60° C.) and exposed for autoradiography.

Example 1

Results from the First Round of Immunoscreenings by SEREX Analysis

Identification of Human Sarcoma Antigens by SEREX Analysis

Preliminary studies were carried out to determine optimum sources of target antigens and immunoreactive patient sera. Three sarcoma cell lines were typed for expression of NY-ESO-1, LAGE-1, MAGE-1, MAGE-3, MAGE-4, MAGE-10, BAGE, SCP-1, CT7, SSX-1, SSX-2, and SSX-4 transcripts by RT-PCR. As shown in Table 2, all 3 sarcoma cell lines expressed at least one of the transcripts in this panel. Specifically, the SW982 and SW1045 synovial sarcoma cell lines expressed 8 and 10 of the 12 CT antigen transcripts in the panel, respectively, while Fuji synovial sarcoma cells expressed 4/12 CT antigen transcripts.

TABLE 2

Cancer/Testis antigen expression in sarcoma cell lines

| CT Antigen | Cell Line | | |
| --- | --- | --- | --- |
| | SW982 (synovial) | SW1045 (synovial) | Fuji |
| NY-ESO-1 | + | + | + |
| LAGE-1 | Neg | + | + |
| MAGE-A1 | + | + | Neg |
| MAGE-A3 | + | + | Neg |
| MAGE-A4 | + | + | |
| MAGE-A10 | + | + | Neg |
| BAGE | + | + | Neg |
| SCP-1 | Neg | Neg | Neg |
| CT7 | + | + | Neg |
| SSX1 | Neg | + | Neg |
| SSX2 | Neg | Neg | |
| SSX4 | + | + | Neg |
| Totals | 8/12 | 10/12 | 4/12 |

In order to identify a subset of sarcoma patients that are actively mounting an immune response against tumor antigens, sera from 54 sarcoma patients (various histologies) were tested by ELISA (Stockert E, et al. 1998. A survey of the humoral immune response of cancer patients to a panel of human tumor antigens. J Exp Med 187:1349-54) for the presence of antibodies against a panel of 8 CT antigens consisting of: NY-ESO-1, SSX-2, MAGE-A1, MAGE-A3, MAGE-A4, MAGE-A10, CT7 and CT10. Only 2/54 sarcoma patients, a malignant fibrous histocytoma (MFH) and fibrosarcoma patient (FS), had detectable serum antibodies against a CT antigen, while the remaining 52 patients lacked detectable anti-CT antigen antibodies. Both seropositive patients had antibodies to NY-ESO-1 but lacked antibodies to the other 7 CT antigens tested. Fibrosarcoma tissue from the NY-ESO-1 seropositive patient, FS, was available for CT antigen typing by RT-PCR and was found to express 11/12 different CT antigen transcripts (NY-ESO-1, LAGE-1, MAGE-A1, -A3, -A4, -A10, BAGE, CT7, SSX1, -2 and -4). Tissue from the NY-ESO-1 seropositive patient, MFH, was not available for CT antigen typing by RT-PCR.

Although it was determined that CT antigen expression is frequent in sarcoma tissue, serum antibody responses were not as frequent. This lack of immunogenicity in sarcoma may be an indication of immune escape by sarcoma cells, whereby the immune system fails to recognize CT antigens and eliminate tumor cells expressing these antigens, resulting in the expansion of a homogenous population CT antigen expressing sarcoma cells. Relevant escape mechanisms include defective antigen presentation (Garrido F, Algarra I. MHC antigens and tumor escape from immune surveillance. Adv Cancer Res 2001; 83:117-58) and/or production of immuno-inhibitory cytokines, such as TGF-β and IL-10 (Conrad C T, et al. Differential expression of transforming growth factor beta 1 and interleukin 10 in progressing and regressing areas of primary melanoma. J Exp Clin Cancer Res 1999 June; 18(2):225-32). It is also possible that homogeneous NY-ESO-1 and MAGE expression in synovial sarcoma (Jungbluth A A, et al. 2001. Monophasic and biphasic synovial sarcomas abundantly express cancer/testis antigen NY-ESO-1 but not MAGE-A1 or CT7. Int J Cancer 94:252-6; Antonescu C R, et al. MAGE antigen expression in monophasic and biphasic synovial sarcoma. Hum Pathol 2002 February; 33(2):225-9), as opposed to heterogeneous CT antigen expression observed in many other tumor types (Jungbluth A A, et al. 2001. Immunohistochemical analysis of NY-ESO-1 antigen expression in normal and malignant human tissues. Int J Cancer 92:856-60; Jungbluth A A, et al. 2000. Expression of MAGE-antigens in normal tissues and cancer. Int J Cancer 85:460-5), may also be a contributing factor to immune escape.

These 2 patients were chosen as the serum sources for SEREX immunoscreening of cDNA libraries prepared from the SW982 and SW1045 synovial sarcoma cell lines. A total of 4 SEREX immunoscreenings were performed, leading to the identification of 72 distinct sarcoma antigens, designated NY-SAR-1 through NY-SAR-72. As shown in Table 3, immunoscreening with sera from an NY-ESO-1 serum antibody positive MFH patient led to the identification of 28 antigens, including 8 overlapping antigens derived from both the SW982 and SW1045 cDNA libraries, as well as 13 antigens derived solely from the SW982 cDNA library, and 7 antigens derived solely from the SW1045 cDNA library.

Immunoscreening with sera from an NY-ESO-1 serum antibody positive fibrosarcoma patient defined 46 antigens, including 2 overlapping antigens derived from both the SW982 and SW1045 cDNA libraries, as well as 25 antigens derived solely from the SW982 cDNA library, and 19 antigens derived solely from the SW1045 cDNA library. There was little overlap between the antigens recognized by serum antibodies from the MFH and FS patients. Only three antigens, NY-SAR-1/TMF1, NY-SAR-4/FH and NY-SAR-17/LAGE-1 were identified with both the MFH and FS sera. Because serological reactivity to NY-ESO-1 was the criteria used in selecting sera for cDNA library screening, mutual immunoreactivity to the highly homologous (84% amino acid identity) NY-SAR-17/LAGE-1 antigen was expected, and, although not intending to be bound by a particular theory, is likely to be due to shared epitopes. The 72 antigens (Tables 4-6) represent 58 known proteins and 14 uncharacterized gene products.

TABLE 3

Immunoscreening of synovial sarcoma cDNA expression libraries with allogeneic sarcoma patient sera

| Sarcoma Serum | Synovial sarcoma cDNA expression library | Number of recombinants screened | Number of different antigens identified | Total number of distinct antigens |
|---|---|---|---|---|
| Malignant Fibrous Histocytoma | SW982 | $5 \times 10^5$ | 21 | 28 |
|  | SW1045 | $5 \times 10^5$ | 15 |  |
| Fibrosarcoma | SW982 | $2.5 \times 10^5$ | 27 | 46 |
|  | SW1045 | $2.5 \times 10^5$ | 21 |  |

TABLE 4

SEREX-defined sarcoma antigens: antigens reactive with sera from multiple cancer patients

| NY-SAR-Antigen | Identity (Unigene cluster) | Reactivity with Sarcoma Sera | Source of Reactive Sera[1] | SEREX Database ID Number[2] of Equivalent Isolate (Tumor Source[1]) |
|---|---|---|---|---|
| 2 | STAU (Hs.6113) | 2/39 | MFH (#3), OS (#2) | 614 (PRC), 1273 (BC) |
| 4 | FH (Hs.75653) | 5/39 | MFH (#3), OS (#4, #7), ES (#1), FS (#2) | No Match |
| 12 | NESG1 (Hs.158450) | 2/39 | MFH (#3), LS (#4) | No Match |
| 13 | ACTN1 (Hs.119000) | 1/39 | MFH (#3) | 855 (BC) |
| 15 | RBM6 (Hs.173993) | 1/39 | MFH (#3) | 76 (LC) |
| 16 | FLJ12785 (Hs.192742) | 1/39 | MFH (#3) | 756 (TALL) |
| 17 | LAGE-1a (Hs.87225) | 2/39 | MFH (#3), FS (#2) | 1160 (BC) |
| 18 | SSSCA1 (Hs.25723) | 1/39 | MFH (#3) | 1799 (CC) |
| 28 | MGC: 9727 (Hs.11065) | 1/39 | MFH (#3) | 71 (BC) |
| 30 | SNK (Hs.3838) | 2/39 | FS (#2), RS (#1) | No Match |
| 44 | LGALS1 (Hs.227751) | 1/39 | FS (#2) | 704 (RC) |
| 47 | MIF (Hs.73798) | 1/39 | FS (#2) | 989 (MEL) |
| 50 | PYCR1 (Hs.79217) | 3/39 | FS (#2), MFH (#2, #4) | No Match |
| 71 | None (Hs.314941) | 1/39 | FS (#2) | 1938 (GL) |
| 72 | HSPE1 (Hs.1197) | 1/39 | FS (#2) | 882 (HC), 1202 (MEL) |

Antigens did not react with sera from normal blood donors (0/33).
[1]Abbreviations: BC, breast cancer; CC, colon cancer; ES, Ewing sarcoma; FS, fibrosarcoma; GC, gastric cancer; GL, glioma; HC, hepatocellular carcinoma; LC, lung cancer; LS, leimyosarcoma; MEL, melanoma; MFH, malignant fibrous histocytoma; OC, ovarian cancer; OS, osteosarcoma; PRC, prostate cancer; RC, renal cancer; RS, rhabdomyosarcoma; TALL, T-cell acute lymphocytic leukemia.
[2]SEREX database ID numbers from the LICR's SEREX database (licr.org/SEREX.html).

TABLE 5

SEREX-defined sarcoma antigens: antigens reactive with sera from both normal donors and sarcoma patients

| NY-SAR-Antigen | Identity (Unigene cluster) | SEREX Database ID Number[1] of Equivalent Isolate (Tumor Source[2]) | Reactivity with Normal Sera | Reactivity with Sarcoma Sera |
|---|---|---|---|---|
| 1 | TMF1 (Hs.267632) | 246 (G), 1241 (BC) | 2/33 | 3/39 |
| 3 | KIAA1536 (Hs.156667) | 89 (BR) | 2/33 | 3/39 |
| 6 | RHAMM (Hs.72550) | 1513 (OC) | 1/33 | 3/39 |
| 7 | PINCH (Hs.112378) | 344 (CC), 550 (GC), 1152 (RC), 1281 (BR) | 16/21 | 14/39 |
| 10 | KIAA0603 (Hs.173802) | No Match | 11/33 | 4/39 |
| 11 | U2AF1RS2 (Hs.171909) | 430 (RC), 786 (HD), 1236 (BC), 1334 (GC) | 6/33 | 17/39 |
| 14 | SC65 (Hs.207251) | No Match | 8/33 | 4/39 |
| 19 | HEF1 (Hs.80261) | 421 (RC) | 3/33 | 7/39 |
| 22 | NELIN (Hs.216381) | No Match | 4/33 | 19/39 |
| 29 | FLJ13441 (Hs.232146) | 974 (PC) | 6/33 | 3/39 |
| 31 | HUMAUANTIG (Hs.75528) | 1017 (BC), 1331 (GC), 1475 (OC) | 2/33 | 6/39 |
| 32 | PDAP1 (Hs.278426) | No Match | 4/33 | 8/39 |
| 33 | SURF6 (Hs.274430) | No Match | 2/33 | 2/39 |
| 41 | None (Hs.166670) | No Match | 1/33 | 1/39 |
| 45 | STIP1 (Hs.75612) | 430 (RC) | 4/33 | 2/39 |

TABLE 5-continued

SEREX-defined sarcoma antigens: antigens reactive with
sera from both normal donors and sarcoma patients

| NY-SAR-Antigen | Identity (Unigene cluster) | SEREX Database ID Number[1] of Equivalent Isolate (Tumor Source[2]) | Reactivity with Normal Sera | Reactivity with Sarcoma Sera |
|---|---|---|---|---|
| 53 | FXYD5 (Hs.333418) | No Match | 1/33 | 1/39 |
| 54 | LMOD1 (Hs.79386) | No Match | 7/33 | 13/39 |
| 55 | RBM10 (Hs.154583) | No Match | 1/33 | 1/39 |
| 58 | LIP8 (Hs.348012) | No Match | 1/33 | 3/39 |
| 61 | ZNF282 (Hs.58167) | No Match | 1/33 | 2/39 |
| 64 | USP16 (Hs.99819) | No Match | 2/33 | 2/39 |
| 65 | FDFT1 (Hs.48876) | No Match | 2/33 | 1/39 |
| 66 | ROCK1 (Hs.109450) | 444 (RC) | 1/33 | 1/39 |
| 68 | P38IP (Hs.333500) | No Match | 1/33 | 3/39 |

[1]The LICR's SEREX database ID numbers from licr.org/SEREX.html.
[2]Abbreviations: BC, breast cancer; CC, colon cancer; HD, Hodgkins disease; GC, gastric cancer; OC, ovarian cancer; PC, pancreatic cancer; RC, renal cancer.

TABLE 6

SEREX-defined sarcoma antigens: antigens reactive
with sera from a single sarcoma patient

| NY-SAR-Antigen | Gene Identity (Unigene Cluster) |
|---|---|
| 5 | TBC1D1(Hs.278586) |
| 8 | BIRC2 (Hs.289107) |
| 9 | ATP5B (Hs.25) |
| 20 | TCEB3 (Hs.155202) |
| 21 | GTF3C3 (Hs.90847) |
| 23 | C20orf81 (Hs.29341) |
| 24 | None (not clustered) |
| 25 | PDE4DIP (Hs.265848) |
| 26 | PIASX-BETA (Hs.111323) |
| 27 | FLJ10330(Hs.342307) |
| 34 | SEC23B (Hs.173497) |
| 35 | None (Hs.128580) |
| 36 | SSX1(Hs.194759) |
| 37 | MP1 (Hs.260116) |
| 38 | HMG20B (Hs.32317) |
| 39 | PSMD4 (Hs.148495) |
| 40 | INPP1 (Hs.32309) |
| 42 | BTG3 (Hs.77311) |
| 43 | SSX4 (Hs.278632) |
| 46 | ARNTL2 (Hs.222024) |
| 48 | MGC20533 (Hs.69280) |
| 49 | EMK1 (Hs.157199) |
| 51 | EDF1 (Hs.174050) |
| 52 | Actin (Hs.288061) |
| 56 | MLF1Hs.85195) |
| 57 | GCN5L2 (Hs.101067) |
| 59 | UPF3B (Hs.103832) |
| 60 | EGLN1 (Hs.6523) |
| 62 | AD034(Hs.281397) |
| 63 | USP19(Hs.301373) |
| 67 | LUC7L (Hs.16803) |
| 69 | ARL1 (Hs.242894) |
| 70 | RPL10A (Hs.334895) |

[1]Antigens reacted with sera from single sarcoma patient (1/39), but not with sera from normal individuals (0/33). The antigens listed had no matches with existing entries in the SEREX database (licr.org/SEREX.html).

The nucleotide sequences of all uncharacterized gene products (NY-SAR-3, -10, -16, -22, -23, -24, -27, -28, -29, -35, -41, -48, -62, -71) have been deposited in the GenBank database (SEQ ID NOs: 1-14, respectively). The cDNA sequences encoding the 72 sarcoma antigens were also compared to sequences deposited in the SEREX database accessible through a website of the Ludwig Institute for Cancer Research (licr.org/SEREX.html). Examination of this database revealed that 21 of the 72 sarcoma antigens defined in this study (29%) were also identified through SEREX analysis of other tumor types (Tables 4 and 5).

Reactivity Patterns of Sera from Normal Individuals and Cancer Patients with SEREX-Defined Sarcoma Antigens To determine whether immune recognition of the isolated antigens was cancer-related, allogeneic sera samples obtained from 33 normal blood donors and 39 sarcoma patients (various histologies) were tested for reactivity against the 72 sarcoma antigens defined in the current study using serum antibody detection arrays (SADA). Twenty-four of the 72 antigens (33%) had a serological profile that was not restricted to cancer patients, as evidenced by their reactivity with normal sera. These antigens have been listed in Table 5.

Sera from two normal individuals and three sarcoma patients reacted with NY-SAR-1/TMF1, suggesting the reactivity was unrelated to cancers. With one notable exception (NY-SAR-22/NELIN), the frequency of antibody responses to 23 of the 24 antigens associated with normal sera reactivity was similar in normal blood donors and cancer patients. In the case of NY-SAR-22/NELIN (UniGene cluster Hs.216381), the frequency of antibody responses was considerably higher in cancer patients, in which 19/39 (49%) of sarcoma patients and 4/33 (12%) of normal individuals had a detectable antibody response. The remaining 48 antigens had a cancer-related serological profile, reacting only with sera from cancer patients.

The 48 antigens having a cancer-related serological profile could be subdivided into 4 categories; a) antigens identified by serum from only a single sarcoma patient; b) antigens that reacted with sera from a single sarcoma patient and, as determined by an analysis of the SEREX database, with sera from patients having other forms of cancer; c) antigens that reacted exclusively with sera from 2 or more sarcoma patients; and d) antigens that reacted with sera from 2 or more sarcoma patients and with sera from patients having other forms of cancer. Of the 48 antigens having a cancer-related serological profile, 33 antigens reacted with sera from a single sarcoma patient (Table 6).

As shown in Table 4, the remaining 15 antigens reacted with sera from 2 or more cancer patients, but not with sera from normal individuals. Nine antigens reacted with sera from a single sarcoma patient, and with sera from patients with other tumor types (NY-SAR-13, -15, -16, -18, -28, -44, -47, -71, -72). Four antigens reacted exclusively with sera from 2 or more sarcoma patients (NY-SAR, -4, -12, -30, -50). The remaining two antigens, NY-SAR-2/STAU and the CT antigen, NY-SAR-17/LAGE-1A, reacted with sera from 2 or more sarcoma patients and with sera from patients with other types of cancer. A cancer-related serological response to NY-SAR-4/FH occurred most frequently. In this case, serum samples from 5/39 (13%) sarcoma patients were reactive with NY-SAR-4/FH, including 2/10 sera samples from osteosarcoma patients, 1/6 sera samples from malignant fibrous histiocytoma patients, 1/2 patients sera samples from fibrosarcoma patients, and 1/7 sera samples from Ewing sarcoma patients. No serological responses to NY-SAR-4/FH were detected in normal blood donors.

This serological response to NY-SAR-4/FH is of interest as germ-line mutations in the FH gene have been associated with a predisposition to uterine and cutaneous leiomyomata and also renal cell carcinoma (Tomlinson I P, et al. Germline mutations in FH predispose to dominantly inherited uterine fibroids, skin leiomyomata and papillary renal cell cancer. Nat Genet 2002 April; 30(4):406-10) and is a target of somatic mutation in sarcoma (Kiuru, M., et al. (2002) Cancer Res. 62, 4554-4557) suggesting that the immune response is directed against mutated epitopes.

Expression Patterns of mRNA Encoding Serologically Defined Sarcoma Antigens in Normal and Malignant Tissues A preliminary in silico mRNA expression profile of all gene products identified in this study was carried out based on the tissue distribution of expressed sequence tags (ESTs) in the human EST database. Products with no EST matches, or those having EST matches limited to tumor tissue, fetal tissue, and/or less than 3 normal adult tissues were further examined by RT-PCR. Gene products with restricted EST profiles include the three well-characterized cancer-testis antigens, LAGE-1/NY-SAR-17, NY-SAR-36/SSX1, and NY-SAR-43/SSX4, which are expressed exclusively in normal testis and a range of different tumor types (Lethe B, et al. 1998. LAGE-1, a new gene with tumor specificity. Int. J. Cancer 76:903-8; Türeci Ö, et al. 1998. Expression of SSX genes in human tumors. Int. J. Cancer 77:19-23; Gure A O, et al. 1997. SSX: a multigene family with several members transcribed in normal testis and human cancer. Int. J. Cancer 72:965-971), and 3 putative tissue restricted antigens, including a known gene product, nasopharyngeal specific protein 1(NESG1)/NY-SAR-12 (Li Z, Yao K, Cao Y. Molecular cloning of a novel tissue-specific gene from human nasopharyngeal epithelium. Gene 1999 Sep. 3; 237(1):235-40), and 2 uncharacterized gene products, NY-SAR-35 (UniGene cluster Hs.128580) and NY-SAR-41 (UniGene cluster Hs.166670). With the exception of serum reactivity to NY-SAR-41 occurring in 1/33 normal blood donors, these differentially expressed antigens showed a cancer-related serological profile.

Figure 1B:
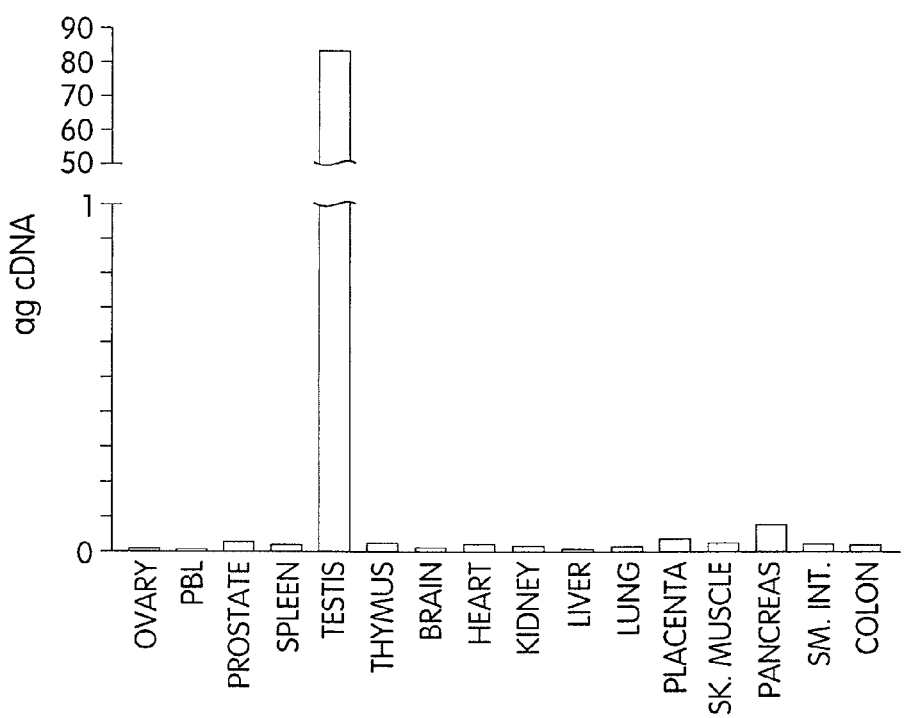
FIG. 1B provides the results of the quantitative real-time RT-PCR analysis of NY-SAR-35 in various normal tissues.

As shown in FIG. 1A, mRNA expression patterns of NY-SAR-12, -35, and -41 were examined in 17 different human tissues by RT-PCR. NESG1/NY-SAR-12 mRNA was detected in normal placenta, testis, colon, lung, and ovary (0/12 other normal tissues). NY-SAR-35 mRNA was detected only in normal testis (0/15 other normal tissues), while a lower molecular weight transcript was detected in normal ovary. NY-SAR-41 was detected in normal testis, fetal brain, colon, lung, and bladder (0/12 other normal tissues). As shown in FIG. 1B, the testis restricted expression pattern of NY-SAR-35 was confirmed by real time quantitative RT-PCR at 40 amplification cycles. In these studies, NY-SAR-35 was expressed in normal testis at a level corresponding to 83.2 ag, which was more than 1000 times the level detected in the remaining 15 normal tissues.

Figure 1C:
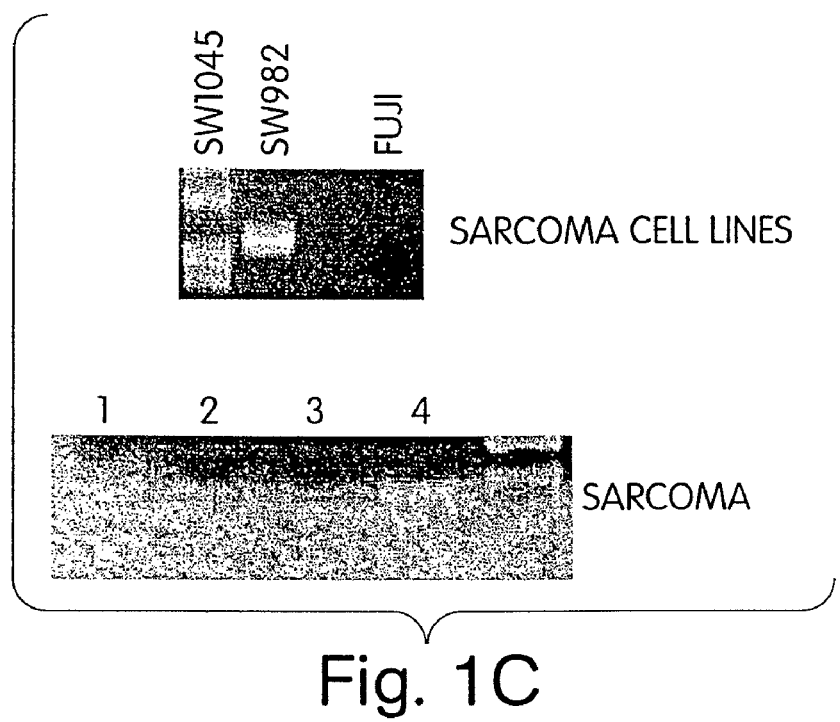
FIG. 1C shows the results of the RT-PCR analysis of NY-SAR-35 expression in sarcoma cell lines and sarcoma tissue (Lane 1, fibrosarcoma; 2, rhabdomyosarcoma; 3, leiomyosarcoma; and 4, normal testis).

The expression of NY-SAR-35 mRNA was also examined in 26 sarcoma specimens of various histologies, and was detected in fibrosarcoma and rhabdomyosarcoma specimens (2/26), as well as the SW1045 synovial sarcoma cell line (Table 7 and FIG. 1C). With regard to other tumor types, transcripts encoding NY-SAR-35 were detected in 1/16 (6%) melanoma specimens, 5/29 (21%) lung cancer specimens, and 3/13 (23%) breast cancer specimens. NY-SAR-35 mRNA was not detected in small number of colon cancer specimens (%) or in small numbers of renal cancer specimens (%). Thus, on the basis of its immunogenicity in cancer patients, and its restricted mRNA expression profile, NY-SAR-35 can be considered a novel CT antigen.

TABLE 7

Expression of NY-SAR-35 in sarcoma, sarcoma cell lines and other malignant tissues

| Histology | Expression Frequency |
| --- | --- |
| Sarcomas | |
| Synovial sarcoma | 0/8 |
| Leimyosarcoma | 0/4 |
| Malignant Fibrous Histocytoma | 0/4 |
| Ewing Sarcoma | 0/2 |
| Osteosarcoma | 0/2 |
| Rhabdomyosarcoma | 1/1 |
| Fibrosarcoma | 1/1 |
| Liposarcoma | 0/1 |
| Neurosarcoma | 0/1 |
| Chondrosarcoma | 0/1 |
| DFSP | 0/1 |
| SW1045 synovial sarcoma cell line | positive |
| SW982 synovial sarcoma cell line | negative |
| Fuji synovial sarcoma cell line | negative |
| Other Malignancies | |
| Melanoma | 1/16 |
| Lung Cancer | 5/29 |
| Colon Cancer | 0/9 |
| Breast Cancer | 3/13 |
| Renal Cancer | 0/8 |
| Esophageal Cancer | 1/12 |
| Ovarian Cancer | 1/12 |
| Gastric Cancer | 5/6 |

The NY-SAR-35 Gene, Transcript and Putative Protein and Orthologous Gene

An analysis of the human genome database, mapped the NY-SAR-35 cDNA sequence to Xq28, approximately 5.9 Mbp downstream (3') of the CT10/MAGE-E1 gene and 6.8 Mbp upstream (5') of the NY-ESO-1 gene. The NY-SAR-35 gene is approximately 44 kb in length and spans 6 exons. Analyses of the human genome databases (NCBI GenBank, ncbi.nlm nih gov/genome, and Celera Genomics, Rockville, Md., celera.com) revealed no genomic sequences of high similarity, suggesting that it is a single copy gene with no additional family members. These results were verified by probing Southern blots of human genomic DNA with the NY-SAR-35 cDNA.

Figure 1D:
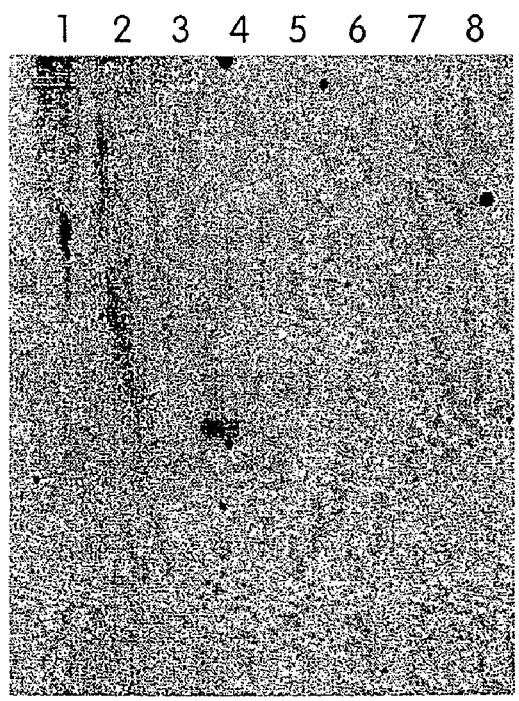
FIG. 1D provides the results of the Northern blot analysis of NY-SAR-35 in various normal tissues (Lane 1, spleen; 2, thymus; 3, prostate; 4, testis; 5, ovary; 6, small intestine; 7, colon mucosa; and 8, peripheral blood leukocytes).

The present SEREX immunoscreening provided 4 overlapping NY-SAR-35 cDNA clones, ranging from 677-767 by in length, all contained identical 3' sequences originating from the poly A region. The NY-SAR-35 cDNA sequence was identical to 3 ESTs (GenBank accession nos. AA909915, AA906131, and AW593050) which were all derived from the NFL_T_GBC_S1 mixed tissue (fetal lung, testis, germinal center B cell) cDNA library and found in UniGene cluster Hs.128580 as well as 4 ESTs (GenBank accession nos. BC034320, AK098602, BG771667 and BI465380) derived from a testis cell line and found in Unigene cluster Hs.375082. As shown in FIG. 1D, Northern blot analysis revealed a single NY-SAR-35 mRNA transcript of 1.1 kB in normal testis, indicating the SEREX-defined clones and EST sequences represent partial transcripts. To obtain a full-length NY-SAR-35 transcript, 5' RACE was performed, yielding 262 by of additional 5' DNA sequence. Thus, the total length of the NY-SAR-35 transcript is 1029 by (SEQ ID NO: 10, GenBank accession no. AY211917), a size that is in agreement with the 1.1 kb hybridization signal seen in Northern blots of testis mRNA probed with NY-SAR-35 cDNA.

The NY-SAR-35 transcript encodes an open reading frame of 255 amino acids (SEQ ID NO: 55, by 68-895) with a predicted molecular mass of 29.2kDa. It is identical to a hypothetical protein, XM098959, predicted from Genefinder analysis of human chromosome X sequences. The putative NY-SAR-35 protein has a signal peptide, a transmembrane domain and a cysteine-rich trefoil/P-domain, found in several secreted proteins of the gastrointestinal tract (Hoffmann W, Hauser F. The P-domain or trefoil motif: a role in renewal and pathology of mucous epithelial Trends Biochem Sci 1993 July; 18(7):239-43). These data suggest that NY-SAR-35 is a-secreted or membrane bound protein.

To identify a murine orthologue of NY-SAR-35, the putative human NY-SAR-35 protein sequence was used to search a translated nonredundant nucleotide database by using the TBLASTN tool of the NCBI (ncbi.nlm nih gov/blast/Blast.cgi). A hypothetical mouse protein, termed XP_150408, generated from a conceptual translation of the mouse X chromosome, was found to have 57% identity (49/85 amino acids) with NY-SAR-35. Using nucleotide primers corresponding to sequences encoding XP_150408, 5' and 3' RACE reactions were undertaken by using mouse testis cDNA. By combining 5' and 3' RACE products, a 1,202 by cDNA was identified (GenBank accession no. AY214130, SEQ ID NO: 133). This cDNA encoded a putative full length mouse protein of 238 amino acids (SEQ ID NO: 134) which is 41% identical to human NY-SAR-35, with conservation of the trefoil and transmembrane domains. This murine NY-SAR-35 (mNY-SAR-35) cDNA sequence was used to search mouse genome sequences (ncbi.nlm nih gov/genome/seq/MmBlast.html) yielding an identical genome sequence, NW 042622, from mouse chromosome X. Analysis of this sequence showed the mNY-SAR-35 gene is composed of approximately 42,600 nucleotides and seven exons.

Example 2

Analysis of the NY-SAR-35 Protein and its Expression

Purification of Recombinant NY-SAR-35 Protein in *E. coli* to Produce Monoclonal Antibodies and to Perform ELISA Assays There are four ATG codons in exon 1 of the NY-SAR-35 gene. It is expected that the fourth ATG codon in the full length sequence of NY-SAR-35 is the first ATG codon of the translated NY-SAR-35 sequence. It appears then that the predicted protein has two interesting domains. The protein revealed two distinctive hydrophobic domains followed by two hydrophilic turns. One hydrophobic domain is a signal peptide, which are predicted in proteins with cleavage sites between amino acids 25 and 26 with SignalP software tool available at the website cbs.dtu.dk/services/SignalP. The other hydrophobic region is predicted to be a transmembrane domain with the TMHMM2.0 program available at the website cbs.dtu.dk/services/TMHMM/TMHMM2.0b.guide.html. Therefore, the NY-SAR-35 gene encodes a signal peptide and a transmembrane domain (FIG. 2).

Three kinds of NY-SAR-35 vectors were designed for the purification of the proteins in an *E. coli* expression system (pET System) (Novagen, Madison, Wisc.). The first encoded the largest possible NY-SAR-35 protein from the first ATG codon (SEQ ID NO: 150), the second encoded the NY-SAR-35 protein from the fourth ATG codon (MH7) (SEQ ID NO: 152), and the third encoded the expected extracellular domain from the fourth ATG codon (SEQ ID NO: 154). An illustration of these vectors is provided below. The expected sizes of the resulting proteins are 29 kD (263 amino acids) (SEQ ID NO: 151), 22 kD (201 amino acids) (SEQ ID NO: 153) and 14.6 kD (133 amino acids) (SEQ ID NO: 155), respectively.

I. Whole protein (NY-SAR-35 from the First ATG)

Vector:pET23a(NdeI/XhoI): C-terminal His tag vector

Primer;

SAR35/NdeI:
(SEQ ID NO: 156)
CACACACACATATGTCTTCACATAGGAGGAAAGCGAAG

SAR35/XhoI:
(SEQ ID NO: 157)
CACACACTCGAGCTCGTCACCATGTTCCTCACGTC (SEQ ID NO: 150)
CATATGTCTTCACATAGGAGGAAAGCGAAGGGGAGGAATAGGAGAAGTCA
CCGTGCCATGCGTGTGGCTCACTTAGAGCTGGCAACTTATGAGTTGGCGG
CAACTGAGTCGAATCCCGAGAGCAGCCATCCTGGATACGAGGCCGCCATG
GCTGACAGGCCTCAGCCAGGATGGCGGGAATCTCTAAAGATGCGGGTCAG
CAAACCCTTTGGGATGCTCATGCTCTCCATTTGGATCCTGCTGTTCGTGT
GCTACTACCTGTCCTACTACCTGTGCTCCGGGTCCTCATATTTTGTGCTT
GCAAATGGACATATCCTGCCCAACAGTGAAAATGCTCATGGCCAATCTCT
GGAAGAAGATTCCGCATTGGAAGCTTTGCTGAATTTTTTCTTTCCAACAA
CTTGCAATCTGAGGGAAAATCAGGTGGCAAAGCCTTGTAATGAGCTGCAA
GATCTTAGTGAGAGTGAATGTTTGAGACACAAATGCTGTTTTTCATCATC
GGGGACCACGAGCTTCAAATGTTTTGCTCCATTTAGAGATGTGCCTAAAC
AGATGATGCAAATGTTTGGGCTTGGTGCGATCAGCCTTATCCTGGTATGT
CTGCCCATTTATTGCCGCTCTCTTTTCTGGAGGAGCGAACCGGCCGATGA
TTTACAAAGGCAGGACAACAGAGTTGTAACGGGTTTGAAGAAACAAAGAA
GGAAGCGAAAGAGGAAGTCTGAAATGTTACAGAAAGCAGCAAGAGGACGT
GAGGAACATGGTGACGAGCTCGAGCACCACCACCACCACCACTGA (SEQ ID NO: 151)
MSSHRRKAKGRNRRSHRAMRVAHLELATYELAATESNPESSHPGYEAAMA
DRPQPGWRESLKMRVSKPFGMLMLSIWILLFVCYYLSYYLCSGSSYFVLA
NGHILPNSENAHGQSLEEDSALEALLNFFPPTTCNLRENQVAKPCNELQD
LSESECLRHKCCFSSSGTTSFKCFAPFRDVPKQMMQMFGLGAISLILVCL
PIYCRSLFWRSEPADDLQRQDNRVVTGLKKQRRKRKRKSEMLQKAARGRE
EHGDELEHHHHHH

II. Partial Protein (MH7 from the Fourth ATG)

Vector; pET23a(NdeI/XhoI)

Primer;

MH7/NdeI:
(SEQ ID NO: 158)
CACACACACATATGCGGGTCAGCAAACCCTTTGGGA

SAR35/XhoI:
(SEQ ID NO: 159)
CACACACTCGAGCTCGTCACCATGTTCCTCACGTC (SEQ ID NO: 152)
CATATGCGGGTCAGCAAACCCTTTGGGATGCTCATGCTCTCCATTTGGAT
CCTGCTGTTCGTGTGCTACTACCTGTCCTACTACCTGTGCTCCGGGTCCT
CATATTTTGTGCTTGCAAATGGACATATCCTGCCCAACAGTGAAAATGCT
CATGGCCAATCTCTGGAAGAAGATTCCGCATTGGAAGCTTTGCTGAATTT
TTTCTTTCCAACAACTTGCAATCTGAGGGAAAATCAGGTGGCAAAGCCTT
GTAATGAGCTGCAAGATCTTAGTGAGAGTGAATGTTTGAGACACAAATGC
TGTTTTTCATCATCGGGGACCACGAGCTTCAAATGTTTTGCTCCATTTAG
AGATGTGCCTAAACAGATGATGCAAATGTTTGGGCTTGGTGCGATCAGCC
TTATCCTGGTATGTCTGCCCATTTATTGCCGCTCTCTTTTCTGGAGGAGC
GAACCGGCCGATGATTTACAAAGGCAGGACAACAGAGTTGTAACGGGTTT
GAAGAAACAAAGAAGGAAGCGAAAGAGGAAGTCTGAAATGTTACAGAAAG
CAGCAAGAGGACGTGAGGAACATGGTGACGAGCTCGAGCACCACCACCAC
CACCACTGA (SEQ ID NO: 153)
MRVSKPFGMLMLSIWILLFVCYYLSYYLCSGSSYFVLANGHILPNSENAH
GQSLEEDSALEALLNFFPPTTCNLRENQVAKPCNELQDLSESECLRHKCC
FSSSGTTSFKCFAPFRDVPKQMMQMFGLGAISLILVCLPIYCRSLFWRSE
PADDLQRQDNRVVTGLKKQRRKRKRKSEMLQKAARGREEHGDELEHHHHH
H

III. Expected Extracellular Domain of NY-SAR-35 from the Fourth ATG
  Vector:pET23a(NdeI/XhoI)
  Primer;

MH7/NdeI:
(SEQ ID NO: 160)
CACACACACATATGCGGGTCAGCAAACCCTTTGGGA

MH7/XhoI:
(SEQ ID NO: 161)
CACACACTCGAGCATTTGCATCATCTGTTTAGGC (SEQ ID NO: 154)
CATATGCGGGTCAGCAAACCCTTTGGGATGCTCATGCTCTCCATTTGGAT
CCTGCTGTTCGTGTGCTACTACCTGTCCTACTACCTGTGCTCCGGGTCCT
CATATTTTGTGCTTGCAAATGGACATATCCTGCCCAACAGTGAAAATGCT
CATGGCCAATCTCTGGAAGAAGATTCCGCATTGGAAGCTTTGCTGAATTT
TTTCTTTCCAACAACTTGCAATCTGAGGGAAAATCAGGTGGCAAAGCCTT
GTAATGAGCTGCAAGATCTTAGTGAGAGTGAATGTTTGAGACACAAATGC
TGTTTTTCATCATCGGGGACCACGAGCTTCAAATGTTTTGCTCCATTTAG
AGATGTGCCTAAACAGATGATGCAAATGCTCGAGCACCACCACCACCACC
ACTGA (SEQ ID NO: 155)
MRVSKPFGMLMLSIWILLFVCYYLSYYLCSGSSYFVLANGHILPNSENAH
GQSLEEDSALEALLNFFFPTTCNLRENQVAKPCNELQDLSESECLRHKCC
FSSSGTTSFKCFAPFRDVPKQMMQMLEHHHHHH

Figure 3:
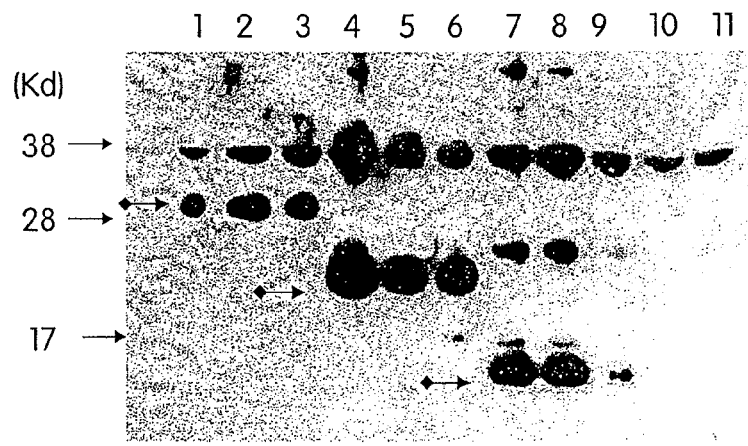
FIG. 3 provides the results of Western blot assay of recombinant NY-SAR-35 proteins in E. coli. Three colonies of each domain cloned plasmid were picked and cultured by IPTG induction. After a four hour induction, total proteins from each of the colonies were separated by SDS-gel electrophoresis. The protein gel was immunoblotted on a membrane with a His-epitope monoclonal antibody. Lanes 1, 2, and 3-whole protein (from the first ATG codon); Lanes 4, 5 and 6—MH7 protein; Lanes 7, 8, and 9-extracellular protein and Lanes 10 and 11-E. coli lysate as negative control.

Protein expression was induced in *E. coli*. Three colonies of each domain cloned plasmid were selected and cultured by IPTG induction for 4 hours. When total proteins were separated by SDS-electrophoresis and stained by Simply Blue SafeStain (Invitrogen) the highly expressed protein bands were not detected. However, when total proteins, separated by SDS-polyacrylamide gel, were immunoblotted using an anti-His epitope antibody, the His-tagged NY-SAR-35 proteins were detected. The results are shown in FIG. 3 with the expected sizes of the expressed proteins.

Functional Study of NY-SAR-35

Most cancer-testis antigens (11/13) have been found to be expressed in non-malignant human kidney embryonic 293 cell while NY-SAR-35 is not. Human 293 cell and monkey Cos-1 cells were used to stably express the NY-SAR-35 gene for functional and immunolocalization studies.

The expected NY-SAR-35 open reading frame (including the 5' untranslated region) was cloned into pcDNA3.1/V5-HisA vector which had a C-terminal fusion tag (V5 epitope and 6×His epitope). The cloned NY-SAR-35 nucleotide sequence and expected amino acid sequence are as follows:

A. Cloned NY-SAR-35 Nucleotide Sequence (SEQ ID NO: 162)

GAATTCCTTCTGGGCCACGGACTGCCGGACCGTTGGGCTGTGAGGCAGCG
EcoRI

TCTCAGCGAGGCGGCACCCGGAGCCATGTCTTCACATAGGAGGAAAGCGA

AGGGGAGGAATAGGAGAAGTCACCGTGCCATGCGTGTGGCTCACTTAGAG

CTGGCAACTTATGAGTTGGCGGCAACTGAGTCGAATCCCGAGAGCAGCCA

TCCTGGATACGAGGCCGCCATGGCTGACAGGCCTCAGCCAGGATGGCGGG

AATCTCTAAAGATGCGGGTCAGCAAACCCTTTGGGATGCTCATGCTCTCC

ATTTGGATCCTGCTGTTCGTGTGCTACTACCTGTCCTACTACCTGTGCTC

CGGGTCCTCATATTTTGTGCTTGCAAATGGACATATCCTGCCCAACAGTG

AAAATGCTCATGGCCAATCTCTGGAAGAAGATTCCGCATTGGAAGCTTTG

CTGAATTTTTTCTTTCCAACAACTTGCAATCTGAGGGAAAATCAGGTGGC

-continued

AAAGCCTTGTAATGAGCTGCAAGATCTTAGTGAGAGTGAATGTTTGAGAC

ACAAATGCTGTTTTTCATCATCGGGGACCACGAGCTTCAAATGTTTTGCT

CCATTTAGAGATGTGCCTAAACAGATGATGCAAATGTTTGGGCTTGGTGC

GATCAGCCTTATCCTGGTATGTCTGCCCATTTATTGCCGCTCTCTTTTCT

GGAGGAGCGAACCGGCCGATGATTTACAAAGGCAGGACAACAGAGTTGTA

ACGGGTTTGAAGAAACAAAGAAGGAAGCGAAAGAGGAAGTCTGAAATGTT

ACAGAAAGCAGCAAGAGGACGTGAGGAACATGGTGACGAGCTCGAGTCTA
XhoI

GAGGGCCCTTCGAA*GGTAAGCC TAT CCCTAACC CTCTCCTC*
V5 epitope

*GGTCTCGATTCTACG*CGTACCGGT*CATCATCACCATCACCAT*TGA
His tag

B. Expected Amino Acid Sequence and Expected Size of Expressed Proteins (SEQ ID NO: 163)

→ 31 Kd

EFLLGHGLPDRWAVRQRLSEAAPGAMSSHRRKAKGRNRRSHRA

→ 29 Kd → 26 Kd

MRVAHLELATYELAATESNPESSHPGYEAAMADRPQPGWRESLK

→ 24 Kd

MRVSKPFGMLMLSIWILLFVCYYLSYYLCSGSSYFVLANGHILPNSENAH

GQSLEEDSALEALLNFFFPPTTCNLRENQVAKPCNELQDLSESECLRHKCC

FSSSGTTSFKCFAPFRDVPKQMMQMFGLGAISLILVCLPIYCRSLFWRSE

PADDLQRQDNRVVTGLKKQRRKRKRKSEMLQKAARGREEHGDELESRGPF

EGKPIPNPLLGLDSTRTGHHHHHH
V5 epitope His tag

Human 293 cells and monkey Cos-1 cell that stably express the NY-SAR-35 gene were tested by RT-PCR and Western blotting. The cells transfected with 0.5 μg pcDNA3.1/V5/HisA/NY-SAR-35 plasmid were selected with 1 mg/ml neomycin for 14 days. Clones were picked and expanded for an additional 1 month and analyzed for NY-SAR-35 mRNA and protein expression. Three sets of NY-SAR-35 5'/3' primers were used and are provided below:

lane 1 (ORF including 5' untranslated region)
(SEQ ID NO: 164)
GGGAATTCATGTCTTCACATAGGAGGAAAGCG/CACACACTCGAGCTCGT
CACCATGTTCCTCACGTC lane 2 (ORF from the last ATG)
(SEQ ID NO: 165)
CACACACACATATGTCTTCACATAGGAGGAAAGCGAAG/CACACACTCGA
GCTCGTCACCATGTTCCTCACGTC lane 3 (ORF from the fourth ATG)
(SEQ ID NO: 166)
CACACACACATATGCGGGTCAGCAAACCCTTTGGGA/CACACACACATAT
GTCTTCACATAGGAGGAAAGCGAAG lane 4 (p53 5'/3')
(SEQ ID NO: 167)
TACTCCCCTGCCCTCAACAAG/CTCAGGCGGCTCATAGGG Whole cell extracts were made from the same cloned cells. Total proteins were separated by SDS-polyacrylamide gel electrophoresis and immunoblotted to detect NY-SAR-35 proteins by anti-V5 epitope monoclonal antibody(Invitrogen). The size of the stably expressed NY-SAR-35 proteins in 293 and Cos-1 cells was found to be 24 kD. This is, therefore, consistent with translation of NY-SAR-35 beginning at the fourth ATG.

Example 3

Results from the Second Round of Immunoscreenings by SEREX Analysis

Identification of Human Sarcoma Antigens by SEREX Analysis

Serum from the two NY-ESO-1 seropositive patients (FS and MFH) were again used to immunoscreen cDNA libraries prepared from the SW982 and SW1045 synovial sarcoma cell lines, both of which were shown to express eight or more known CT antigen transcripts (Table 2). Sera from the FS patient was also used to immunoscreen a cDNA library derived from normal testis. In total, the results from Examples 1 and 3 represent five independent SEREX immunoscreenings performed, which lead to the identification of 113 distinct antigens, designated NY-SAR-1 through NY-SAR-113.

The 113 SEREX-defined antigens represent 91 known proteins and 22 uncharacterized gene products (novel, ESTs, KIAA series, FLJ series, ORFs, DKFZ series). In addition to the uncharacterized gene products described above in Example 1 (NY-SAR-3, -10, -16, -22, -23, -24, -27, -29, -35, -41, -48 and -71) additional immunoscreening identified another 11 uncharacterized gene products (NY-SAR-77, -79, -80, -84, -88, -91, -95, -97, -104, -105 and -113). All of the sequences for these uncharacterized gene products have been deposited in the GenBank database and given the sequential accession numbers AY211909-AY211931. In terms of the serum sources, 27 of the 113 antigens were identified by using sera from a MFH patient and 86 were identified with FS sera. Of the 113 antigens identified, 95 were unique to a particular cDNA library screening and 18 antigens were identified in more than one library. This underlines the beneficial nature of incorporating multiple cDNA libraries into large-scale SEREX analyses of the cancer immunome.

Seroepidemiology of SEREX-Defined Sarcoma Antigens

The cDNA sequences encoding the 113 sarcoma antigens were compared with sequences deposited in the cancer immunome or SEREX database (licr.org/CancerImmunomeDB, formerly licr.org/SEREX.html). These comparisons are in addition to the comparisons presented above in Example 1. In a preliminary analysis, it was found that 39 of the 113 sarcoma antigens defined in this study (34%) were also identified through SEREX analysis of other tumor types (Table 8). Table 9 below provides a complete list of all 113 antigens along with their respective Unigene cluster information, if any. These results represent the information available after all rounds of immunoscreening. Contrary to the results shown, NY-SAR-39, -57, -61, -63 and -64 after the first round of immunoscreenings had not been found in the SEREX database.

TABLE 8

Immunomic analysis of sarcoma/testis antigens: Reactivity with sera from sarcoma patients, patients with other forms of cancer, and normal individuals

| NY-SAR-antigen | Gene identity (ugene cluster) | Cancer patient seroreactivity* | Normal seroreactivity |
|---|---|---|---|
| 1 | TMF1 (Hs.267632) | GC, BC, CC, SRC | 2/33 |
| 2 | STAU (Hs.6113) | PC, BC, SRC | 3/30 |
| 3 | KIAA1536 (Hs.156667) | BC, SRC | 2/33 |
| 6 | RHAMM (Hs.72550) | OC, SRC | 1/33 |
| 7 | PINCH (Hs.112378) | CC, GC, RC, BC HN, ESO, AML, SRC | 16/21 |
| 11 | U2AF1RS2 (Hs.171909) | RC, HD, BC, GC, SRC | 6/33 |
| 13 | ACTN1 (Hs.119000) | BC, SRC | 5/30 |
| 15 | RBM6 (Hs.173993) | LC, SRC | 0/33 |
| 16 | FLJ12785 (Hs.192742) | TALL, SRC | 0/33 |
| 17 | LAGE-1a (Hs.87225) | BC, SRC | 0/33 |
| 18 | SSSCA1(Hs.25723) | CC, SRC | 0/33 |
| 19 | HEF1 (Hs.80261) | RC, SRC | 3/33 |
| 28 | PPIL4 (Hs.11065) | BC, SRC | 0/33 |
| 29 | FLJ13441 (Hs.232146) | PN, SRC | 6/33 |
| 31 | AUANTIG (Hs.75528) | BC, GC, OC, SRC | 2/33 |
| 39 | PSMD4 (Hs.148495) | MEL, SRC | 0/33 |
| 44 | LGALS1 (Hs.227751) | RC, SRC | 0/33 |
| 45 | STIP1 (Hs.75612) | RC, SRC | 4/33 |
| 47 | MIF (Hs.73798) | MEL, SRC | 0/33 |
| 57 | GCN5L2 (Hs.101067) | PC, SRC | 0/33 |
| 61 | ZNF282 (Hs.58167) | RC, SRC | 1/33 |
| 63 | USP19 (Hs.301373) | OC, SRC | 0/33 |
| 64 | USP16 (Hs.99819) | PN, SRC | 2/33 |
| 66 | ROCK1 (Hs.17820) | RC, BC, CC, SRC | 1/33 |
| 74 | RANBP2 (Hs.199179) | BC, GL, BC, SRC | 2/33 |
| 77 | KIAA0992 (Hs.194431) | PC, SRC | 4/15 |
| 80 | FLJ12577 (Hs.87159) | GC, SRC | 0/33 |
| 81 | SDS3 (Hs.20104) | GC, SRC | 4/16 |
| 82 | NYCO45 (Hs.160881) | CC, SRC | 0/33 |
| 89 | SSX2 (Hs.289105) | BC, MEL, SRC | 0/33 |
| 90 | UACA (Hs.49753) | BC, ESO, SRC | 4/25 |
| 93 | NYBR15 (Hs.178175) | BC, SRC | 1/12 |
| 98 | OIP2 (Hs.274170) | BC, SRC | 0/33 |
| 99 | SSX3 (Hs.178749) | BC, MEL, SRC | 2/30 |
| 101 | RANBP2L1 (Hs.179825) | GL, BC, SRC | 3/33 |
| 102 | RBPJK (Hs.356806) | GC, RC, BC, MEL, SRC | 1/16 |
| 103 | Hsp40 (Hs.94) | HN, NCC, SRC | 0/33 |
| 108 | EIF4G (Hs.25732) | GC, SRC | 5/27 |
| 112 | PMSCL1 (Hs.91728) | CC, SRC | 0/33 |

AML, acute myelogenous leukemia; BC, breast cancer; CC, colon cancer; GC, gastric cancer; GL, glioma; HCC, hepatocellular carcinoma; HN, head and nech cancer; LC, lung cancer; MEL, melanoma; OC, ovarian cancer; PC, prostate cancer; PN, pancreatic cancer; RC, renal cancer; SRC, sarcoma; TALL, T cell acute lymphocytic leukemia.
*Determined by sequence comparisons with the SEREX database (licr.org/CancerImmunomeDB/).

TABLE 9

Sarcoma/testes antigens defined by serological analysis of cDNA expression libraries

| NY-SAR-antigen | Gene identity (Unigene Cluster) | Sera source | Library source |
|---|---|---|---|
| 1 | TMF1 (Hs.267632) | MFH, FS | A, T |
| 2 | STAU (Hs.6113) | MFH | A |
| 3 | KIAA1536 (Hs.156667) | MFH | A |
| 4 | FH (Hs.75653) | MFH, FS | A, B |
| 5 | TBC1D1(Hs.278586) | MFH | A |
| 6 | RHAMM (Hs.72550) | MFH | A, B |
| 7 | PINCH (Hs.112378) | MFH | A, B |
| 8 | BIRC2 (Hs.289107) | MFH | A, B |
| 9 | ATP5B (Hs.25) | MFH | A, B |
| 10 | KIAA0603 (Hs.173802) | MFH | A |
| 11 | U2AF1RS2 (Hs.171909) | MFH | A, B |
| 12 | NESG1 (Hs.158450) | MFH | B |

TABLE 9-continued

Sarcoma/testes antigens defined by serological analysis of cDNA expression libraries

| NY-SAR-antigen | Gene identity (Unigene Cluster) | Sera source | Library source |
|---|---|---|---|
| 13 | ACTN1 (Hs.119000) | MFH | A |
| 14 | SC65 (Hs.207251) | MFH | A |
| 15 | RBM6 (Hs.173993) | MFH | A |
| 16 | FLJ12785 (Hs.192742) | MFH | A |
| 17 | LAGE-1a (Hs.87225) | MFH, FS | B |
| 18 | SSSCA1 (Hs.25723) | MFH | A, B |
| 19 | HEF1 (Hs.80261) | MFH | A, B |
| 20 | TCEB3 (Hs.155202) | MFH | B |
| 21 | GTF3C3 (Hs.90847) | MFH | A |
| 22 | NELIN (Hs.216381) | MFH | A |
| 23 | C20orf81 (Hs.29341) | MFH | A |
| 24 | None (not clustered) | MFH | A |
| 25 | PDE4DIP (Hs.265848) | MFH | B |
| 26 | PIASX-BETA (Hs.111323) | MFH | B |
| 27 | FLJ10330(Hs.342307) | MFH | B |
| 28 | PPIL4 (Hs.11065) | FS | B |
| 29 | FLJ13441 (Hs.232146) | FS | A |
| 30 | SNK (Hs.3838) | FS | A |
| 31 | HUMAUANTIG (Hs.75528) | FS | A, B, T |
| 32 | PDAP1 (Hs.278426) | FS | A |
| 33 | SURF6 (Hs.274430) | FS | B |
| 34 | SEC23B (Hs.173497) | FS | B |
| 35 | EST (Hs.128580) | FS | B, T |
| 36 | SSX1(Hs.194759) | FS | B, T |
| 37 | MP1 (Hs.260116) | FS | A, T |
| 38 | HMG20B (Hs.32317) | FS | A |
| 39 | PSMD4 (Hs.148495) | FS | A |
| 40 | INPP1 (Hs.32309) | FS | A |
| 41 | EST (Hs.166670) | FS | B |
| 42 | BTG3 (Hs.77311) | FS | B, T |
| 43 | SSX4 (Hs.278632) | FS | B |
| 44 | LGALS1 (Hs.227751) | FS | B |
| 45 | STIP1 (Hs.75612) | FS | A |
| 46 | ARNTL2 (Hs.222024) | FS | B |
| 47 | MIF (Hs.73798) | FS | A |
| 48 | MGC20533 (Hs.69280) | FS | A |
| 49 | EMK1 (Hs.157199) | FS | A |
| 50 | PYCR1 (Hs.79217) | FS | A |
| 51 | EDF1 (Hs.174050) | FS | A |
| 52 | Actin (Hs.288061) | FS | A |
| 53 | FXYD5 (Hs.333418) | FS | A |
| 54 | LMOD1 (Hs.79386) | FS | A |
| 55 | RBM10 (Hs.154583) | FS | A |
| 56 | MLF1(Hs.85195) | FS | A, T |
| 57 | GCN5L2 (Hs.101067) | FS | A |
| 58 | LIP8 (Hs.348012) | FS | A |
| 59 | UPF3B (Hs.103832) | FS | A |
| 60 | EGLN1 (Hs.6523) | FS | A |
| 61 | ZNF282 (Hs.58167) | FS | A |
| 62 | AD034(Hs.281397) | FS | A |
| 63 | USP19(Hs.301373) | FS | A |
| 64 | USP16 (Hs.99819) | FS | B, T |
| 65 | FDFT1 (Hs.48876) | FS | B |
| 66 | ROCK1 (Hs.17820) | FS | B, T |
| 67 | LUC7L (Hs.16803) | FS | B |
| 68 | P38IP (Hs.333500) | FS | B |
| 69 | ARL1 (Hs.242894) | FS | B |
| 70 | RPL10A (Hs.334895) | FS | B |
| 71 | EST (Hs.314941) | FS | B |
| 72 | HSPE1 (Hs.1197) | FS | B, T |
| 73 | PRM2 (Hs.2324) | FS | T |
| 74 | RANBP2 (Hs.199179) | FS | T |
| 75 | GKAP42 (Hs.36752) | FS | T |
| 76 | TIAL1 (Hs.182741) | FS | T |
| 77 | KIAA0992 (Hs.194431) | FS | T |
| 78 | TSP-NY (Hs.97643) | FS | T |
| 79 | Novel (not clustered) | FS | T |
| 80 | FLJ12577 (Hs.87159) | FS | T |
| 81 | SDS3 (Hs.20104) | FS | T |
| 82 | NYCO45 (Hs.160881) | FS | T |
| 83 | SOX6 (Hs.326876) | FS | T |
| 84 | DKFZp434 (Hs.131834) | FS | T |
| 85 | RAD50 (Hs.41587) | FS | T |
| 86 | EPIM (Hs.99865) | FS | T |
| 87 | SOX5 (Hs.87224) | FS | T |
| 88 | DKFZp564 (Hs.93589) | FS | T |
| 89 | SSX2 (Hs.289105) | FS | T |
| 90 | UACA (Hs.49753) | FS | T |
| 91 | FLJ11730 (Hs.17118) | FS | T |
| 92 | ESTs (Hs.368781) | FS | T |
| 93 | NYBR15 (Hs.178175) | FS | T |
| 94 | CG005 (Hs.23518) | FS | T |
| 95 | FLJ10637 (Hs.22595) | FS | T |
| 96 | MCSP (Hs.111850) | FS | T |
| 97 | EST (Hs.128836) | FS | T |
| 98 | OIP2 (Hs.274170) | FS | T |
| 99 | SSX3 (Hs.178749) | FS | T |
| 100 | PGAM2 (Hs.46039) | FS | T |
| 101 | RANBP2L1 (Hs.179825) | FS | T |
| 102 | RBPJK (Hs.356806) | FS | T |
| 103 | Hsp40 (Hs.94) | FS | T |
| 104 | DKFZp434 (Hs.131834) | FS | T |
| 105 | C11orf14 (Hs.32017) | FS | T |
| 106 | CEP11 (Hs.97437) | FS | T |
| 107 | UBE1 (Hs.2055) | FS | T |
| 108 | EIF4G (Hs.25732) | FS | T |
| 109 | SYNJ1 (Hs.127416) | FS | T |
| 110 | NYD-SP14 (Hs.98105) | FS | T |
| 111 | NDP52 (Hs.154230) | FS | T |
| 112 | PMSCL1 (Hs.91728) | FS | T |
| 113 | KIAA0442 (Hs.32168) | FS | T |

To determine whether immune recognition of these 39 antigens was cancer-related, serum samples from normal individuals (n=33) were tested for reactivity to these antigens. 23 of the 39 antigens (59%) had a serological profile that was not restricted to cancer patients, whereas the remaining 16 antigens had a cancer-related serological profile, reacting only with sera from cancer patients (sarcoma patients and serum source of SEREX database entry), and not with sera from normal individuals. 14 of these 16 antigens reacted only with sera from a single sarcoma patient when tested for reactivity with additional allogeneic sarcoma sera (n=39). The remaining 2 antigens, NY-SAR-17/LAGE-1 and NY-SAR-80/FLJ12577, reacted with 2 of 39 and 3 of 39 sarcoma sera, respectively, and not with sera from normal individuals (n=33).

NY-SAR-80/FLJ12577 is an uncharacterized member of the Mo25 protein family, an evolutionary conserved family of proteins with no known function. Analysis of the tissue distribution and frequency of EST sequences homologous to NY-SAR-80/FLJ12577 indicate widespread mRNA expression, with a preponderance of malignant tissue-derived homologous ESTs suggesting possible overexpression in cancer.

Overall, the relative infrequency of overlapping humoral immune responses among the population of sarcoma patients analyzed is contrary to previous findings for colon (Scanlan M J. et al. 2002. Cancer-Related Serological Recognition of Human Colon Cancer: Identification of Potential Diagnostic and Immunotherapeutic Targets. Cancer Res., 2002; Jul. 15; 62(14), 4041-7.), breast (Scanlan M J, et al. Humoral immunity to human breast cancer: antigen definition and quantitative analysis of mRNA expression. Cancer Immunity 1:4 [epub]) and renal cancers (Scanlan, M. J., et al., and Old, L. J. Antigens recognized by autologous antibody in patients with renal-cell carcinoma. *Int. J. Cancer* 1999; 83: 456-64) in which a subset of antigens were mutually seroreactive in a cancer related manner These results suggest that the immune response to sarcoma is either highly variable or that distinct sarcoma histiotypes have distinct immunomes.

Expression Patterns of mRNA Encoding Serologically Defined Sarcoma/Testis Antigens in Normal and Malignant Tissues In addition to the three well-known CT antigens described in Example 1, NY-SAR-89/SSX-2 and NY-SAR-99/SSX-3 were found to have restricted EST profiles, being expressed exclusively in normal testis and a range of different tumor types (Lethe B, et al. 1998. LAGE-1, a new gene with tumor specificity. Int. J. Cancer 76:903-8; Türeci Ö, et al. 1998. Expression of SSX genes in human tumors. Int J Cancer 77:19-23; Gure A O, et al. 1997. SSX: a multigene family with several members transcribed in normal testis and human cancer. Int J Cancer 72:965-971). Six other putative tissue-restricted antigens were identified, including four other known gene products, NY-SAR-73/Protamine 2 (PRM2, Domenjoud, L., Fronia, C., Uhde, F. & Engel, W. (1998) Nucleic Acids Res. 16, 7773), NY-SAR-78/TSP-NY (Uni-Gene cluster Hs.97643), NY-SAR-96/mitochondrial capsule selenoprotein (MCSP, Aho, H., et al. (1996) Geonomics 32, 184-190) and NY-SAR-110/NYD-SP14 (Hs.98105) and two additional uncharacterized gene products, NY-SAR-92 (Hs.368781) and NY-SAR-97 (not clustered).

Two of the six putative tissue restricted antigens, NY-SAR-73/PRM2 and NY-SAR-110/NYD-SP14, were ubiquitously expressed in a panel of 20 normal tissues as determined by RT-PCR (Table 10). The remaining four genes, in addition to NY-SAR-12/nasopharyngeal specific protein 1 (NESG1, Li Z, Yao K, Cao Y. Molecular cloning of a novel tissue-specific gene from human nasopharyngeal epithelium. Gene 1999 Sep. 3; 237(1):235-40), NY-SAR-35 and NY-SAR-41, were found to be expressed with frequencies ranging from 1 to 9 of 20 normal tissues. NY-SAR-35 and NY-SAR-78 were both testis-specific. The mRNA expression profiles of NY-SAR-35 and NY-SAR-78 were then analyzed in various malignant tissues by RT-PCR. Transcripts encoding NY-SAR-78/TSP-NY were not detected in cancer. The tumor specimens examined included, lung cancer (0 of 9), colon cancer (0 of 9), breast cancer (0 of 18), renal cancer (0 of 11), esophageal cancer (0 of 12), ovarian cancer (0 of 14), melanoma (0 of 18) and sarcoma (0 of 8). Thus, although NY-SAR-78/TSP-NY is a "virtual CT antigen" with 100% identity with ESTs derived from prostate cancer and leukemia, its expression in cancer could not be verified in our RT-PCR series.

TABLE 10

Analysis of mRNA expression by RT-PCR of 9 of the 113 sarcoma/testis antigens

| Tissue | NY-SAR antigen* | | | | | | | | |
|---|---|---|---|---|---|---|---|---|---|
| | 12 | 35 | 41 | 73 | 78 | 92 | 96 | 97 | 110 |
| Brain | − | − | − | + | − | − | − | − | + |
| Kidney | − | − | − | + | − | − | − | − | + |
| Liver | − | − | − | + | − | − | − | − | + |
| Pancreas | − | − | − | + | − | − | − | − | + |
| Placenta | + | − | − | + | − | − | − | − | + |
| Testis | + | + | + | + | + | + | + | + | + |
| Fetal brain | − | − | + | + | − | − | + | + | + |
| Small intestine | − | − | − | + | − | − | − | − | + |
| Heart | − | − | − | + | − | − | − | − | + |
| Prostate | − | − | − | + | − | − | + | + | + |
| Adrenal | − | − | − | + | − | − | + | + | + |
| Spleen | + | − | − | + | − | + | + | + | + |
| Colon | + | − | + | + | − | − | − | − | + |
| Stomach | − | − | − | + | − | − | − | − | + |
| Lung | + | − | + | + | − | − | − | + | + |
| Bladder | − | − | + | + | − | − | − | + | + |
| Ovary | + | − | + | + | − | − | − | + | + |
| Breast | − | − | − | + | − | − | − | + | + |
| Cervix | − | − | − | + | − | − | − | − | + |
| Skeletal muscle | − | − | − | + | − | − | − | − | + |
| Total no. of positive tissues | 6/20 | 1/20 | 6/20 | 20/20 | 1/20 | 2/20 | 5/20 | 9/20 | 20/20 |

*Unigene clusters: NY-SAR-12, Hs.158450; NY-SAR-35, Hs.128580; NY-SAR-41, Hs.166670; NY-SAR-73, Hs.2324; NY-SAR-78, Hs.97643; NY-SAR-92, Hs.368781; NY-SAR-96, Hs.111850; NY-SAR-97, Hs.128836; NY-SAR-110, Hs.98105.

The antigens presented herein are of interest for their immunotherapeutic and diagnostic potential. For example, the six known testis-restricted gene antigens (NY-SAR-17/LAGE-1, NY-SAR-36/SSX1, NY-SAR-43/SSX4, NY-SAR-78/TSP-NY, NY-SAR-89/SSX2 and NY-SAR-99/SSX3), four novel gene products that are also differentially expressed antigens (NY-SAR-35, -41, -92 and -91) and two tissue-restricted antigens (NY-SAR-12/NESG1 and NY-SAR-96/MCSP) not previously studied in relation to cancer have are potential vaccine targets and/or targets for therapeutic antibodies as well as for diagnosis of cancer, particularly by screening patient samples for antibodies that recognize the proteins.

Figure 4:
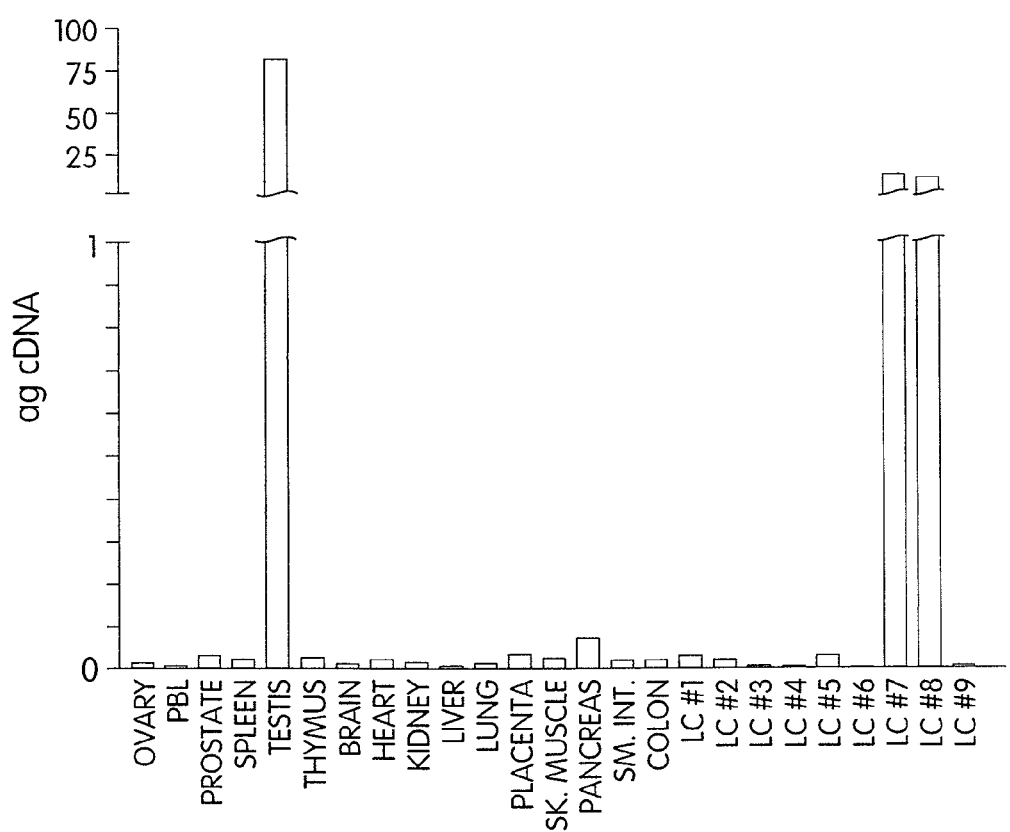
FIG. 4 provides the real-time RT-PCR analysis of NY-SAR-35 mRNA in various normal tissues and non-small cell lung cancer specimens. NY-SAR-35 was expressed in normal lung cancer specimens. NY-SAR-35 was expressed in normal testis (83.2 ag) at a level that was >1,000 times the level detected in all other normal tissues. In 2 of 9 cases of non-small cell lung cancer examined, the level of NY-SAR-35 expression was equivalent to 0.15 (12.5 ag) and 0.13 (10.8 ag) times the level detected in normal testis, or approximately 100 times the level detected in normal tissues.

NY-SAR-35 mRNA was detected in a variety of tumor specimens, such as melanoma (1 of 16 specimens), sarcoma (2 of 26 specimens), lung cancer (5 of 29 specimens), breast cancer (3 of 13 specimens), bladder cancer (5 of 12 specimens), esophageal cancer (1 of 12 specimens) and ovarian cancer (1 of 12 specimens). As also shown before in Example 1, NY-SAR-35 was not detected in colon cancer (n=9) or renal cancer (n=8). The CT-restricted expression profile of NY-SAR-35 was confirmed by real-time quantitative RT-PCR at 40 amplification cycles (FIG. 4). In two of the nine non-small lung cancer specimens tested, NY-SAR-35 was expressed at levels that were 0.13 and 0.15 times the level detected in normal testis. In conformity with the proposed nomenclature for CT antigens (Chen Y T, et al. 1998. Identification of multiple cancer/testis antigens by allogeneic antibody screening of a melanoma cell line library. Proc. Natl. Acad. Sci. USA. 95:6919-23), NY-SAR-35 is designated CT-20.

REFERENCES 1. van der Bruggen P, et al. 1991. A gene encoding an antigen recognized by cytolytic T lymphocytes on a human melanoma. Science 254:1643-47.
2. Gaugler, B., Van den Eynde, B., van der Bruggen, P., Romero, P., Gaforio, J. J., De Plaen, E., Lethe, B., Brasseur, F., and Boon, T. Human gene MAGE-3 codes for an antigen recognized on a melanoma by autologous cytolytic T lymphocytes. J. Exp. Med. 1994; 179: 921-30.
3. Kawakami, Y., Eliyahu, S., Delgado, C. H., Robbins, P. F., Rivoltini, L., Topalian, S., L., Miki, T., and Rosenberg, S. A. Cloning of the gene for a shared human melanoma antigen recognized by autologous T cells infiltrating into tumor. Proc. Natl. Acad. Sci. USA. 1994; 91: 3515-19.
4. Chen, Y.-T., Scanlan, M. J., Sahin, U., Tureci, O., Gure, A. O., Tsang, S., Williamson, B., Stockert, E., Pfreundschuh, M., and Old, L. J. A testicular antigen aberrantly expressed in human cancers detected by autologous antibody screening. Proc. Natl. Acad. Sci. USA. 1997; 94: 1914-18.
5. Jager D, Stockert E, Gure A O, Scanlan M J, Karbach J, Jager E, Knuth A, Old L J, Chen Y T. Identification of a tissue-specific putative transcription factor in breast tissue by serological screening of a breast cancer library. Cancer Res 2001 Mar. 1; 61(5):2055-61.
6. Boel, P., Wildmann, C., Sensi, M. L., Brasseur, R., Renauld, J. C., Coulie, P., Boon, T., and van der Bruggen, P. BAGE: a new gene encoding an antigen recognized on human melanomas by cytolytic T lymphocytes. Immunity 1995; 2: 167-75. (PMID: 7895173).
7. Van den Eynde, B., Peeters, O., De Backer, O., Gaugler, B., Lucas, S., and Boon, T. A new family of genes coding for an antigen recognized by autologous cytolytic T lymphocytes on a human melanoma. J. Exp. Med. 1995; 182: 689-98. (PMID: 7544395).
8. Skipper J C, Hendrickson R C, Gulden P H, Brichard V, Van Pel A, Chen Y, Shabanowitz J, Wolfel T, Slingluff C L Jr, Boon T, Hunt D F, Engelhard V H. An HLA-A2-restricted tyrosinase antigen on melanoma cells results from post-translational modification and suggests a novel pathway for processing of membrane proteins. J Exp Med 1996 Feb. 1; 183(2):527-34.
9. Cox A L, Skipper J, Chen Y, Henderson R A, Darrow T L, Shabanowitz J, Engelhard V H, Hunt D F, Slingluff C L Jr. Identification of a peptide recognized by five melanoma-specific human cytotoxic T cell lines. Science 1994 Apr. 29; 264(5159):716-9.
10. Pascolo S, Schirle M, Guckel B, Dumrese T, Stumm S, Kayser S, Moris A, Wallwiener D, Rammensee H G, Stevanovic S. A MAGE-A1 HLA-A A*0201 epitope identified by mass spectrometry. Cancer Res 2001 May 15; 61(10):4072-7.
11. Sahin, U., Türeci, Ö., Schmitt, H., Cochlovius, B., Johannes, T., Schmits, R., Stenner, F., Luo, G., Schobert, I., and Pfreundschuh, M. Human neoplasms elicit multiple specific immune responses in the autologous host. Proc. Natl. Acad. Sci. USA 1995; 92: 11810-13.
12. Scanlan, M. J., Chen, Y. T., Williamson, B., Gure, A. O., Stockert, E., Gordan, J. D., Tureci, O., Sahin, U., Pfreundschuh, M., and Old, L. J. Characterization of human colon cancer antigens recognized by autologous antibodies. Int. J. Cancer 1998; 76: 652-8.
13. Scanlan, M. J., Gordan, J. D., Williamson, B., Stockert, E., Bander, N. H., Jongeneel, V., Gure, A. O., Jäger, D., Jäger, E., Kneuth, A., Chen, Y.-T., and Old, L. J. Antigens recognized by autologous antibody in patients with renal-cell carcinoma. Int. J. Cancer 1999; 83: 456-64.
14. Scanlan M J, et al. Humoral immunity to human breast cancer: antigen definition and quantitative analysis of mRNA expression. Cancer Immunity 1:4 [epub].
15. Jager D, Stockert E, Jager E, Gure A O, Scanlan M J, Knuth A, Old L J, Chen Y T. Serological cloning of a melanocyte rab guanosine 5'-triphosphate-binding protein and a chromosome condensation protein from a melanoma complementary DNA library. Cancer Res 2000 Jul. 1; 60(13):3584-91.
16. Chen, Y.-T., Scanlan, M. J., Obata, Y., and Old, L. J. Identification of human tumor antigens by serological expression cloning. In: S. A. Rosenberg (ed.). Principles and Practice of Biologic Therapy of Cancer, pp. 557-570. Philadelphia: Lippincott Williams & Wilkins, 2000.
17. Sahin U, et al. 1998. Expression of multiple cancer/testis antigens in breast cancer and melanoma: basis for polyvalent CT vaccine strategies. Int J Cancer 78:387-89.
18. Scanlan M J et al. 2000. Expression of cancer-testis antigens in lung cancer: definition of bromodomain testis-specific gene (BRDT) as a new CT gene, CT9. Cancer Lett. 150:155-64.
19. Van den Eynde B J van der Bruggen P. 1997. T cell defined tumor antigens. Curr Opin Immunol 9:684-693.
20. Jungbluth A A, et al. 2001. Monophasic and biphasic synovial sarcomas abundantly express cancer/testis antigen NY-ESO-1 but not MAGE-A1 or CT7. Int J Cancer 94:252-6.
21. Antonescu C R, Busam K J, Iversen K, Kolb D, Coplan K, Spagnoli G C, Ladanyi M, Old L J, Jungbluth A A. MAGE antigen expression in monophasic and biphasic synovial sarcoma. Hum Pathol 2002 February; 33(2):225-9.
22. Stockert E, et al. 1998. A survey of the humoral immune response of cancer patients to a panel of human tumor antigens. J Exp Med 187:1349-54.
23. Scanlan M J. et al. 2002. Cancer-Related Serological Recognition of Human Colon Cancer: Identification of Potential Diagnostic and Immunotherapeutic Targets. Cancer Res., 2002; Jul. 15; 62(14), 4041-7.
24. Lethe B, et al. 1998. LAGE-1, a new gene with tumor specificity. Int. J. Cancer 76:903-8.
25. Türeci Ö, et al. 1998. Expression of SSX genes in human tumors. Int J Cancer 77:19-23.
26. Gure A O, et al. 1997. SSX: a multigene family with several members transcribed in normal testis and human cancer. Int J Cancer 72:965-971.
27. Li Z, Yao K, Cao Y. Molecular cloning of a novel tissue-specific gene from human nasopharyngeal epithelium. Gene 1999 Sep. 3; 237(1):235-40.
28. Hoffmann W, Hauser F. The P-domain or trefoil motif: a role in renewal and pathology of mucous epithelial Trends Biochem Sci 1993 July; 18(7):239-43.
29. Chen Y T, et al. 1998. Identification of multiple cancer/testis antigens by allogeneic antibody screening of a melanoma cell line library. Proc. Natl. Acad. Sci. USA. 95:6919-23.
30. Niwa M, Maruyama H, Fujimoto T, Dohi K, Maruyama I N. Affinity selection of cDNA libraries by lambda phage surface display. Gene 2000 Oct. 3; 256(1-2):229-36.
31. Le Naour F, Misek D E, Krause M C, Deneux L, Giordano T J, Scholl S, Hanash S M. Proteomics-based identification of RS/DJ-1 as a novel circulating tumor antigen in breast cancer. Clin Cancer Res 2001 November; 7(11):3328-35.

32. Yang X F, Wu C J, McLaughlin S, Chillemi A, Wang K S, Canning C, Alyea E P, Kantoff P, Soiffer R J, Dranoff G, Ritz J. CML66, a broadly immunogenic tumor antigen, elicits a humoral immune response associated with remission of chronic myelogenous leukemia. Proc Natl Acad Sci USA 2001 Jun. 19; 98(13):7492-7.
33. Jungbluth A A, et al. 2001 Immunohistochemical analysis of NY-ESO-1 antigen expression in normal and malignant human tissues. Int J Cancer 92:856-60.
34. Jungbluth A A, et al. 2000. Expression of MAGE-antigens in normal tissues and cancer. Int J Cancer 85:460-5.
35. Garrido F, Algarra I. MHC antigens and tumor escape from immune surveillance. Adv Cancer Res 2001; 83:117-58.
36. Conrad C T, Ernst N R, Dummer W, Brocker E B, Becker J C. Differential expression of transforming growth factor beta 1 and interleukin 10 in progressing and regressing areas of primary melanoma. J Exp Clin Cancer Res 1999 June; 18(2):225-32.
37. Tomlinson I P, et al. Germline mutations in FH predispose to dominantly inherited uterine fibroids, skin leiomyomata and papillary renal cell cancer. Nat Genet 2002 April; 30(4):406-10.
38. Ayyoub M, et al. 2002. Proteasome-assisted identification of a SSX-2-derived epitope recognized by tumor-reactive CTL infiltrating metastatic melanoma J Immunol 168:1717-22.
39. Van Der Bruggen, P., Zhang, Y., Chaux, P., Stroobant, V., Panichelli, C., Schultz, E. S., Chapiro, J., Van Den Eynde, B. J., Brasseur, F. & Boon, T. (2002) Immunol. Rev. 188, 51-64.
40. Rosenberg, S. A. (2001) Nature 411, 380-384.
41. Preuss, K. D., Zwick, C., Bormann, C., Neumann, F. & Pfeundschuh, M. (2002) Immunol. Rev. 188, 43-50.
42. Scanlan, M. J., Gure, A. O., Jungbluth, A. A., Old, L. J. & Chen, Y. T. (2002) Immunol. Rev. 188, 22-32.
43. Guillaudeux, T., Gomez, E., Onno, M., Drenou, B., Segretain, D., Alberti, S., Lejeune, H., Fauchet, R., Jegou, B. & Le Bouteiller, P. (1996) Biol. Reprod. 55, 99-110.
44. Domenjoud, L., Fronia, C., Uhde, F. & Engel, W. (1998) Nucleic Acids Res. 16, 7773.
45. Aho, H., Schwemmer, M., Tessman, D., Murphy, D., Mattei, G., Engel, W. & Adham, I. M. (1996) Geonomics 32, 184-190.
46. Naka, N., Araki, N., Nakanishi, H., Itoh, K., Mano, M., Ishiguro, S., de Bruijn, D. R. Myoui, A., Ueda, T. & Yoshikawa, H. (2002) Int. J. Cancer 98, 640-642.
47. Martelange, V., De Smet, C., De Plaen, E., Lurquin, C. & Boon, T. (2000) Cancer Res. 60, 3848-3855.
48. Kiuru, M., Lehtonen, R., Arola, J., Salovaara, R., Jarvinen, H., Aittomaki, K., Sjobeg, J., Visakorpi, T., Knuutila, S., et al. (2002) Cancer Res. 62, 4554-4557.

EQUIVALENTS

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

What is claimed is:

1. An isolated antibody or antigen-binding antibody fragment that selectively binds to an extracellular domain of NY-SAR-35 as set forth as SEQ ID NO: 155 or a fragment thereof that is at least 8 amino acids in length.

2. The isolated antibody or antigen-binding antibody fragment of claim 1, wherein the fragment of the NY-SAR-35 extracellular domain is at least 9, 10, 11, 12, 13, 14, 15, 16, 17, 18, 19, 20, 25, 30, 35, 40, 45, 50, 75 or 100 amino acids in length.

3. A method for diagnosing cancer in a subject comprising:
obtaining a biological sample from a subject, and
determining the expression of a sarcoma-associated antigen in the biological sample by contacting the sample with an isolated antibody or antigen-binding antibody fragment of claim 1,
wherein the expression of the sarcoma-associated antigen in the sample is diagnostic for cancer in the subject.

4. The method of claim 3, wherein the antibody is a monoclonal, chimeric, human, humanized or single chain antibody; or wherein the antigen-binding antibody fragment is a F(ab')$_2$, Fab, Fd, or Fv fragment.

5. The isolated antibody or antigen-binding antibody fragment of claim 1, wherein the antibody is a monoclonal, chimeric, human, humanized or single chain antibody; or wherein the antigen-binding fragment is a F(ab')$_2$, Fab, Fd, or Fv fragment.

6. The isolated antibody or antigen-binding antibody fragment of claim 1, wherein the antibody or antigen-binding fragment is labeled with a detectable label.

7. The isolated antibody or antigen-binding antibody fragment of claim 6, wherein the detectable label is a fluorescent or radioactive label.

8. The method of claim 3, wherein the sample is selected from the group consisting of tissue, cells, and blood.

9. The method of claim 3, wherein the cancer is a sarcoma.

10. A kit for the diagnosis of cancer in a subject, comprising:
one or more isolated antibodies or antigen-binding antibody fragments of claim 1 and instructions for the use of the one or more isolated binding polypeptides in the diagnosis of cancer.

11. The kit of claim 10, wherein the one or more isolated antibodies or antigen-binding antibody fragments are antibodies or antigen-binding fragments thereof.

12. The kit of claim 10, wherein the one or more isolated antibodies or antigen-binding antibody fragments are bound to a substrate.

13. A kit for the diagnosis of cancer in a subject, comprising:
one or more isolated antibodies or antigen-binding antibody fragments, that selectively binds to a polypeptide consisting of a sequence as set forth as SEQ ID NO: 55, or a fragment thereof that is at least 8 amino acids in length;
instructions for the use of the one or more isolated antibodies or antigen-binding antibody fragments in the diagnosis of cancer; and
one or more agents that bind specifically to a cancer-associated antigen other than a polypeptide consisting of a sequence as set forth as SEQ ID NO: 55 or a fragment thereof that is at least 8 amino acids in length.

14. A kit for the diagnosis of cancer in a subject, comprising:
one or more isolated antibodies or antigen-binding antibody fragments that selectively binds to a polypeptide consisting of a sequence as set forth as SEQ ID NO: 155, or a fragment thereof that is at least 8 amino acids in length; and
instructions for the use of the one or more isolated antibodies or antigen-binding antibody fragments in the diagnosis of cancer,
wherein the cancer is a sarcoma.

15. A composition, comprising:
an isolated antibody or antigen-binding antibody fragment of claim 1.

16. The composition of claim 15, wherein the antibody is a monoclonal, chimeric, human, humanized or single chain antibody; or wherein the antigen-binding antibody fragment is a F(ab')$_2$, Fab, Fd, or Fv fragment.

17. A composition, comprising
an isolated binding polypeptide that selectively binds to a polypeptide consisting of a sequence as set forth as SEQ ID NO: 55, or a fragment thereof that is at least 8 amino acids in length, wherein the isolated binding polypeptide is an antibody or antigen-binding fragment thereof, and wherein the antibody or antigen-binding fragment is conjugated to a cytotoxic or chemotherapeutic agent.

18. A composition, comprising
an isolated binding polypeptide that selectively binds to a polypeptide consisting of a sequence as set forth as SEQ ID NO: 55, or a fragment thereof that is at least 8 amino acids in length, wherein the isolated binding polypeptide is an antibody or antigen-binding fragment thereof, and
a cytotoxic or chemotherapeutic agent.

19. The composition of claim 15, further comprising a pharmaceutically acceptable carrier.

20. The isolated antibody or antigen-binding antibody fragment of claim 1, wherein the extracellular domain of NY-SAR-35 comprises SEQ ID NO:155.

21. The isolated antibody or antigen-binding antibody fragment of claim 20, wherein the fragment of the NY-SAR-35 extracellular domain is at least 9, 10, 11, 12, 13, 14, 15, 16, 17, 18, 19, 20, 25, 30, 35, 40, 45, 50, 75 or 100 amino acids of SEQ ID NO:155.

22. The isolated antibody or antigen-binding antibody fragment of claim 20, wherein the antibody is a monoclonal, chimeric, human, humanized or single chain antibody; or wherein the antigen-binding fragment is a F(ab')$_2$, Fab, Fd, or Fv fragment.

23. The isolated antibody or antigen-binding antibody fragment of claim 20, wherein the antibody or antigen-binding fragment is labeled with a detectable label.

24. The isolated antibody or antigen-binding antibody fragment of claim 23, wherein the detectable label is a fluorescent or radioactive label.

* * * * *

SEQUENCE LISTING

```
<160> NUMBER OF SEQ ID NOS: 167

<210> SEQ ID NO 1
<211> LENGTH: 1148
<212> TYPE: DNA
<213> ORGANISM: homo sapiens
<220> FEATURE:
<221> NAME/KEY: misc_feature
<222> LOCATION: (3)..(3)
<223> OTHER INFORMATION: n = a, c, g or t/u
<220> FEATURE:
<221> NAME/KEY: misc_feature
<222> LOCATION: (195)..(195)
<223> OTHER INFORMATION: n = a, c, g or t/u
<220> FEATURE:
<221> NAME/KEY: misc_feature
<222> LOCATION: (507)..(507)
<223> OTHER INFORMATION: n = a, c, g or t/u
<220> FEATURE:
<221> NAME/KEY: misc_feature
<222> LOCATION: (614)..(614)
<223> OTHER INFORMATION: n = a, c, g or t/u
<220> FEATURE:
<221> NAME/KEY: misc_feature
<222> LOCATION: (625)..(625)
<223> OTHER INFORMATION: n = a, c, g or t/u
<220> FEATURE:
<221> NAME/KEY: misc_feature
<222> LOCATION: (634)..(634)
<223> OTHER INFORMATION: n = a, c, g or t/u
<220> FEATURE:
<221> NAME/KEY: misc_feature
<222> LOCATION: (651)..(651)
<223> OTHER INFORMATION: n = a, c, g or t/u
<220> FEATURE:
<221> NAME/KEY: misc_feature
<222> LOCATION: (686)..(686)
```

-continued

```
<223> OTHER INFORMATION: n = a, c, g or t/u
<220> FEATURE:
<221> NAME/KEY: misc_feature
<222> LOCATION: (690)..(690)
<223> OTHER INFORMATION: n = a, c, g or t/u
<220> FEATURE:
<221> NAME/KEY: misc_feature
<222> LOCATION: (693)..(693)
<223> OTHER INFORMATION: n = a, c, g or t/u
<220> FEATURE:
<221> NAME/KEY: misc_feature
<222> LOCATION: (696)..(696)
<223> OTHER INFORMATION: n = a, c, g or t/u
<220> FEATURE:
<221> NAME/KEY: misc_feature
<222> LOCATION: (707)..(707)
<223> OTHER INFORMATION: n = a, c, g or t/u
<220> FEATURE:
<221> NAME/KEY: misc_feature
<222> LOCATION: (720)..(720)
<223> OTHER INFORMATION: n = a, c, g or t/u
<220> FEATURE:
<221> NAME/KEY: misc_feature
<222> LOCATION: (758)..(758)
<223> OTHER INFORMATION: n = a, c, g or t/u
<220> FEATURE:
<221> NAME/KEY: misc_feature
<222> LOCATION: (782)..(782)
<223> OTHER INFORMATION: n = a, c, g or t/u
<220> FEATURE:
<221> NAME/KEY: misc_feature
<222> LOCATION: (793)..(793)
<223> OTHER INFORMATION: n = a, c, g or t/u
<220> FEATURE:
<221> NAME/KEY: misc_feature
<222> LOCATION: (798)..(798)
<223> OTHER INFORMATION: n = a, c, g or t/u
<220> FEATURE:
<221> NAME/KEY: misc_feature
<222> LOCATION: (807)..(807)
<223> OTHER INFORMATION: n = a, c, g or t/u
<220> FEATURE:
<221> NAME/KEY: misc_feature
<222> LOCATION: (819)..(819)
<223> OTHER INFORMATION: n = a, c, g or t/u
<220> FEATURE:
<221> NAME/KEY: misc_feature
<222> LOCATION: (822)..(822)
<223> OTHER INFORMATION: n = a, c, g or t/u
<220> FEATURE:
<221> NAME/KEY: misc_feature
<222> LOCATION: (828)..(828)
<223> OTHER INFORMATION: n = a, c, g or t/u
<220> FEATURE:
<221> NAME/KEY: misc_feature
<222> LOCATION: (831)..(831)
<223> OTHER INFORMATION: n = a, c, g or t/u
<220> FEATURE:
<221> NAME/KEY: misc_feature
<222> LOCATION: (837)..(837)
<223> OTHER INFORMATION: n = a, c, g or t/u
<220> FEATURE:
<221> NAME/KEY: misc_feature
<222> LOCATION: (841)..(841)
<223> OTHER INFORMATION: n = a, c, g or t/u
<220> FEATURE:
<221> NAME/KEY: misc_feature
<222> LOCATION: (843)..(844)
<223> OTHER INFORMATION: n = a, c, g or t/u
<220> FEATURE:
<221> NAME/KEY: misc_feature
<222> LOCATION: (856)..(857)
<223> OTHER INFORMATION: n = a, c, g or t/u
<220> FEATURE:
<221> NAME/KEY: misc_feature
<222> LOCATION: (867)..(867)
<223> OTHER INFORMATION: n = a, c, g or t/u
<220> FEATURE:
<221> NAME/KEY: misc_feature
<222> LOCATION: (880)..(880)
```

-continued

```
<223> OTHER INFORMATION: n = a, c, g or t/u
<220> FEATURE:
<221> NAME/KEY: misc_feature
<222> LOCATION: (886)..(886)
<223> OTHER INFORMATION: n = a, c, g or t/u
<220> FEATURE:
<221> NAME/KEY: misc_feature
<222> LOCATION: (892)..(893)
<223> OTHER INFORMATION: n = a, c, g or t/u
<220> FEATURE:
<221> NAME/KEY: misc_feature
<222> LOCATION: (897)..(897)
<223> OTHER INFORMATION: n = a, c, g or t/u
<220> FEATURE:
<221> NAME/KEY: misc_feature
<222> LOCATION: (908)..(908)
<223> OTHER INFORMATION: n = a, c, g or t/u
<220> FEATURE:
<221> NAME/KEY: misc_feature
<222> LOCATION: (913)..(913)
<223> OTHER INFORMATION: n = a, c, g or t/u
<220> FEATURE:
<221> NAME/KEY: misc_feature
<222> LOCATION: (925)..(925)
<223> OTHER INFORMATION: n = a, c, g or t/u
<220> FEATURE:
<221> NAME/KEY: misc_feature
<222> LOCATION: (943)..(943)
<223> OTHER INFORMATION: n = a, c, g or t/u
<220> FEATURE:
<221> NAME/KEY: misc_feature
<222> LOCATION: (949)..(949)
<223> OTHER INFORMATION: n = a, c, g or t/u
<220> FEATURE:
<221> NAME/KEY: misc_feature
<222> LOCATION: (953)..(953)
<223> OTHER INFORMATION: n = a, c, g or t/u
<220> FEATURE:
<221> NAME/KEY: misc_feature
<222> LOCATION: (957)..(958)
<223> OTHER INFORMATION: n = a, c, g or t/u
<220> FEATURE:
<221> NAME/KEY: misc_feature
<222> LOCATION: (962)..(963)
<223> OTHER INFORMATION: n = a, c, g or t/u
<220> FEATURE:
<221> NAME/KEY: misc_feature
<222> LOCATION: (968)..(968)
<223> OTHER INFORMATION: n = a, c, g or t/u
<220> FEATURE:
<221> NAME/KEY: misc_feature
<222> LOCATION: (971)..(971)
<223> OTHER INFORMATION: n = a, c, g or t/u
<220> FEATURE:
<221> NAME/KEY: misc_feature
<222> LOCATION: (983)..(983)
<223> OTHER INFORMATION: n = a, c, g or t/u
<220> FEATURE:
<221> NAME/KEY: misc_feature
<222> LOCATION: (985)..(988)
<223> OTHER INFORMATION: n = a, c, g or t/u
<220> FEATURE:
<221> NAME/KEY: misc_feature
<222> LOCATION: (994)..(995)
<223> OTHER INFORMATION: n = a, c, g or t/u
<220> FEATURE:
<221> NAME/KEY: misc_feature
<222> LOCATION: (998)..(998)
<223> OTHER INFORMATION: n = a, c, g or t/u
<220> FEATURE:
<221> NAME/KEY: misc_feature
<222> LOCATION: (1003)..(1003)
<223> OTHER INFORMATION: n = a, c, g or t/u
<220> FEATURE:
<221> NAME/KEY: misc_feature
<222> LOCATION: (1008)..(1009)
<223> OTHER INFORMATION: n = a, c, g or t/u
<220> FEATURE:
<221> NAME/KEY: misc_feature
<222> LOCATION: (1012)..(1013)
```

-continued

```
<223> OTHER INFORMATION: n = a, c, g or t/u
<220> FEATURE:
<221> NAME/KEY: misc_feature
<222> LOCATION: (1020)..(1021)
<223> OTHER INFORMATION: n = a, c, g or t/u
<220> FEATURE:
<221> NAME/KEY: misc_feature
<222> LOCATION: (1029)..(1029)
<223> OTHER INFORMATION: n = a, c, g or t/u
<220> FEATURE:
<221> NAME/KEY: misc_feature
<222> LOCATION: (1033)..(1033)
<223> OTHER INFORMATION: n = a, c, g or t/u
<220> FEATURE:
<221> NAME/KEY: misc_feature
<222> LOCATION: (1035)..(1036)
<223> OTHER INFORMATION: n = a, c, g or t/u
<220> FEATURE:
<221> NAME/KEY: misc_feature
<222> LOCATION: (1043)..(1043)
<223> OTHER INFORMATION: n = a, c, g or t/u
<220> FEATURE:
<221> NAME/KEY: misc_feature
<222> LOCATION: (1050)..(1052)
<223> OTHER INFORMATION: n = a, c, g or t/u
<220> FEATURE:
<221> NAME/KEY: misc_feature
<222> LOCATION: (1057)..(1057)
<223> OTHER INFORMATION: n = a, c, g or t/u
<220> FEATURE:
<221> NAME/KEY: misc_feature
<222> LOCATION: (1062)..(1062)
<223> OTHER INFORMATION: n = a, c, g or t/u
<220> FEATURE:
<221> NAME/KEY: misc_feature
<222> LOCATION: (1065)..(1065)
<223> OTHER INFORMATION: n = a, c, g or t/u
<220> FEATURE:
<221> NAME/KEY: misc_feature
<222> LOCATION: (1069)..(1069)
<223> OTHER INFORMATION: n = a, c, g or t/u
<220> FEATURE:
<221> NAME/KEY: misc_feature
<222> LOCATION: (1071)..(1071)
<223> OTHER INFORMATION: n = a, c, g or t/u
<220> FEATURE:
<221> NAME/KEY: misc_feature
<222> LOCATION: (1074)..(1074)
<223> OTHER INFORMATION: n = a, c, g or t/u
<220> FEATURE:
<221> NAME/KEY: misc_feature
<222> LOCATION: (1077)..(1077)
<223> OTHER INFORMATION: n = a, c, g or t/u
<220> FEATURE:
<221> NAME/KEY: misc_feature
<222> LOCATION: (1083)..(1083)
<223> OTHER INFORMATION: n = a, c, g or t/u
<220> FEATURE:
<221> NAME/KEY: misc_feature
<222> LOCATION: (1086)..(1086)
<223> OTHER INFORMATION: n = a, c, g or t/u
<220> FEATURE:
<221> NAME/KEY: misc_feature
<222> LOCATION: (1090)..(1090)
<223> OTHER INFORMATION: n = a, c, g or t/u
<220> FEATURE:
<221> NAME/KEY: misc_feature
<222> LOCATION: (1092)..(1092)
<223> OTHER INFORMATION: n = a, c, g or t/u
<220> FEATURE:
<221> NAME/KEY: misc_feature
<222> LOCATION: (1094)..(1094)
<223> OTHER INFORMATION: n = a, c, g or t/u
<220> FEATURE:
<221> NAME/KEY: misc_feature
<222> LOCATION: (1096)..(1096)
<223> OTHER INFORMATION: n = a, c, g or t/u
<220> FEATURE:
<221> NAME/KEY: misc_feature
<222> LOCATION: (1099)..(1099)
```

```
<223> OTHER INFORMATION: n = a, c, g or t/u
<220> FEATURE:
<221> NAME/KEY: misc_feature
<222> LOCATION: (1102)..(1102)
<223> OTHER INFORMATION: n = a, c, g or t/u
<220> FEATURE:
<221> NAME/KEY: misc_feature
<222> LOCATION: (1107)..(1107)
<223> OTHER INFORMATION: n = a, c, g or t/u
<220> FEATURE:
<221> NAME/KEY: misc_feature
<222> LOCATION: (1113)..(1113)
<223> OTHER INFORMATION: n = a, c, g or t/u
<220> FEATURE:
<221> NAME/KEY: misc_feature
<222> LOCATION: (1115)..(1115)
<223> OTHER INFORMATION: n = a, c, g or t/u
<220> FEATURE:
<221> NAME/KEY: misc_feature
<222> LOCATION: (1136)..(1137)
<223> OTHER INFORMATION: n = a, c, g or t/u
<220> FEATURE:
<221> NAME/KEY: misc_feature
<222> LOCATION: (1139)..(1139)
<223> OTHER INFORMATION: n = a, c, g or t/u
<220> FEATURE:
<221> NAME/KEY: misc_feature
<222> LOCATION: (1142)..(1144)
<223> OTHER INFORMATION: n = a, c, g or t/u

<400> SEQUENCE: 1
ttnggacagg ggaactgtgt tcagaaccag ctcgatgaga gccagcaaga acggaatgac      60
ctgatgcagc tgaagctaca gctggaggga caggtgacag agctgaggag ccgagtgcag     120
gagctcgaga gggctctggc aactgccagg caggagcaca ctggagctga tggaacagta     180 caagggatt tcccnggtcc catggggaga tcacagaaga gagggacatc ctgagccggc      240
aacagggaga ccatgtggca cgcatcctgg agctagagga tgacatccag accatcagtg     300
agaaagtgct gacgaaggaa gtggagcctg acaggctta gagacacagt gaaggccctg      360
actcgggaac aagagaagct ccttgggcaa ctgaaagaag tacaagcaga caaggagcaa     420
agtgaggctg agctccaagt ggcacaacag gagaaccatc acttaaattt ggacctgaag     480
gaggcgaaga gctggcaaga ggagcanagt gctcaggctc agcgactgaa agacaaggtg     540
gcccagatga aggacaccct atgccaggcc cagcagcggg tggcccagct ggagcccttg     600
aaggagcagc ttcnaggggc ccaangagcc ttgncagcct caagccagca naaagccacc     660
ctttcttggg gaggagtttg ccagcngcan cancanccag ggaccontcc atatgccgan    720 ctacaccgga gccgtcctgg aagtggctga agttaacngc aagtggctg acctcgtttt      780 gnctttgaag ganaaaantc ccatggnccea aggaccggnc anggctgntc ncaatgngga    840
ngnncaaaag acaaanncttt gaactcnatg caaaatcctn tattgnaaaa gnncttngga    900
ggaaagancc aanccagtgt caaangactg gccggaaaag atnttcctng tcnattnnca    960
annaatcngg nattccaaat ttngnnnncc tgtnngtnca aangaaannc gnncctgggn   1020
naccgaatnt tancnntaaa acnaagcccn nngaagnggc anaancggnt ngtnccncac   1080
agntgngccn tngntnatnc cncttanaca agnanccaaa atagtccctg gctgtnngna   1140 cnnntttt                                                             1148

<210> SEQ ID NO 2
<211> LENGTH: 914
<212> TYPE: DNA
<213> ORGANISM: homo sapiens
<220> FEATURE:
<221> NAME/KEY: misc_feature
<222> LOCATION: (10)..(10)
```

```
<223> OTHER INFORMATION: n = a, c, g or t/u
<220> FEATURE:
<221> NAME/KEY: misc_feature
<222> LOCATION: (239)..(239)
<223> OTHER INFORMATION: n = a, c, g or t/u
<220> FEATURE:
<221> NAME/KEY: misc_feature
<222> LOCATION: (863)..(863)
<223> OTHER INFORMATION: n = a, c, g or t/u
<220> FEATURE:
<221> NAME/KEY: misc_feature
<222> LOCATION: (900)..(900)
<223> OTHER INFORMATION: n = a, c, g or t/u
<220> FEATURE:
<221> NAME/KEY: misc_feature
<222> LOCATION: (912)..(912)
<223> OTHER INFORMATION: n = a, c, g or t/u

<400> SEQUENCE: 2
ggagctcgcn cgcctgcagg tcgacactag tggatccaaa gaattcggca cgaggcgcca      60
gcgtccccac cgtcctcagc ttggcaaacg tttcccgaag aggattccga ctccccgcag     120
tttcgaagac gggcacacac gttcagccac ccaccttcaa gcacaaagag aaagctgaat     180
ttgcaggatg ggagggctca gggtgtgcgt tccctctgc tgaggcagag ctccagtcna     240
acagtgcagt gatggagaag ggagaaaaag gacctcatct acctgcagca atgagtccct     300
aagtgtggga ggaaccctct gtcactcctcg ccggatctcc tggcggcagc gcattttcct     360
cagggttgct tctcccatga acaaatctcc ctcagcaatg caacagcaag atggattgga     420
caggaacgag ctgctgccac tgtccccct ctctccaacc atggaggagg aaccgctggt      480
tgtattcctg tctggggagg atgacccaga aaagattgaa gaaagaaaga atcaaaaga     540 actgaggagc ttgtggagaa agctataca ccaacaaatc ttgttacttc gaatggaaaa     600
agaaaaccag aaacttgaag caagcagaga tgaactccag tccagaaaag ttaaattaga     660
ctatgaagaa gttggtgcat gtcagaaaga ggtcttaata acttgggata agaagttgtt     720
aaactgcaga gctaaaatca gatgtgatat ggaagatatt catactcttc ttaagaagga     780
gttcccaaag tcgacgagga gaatttggca gtttctggct tacagtaccg actcaacaca     840
gattgcctaa taacaacagc ctnctgacta ttcttaagga ctttgagcag ctactgctan     900
cagcatgcga tntt                                                      914

<210> SEQ ID NO 3
<211> LENGTH: 891
<212> TYPE: DNA
<213> ORGANISM: homo sapiens
<220> FEATURE:
<221> NAME/KEY: misc_feature
<222> LOCATION: (9)..(9)
<223> OTHER INFORMATION: n = a, c, g or t/u
<220> FEATURE:
<221> NAME/KEY: misc_feature
<222> LOCATION: (677)..(677)
<223> OTHER INFORMATION: n = a, c, g or t/u
<220> FEATURE:
<221> NAME/KEY: misc_feature
<222> LOCATION: (775)..(775)
<223> OTHER INFORMATION: n = a, c, g or t/u
<220> FEATURE:
<221> NAME/KEY: misc_feature
<222> LOCATION: (785)..(785)
<223> OTHER INFORMATION: n = a, c, g or t/u
<220> FEATURE:
<221> NAME/KEY: misc_feature
<222> LOCATION: (807)..(807)
<223> OTHER INFORMATION: n = a, c, g or t/u
<220> FEATURE:
<221> NAME/KEY: misc_feature
<222> LOCATION: (847)..(847)
```

<223> OTHER INFORMATION: n = a, c, g or t/u
<220> FEATURE:
<221> NAME/KEY: misc_feature
<222> LOCATION: (858)..(858)
<223> OTHER INFORMATION: n = a, c, g or t/u
<220> FEATURE:
<221> NAME/KEY: misc_feature
<222> LOCATION: (879)..(879)
<223> OTHER INFORMATION: n = a, c, g or t/u

<400> SEQUENCE: 3

| | | | | | |
|---|---|---|---|---|---|
| ggagctcgng | cgcctgcagg | tcgacactag | tggatccaaa | gaattcggca | cgaggggcac | 60 |
| ggggcgcgtc | gggcccgcag | gtggggaacg | ctctgggcag | cctggagcca | ctgcgctgga | 120 |
| tgctgcgctc | gcccttcgac | cgcaacgtgc | cggtcaacct | ggagcttcag | gagttgctgc | 180 |
| tggactacag | cttccagcac | ctgggtgtct | cctcacaggg | ctgtgttgat | catcccatag | 240 |
| ttttgacaga | agctgtgtgc | aacccactgt | attcacggca | aatgatgtct | gagcttcttt | 300 |
| ttgagtgcta | cgggattccc | aaggttgcct | atggaataga | cagcctcttc | agcttctacc | 360 |
| acaataagcc | aaagaactcg | atgtgcagtg | ggctaatcat | ttcatctgga | taccagtgta | 420 |
| cgcatgtttt | acccatctta | gaagggagat | tagatgctaa | aaactgcaag | cgcatcaatc | 480 |
| ttggaggaag | ccaagcagct | ggttacctcc | agcgtctcct | ccagctgaag | taccctgggc | 540 |
| acctggcagc | catcaccctc | agccgcatgg | aggagattct | gcatgagcac | agctacatcg | 600 |
| ctgaggatta | tgtggaagaa | ttacacaaat | ggcggtgtcc | tgattattat | gagaataatg | 660 |
| tccacaagat | gcagctncca | ttttccagca | agctcctggg | cagcactctg | acctctgagg | 720 |
| agaaacaaga | aaggcggcag | cagcaattgc | ggcggctgca | ggagctcaat | gcccngcggc | 780 |
| gggangagaa | gctgcagctt | ggatcangag | cgtctggacc | gactgctata | tgtgcaggaa | 840 |
| cttctanagg | atggccanat | ggatcagttt | acaaagctnt | gatgagctga | t | 891 |

<210> SEQ ID NO 4
<211> LENGTH: 880
<212> TYPE: DNA
<213> ORGANISM: homo sapiens
<220> FEATURE:
<221> NAME/KEY: misc_feature
<222> LOCATION: (654)..(654)
<223> OTHER INFORMATION: n = a, c, g or t/u
<220> FEATURE:
<221> NAME/KEY: misc_feature
<222> LOCATION: (693)..(693)
<223> OTHER INFORMATION: n = a, c, g or t/u
<220> FEATURE:
<221> NAME/KEY: misc_feature
<222> LOCATION: (698)..(698)
<223> OTHER INFORMATION: n = a, c, g or t/u
<220> FEATURE:
<221> NAME/KEY: misc_feature
<222> LOCATION: (784)..(784)
<223> OTHER INFORMATION: n = a, c, g or t/u
<220> FEATURE:
<221> NAME/KEY: misc_feature
<222> LOCATION: (803)..(803)
<223> OTHER INFORMATION: n = a, c, g or t/u
<220> FEATURE:
<221> NAME/KEY: misc_feature
<222> LOCATION: (813)..(813)
<223> OTHER INFORMATION: n = a, c, g or t/u
<220> FEATURE:
<221> NAME/KEY: misc_feature
<222> LOCATION: (842)..(842)
<223> OTHER INFORMATION: n = a, c, g or t/u
<220> FEATURE:
<221> NAME/KEY: misc_feature
<222> LOCATION: (867)..(867)
<223> OTHER INFORMATION: n = a, c, g or t/u

<400> SEQUENCE: 4

```
ggcacgaggc ggcggcggcg gcggcggcag cggcagccag aggactccca gcggctggag      60
cagaagtgtt agcggccaga gctcccagac ccctacccac agccaggcgg gacgcgcaca     120
gtccctccac gcggaaagaa gtaccttcgc cggtcaccgg ctcctgcagg gtgcaaatat     180
atacagagct tcataatcag cccaagacca catagagcaa acatgaatga tatttcccaa     240
aaggctgaga ttctgctttc ttcatctaaa cctgtcccaa aaacctatgt accaaaactt     300
ggcaagggtg atgtaaagga taagtttgaa gccatgcaga gagccaggga agaaagaaat     360
caaaggagat ctagagacga aaacaaaga agaaagaac aatatattag agagagagaa       420
tggaacagga gaaagcagga gattaaagaa atgcttgctt ctgatgatga ggaagatgta     480
tcttctaaag tagaaaaggc ttatgttcca aaattaacag gaactgtgaa gggtagattt     540
gctgaaatgg agaaacaaag acaagaggaa caaaggaaga gaacggagga ggaacgaaaa     600
cgcagaattg agcaggatat gttagaaaag aggaaaatac agcgtgaatt agcnaaaagg     660
gctgaacagg aaggagatga ttcactactt atnactgngg tacctgtcaa tcatataaac     720
atctggaaaa tgaaaagaat tttgagatct agaaaaagac gtgaagagaa gaaagatcca     780
gtcnaggaga taaagattag atntgagaca cgncctctct caggagcaag ggcttcttag     840
tntggtgtga ataaaaggga gcaaaanatc cttctcccca                           880
```

<210> SEQ ID NO 5
<211> LENGTH: 924
<212> TYPE: DNA
<213> ORGANISM: homo sapiens
<220> FEATURE:
<221> NAME/KEY: misc_feature
<222> LOCATION: (754)..(754)
<223> OTHER INFORMATION: n = a, c, g or t/u
<220> FEATURE:
<221> NAME/KEY: misc_feature
<222> LOCATION: (772)..(772)
<223> OTHER INFORMATION: n = a, c, g or t/u
<220> FEATURE:
<221> NAME/KEY: misc_feature
<222> LOCATION: (783)..(783)
<223> OTHER INFORMATION: n = a, c, g or t/u
<220> FEATURE:
<221> NAME/KEY: misc_feature
<222> LOCATION: (799)..(799)
<223> OTHER INFORMATION: n = a, c, g or t/u
<220> FEATURE:
<221> NAME/KEY: misc_feature
<222> LOCATION: (873)..(875)
<223> OTHER INFORMATION: n = a, c, g or t/u
<220> FEATURE:
<221> NAME/KEY: misc_feature
<222> LOCATION: (898)..(898)
<223> OTHER INFORMATION: n = a, c, g or t/u
<220> FEATURE:
<221> NAME/KEY: misc_feature
<222> LOCATION: (918)..(918)
<223> OTHER INFORMATION: n = a, c, g or t/u
<220> FEATURE:
<221> NAME/KEY: misc_feature
<222> LOCATION: (920)..(920)
<223> OTHER INFORMATION: n = a, c, g or t/u

<400> SEQUENCE: 5

```
ctggagctcg cgcgcctgca ggtcgacact agtggatcca aagaattcgg cacgaggctc      60
actgctcaca gctgcccagc tgaaagccaa gggggagctg agctttgaac aggaccagct     120
ggtggctggg ggccagctgg gcgagctgca caacgggaca cagtatcgtg aggtccgcca     180
gttctgctcg ggctctggcc accaccttgt gcgcttctac ttcctcactc gtgtttactc     240
```

-continued

```
cgagtacctt gaggatgttc tggaagagct gacatatgga cctgccccgg acctggtgat    300
catcaactcc tgcctctggg atctctccag atatggtcgc tgctcaatgg agagctaccg    360
ggagaacctg gagcgggtgt tgtgcgcat ggaccaagta ttgccagact cctgcctgct    420
ggtgtggaac atggcgatgc ccctcgggga acgtatcact gggggtttcc tcctgccaga    480
gctccagccc ctggcaggct ccctgcggcg ggatgtggtt gaagggaact tctacagtgc    540
tacgctggcc ggggaccact gctttgatgt cctagacctc cactttcact ccggcatgc    600 agtacagcac cgtcatcggg atggtgtcca ctgggaccag catgcacacc gccacctctc    660
acacctgctt ctgacccatg tggctgacgc ctggggcgtg gagctgccca gcgtggcta    720 tcccctgac ccgtggattg aggactgggc aganatgaat catccattcc anggaagcca    780
tangcagacc caaacttcng ggagacctgg gccttgctcc accccacttc ttcttgctct    840
ccatgccttt tcctaccggt tctaggcctg cannnttcct tttccaccct gccagganac    900 cctttccag gcagcctncn ccca                                            924
```

```
<210> SEQ ID NO 6
<211> LENGTH: 929
<212> TYPE: DNA
<213> ORGANISM: homo sapiens
<220> FEATURE:
<221> NAME/KEY: misc_feature
<222> LOCATION: (11)..(11)
<223> OTHER INFORMATION: n = a, c, g or t/u
<220> FEATURE:
<221> NAME/KEY: misc_feature
<222> LOCATION: (640)..(640)
<223> OTHER INFORMATION: n = a, c, g or t/u
<220> FEATURE:
<221> NAME/KEY: misc_feature
<222> LOCATION: (672)..(672)
<223> OTHER INFORMATION: n = a, c, g or t/u
<220> FEATURE:
<221> NAME/KEY: misc_feature
<222> LOCATION: (715)..(715)
<223> OTHER INFORMATION: n = a, c, g or t/u
<220> FEATURE:
<221> NAME/KEY: misc_feature
<222> LOCATION: (724)..(724)
<223> OTHER INFORMATION: n = a, c, g or t/u
<220> FEATURE:
<221> NAME/KEY: misc_feature
<222> LOCATION: (768)..(768)
<223> OTHER INFORMATION: n = a, c, g or t/u
<220> FEATURE:
<221> NAME/KEY: misc_feature
<222> LOCATION: (782)..(782)
<223> OTHER INFORMATION: n = a, c, g or t/u
<220> FEATURE:
<221> NAME/KEY: misc_feature
<222> LOCATION: (795)..(795)
<223> OTHER INFORMATION: n = a, c, g or t/u
<220> FEATURE:
<221> NAME/KEY: misc_feature
<222> LOCATION: (800)..(800)
<223> OTHER INFORMATION: n = a, c, g or t/u
<220> FEATURE:
<221> NAME/KEY: misc_feature
<222> LOCATION: (813)..(813)
<223> OTHER INFORMATION: n = a, c, g or t/u
<220> FEATURE:
<221> NAME/KEY: misc_feature
<222> LOCATION: (818)..(818)
<223> OTHER INFORMATION: n = a, c, g or t/u
<220> FEATURE:
<221> NAME/KEY: misc_feature
<222> LOCATION: (820)..(820)
<223> OTHER INFORMATION: n = a, c, g or t/u
<220> FEATURE:
<221> NAME/KEY: misc_feature
<222> LOCATION: (827)..(827)
```

```
<223> OTHER INFORMATION: n = a, c, g or t/u
<220> FEATURE:
<221> NAME/KEY: misc_feature
<222> LOCATION: (829)..(829)
<223> OTHER INFORMATION: n = a, c, g or t/u
<220> FEATURE:
<221> NAME/KEY: misc_feature
<222> LOCATION: (840)..(840)
<223> OTHER INFORMATION: n = a, c, g or t/u
<220> FEATURE:
<221> NAME/KEY: misc_feature
<222> LOCATION: (846)..(846)
<223> OTHER INFORMATION: n = a, c, g or t/u
<220> FEATURE:
<221> NAME/KEY: misc_feature
<222> LOCATION: (849)..(849)
<223> OTHER INFORMATION: n = a, c, g or t/u
<220> FEATURE:
<221> NAME/KEY: misc_feature
<222> LOCATION: (852)..(852)
<223> OTHER INFORMATION: n = a, c, g or t/u
<220> FEATURE:
<221> NAME/KEY: misc_feature
<222> LOCATION: (862)..(862)
<223> OTHER INFORMATION: n = a, c, g or t/u
<220> FEATURE:
<221> NAME/KEY: misc_feature
<222> LOCATION: (873)..(873)
<223> OTHER INFORMATION: n = a, c, g or t/u
<220> FEATURE:
<221> NAME/KEY: misc_feature
<222> LOCATION: (875)..(875)
<223> OTHER INFORMATION: n = a, c, g or t/u
<220> FEATURE:
<221> NAME/KEY: misc_feature
<222> LOCATION: (887)..(887)
<223> OTHER INFORMATION: n = a, c, g or t/u
<220> FEATURE:
<221> NAME/KEY: misc_feature
<222> LOCATION: (889)..(889)
<223> OTHER INFORMATION: n = a, c, g or t/u
<220> FEATURE:
<221> NAME/KEY: misc_feature
<222> LOCATION: (903)..(903)
<223> OTHER INFORMATION: n = a, c, g or t/u
<220> FEATURE:
<221> NAME/KEY: misc_feature
<222> LOCATION: (909)..(909)
<223> OTHER INFORMATION: n = a, c, g or t/u
<220> FEATURE:
<221> NAME/KEY: misc_feature
<222> LOCATION: (913)..(913)
<223> OTHER INFORMATION: n = a, c, g or t/u
<220> FEATURE:
<221> NAME/KEY: misc_feature
<222> LOCATION: (928)..(928)
<223> OTHER INFORMATION: n = a, c, g or t/u

<400> SEQUENCE: 6
gcggtcacct ngtggatcca agaattcggc acgaggcttg tcttgcattt gaatcaattg      60
gaaggaaata aggaaaagtt tgaaaaacag ttaaagaaga atctgaaga ggtatattgt     120 ttacagaaag agctaaagat aaaaaatcac agtcttcaag agacttctga gcaaaacgtt     180
attctacagc atactcttca gcaacagcag caaatgttac aacaagagac aattagaaat     240
ggagagctag aagatactca aactaaactt gaaaaacagg tgtcaaaact ggaacaagaa     300
cttcaaaaac aaagggaaag ttcagctgaa aagttgagaa aaatggagga gaaatgtgaa     360
tcagctgcac atgaagcaga tttgaaaagg caaaaagtga ttgagcttac tggcactgcc     420
aggcaagtaa agattgagat ggatcagtac aaagaagagc tgtctaaaat ggaaaaggaa     480
ataatgcacc taaaacgaga tggagaaaat aaagcaatgc acctctctca attagatatg     540
atcttagatc agacaaagac agagctagaa aagaaaacca atgctgtaaa ggagttagaa     600
```

| | |
|---|---|
| aagttacagc acagtactga aactgaacta acagaagccn tgcaaaacgg gaagtacttg | 660 |
| agactgacta cnaaatgctc atgggagatt taaaaagtac tttaagacaa ctccnggaat | 720 |
| tggngagatg tactacagaa ggctccattt tcattagagg aaaatacnct actataagga | 780 |
| tnccccgct ggacntaaan aatgcaagat ggnattgnan acaaaancng gagctcctgn | 840 |
| aatggnccng cncttaagag anaattggga ctnangcaaa aacagcncng gtaccctttg | 900 |
| ganttgctnt tcnggacccg aggaaaang | 929 |

<210> SEQ ID NO 7
<211> LENGTH: 935
<212> TYPE: DNA
<213> ORGANISM: homo sapiens
<220> FEATURE:
<221> NAME/KEY: misc_feature
<222> LOCATION: (1)..(1)
<223> OTHER INFORMATION: n = a, c, g or t/u
<220> FEATURE:
<221> NAME/KEY: misc_feature
<222> LOCATION: (792)..(792)
<223> OTHER INFORMATION: n = a, c, g or t/u
<220> FEATURE:
<221> NAME/KEY: misc_feature
<222> LOCATION: (799)..(799)
<223> OTHER INFORMATION: n = a, c, g or t/u
<220> FEATURE:
<221> NAME/KEY: misc_feature
<222> LOCATION: (820)..(820)
<223> OTHER INFORMATION: n = a, c, g or t/u
<220> FEATURE:
<221> NAME/KEY: misc_feature
<222> LOCATION: (856)..(856)
<223> OTHER INFORMATION: n = a, c, g or t/u
<220> FEATURE:
<221> NAME/KEY: misc_feature
<222> LOCATION: (872)..(872)
<223> OTHER INFORMATION: n = a, c, g or t/u
<220> FEATURE:
<221> NAME/KEY: misc_feature
<222> LOCATION: (875)..(875)
<223> OTHER INFORMATION: n = a, c, g or t/u
<220> FEATURE:
<221> NAME/KEY: misc_feature
<222> LOCATION: (886)..(886)
<223> OTHER INFORMATION: n = a, c, g or t/u
<220> FEATURE:
<221> NAME/KEY: misc_feature
<222> LOCATION: (899)..(899)
<223> OTHER INFORMATION: n = a, c, g or t/u
<220> FEATURE:
<221> NAME/KEY: misc_feature
<222> LOCATION: (904)..(904)
<223> OTHER INFORMATION: n = a, c, g or t/u
<220> FEATURE:
<221> NAME/KEY: misc_feature
<222> LOCATION: (906)..(906)
<223> OTHER INFORMATION: n = a, c, g or t/u
<220> FEATURE:
<221> NAME/KEY: misc_feature
<222> LOCATION: (922)..(922)
<223> OTHER INFORMATION: n = a, c, g or t/u
<220> FEATURE:
<221> NAME/KEY: misc_feature
<222> LOCATION: (926)..(927)
<223> OTHER INFORMATION: n = a, c, g or t/u
<220> FEATURE:
<221> NAME/KEY: misc_feature
<222> LOCATION: (935)..(935)
<223> OTHER INFORMATION: n = a, c, g or t/u

<400> SEQUENCE: 7

| | |
|---|---|
| ngctggagct cgcgcgcctg caggtcgaca ctagtggatc caaagaattc ggcacgaggg | 60 |
| aaacataaag aagacaaaga tgataggcgg cacagagatg acaaaagaga ttccaagaaa | 120 |

```
gagaaaaaac acagtagaag cagaagcaga gaaaggaaac acagaagtag gagtcgaagt    180
agaaatgcag ggaaacgaag tagaagtaga agcaaagaga aatcaagtaa acataaaaat    240
gaaagtaaag aaaaatcaaa taaacgaagt cgaagtggca gtcaaggaag aactgacagt    300
gttgaaaaat caaaaaaacg ggaacatagt cccagcaaag aaaaatctag aaagcgtagt    360
agaagcaaag aacgttccca caaacgagat cacagtgata gtaaggacca gtcagacaaa    420
catgatcgtc gaaggagcca aagtatagaa caagagagcc aagaaaaaca gcataaaaac    480
aaagatgaga ctgtgtgaaa atattttgta aaagtggatc acattgaatc ctataaatga    540
ttaaatctgc ttttttcccc cacgttgaga ttgtgcagta gttcgcactc ctcaagctct    600
ccctgtaggc tgcattttca tttcctcttt cgtgtaggga agtgcctttg taattccatt    660
tattgcattg gtgttttcac ccaattgtta agtttgatac atgatgcaca gattggtctt    720
gcatttttat tgtttggttt tgaatgtaca gtctgtacta tgtcctgaaa tggtttattc    780
ctttggcatg gntgcctgnt ggttaatttg tataggcatn aactgcccta tctaaaaaaa    840
aaaaaaaaaa ctcgangtct ttaaagcggc gnggncctcg atttcnccgg gggggaccng    900
taangnccca tccccttag gngcgnntaa atccn                               935
```

<210> SEQ ID NO 8
<211> LENGTH: 943
<212> TYPE: DNA
<213> ORGANISM: homo sapiens
<220> FEATURE:
<221> NAME/KEY: misc_feature
<222> LOCATION: (4)..(4)
<223> OTHER INFORMATION: n = a, c, g or t/u
<220> FEATURE:
<221> NAME/KEY: misc_feature
<222> LOCATION: (741)..(741)
<223> OTHER INFORMATION: n = a, c, g or t/u
<220> FEATURE:
<221> NAME/KEY: misc_feature
<222> LOCATION: (796)..(796)
<223> OTHER INFORMATION: n = a, c, g or t/u
<220> FEATURE:
<221> NAME/KEY: misc_feature
<222> LOCATION: (823)..(823)
<223> OTHER INFORMATION: n = a, c, g or t/u
<220> FEATURE:
<221> NAME/KEY: misc_feature
<222> LOCATION: (842)..(842)
<223> OTHER INFORMATION: n = a, c, g or t/u
<220> FEATURE:
<221> NAME/KEY: misc_feature
<222> LOCATION: (857)..(857)
<223> OTHER INFORMATION: n = a, c, g or t/u
<220> FEATURE:
<221> NAME/KEY: misc_feature
<222> LOCATION: (869)..(869)
<223> OTHER INFORMATION: n = a, c, g or t/u
<220> FEATURE:
<221> NAME/KEY: misc_feature
<222> LOCATION: (873)..(873)
<223> OTHER INFORMATION: n = a, c, g or t/u
<220> FEATURE:
<221> NAME/KEY: misc_feature
<222> LOCATION: (898)..(898)
<223> OTHER INFORMATION: n = a, c, g or t/u
<220> FEATURE:
<221> NAME/KEY: misc_feature
<222> LOCATION: (911)..(911)
<223> OTHER INFORMATION: n = a, c, g or t/u
<220> FEATURE:
<221> NAME/KEY: misc_feature
<222> LOCATION: (915)..(916)
<223> OTHER INFORMATION: n = a, c, g or t/u

<400> SEQUENCE: 8

-continued

```
aaangctgga gctcgcgcgc ctgcaggtcg acactagtgg atccaaagaa ttcggcacga      60
ggcaagagtg atttcaagga gtatgaaaaa gaacaggata aaccacctaa tttggttctg     120
aaagataaag taaagcccaa acaggataca aaatacgatc ttatattaga tgagcaggcc     180
gaagactcaa aatcaagtca ctcacacaca agtaaaaaac acaagaagaa aacccatcac     240
tgttctgaag agaaagaaga tgaggactac atgccaatca aaatactaa tcaggatatc      300
tatagagaaa tggggtttgg tcactatgaa gaagaagaaa gctgttggga gaaacaaaag     360
agtgaaaaga gagaccgaac tcagaaccga agtcgtagcc gatctcgaga gagggatggc     420
cattatagta atagtcataa atcaaaatac caaacagatc tttatgaaag agaaaggagt     480
aaaaagagag accgaagcag aagtccaaag aagtccaaag ataaagaaaa atctaagtat     540
agatgaaaga tgaagaggca gaattgagag gctaacatat ttactcttgt ctaacttaag     600
agtgccagga aagcagatgc ttagattttg tgtcaaagct tgttattttt ttcatactag     660
gattatggtc tttagattaa tactgattat atagagcacg gaaagataaa gaattgacat     720
tttctttgta tactttttac nctaattttt atggtataca taatggtagt cttcattttt     780
gaagtcttca ttttcnctct tttttatgg agtatttcta ctncaaaatc cttaacgttt      840
tntagggta ataatgnaat atctggtcnc tcncacttag atacgtgtgc gacttttnag     900
tccctaggcc ncccnnccaa aatatttgga tttgggtggc ttg                       943
```

```
<210> SEQ ID NO 9
<211> LENGTH: 910
<212> TYPE: DNA
<213> ORGANISM: homo sapiens
<220> FEATURE:
<221> NAME/KEY: misc_feature
<222> LOCATION: (4)..(4)
<223> OTHER INFORMATION: n = a, c, g or t/u
<220> FEATURE:
<221> NAME/KEY: misc_feature
<222> LOCATION: (584)..(584)
<223> OTHER INFORMATION: n = a, c, g or t/u
<220> FEATURE:
<221> NAME/KEY: misc_feature
<222> LOCATION: (626)..(626)
<223> OTHER INFORMATION: n = a, c, g or t/u
<220> FEATURE:
<221> NAME/KEY: misc_feature
<222> LOCATION: (723)..(723)
<223> OTHER INFORMATION: n = a, c, g or t/u
<220> FEATURE:
<221> NAME/KEY: misc_feature
<222> LOCATION: (751)..(751)
<223> OTHER INFORMATION: n = a, c, g or t/u
<220> FEATURE:
<221> NAME/KEY: misc_feature
<222> LOCATION: (756)..(756)
<223> OTHER INFORMATION: n = a, c, g or t/u
<220> FEATURE:
<221> NAME/KEY: misc_feature
<222> LOCATION: (775)..(775)
<223> OTHER INFORMATION: n = a, c, g or t/u
<220> FEATURE:
<221> NAME/KEY: misc_feature
<222> LOCATION: (784)..(784)
<223> OTHER INFORMATION: n = a, c, g or t/u
<220> FEATURE:
<221> NAME/KEY: misc_feature
<222> LOCATION: (796)..(796)
<223> OTHER INFORMATION: n = a, c, g or t/u
<220> FEATURE:
<221> NAME/KEY: misc_feature
<222> LOCATION: (833)..(833)
<223> OTHER INFORMATION: n = a, c, g or t/u
<220> FEATURE:
<221> NAME/KEY: misc_feature
<222> LOCATION: (844)..(844)
```

<223> OTHER INFORMATION: n = a, c, g or t/u
<220> FEATURE:
<221> NAME/KEY: misc_feature
<222> LOCATION: (870)..(870)
<223> OTHER INFORMATION: n = a, c, g or t/u
<220> FEATURE:
<221> NAME/KEY: misc_feature
<222> LOCATION: (884)..(884)
<223> OTHER INFORMATION: n = a, c, g or t/u
<220> FEATURE:
<221> NAME/KEY: misc_feature
<222> LOCATION: (894)..(894)
<223> OTHER INFORMATION: n = a, c, g or t/u
<220> FEATURE:
<221> NAME/KEY: misc_feature
<222> LOCATION: (903)..(903)
<223> OTHER INFORMATION: n = a, c, g or t/u

<400> SEQUENCE: 9

| | | | | | |
|---|---|---|---|---|---|
| aatngctgga | gctcgcgcgc | ctgcaggtcg | acactagtgg | atccaaagaa | ttcggcacga | 60 |
| gggcgagctc | ggcaacctcg | gcgcagcgag | cgcgggcggc | cagccagggc | caggggggcgg | 120 |
| tggcggccaa | ggtccgaccg | ggtgccagct | gttcccagcc | ccgcctcgg | gcccgccgcc | 180 |
| ggcgccgcca | tgggcaagaa | gcacaagaag | cacaaggccg | agtggcgctc | gtcctacgag | 240 |
| gattatgccg | acaagcccct | ggagaagcct | ctaaagctag | tcctgaaggt | cggaggaagt | 300 |
| gaagtgactg | aactctcagg | atccggccac | gactccagtt | actatgatga | caggtcagac | 360 |
| catgagcgag | agaggcacaa | agaaaagaaa | aagaagaaga | agaagaagtc | cgagaaggag | 420 |
| aagcatctgg | acgatgagga | agaaggaag | cgaaaggaag | agaagaagcg | gaagcgagag | 480 |
| agggagcact | gtgacacgga | gggagaggct | gacgactttg | atcctgggaa | gaaggtggag | 540 |
| gtggagccgc | ccccagatcg | gccagtccga | gcgtgccgga | cacngccagc | cgaaaatgag | 600 |
| agcacaccta | ttcagcaact | cctggnaaca | cttcctccgc | cagcttcaga | gaaaagatcc | 660 |
| ccatggattt | tttgcttttc | ctgtcacgga | tgcaattgct | cctgggatat | tccatgataa | 720 |
| tanaacctcc | catggatttt | ggcaccatga | nagacnaaat | tgtagctaat | gaatncaagt | 780 |
| cagntacgga | attnanggca | attccacgct | gatgtgtgat | atgcatggac | ttncataggc | 840 |
| cagntccgtg | tactacagtt | ggcaagagan | cttcccgcag | cttnaagatg | atgngcaacc | 900 |
| gcngctcttt | | | | | 910 |

<210> SEQ ID NO 10
<211> LENGTH: 1029
<212> TYPE: DNA
<213> ORGANISM: Homo sapiens

<400> SEQUENCE: 10

| | | | | | |
|---|---|---|---|---|---|
| tctgggccac | ggactgccgg | accgttgggc | tgtgaggcag | cgtctcagcg | aggcggcacc | 60 |
| cggagccatg | tcttcacata | ggaggaaagc | gaaggggagg | aataggagaa | gtcaccgtgc | 120 |
| catgcgtgtg | gctcacttag | agctggcaac | ttatgagttg | gcggcaactg | agtcgaatcc | 180 |
| cgagagcagc | catcctggat | acgaggccgc | catggctgac | aggcctcagc | caggatggcg | 240 |
| ggaatctcta | agatgcggg | tcagcaaacc | ctttgggatg | ctcatgctct | ccatttggat | 300 |
| cctgctgttc | gtgtgctact | acctgtccta | ctacctgtgc | tccgggtcct | catattttgt | 360 |
| gcttgcaaat | ggacatatcc | tgcccaacag | tgaaaatgct | catggccaat | ctctggaaga | 420 |
| agattccgca | ttggaagctt | tgctgaattt | tttctttcca | acaacttgca | atctgaggga | 480 |
| aaatcaggtg | gcaaagcctt | gtaatgagct | gcaagatctt | agtgagagtg | aatgtttgag | 540 |
| acacaaatgc | tgttttttcat | catcggggac | cacgagcttc | aaatgttttg | ctccatttag | 600 |

| | | |
|---|---|---|
| agatgtgcct aaacagatga tgcaaatgtt tgggcttggt gcgatcagcc ttatcctggt | 660 |
| atgtctgccc atttattgcc gctctctttt ctggaggagc gaaccggccg atgatttaca | 720 |
| aaggcaggac aacagagttg taacgggttt gaagaaacaa agaaggaagc gaaagaggaa | 780 |
| gtctgaaatg ttacagaaag cagcaagagg acgtgaggaa catggtgacg agtagcaaga | 840 |
| gaccaaagca ttattttccc ctcaagacaa cagaaaccat tcagagcaga ggggactgtc | 900 |
| tcagccatgc aaacctcatg gagcattttg gaaagttaaa attgattctt atttttgtca | 960 |
| tgtttacttt caaacatgaa ataaaattga gttctgtttt catgcatcaa aaaaaaaaaa | 1020 |
| aaaaaaaaa | 1029 |

```
<210> SEQ ID NO 11
<211> LENGTH: 924
<212> TYPE: DNA
<213> ORGANISM: homo sapiens
<220> FEATURE:
<221> NAME/KEY: misc_feature
<222> LOCATION: (4)..(4)
<223> OTHER INFORMATION: n = a, c, g or t/u
<220> FEATURE:
<221> NAME/KEY: misc_feature
<222> LOCATION: (204)..(204)
<223> OTHER INFORMATION: n = a, c, g or t/u
<220> FEATURE:
<221> NAME/KEY: misc_feature
<222> LOCATION: (752)..(752)
<223> OTHER INFORMATION: n = a, c, g or t/u
<220> FEATURE:
<221> NAME/KEY: misc_feature
<222> LOCATION: (754)..(754)
<223> OTHER INFORMATION: n = a, c, g or t/u
<220> FEATURE:
<221> NAME/KEY: misc_feature
<222> LOCATION: (756)..(759)
<223> OTHER INFORMATION: n = a, c, g or t/u
<220> FEATURE:
<221> NAME/KEY: misc_feature
<222> LOCATION: (761)..(761)
<223> OTHER INFORMATION: n = a, c, g or t/u
<220> FEATURE:
<221> NAME/KEY: misc_feature
<222> LOCATION: (765)..(765)
<223> OTHER INFORMATION: n = a, c, g or t/u
<220> FEATURE:
<221> NAME/KEY: misc_feature
<222> LOCATION: (770)..(770)
<223> OTHER INFORMATION: n = a, c, g or t/u
<220> FEATURE:
<221> NAME/KEY: misc_feature
<222> LOCATION: (773)..(775)
<223> OTHER INFORMATION: n = a, c, g or t/u
<220> FEATURE:
<221> NAME/KEY: misc_feature
<222> LOCATION: (777)..(779)
<223> OTHER INFORMATION: n = a, c, g or t/u
<220> FEATURE:
<221> NAME/KEY: misc_feature
<222> LOCATION: (781)..(781)
<223> OTHER INFORMATION: n = a, c, g or t/u
<220> FEATURE:
<221> NAME/KEY: misc_feature
<222> LOCATION: (802)..(802)
<223> OTHER INFORMATION: n = a, c, g or t/u
<220> FEATURE:
<221> NAME/KEY: misc_feature
<222> LOCATION: (812)..(812)
<223> OTHER INFORMATION: n = a, c, g or t/u
<220> FEATURE:
<221> NAME/KEY: misc_feature
<222> LOCATION: (829)..(829)
<223> OTHER INFORMATION: n = a, c, g or t/u
<220> FEATURE:
<221> NAME/KEY: misc_feature
<222> LOCATION: (833)..(833)
```

<223> OTHER INFORMATION: n = a, c, g or t/u
<220> FEATURE:
<221> NAME/KEY: misc_feature
<222> LOCATION: (849)..(849)
<223> OTHER INFORMATION: n = a, c, g or t/u
<220> FEATURE:
<221> NAME/KEY: misc_feature
<222> LOCATION: (866)..(866)
<223> OTHER INFORMATION: n = a, c, g or t/u
<220> FEATURE:
<221> NAME/KEY: misc_feature
<222> LOCATION: (873)..(873)
<223> OTHER INFORMATION: n = a, c, g or t/u
<220> FEATURE:
<221> NAME/KEY: misc_feature
<222> LOCATION: (879)..(880)
<223> OTHER INFORMATION: n = a, c, g or t/u
<220> FEATURE:
<221> NAME/KEY: misc_feature
<222> LOCATION: (886)..(886)
<223> OTHER INFORMATION: n = a, c, g or t/u
<220> FEATURE:
<221> NAME/KEY: misc_feature
<222> LOCATION: (901)..(901)
<223> OTHER INFORMATION: n = a, c, g or t/u

<400> SEQUENCE: 11

```
aatngctgga gctcgcgcgc ctgcaggtcg acactagtgg atccaaagaa ttcggcacga      60
gggagaaaaa gagtttataa tgctacaaaa tgaacaggag ataagtcaac tgaaaaaaga     120
aattgaaaga acacaacaaa ggatgaaaga atggagagt gttatgaaag agcaagaaca     180
gtacattgcc actcagtaca aggnggccat agatttgggg caagaattga ggctgacccg     240
ggagcaggtg cagaactctc atacagaatt ggcagaggct cgtcatcagc aagtccaagc     300
acagagagaa atagaaaggc tctctagtga actggaggat atgaagcaac tctctaaaga     360
gaaagatgct catggaaacc atttagctga agaactgggg gcttctaaag tacgtgaagc     420
tcatttagaa gcaagaatgc aagcagaaat caagaaattg tcagcagaag tagaatctct     480
caaagaagct tatcatatgg agatgatttc acatcaagag aaccatgcaa agtggaagat     540
ttctgctgac tctcaaaagt cttctgttca gcaactaaac gaacagttag agaaggcaaa     600
attggaatta gaagaagctc aggatactgt aagcaatttg catcaacaag tccaagatag     660
gaatgaagta attgaagctg caaatgaagc attacttact aaagtaagta aacatataaa     720
agtattaaag catatctatg aaaacaaaac cncncnnnnc ngccntcccn ccnnnannnc     780
ntctcgagag tacttctaaa gnggccgcgg gnccctccga tttcccccng ggngggggtac     840
caggtaagng tacccaattc cccctntagg agncgtatnn aattcnctgg ccgccgttta     900
ncacctcgtg ctgggaaaac ctgg                                             924
```

<210> SEQ ID NO 12
<211> LENGTH: 917
<212> TYPE: DNA
<213> ORGANISM: homo sapiens
<220> FEATURE:
<221> NAME/KEY: misc_feature
<222> LOCATION: (4)..(4)
<223> OTHER INFORMATION: n = a, c, g or t/u
<220> FEATURE:
<221> NAME/KEY: misc_feature
<222> LOCATION: (745)..(745)
<223> OTHER INFORMATION: n = a, c, g or t/u
<220> FEATURE:
<221> NAME/KEY: misc_feature
<222> LOCATION: (784)..(784)
<223> OTHER INFORMATION: n = a, c, g or t/u

<400> SEQUENCE: 12

-continued

| | |
|---|---|
| aaanctggag ctcgcgcgcc tgcaggtcga cactagtgga tccaaagaat tcggcacgag | 60 |
| ggggaaaatg gcggattcct cggggcgagg cgctgggaag cctgcaaccg gccccacaaa | 120 |
| ttctagcagt gccaagaaga aggataaaag agttcaaggt ggaagagtga ttgagtcccg | 180 |
| gtatctgcag tatgaaaaga agacaaccca aaaggctcct gcaggagatg ggtcacagac | 240 |
| ccgagggaag atgtctgaag gtggaaggaa atccagcctg ctccagaaaa gcaaagcaga | 300 |
| tagcagtggg gtcggaaagg gtgacctgca gtccacgttg ctggaagggc atggcacagc | 360 |
| tccacctgac ctggatctct ctgctattaa tgacaaaagc atcgtcaaaa agacgccaca | 420 |
| gttagcaaaa acaatatcaa agaaacctga gtcaacatca ttttctgccc ctcggaaaaa | 480 |
| gagcccggat ttatctgaag caatggaaat gatggagtct cagacactac tgctgacgct | 540 |
| actatccgta aagatggaga acaatcttgc tgagtttgaa agaagggcag aaaagaattt | 600 |
| attaataatg tgtaaggaga aggagaagct acagaaaaag gcccacgagc tgaagcgcag | 660 |
| gcttctcctc tctcagagga agcgggagct ggcagatgtc ctggatgccc agatcgagat | 720 |
| gctcagcccc cttcgaggca gtggncacac gcttcaagga gcaatacagg acattcgcca | 780 |
| cggnccttgg acactaccag gcacgagctg cccgtgaggt ccatccacct ggagggagat | 840 |
| gggcagcagc tcttagacgc cctgcagcat gactggtgac cctcagcgcc tcctgggaaa | 900 |
| cttgatgttg gtgatcg | 917 |

<210> SEQ ID NO 13
<211> LENGTH: 921
<212> TYPE: DNA
<213> ORGANISM: homo sapiens
<220> FEATURE:
<221> NAME/KEY: misc_feature
<222> LOCATION: (4)..(4)
<223> OTHER INFORMATION: n = a, c, g or t/u
<220> FEATURE:
<221> NAME/KEY: misc_feature
<222> LOCATION: (742)..(742)
<223> OTHER INFORMATION: n = a, c, g or t/u
<220> FEATURE:
<221> NAME/KEY: misc_feature
<222> LOCATION: (808)..(808)
<223> OTHER INFORMATION: n = a, c, g or t/u
<220> FEATURE:
<221> NAME/KEY: misc_feature
<222> LOCATION: (822)..(822)
<223> OTHER INFORMATION: n = a, c, g or t/u
<220> FEATURE:
<221> NAME/KEY: misc_feature
<222> LOCATION: (842)..(842)
<223> OTHER INFORMATION: n = a, c, g or t/u
<220> FEATURE:
<221> NAME/KEY: misc_feature
<222> LOCATION: (858)..(858)
<223> OTHER INFORMATION: n = a, c, g or t/u
<220> FEATURE:
<221> NAME/KEY: misc_feature
<222> LOCATION: (895)..(895)
<223> OTHER INFORMATION: n = a, c, g or t/u
<220> FEATURE:
<221> NAME/KEY: misc_feature
<222> LOCATION: (912)..(912)
<223> OTHER INFORMATION: n = a, c, g or t/u
<220> FEATURE:
<221> NAME/KEY: misc_feature
<222> LOCATION: (918)..(918)
<223> OTHER INFORMATION: n = a, c, g or t/u
<220> FEATURE:
<221> NAME/KEY: misc_feature
<222> LOCATION: (920)..(920)
<223> OTHER INFORMATION: n = a, c, g or t/u

<400> SEQUENCE: 13

-continued

| | |
|---|---|
| aatngctgga gctcgcgcgc ctgcaggtcg acactagtgg atccaaagaa ttcggcacga | 60 |
| ggtgaggggc ttccggttgg ggtggcaggg tggtggatct gttggtcccg ttttcccgtc | 120 |
| gcacgtggtg gccactgttg gcttctgaat ggtttgcaag gcggatatcc acgccaaggc | 180 |
| cttggatcg gccgtgggta catccgtctg agccgttcct ttccatcgca gagcggcggc | 240 |
| ctccggcggc gctctccagt catggactac cggcggcttc tcatgagccg ggtggtcccc | 300 |
| gggcaattcg acgacgcgga ctcctctgac agtgaaaaca gagacttgaa gacagtcaaa | 360 |
| gagaaggatg acattctgtt tgaagacctt caagacaatg tgaatgagaa tggtgaaggt | 420 |
| gaaatagaag atgaggagga ggagggttat gacgatgatg atgatgactg ggactgggat | 480 |
| gaaggagttg gaaaactcgc caagggttat gtctggaatg gaggaagcaa cccacaggca | 540 |
| aatcgacaga cctccgacag cagttcagcc aaaatgtcta ctccagcaga caaggtctta | 600 |
| cggaaaattt gagaataaaa ttaatttaga taagctaaat gttactgatt ccgtcataaa | 660 |
| taaagtcacc gaaaagtcta gacaaaagga agcagatatg tatcgcatca agataaggc | 720 |
| agacagagca actgtagaac angtgttgga tcccagacca agaatgattt tattcaagat | 780 |
| gttgactaga ggaatcataa cagagatnaa tggctgcatt anccaggaaa aaagctaatg | 840 |
| tnaccatgct acccagcnaa tggagagagc agaccatcaa atttataaac ttctntttgg | 900 |
| ggttcaagat cnggatantn t | 921 |

<210> SEQ ID NO 14
<211> LENGTH: 901
<212> TYPE: DNA
<213> ORGANISM: homo sapiens
<220> FEATURE:
<221> NAME/KEY: misc_feature
<222> LOCATION: (836)..(836)
<223> OTHER INFORMATION: n = a, c, g or t/u
<220> FEATURE:
<221> NAME/KEY: misc_feature
<222> LOCATION: (892)..(892)
<223> OTHER INFORMATION: n = a, c, g or t/u

<400> SEQUENCE: 14

| | |
|---|---|
| gctggagctc gcgcgcctgc aggtcgacac tagtggatcc aaagaattcg gcacgaggaa | 60 |
| gacgctactt cccctatcat agaagagctt atcacctttc atgatcacgc cctcataatc | 120 |
| attttcctta tctgcttcct agtcctgtat gcccttttcc taacactcac aacaaaacta | 180 |
| actaatacta acatctcaga cgctcaggaa atagaaaccg tctgaactat cctgcccgcc | 240 |
| atcatcctag tcctcatcgc cctcccatcc ctacgcatcc tttacataac agacgaggtc | 300 |
| aacgatccct cccttaccat caaatcaatt ggccaccaat ggtactgaac ctacgagtac | 360 |
| accgactacg gcggactaat cttcaactcc tacatacttc cccattatt cctagaacca | 420 |
| ggcgacctgc gactccttga cgttgacaat cgagtagtac tcccgattga agcccccatt | 480 |
| cgtataataa ttacatcaca agacgtcttg cactcatgag ctgtcccac attaggctta | 540 |
| aaaacagatg caattcccgg acgtctaaac caaaccactt tcaccgctac acgaccgggg | 600 |
| gtatactacg gtcaatgctc tgaaatctgt ggagcaaacc acagtttcat gcccatcgtc | 660 |
| ctagaattaa ttcccctaaa aatctttgaa ataggacccg tatttaccct atagcacccc | 720 |
| ctctacccc tctagagcca aaaaaaaaaa aaaaaactc gagactagtt ctctccggac | 780 |
| attcagactg agcgtgccta ccaaaagcag ccgaccatct ttcaaaacaa gaagangtc | 840 |
| ctgctgggag aactggcaag gagaagctcc gcggtactac aagaacatcg gnctgggctt | 900 |
| c | 901 |

<210> SEQ ID NO 15
<211> LENGTH: 1850
<212> TYPE: DNA
<213> ORGANISM: homo sapiens

<400> SEQUENCE: 15

```
cggcgccggg gcggcagcag aagtccggag tcagggcgtg tggctgagga gatgccacta      60
agcacagctg gcatcctgag ctcctcttct gccgcttcca acaggtcaag gaataaggct     120
cgctatcgga ccaaagccgt gagctctgag gtggatgaga gcctctttgg agatatcaag     180
tccccagccc agggccagag cgacagcccc attgtgctgc tccgagataa gcatacccctt    240
caaaaaactc tcactgcttt gggcttggat cgcaagccag agaccatcca gctcatcacc     300
cgggacatgg tccgagaact cattgttccc acagaggatc cctccgggga gtccctaatc     360
atcagccctg aggagtttga gcgaatcaaa tgggcatccc atgtcctgac cagagaagaa     420
cttgaggcca gggaccaggc cttcaagaag gagaaggaag ccaccatgga tgcagtgatg     480
acacgaaaga agatcatgaa acagaaggag atggtgtgga caacaacaa gaagctcagt      540
gacctggagg aggtggccaa ggaacgggcc cagaacctcc tgcagagagc caacaagctg     600
cggatggagc aggaggagga gctcaaggac atgagcaaga ttatcctcaa tgctaagtgc     660
catgccatcc gggatgccca aatcctggag aagcagcaga tccaaaaaga actggacaca     720
gaagagaagc ggttggatca gatgatggaa gtggagcggc agaaatccat tcaaaggcag     780
gaggaactgg agaggaagag gagggaggaa agaattagag gaaggcggca aattgtggaa     840
cagatggaaa agaaccagga ggagcgatcg ctgcttgctg agcagcggga gcaggagaag     900
gagcagatgc tggaatatat ggaacagctc aagaggaag atctaaagga catggaacga     960
aggcagcaac aaaaactgaa gatgcaagct gagattaagc gcatcaatga tgaaaaccag    1020
aaacagaaag cagaactgct ggctcaggag aagctggcag accagatggt gatggagttt    1080
accaagaaga gatggctcg agaagcagag tttgaggctg agcaggagag aatccggagg    1140
gagaaagaga aggagatcgc acgcttgagg gccatgcagg agaaggccca ggattaccag    1200
gcagaacagg atgccttgcg ggccaagcgc aaccaggagg ttgcagacag agagtggcgc    1260
agaaaggaaa aggaaaatgc gcggaagaag atggaaacag aggctgagct gcgaaaaagt    1320
cggctcgaac aggtggcttt caaggagcac gctctggctg ttcaggtgca cgggaccggg    1380
atgagttcga gaggattctt cgggctcaga gagaacagat tgagaaggag cggctggagg    1440
aggagaaaaa ggccacaggg cgcttacagc atgccaatga gctccggcgc caggtgcgcg    1500
agaaccagca gaaggaagtg cagaaccgga ttgccaccct tgaggggggc cggcgcctca    1560
aagaggaggc ccagaaacgc cgtgagcgca tcgatgagat caagaggaaa aagcttgaag    1620
agctgagagc cactggcctt cccgagaagt actgcattga agctgagcgc aaagctaaca    1680
tcctgccagc tacctctgtg aactgagggg agccttcgtg gccctcagga tgccttcggg    1740
ggacagattc tgcccagtct ctgggcatcc ataattgctg ctaacctaga catttcatag    1800
ttacagatta aatctacttg actaaaaaaa aaaaaaaaa aaaaaaaaaa                  1850
```

<210> SEQ ID NO 16
<211> LENGTH: 1791
<212> TYPE: DNA
<213> ORGANISM: homo sapiens

<400> SEQUENCE: 16

```
cccagaaatt ctacccaagc tccctcagca ccatgtaccg agcacttcgg ctcctcgcgc      60
```

| | | | | |
|---|---|---|---|---|
| gctcgcgtcc | cctcgtgcgg | gctccagccg | cagccttagc | ttcggctccc | ggcttgggtg | 120 |
| gcgcggccgt | gccctcgttt | tggcctccga | acgcggctcg | aatggcaagc | caaaattcct | 180 |
| tccggataga | atatgatacc | tttggtgaac | taaaggtgcc | aaatgataag | tattatggcg | 240 |
| cccagaccgt | gagatctacg | atgaacttta | agattggagg | tgtgacagaa | cgcatgccaa | 300 |
| ccccagttat | taaagctttt | ggcatcttga | agcgagcggc | cgctgaagta | aaccaggatt | 360 |
| atggtcttga | tccaaagatt | gctaatgcaa | taatgaaggc | agcagatgag | gtagctgaag | 420 |
| gtaaattaaa | tgatcatttt | cctctcgtgg | tatggcagac | tggatcagga | actcagacaa | 480 |
| atatgaatgt | aaatgaagtc | attagcaata | gagcaattga | atgttaggga | ggtgaacttg | 540 |
| gcagcaagat | acctgtgcat | cccaacgatc | atgttaataa | aagccagagc | tcaaatgata | 600 |
| cttttcccac | agcaatgcac | attgctgctg | caatagaagt | tcatgaagta | ctgttaccag | 660 |
| gactacagaa | gttacatgat | gctcttgatg | caaaatccaa | agagtttgca | cagatcatca | 720 |
| agattggacg | tactcatact | caggatgctg | ttccacttac | tcttgggcag | gaatttagtg | 780 |
| gttatgttca | acaagtaaaa | tatgcaatga | caagaataaa | agctgccatg | ccaagaatct | 840 |
| atgagctcgc | agctggaggc | actgctgttg | gtacaggttt | aaatactaga | attggctttg | 900 |
| cagaaaaggt | tgctgcaaaa | gtggctgcac | ttacaggctt | gccttttgtc | actgctccga | 960 |
| ataaatttga | agctctggct | gctcatgacg | ctctggttga | gctcagtgga | gccatgaaca | 1020 |
| ctactgcctg | cagtctgatg | aagatagcaa | atgatattcg | attttgggt | tctggtcctc | 1080 |
| ggtcaggtct | gggagaattg | atcttgcctg | aaaatgaacc | aggaagcagt | atcatgccag | 1140 |
| gcaaggtgaa | ccctactcag | tgtgaagcaa | tgaccatggt | tgcagcccaa | gtcatgggga | 1200 |
| accatgttgc | tgtcactgtc | ggaggcagca | atggacattt | tgagttgaat | gttttcaagc | 1260 |
| caatgatgat | taaaaatgtg | ttacactcag | ccaggctgct | gggggatgct | tcagtttcct | 1320 |
| ttacagaaaa | ctgcgtggtg | ggaatccagg | ccaatacaga | aaggatcaac | aagctgatga | 1380 |
| atgagtctct | aatgttggtg | acagctctca | atcctcatat | agggtatgac | aaggcagcaa | 1440 |
| agattgctaa | gacagcacac | aaaaatggat | caaccttaaa | ggaaactgct | atcgaacttg | 1500 |
| gctatctcac | agcagagcag | tttgacgaat | gggtaaaacc | taaggacatg | ctgggtccaa | 1560 |
| agtgatttac | ataaatttat | aatgaaaata | acatgtata | aaatttaaaa | aaacagactc | 1620 |
| ccatttctta | aaaacggata | agtttgaaag | gaaactgcta | ttgaacttaa | gcatctctag | 1680 |
| cagagcaatt | tgatcagtat | ataaaaccct | aggatgtgct | aggtctaaga | tggattaaac | 1740 |
| aagtataaaa | taaatacat | ttataaaata | aaaggaaaa | cagacttaaa | a | 1791 |

<210> SEQ ID NO 17
<211> LENGTH: 3258
<212> TYPE: DNA
<213> ORGANISM: homo sapiens

<400> SEQUENCE: 17

| | | | | |
|---|---|---|---|---|
| cggccgcgtg | acggtggcgc | acaagaaggc | tccgccggcc | ctgatcgacg | agtgcatcga | 60 |
| gaagttcaat | cacgtcagcg | gcagccgggg | gtccgagagc | cccgccccca | acccgccca | 120 |
| tgccgcgccc | acagggagcc | aggagcctgt | gcgcaggccc | atgcgcaagt | ccttctccca | 180 |
| gcccggcctg | cgctcgctgg | cctttaggaa | ggagctgcag | gatgggggcc | tccgaagcag | 240 |
| cggcttcttc | agctccttcg | aggagagcga | cattgagaac | cacctcatta | gcggacacaa | 300 |
| tattgtgcag | cccacagata | tcgaggaaaa | tcgaactatg | ctcttcacga | ttggccagtc | 360 |
| tgaagtttac | ctcatcagtc | ctgacaccaa | aaaaatagca | ttggagaaaa | attttaagga | 420 |

-continued

```
gatatccttt tgctctcagg gcatcagaca cgtggaccac tttgggttta tctgtcggga    480
gtcttccgga ggtggcggct ttcattttgt ctgttacgtg tttcagtgca caaatgaggc    540
tctggttgat gaaattatga tgaccctgaa acaggccttc acggtggccg cagtgcagca    600
gacagctaag gcgccagccc agctgtgtga gggctgcccc ctgcaaagcc tgcacaagct    660
ctgtgagagg atagagggaa tgaattcttc caaaacaaaa ctagaactgc aaaagcacct    720
gacgacatta accaatcagg agcaggcgac tattttgaa gaggttcaga aattgagacc    780
gagaaatgag cagcgagaga tgaattgat tattctttt ctgagatgtt tatatgaaga    840
gaaacagaaa gaacacatcc atattgggga gatgaagcag acatcgcaga tggcagcaga    900
gaatattgga agtgaattac cacccagtgc cactcgattt aggctagata tgctgaaaaa    960
caaagcaaag agatctttaa cagagtcttt agaaagtatt ttgtcccggg gtaataaagc   1020
cagaggcctg caggaacact ccatcagtgt ggatctggat agctccctgt ctagtacatt   1080
aagtaacacc agcaaagagc catctgtgtg tgaaaaggag ccttgccca tctctgagag   1140
ctcctttaag ctcctcggct cctcggagga cctgtccagt gactcggaga gtcatctccc   1200
agaagagcca gctccgctgt cgccccagca ggccttcagg aggcgagcaa acaccctgag   1260
tcacttcccc atcgaatgcc aggaacctcc acaacctgcc cggggtccc cggggtttc    1320
gcaaaggaaa cttatgaggt atcactcagt gagcacagag acgcctcatg aacgaaagga   1380
ctttgaatcc aaagcaaacc atcttggtga ttctggtggg actcctgtga agacccggag   1440
gcattcctgg aggcagcaga tattcctccg agtagccacc ccgcagaagg cgtgcgattc   1500
ttccagcaga tatgaagatt attcagagct gggagagctt cccccacgat ctcctttaga   1560
accagtttgt gaagatgggc cctttggccc cccaccagag gaaaagaaaa ggacatctcg   1620
tgagctccga gagctgtggc aaaaggctat tcttcaacag atactgctgc ttagaatgga   1680
gaaggaaaat cagaagctcc aagcctctga aatgatttg ctgaacaagc gcctgaagct   1740
cgattatgaa gaaattactc cctgtcttaa agaagtaact acagtgtggg aaaagatgct   1800
tagcactcca ggaagatcaa aaattaagtt tgacatggaa aaaatgcact cggctgttgg   1860
gcaaggtgtg ccacgtcatc accgaggtga atctggaaa tttctagctg agcaattcca   1920
ccttaaacac cagtttccca gcaaacagca gccaaaggat gtgccataca agaactctt   1980
aaagcagctg acttcccagc agcatgcgat tcttattgac cttgggcgaa cctttcctac   2040
acacccatac ttctctgccc agcttggagc aggacagcta tcgctttaca acattttgaa   2100
ggcctactca cttctagacc aggaagtggg atattgccaa ggtctcagct ttgtagcagg   2160
cattttgctt cttcatatga gtgaggaaga ggcgtttaaa atgctcaagt ttctgatgtt   2220
tgacatgggc ctgcggaaac agtatcggcc agacatgatt atttacaga tccagatgta   2280
ccagctctcg aggttgcttc atgattacca cagagacctc tacaatcacc tggaggagca   2340
cgagatcggc cccagcctct acgctgcccc ctggttcctc accatgtttg cctcacagtt   2400
cccgctggga ttcgtagcca gagtctttga tatgattttt cttcagggaa cagaggtcat   2460
atttaaagtg gctttaagtc tgttgggaag ccataagccc ttgattctgc agcatgaaaa   2520
cctagaaacc atagttgact ttataaaaag cacgctaccc aaccttggct tggtacagat   2580
ggaaaagacc atcaatcagg tatttgaaat ggacatcgct aaacagttac aagcttatga   2640
agttgagtac cacgtccttc aagaagaact tatcgattcc tctcctctca gtgacaacca   2700
aagaatggat aaattagaga aaccaacag cagcttacgc aaacagaacc ttgacctcct   2760
tgaacagttg caggtggcaa atggtaggat ccaaagcctt gaggccacca ttgagaagct   2820
```

```
cctgagcagt gagagcaagc tgaagcaggc catgcttacc ttagaactgg agcggtcggc   2880
cctgctgcag acggtggagg agctgcggcg gcggagcgca gagcccagcg accgggagcc   2940
tgagtgcacg cagcccgagc ccacgggcga ctgacagctc tgcaggagag attgcaacac   3000
catcccacac tgtccaggcc ttaactgaga gggacagaag acgctggaag agagaagga   3060 agcgggaagt gtgcttctca gggaggaaac cggcttgcca gcaagtagat tcttacgaac   3120
tccaacttgc aattcagggg gcatgtccca gtgttttttt tgttgttttt agatactaaa   3180
tcgtcccttc tccagtcctg attactgtac acagtagctt tagatggcgt ggacgtgaat   3240
aaatgcaact tatgtttt                                                 3258

<210> SEQ ID NO 18
<211> LENGTH: 3496
<212> TYPE: DNA
<213> ORGANISM: homo sapiens

<400> SEQUENCE: 18
gaattctatg gagtgtaatt tgtgtatga attatatttt taaaacattg aagagttttc    60
agaaagaagg ctagtagagt tgattactga tactttatgc taagcagtac ttttttggta   120
gtacaatatt ttgttaggcg tttctgataa cactagaaag acaagttttt atcttgtgat   180
aaattgatta atgtttacaa catgactgat aattatagct gaatagtcct taaatgatga   240
acaggttatt tagttttaa atgcagtgta aaaagtgtgc tgtggaaatt ttatggctaa    300
ctaagtttat ggagaaaata ccttcagttg atcaagaata atagtggtat acaaagttag   360
gaagaaagtc aacatgatgc tgcaggaaat ggaaacaaat acaaatgata tttaacaaag   420
atagagttta cagttttga actttaagcc aaattcattt gacatcaagc actatagcag    480
gcacaggttc aacaaagctt gtgggtattg acttccccca aaagttgtca gctgaagtaa   540
tttagcccac ttaagtaaat actatgatga taagctgtgt gaacttagct tttaaatagt   600
gtgaccatat gaaggtttta attactttg tttattggaa taaaatgaga ttttttgggt    660
tgtcatgtta aagtgcttat agggaaagaa gcctgcatat aatttttac cttgtggcat    720 aatcagtaat tggtctgtta ttcaggcttc atagcttgta accaaatata aataaaaggc   780
ataatttagg tattctatag ttgcttagaa ttttgttaat ataaatctct gtgaaaaatc   840
aaggagtttt aatattttca gaagtgcatc caccttttcag ggcttttaagt tagtattact  900 caagattatg aacaaatagc acttaggtta cctgaaagag ttactacaac cccaaagagt   960
tgtgttctaa gtagtatctt ggaaattcag agagatactc atcctacctg aatataaact  1020
gagataaatc cagtaaagaa agtgtagtaa attctacata agagtctatc attgatttct  1080
tttggtggta aaaatcttag ttcatgtgaa gaaatttcat gtgaatgttt tagctatcaa  1140
acagcactgt cacctactca tgcacaaaac tgcctcccaa agactttcc caggtccctc   1200 gtatcaaaac attaagagta taatggaaga tagcacgatc ttgtcagatt ggacaaacag  1260
caacaaacaa aaaatgaagt atgacttttc ctgtgaactc tacagaatgt ctacatattc  1320
aactttcccc gccggggtgc ctgtctcaga aaggagtctt gctcgtgctg ttttttatta  1380
tactggtgtg aatgacaagg tcaaatgctt ctgttgtggc ctgatgctgg ataactggaa  1440
actaggagac agtcctattc aaaagcataa acagctatat cctagctgta gctttattca  1500
gaatctggtt tcagctagtc tgggatccac ctctaagaat acgtctccaa tgagaaacag  1560
ttttgcacat tcattatctc ccaccttgga acatagtagc ttgttcagtg gttcttactc  1620
cagccttcct ccaaacccct caattctag agcagttgaa gacatctctt catcgaggac   1680
```

| | |
|---|---|
| taaccccctac agttatgcaa tgagtactga agaagccaga tttcttacct accatatgtg | 1740 |
| gccattaact tttttgtcac catcagaatt ggcaagagct ggttttatt atataggacc | 1800 |
| tggagatagg gtagcctgct ttgcctgtgg tgggaagctc agtaactggg aaccaaagga | 1860 |
| tgatgctatg tcagaacacc ggaggcattt tcccaactgt ccattttgg aaaattctct | 1920 |
| agaaactctg aggtttagca tttcaaatct gagcatgcag acacatgcag ctcgaatgag | 1980 |
| aacatttatg tactggccat ctagtgttcc agttcagcct gagcagcttg caagtgctgg | 2040 |
| tttttattat gtgggtcgca atgatgatgt caaatgcttt tgttgtgatg gtggcttgag | 2100 |
| gtgttgggaa tctggagatg atccatgggt agaacatgcc aagtggtttc caaggtgtga | 2160 |
| gttcttgata cgaatgaaag gccaagagtt tgttgatgag attcaaggta gatatcctca | 2220 |
| tcttcttgaa cagctgttgt caacttcaga taccactgga gaagaaatg ctgacccacc | 2280 |
| aattattcat tttggacctg agaaagttc ttcagaagat gctgtcatga tgaatacacc | 2340 |
| tgtggttaaa tctgccttgg aaatgggctt aatagagac ctggtgaaac aaacagttca | 2400 |
| aagtaaaatc ctgacaactg gagagaacta taaaacagtt aatgatattg tgtcagcact | 2460 |
| tctaaatgct gaagatgaaa aagagagga ggagaaggaa aaacaagctg aagaaatggc | 2520 |
| atcagatgat ttgtcattaa ttcggaagaa cagaatggct ctctttcaac aattgacatg | 2580 |
| tgtgcttcct atcctggata atctttaaa ggccaatgta attaataaac aggaacatga | 2640 |
| tattattaaa caaaaacac agataccttt acaagcgaga gaactgattg ataccatttt | 2700 |
| ggttaaagga aatgctgcgg ccaacatctt caaaaactgt ctaaaagaaa ttgactctac | 2760 |
| attgtataag aacttatttg tggataagaa tatgaagtat attccaacag aagatgtttc | 2820 |
| aggtctgtca ctggaagaac aattgaggag gttgcaagaa gaacgaactt gtaaagtgtg | 2880 |
| tatgacaaaa gaagtttctg ttgtatttat tccttgtggt catctggtag tatgccagga | 2940 |
| atgtgcccct tctctaagaa aatgccctat ttgcagggt ataatcaagg gtactgttcg | 3000 |
| tacatttctc tcttaaagaa aaatagtcta tattttaacc tgcataaaaa ggtctttaaa | 3060 |
| atattgttga acacttgaag ccatctaaag taaaaggga attatgagtt tttcaattag | 3120 |
| taacattcat gttctagtct gctttggtac taataatctt gtttctgaaa agatggtatc | 3180 |
| atatatttaa tcttaatctg tttatttaca agggaagatt tatgtttggt gaactatatt | 3240 |
| agtatgtatg tgtacctaag ggagtagtgt cactgcttgt tatgcatcat ttcaggagtt | 3300 |
| actggatttg ttgttctttc agaaagcttt gaatactaaa ttatagtgta gaaaagaact | 3360 |
| ggaaccagg aactctggag ttcatcagag ttatggtgcc gaattgtctt tggtgctttt | 3420 |
| cacttgtgtt ttaaaataag gattttctc ttatttctcc ccctagtttg tgagaaacat | 3480 |
| ctcaataaag tgcttt | 3496 |

<210> SEQ ID NO 19
<211> LENGTH: 1807
<212> TYPE: DNA
<213> ORGANISM: homo sapiens

<400> SEQUENCE: 19

| | |
|---|---|
| gaattctttc ttcagcccat gtaaacatga aaataagggt taaaaatgac ttcattatgg | 60 |
| ggaaaaggga caggatgcaa attgttcaaa ttccgggtgg ccgctgctcc ggcctccggg | 120 |
| gccttgcgga gactcacccc ttcagcgtcg ctgcccccag ctcagctctt actgcgggcc | 180 |
| gtccgacggc ggtcccatcc tgtcagggac tatgcgcgc aaacatctcc ttcgccaaaa | 240 |
| gcaggcgccg ccaccgggcg catcgtggcg gtcattggcg cagtggtgga cgtccagttt | 300 |

-continued

```
gatgagggac taccaccaat tctaaatgcc ctggaagtgc aaggcaggga gaccagactg    360
gttttggagg tggcccagca tttgggtgag agcacagtaa ggactattgc tatggatggt    420
acagaaggct tggttagagg ccagaaagta ctggattctg gtgcaccaat caaaattcct    480
gttggtcctg agactttggg cagaatcatg aatgtcattg agaacctat tgatgaaaga     540
ggtcccatca aaccaaaca atttgctccc attcatgctg aggctccaga gttcatggaa     600
atgagtgttg agcaggaaat tctggtgact ggtatcaagg ttgtcgatct gctagctccc    660
tatgccaagg gtggcaaaat tgggcttttt ggtggtgctg gagttggcaa gactgtactg    720
atcatggagt taatcaacaa tgtcgccaaa gcccatggtg ttactctgt gtttgctggt     780
gttggtgaga ggacccgtga aggcaatgat ttataccatg aaatgattga atctggtgtt    840
atcaacttaa aagatgccac ctctaaggta gcgctggtat atggtcaaat gaatcaacca    900
cctggtgctc gtgcccgggt agctctgact gggctgactg tggctgaata cttcagagac    960
caagaaggtc aagatgtact gctatttatt gataacatct ttcgcttcac ccaggctggt   1020
tcagaggtgt ctgcattatt gggccgaatc ccttctgctg tgggctatca gcctacctg    1080
gccactgaca tgggcactat gcaggaaaga attaccacta ccaagaaggg atctatcacc   1140
tctgtacagg ctatctatgt gcctgctgat gacttgactg accctgcccc tgctactacg   1200
tttgcccatt tggatgctac cactgtactg tcgcgtgcca ttgctgagct gggcatctat   1260
ccagctgtgg atcctctaga ctccacctct cgtatcatgg atcccaacat tgttggcagt   1320
gagcattacg atgttgcccg tggggtgcaa aagatcctgc aggactacaa atccctccag   1380
gatatcattg ccatcctggg tatggatgaa ctttctgagg aagacaagtt gaccgtgtcc   1440
cgtgcacgga aaatacagcg tttcttgtct cagccattcc aggttgctga ggtcttcaca   1500
ggtcatatgg ggaagctggt accccctgaag agaccatca aaggattcca gcagattttg   1560
gcaggtgaat atgaccatct cccagaacag gccttctata tggtgggacc cattgaagaa   1620
gctgtggcaa aagctgataa gctggctgaa gagcattcat cgtgagggt ctttgtcctc    1680
tgtacttgtc tctctccttg cccctaaccc aaaaagcttc attttctat ataggctgca    1740
caagagcctt gattgaagat atattctttc tgaacagtat ttaaggtttc caataaaatc   1800
ggaattc                                                              1807
```

<210> SEQ ID NO 20
<211> LENGTH: 2676
<212> TYPE: DNA
<213> ORGANISM: homo sapiens

<400> SEQUENCE: 20

```
gttccggcga ggaggccgcg ccagtgacag cgatggcggc ggagtcggcg ctccaagttg     60
tggagaagct gcaggcgcgc ctggccgcga acccggaccc taagaagcta ttgaaatatt    120
tgaagaaact ctccaccctg cctattacag tagacattct tgcggagact ggggttggga    180
aaacagtaaa tagcttgcga aaacacgagc atgttggaag ctttgccagg gacctagtgg    240
cccagtggaa gaagctggtt cctgtggaac gaaatgctga gcctgatgaa caggactttg    300
agaagagcaa ttcccgaaag cgccctcggg atgccctgca gaaggaggag gagatggagg    360
gggactacca agaaacctgg aaagccacgg ggagccgatc ctatagccct gaccacaggc    420
agaagaaaca taggaaactc tcggagctcg agagacctca caagtgtct cacggtcatg     480
agaggagaga tgagagaaag aggtgtcaca gaatgtcacc aacttactct tcagaccctg    540
agtcttctga ttatggccat gttcaatccc ctccatcttg taccagtcct catcagatgt    600
```

| | |
|---|---:|
| acgtcgacca ctacagatcc ctggaggagg accaggagcc cattgtttca caccagaagc | 660 |
| ctgggaaagg ccacagcaat gcctttcagg acagactcgg ggccagccaa gaacgacacc | 720 |
| tgggtgaacc ccatgggaaa ggggttgtga gtcaaaacaa ggagcacaaa tcttcccaca | 780 |
| aggacaaacg ccccgtggat gccaagagtg atgagaaggc ctctgtggtg agcagagaga | 840 |
| aatcacacaa ggccctctcc aaagaggaga accgaaggcc accctcaggg acaatgcaa | 900 |
| gggagaaacc gccctctagt ggcgtaaaga aagagaagga cagagagggc agcagcctga | 960 |
| agaagaagtg tttgcctccc tcagaggccg cttcagacaa ccacctgaaa agccaaagc | 1020 |
| acagagaccc agagaaagcc aaattggaca aaagcaagca aggtctggac agctttgaca | 1080 |
| caggaaaagg agcaggagac ctgttgccca aggtaaaaga aagggttct aacaacctaa | 1140 |
| agactccaga agggaaagtc aaaactaatt tggatagaaa gtcactgggc tccctcccta | 1200 |
| aagttgagga gacagatatg gaggatgaat tcgagcagcc aaccatgtct tttgaatcct | 1260 |
| acctcagcta tgaccagccc cggaagaaaa agaaaaagat tgtgaaaact tcagccacgg | 1320 |
| cacttggaga taaaggactt aaaaaaaatg actctaaaag cactggtaaa aacttggact | 1380 |
| cagttcagaa attacccaag gtgaacaaaa ccaagtcaga gaagccggct ggagctgatt | 1440 |
| tagccaagct gagaaaggtg cctgatgtgt tgccagtgtt gccagacctc ccgttacccg | 1500 |
| cgatacaggc caattaccgt ccactgcctt ccctcgagct gatatcctcc ttccagccaa | 1560 |
| agcgaaaagc gttctcttca ccccaggaag aagaagaagc tggatttact gggcgcagaa | 1620 |
| tgaattccaa gatgcaggtg tattctggtt ccaagtgtgc ctatctccct aaaatgatga | 1680 |
| ccttgcacca gcaatgcatc cgagtactta aaaacaacat cgattcaatc tttgaagtgg | 1740 |
| gaggagtccc atactctgtt cttgaacccg ttttggagag gtgtacacct gatcagctgt | 1800 |
| atcgcataga ggaatacaat catgtattaa ttgaagaaac agatcaatta tggaaagttc | 1860 |
| attgtcaccg agactttaag gaagaaagac ccgaagagta tgagtcgtgg cgagagatgt | 1920 |
| acctgcggct tcaggacgcc cgagagcagc ggctacgagt actaacaaag aatatccagt | 1980 |
| tcgcacatgc caataagccc aaaggccgac aagcaaagat ggcctttgtc aactctgtgg | 2040 |
| ccaagccacc tcgtgacgtc cggaggaggc aggaaaagtt tggaacggga ggagcagctg | 2100 |
| tccctgagaa aatcaagatc aagccagccc cgtaccccat gggaagcagc catgcttccg | 2160 |
| ccagtagcat cagctttaac cccagccctg aggagccggc ctatgatggc caagcacca | 2220 |
| gcagtgccca cttggcacca gtggtcagca gcactgtttc ctatgatcct aggaaaccca | 2280 |
| ctgtgaagaa aattgcccca atgatggcca agacaattaa agctttcaag aacagattct | 2340 |
| cccgacgata aactgaggac ttgccttgga aatggaatct ggggaggcag gaatacaagg | 2400 |
| acagtggggg ttggggaatg gaattctaca ggagactgga gtcttgcttt gtggatcctt | 2460 |
| ttggtctccg agtctgcagt ctgcaggtgc tgcccctggg aacctgcgtg ccacagcccc | 2520 |
| gcctccctgc ctggagcaca ctttagaatt ctgaagatgt gaagcctctg tctcactgag | 2580 |
| gattttaaag gtcaattata cttttgttgt tcattagcat cttttgtaaac tataagacgt | 2640 |
| agttttaatt aataaatatt gcccccagat gttaaa | 2676 |

<210> SEQ ID NO 21
<211> LENGTH: 2961
<212> TYPE: DNA
<213> ORGANISM: homo sapiens

<400> SEQUENCE: 21

| | |
|---|---:|
| cggtgctggc cccggcgagg tagcttctgg aaggcgctgc tcttccggtt ctctgtcccg | 60 |

```
gttcctgggg ttgcacagac agaccctgta aacatgtcag ggttcagtcc ggaactcatc    120
gactacttgg aagggaaaat ctcctttgag gagttcgaac ggcggagaga agagagaaaa    180
acccgcgaga agaaaagtct tcaggaaaaa ggcaagttat cagctgaaga aaatcccgat    240
gactctgaag ttccatcatc atcaggaatt aactctacca aatcccaaga caaagatgtc    300
aatgaaggag aaacatcaga tggagtgagg aagtcagttc acaaggtctt tgcttccatg    360
cttggagaga atgaagatga tgaggaggaa aggaagaaag aggaggagga ggaggaggag    420
gaagaaacac ctgagcaacc cactgcgggc gatgtatttg tattggagat ggttctcaat    480
cgtgaaacca agaaaatgat gaaagagaaa aggcctcgga gtaaacttcc cagagctctg    540
agaggtctca tgggtgaagc caacattcgt tttgctcgag gagaacgtga agaggcgata    600
ttgatgtgca tggaaatcat aagacaagct cctctggctt atgagccatt ctctactcta    660
gccatgatat atgaggacca aggtgacatg gaaaaatcat tgcagtttga gttgattgct    720
gcgcatttaa atcccagtga cacagaagaa tgggttagac tggcagaaat gtctctggaa    780
caagacaata ttaagcaggc tatttttttgc tatacaaaag ctcttaaata tgaacctact    840
aatgtccgtt atctgtggga gcgatcaagc ctttatgaac agatgggtga tcataaaatg    900
gccatggatg gttataggcg tattttaaac cttttgtctc catctgatgg cgaacgtttt    960
atgcagctgg ctagagatat ggcaaagagt tactatgaag ccaatgatgt tacttctgct   1020
attaacataa ttgatgaagc tttctcaaag caccagggcc tagtctccat ggaagatgtt   1080
aacatagcag ctgaactata tatttctaac aaacagtatg acaaagcttt ggagataatt   1140
acagattttt ctggaattgt gctggaaaaa aaaacttcag aagaaggcac ctcagaagag   1200
aataaagctc ctgagaatgt tacctgcact ataccctgatg gcgtgccaat agatatcaca   1260
gtgaagttga tggtctgcct tgtacatctc aacattcttg aaccacttaa tcctctcttg   1320
acaacactag tagaacagaa tcctgaagat atgggagacc tatacctaga tgttgctgaa   1380
gcttttctgg atgttggtga atataattct gcacttcccc tcctcagtgc tcttgtttgc   1440
tctgaaagat acaaccttgc agtagtttgg cttcgtcatg cagaatgttt aaaggcctta   1500
ggctatatgg agcgagctgc tgaaagctat ggcaaggtgg ttgatctggc cccactccat   1560
ttggatgcaa ggatttcact ttctacccctt cagcagcagc tgggccagcc tgagaaagct   1620
ctggaagctc tggaaccaat gtatgatcca gatactttag cacaggatgc aaatgctgca   1680
cagcaggaac tgaagttatt gcttcatcgt tctactctgt tgttttcaca aggcaaaatg   1740
tatggttatg tggataccct tacttactatg ttagccatgc ttttaaaggt agcaatgaat   1800
cgagcccaag tttgtttgat atccagttcc aagtctggag agaggcatct ttatcttatt   1860
aaagtatcga gagacaaaat atcagacagc aatgaccaag agtcagcaaa ttgtgatgca   1920
aaagcaatat ttgctgtgct cacaagcgtc ttgacaaagg atgactggtg gaatcttctg   1980
ttgaaggcca tatactcctt atgtgaccta tcccgatttc aagaggctga gttgcttgta   2040
gattcctcat tggaatatta ctcatttftat gatgacaggc aaaaacgcaa agaactagaa   2100
tactttggtc tgtctgctgc aattctggac aaaaatttca gaaaggcata caactatatc   2160
aggataatgg taatggaaaa tgtcaataaa ccccagctct ggaacatttt caatcaagtt   2220
accatgcact cccaagatgt acgacatcat cgcttctgtc tccgtttgat gctgaaaaac   2280
ccagaaaatc atgccctatg tgtcttaaat ggacacaatg catttgtatc tggtagtttt   2340
aagcatgcgc ttgacagta tgtgcaagcc tttcgcactc accctgacga acctctctat   2400
agcttctgta taggcctaac ctttattcat atggcatctc agaagtatgt gttacggaga   2460
```

-continued

```
catgctctta ttgtacaggg cttttccttt cttaatcgat acctcagttt acgtgggccc    2520
tgccaggaat cattctacaa tttgggccgt ggccttcatc agttggggct gattcatctt    2580
gcaatccact attatcagaa ggccctggag ctccctccac ttgtggtaga gggtatagaa    2640
cttgaccagt tagacttacg aagagatatt gcctacaact tgtctctcat ctatcagagc    2700
agtgggaata ccggaatggc tcaaacgctt ttgtatacct attgttctat ataaagcacc    2760
gcaactgaga acagagcaat ggcagctgct gtgtgaggac cagtgtcttc tgtctcaggg    2820
cttattattt gtaactccaa aatagaaatg accatttcag aattacctaa caaacagtgt    2880 atttatttt aatatgtgat catgatcttg tggtatatat gcaaaattat tcctacaaaa     2940
aaaaaaaaaa aaaaaaaaa a                                                2961

<210> SEQ ID NO 22
<211> LENGTH: 5676
<212> TYPE: DNA
<213> ORGANISM: homo sapiens

<400> SEQUENCE: 22
ggatccttga gggcactggt gcgactttca ggtgaggtct tagcagatga aagcggctgg      60
ctgtggcccg cgccagtagt gctttctgct ccgcactcgc cgtgagccag gtgtgcaacc     120
ggatttgggg cgagggtcgc gctggctacc tcgcatgcgc agagccggaa gcccgctgac     180
cggactacag ctcccagaag agccttgtgg aggccgcaga cgcgaagccg ctggcgccat     240
cttgaaatct gatcctccat ccccgaggct ttgcgtctgc gcggccggcc gctgctgctc     300
cgggagccca gtctgctaaa aggggaggac gttgaggacg cggcggctgg cgggagagac     360
agctggggag agacatggca gggtcggagc gcggcctgcg cctctgtcac tcagcatcct     420
cttaggcgtt tccacgcccg cccctgccc gaggggcggg gctgacggct ctggtacccg      480
gagtcggcgc gcggggcagg ggcgcgcccc tgcagagtgg ggaccccact gggctgtgcc     540
atgctgaccg gagaccaccg aggcgggaga cagagcgcgg cgaagagcca ttgagtggtc     600
acccagtagc cgccgccgcc gccgcctcgg gaagcttgcc acccgctagg agggaagatg     660
aaggagattt gcaggatctg tgcccgagag ctgtgtggaa accagcggcg ctggatcttc     720
cacacggcgt ccaagctcaa tctccaggtt ctgctttcgc acgtcttggg caaggatgtc     780
ccccgcgatg gcaaagccga gttcgcttgc agcaagtgtg ctttcatgct tgatcgaatc     840
tatcgattcg acacagttat tgcccggatt gaagcgcttt ctattgagcg cttgcaaaag     900
ctgctactgg agaaggatcg cctcaagttc tgcattgcca gtatgtatcg aagaataac     960 gatgactctg gcgcggagat caaggcgggg aatgggacgg ttgacatgtc cgtcttaccc    1020
gatgcgagat actctgcact gctccaggag gacttcgcct attcagggtt tgagtgctgg    1080
gtggagaatg aggatcagat ccaggagcca cacagctgcc atggttcaga aggccctgga    1140
aaccgaccca ggagatgccg tggttgtgcc gctttgcggg ttgctgattc tgactatgaa    1200
gccatttgta aggtacctcg aaaggtggcc agaagtatct cctgcggccc ttctagcagg    1260
tggtcgacca gcatttgcac tgaagaacca gcgttgtctg aggttgggcc acccgactta    1320
gcaagcacaa aggtaccccc agatggagaa agcatggagg aagagacgcc tggttcctct    1380
gtggaatctt tggatgcaag cgtccaggct agccctccac aacagaaaga tgaggagact    1440
gagagaagtg caaaggaact tggaaagtgt gactgttgtt cagatgatca ggctccgcag    1500
catgggtgta atcacaagct ggaattagct cttagcatga ttaaaggtct tgattataag    1560
cccatccaga gccccgagg gagcaggctt ccgattccag tgaaatccag cctacctgga    1620
```

```
gccaagcctg gccctagcat gacagatgga gttagttccg gtttccttaa caggtctttg      1680 aaacccettt acaagacacc tgtgagttat cccttggagc tttcagacct gcaggagctg      1740
tgggatgatc tctgtgaaga ttatttgccg ctccgggtcc agcccatgac tgaagagttg      1800
ctgaaacaac aaaagctgaa ttcacatgag accactataa ctcagcagtc tgtatctgat      1860
tcccacttgg cagaactcca ggaaaaaatc cagcaaacag aggccaccaa caagattctt      1920
caagagaaac ttaatgaaat gagctatgaa ctaaagtgtg ctcaggagtc gtctcaaaag      1980
caagatggta caattcagaa cctcaaggaa actctgaaaa gcagggaacg tgagactgag      2040
gagttgtacc aggtaattga aggtcaaaat gacacaatgg caaagcttcg agaaatgctg      2100
caccaaagcc agcttggaca acttcacagc tcagagggta cttctccagc tcagcaacag      2160
gtagctctgc ttgatcttca gagtgcttta ttctgcagcc aacttgaaat acagaagctc      2220
cagagggtgg tacgacagaa agagcgccaa ctggctgatg ccaaacaatg tgtgcaattt      2280
gtagaggctg cagcacacga gagtgaacag cagaaagagg cttcttggaa acataaccag      2340
gaattgcgaa aagccttgca gcagctacaa gaagaattgc agaataagag ccaacagctt      2400
cgtgcctggg aggctgaaaa atacaatgag attcgaaccc aggaacaaaa catccagcac      2460
ctaaaccata gtctgagtca caaggagcag ttgcttcagg aatttcggga gctcctacag      2520
tatcgagata actcagacaa aacccttgaa gcaaatgaaa tgttgcttga gaaacttcgc      2580
cagcgaatac atgataaagc tgttgctctg gagcgggcta tagatgaaaa attctctgct      2640
ctagaagaga agaaaaaga actgcgccag cttcgtcttg ctgtgagaga gcgagatcat      2700
gacttagaga gactgcgcga tgtcctctcc tccaatgaag ctactatgca aagtatggag      2760
agtctcctga gggccaaagg cctggaagtg aacagttat ctactacctg tcaaaacctc      2820
cagtggctga agaagaaat ggaaaccaaa tttagccgtt ggcagaagga acaagagagt      2880
atcattcagc agttacagac gtctcttcat gataggaaca agaagtggag ggatcttagt      2940
gcaacactgc tctgcaaact tggaccaggg cagagtgaga tagcagagga gctgtgccag      3000
cgtctacagc gaaaggaaag gatgctgcag gaccttctaa gtgatcgaaa taaacaagtg      3060
ctggaacatg aaatggagat tcaaggcctg cttcagtctg tgagcaccag ggagcaggaa      3120
agccaagctg ctgcagagaa gttggtgcaa gccttaatgg aaagaaattc agaattacag      3180
gccctgcgcc aatatttagg agggagagac tccctgatgt cccaagcacc catctctaac      3240
caacaagctg aagttacccc cactggccgt cttggaaaac agactgatca aggttcaatg      3300 cagataccttt ccagagatga tagcacttca ttgactgcca aagaggatgt cagcataccc      3360
agatccacat taggagactt ggacacagtt gcagggctgg aaaaagaact gagtaatgcc      3420
aaagaggaac ttgaactcat ggctaaaaaa gaaagagaaa gtcagatgga actttctgct      3480
ctacagtcca tgatggctgt gcaggaagaa gagctgcagg tgcaggctgc tgatatggag      3540
tctctgacca ggaacataca gattaaagaa gatctcataa aggacctgca aatgcaactg      3600
gttgatcctg aagacatacc agctatggaa cgcctgaccc aggaagtctt acttcttcgg      3660
gaaaaagttg cttcagtaga atcccagggt caagaaattt caggaaaccg aagacaacag      3720
ttgctgctga tgctagaagg actagtagat gaacggagtc ggctcaatga ggccttacaa      3780
gcagagagac agctctatag cagtctggtg aagttccatg cccatccaga gagctctgag      3840
agagaccgaa ctctgcaggt ggaactgaa gggctcagg tgttacgcag tcggctagaa      3900
gaagttcttg gaagaagctt ggagcgctta acaggctgg agaccctggc cgccattgga      3960
ggtgcagctg caggggatga caccgaagat acaagcactg agttcactga cagtattgag      4020
```

-continued

| | |
|---|---|
| gaggaggctg cacaccatag tcaccagcaa ctatagcttc agaagcattt ttacttgcaa | 4080 |
| gacgatggac acattcccct tgggcttttt gtaactgaaa cgcaccacag aagacaggga | 4140 |
| gtcatcgaag ggctgctcgg ggaggtggca gggcggagga cctgcttggg aagaaactcc | 4200 |
| aagaagattg gaatgcttcc aaagcaagaa tctttctcag tgaaatctca ttatacaaag | 4260 |
| agaaccttat gcaacctgac aaaccactga ggtcatggtg actcagtgat cagcagatgg | 4320 |
| tacttcaaca gcaatcccct gtcaaacctc agaacttgag gctgaaacat tgcttccacc | 4380 |
| caccatcagt gaagatgtaa ctagcatgtt acaagagtga ataatctgga cttcagagat | 4440 |
| taagtcacca atagtgatct cacaagcact caccggaact cctataatgt ctccactttg | 4500 |
| tccatgccat ttagcaatct catctcctaa atggactgtg cctatgattc ttaaggagaa | 4560 |
| agtgaatcat tggtagatat cctgcacaag cagctggact ttccagtaat agctttcttg | 4620 |
| gggctattag gaaaattaaa caagaaatga ggctttctgg gtctgcctgt atgtcttctg | 4680 |
| cataagacaa agaagagaca tcgaatcaac caataagaag agcccaaata agcatcctca | 4740 |
| aatcttttgg gatttggcac ttggggacat gagtagttgt ctgggatacg tcatattctc | 4800 |
| aacagtttct ttgtagtagt aggatcacct tcttataata ggatcacctt cttgttgcta | 4860 |
| tagctgtacc cgaccttccc ttctcccttg agtgcttgca tgagctccac ttttcctttt | 4920 |
| gcttgaacag cttctcctga gtcctcctta ccgatggttg tgactttaat tatatacatc | 4980 |
| tctgtccctc cagacagatc cctctgtcct cactctctga tttcattgag gatcttgggt | 5040 |
| gagagagagg gacctgcagg atgaacaaat gtctactcta agacagctag attgggaggt | 5100 |
| tggctggtca ctgatggtta taatgactgt gggacaggat taacttcaga ataaatgaac | 5160 |
| aggagacaca gatatgaaga aagtttctga ttgatatggt ctgaagtact cctggtattg | 5220 |
| caagtcattt gctctaattc tcaattgtag gcaaactgat ttgtaaattt gcttcttcag | 5280 |
| ccttctttcc tgtagcctag catggagaat ctgaccagac cccatttga aaggtcagc | 5340 |
| ctacactgga atgaactttt tacattaggg catttgtatt tccctcacaa tacttgccac | 5400 |
| attacttggc ataggagaga tgcttagtgt aattataagt taacaagcct ttggatcagg | 5460 |
| gcttgactca tgatagacaa agtatatgcc tgctggatgg aagaatctct tgggcgagca | 5520 |
| ccatttttct ttccatcacc tttccttgaa aatatatctt cagctttggg taggaggaat | 5580 |
| cttggtgtat gaaatcattg caaatttact tcatctttc tggagtttga agttgtgact | 5640 |
| ctcctgctac caattaaata aagcttactt tgccat | 5676 |

<210> SEQ ID NO 23
<211> LENGTH: 1866
<212> TYPE: DNA
<213> ORGANISM: homo sapiens

<400> SEQUENCE: 23

| | |
|---|---|
| atggcggatt tcgaagagtt gaggaatatg gtttctagtt ttagggtttc tgaactacaa | 60 |
| gtattactag gctttgctgg acggaataaa agtggacgca agcatgacct cctgatgagg | 120 |
| gcgctgcatt tattgaagag cggctgcagc cctgcggttc agattaaaat ccagaattg | 180 |
| tatagacgcc gatatccacg aactcttgaa ggactttctg atttatccac aatcaaatca | 240 |
| tcggttttca gtttggatgg tggctcatca cctgtagaac ctgacttggc cgtggctgga | 300 |
| atccactcgt tgccttccac ttcagttaca cctcactcac catcctctcc tgttggttct | 360 |
| gtgctgcttc aagatactaa gcccacattt gagatgcagc agccatctcc cccaattcct | 420 |
| cctgtccatc ctgatgtgca gttaaaaaat ctgcccttt atgatgtcct tgatgttctc | 480 |

| | |
|---|---|
| atcaagccca cgagtttagt tcaaagcagt attcagcgat ttcaagagaa gttttttatt | 540 |
| tttgctttga cacctcaaca agttagagag atatgcatat ccagggattt tttgccaggt | 600 |
| ggtaggagag attatacagt ccaagttcag ttgagacttt gcctggcaga gacaagttgc | 660 |
| cctcaagaag ataactatcc aaatagtcta tgtataaaag taaatgggaa gctatttcct | 720 |
| ttgcctggct atgcaccacc gcctaaaaat gggattgaac agaagcgccc tggacgcccc | 780 |
| ttgaatatta catctttagt taggttatct tcagctgtgc caaaccaaat ttccatttct | 840 |
| tgggcatcag aaattgggaa gaattactct atgtctgtat atcttgtacg gcagcttaca | 900 |
| tcagccatgt tattacagag attaaaaatg aaaggtatta gaaaccctga tcattccaga | 960 |
| gcactaatta agaaaaaact tactgcagat cctgatagtg aaattgctac aactagcctt | 1020 |
| cgggtatcct tgatgtgccc tttaggaaaa atgaggctga caatcccatg ccgtgcagtg | 1080 |
| acttgtacac atctgcagtg ttttgatgct gccctctatc tacaaatgaa tgagaaaaag | 1140 |
| cccacctgga tttgtcctgt gtgtgacaaa aaagctgcct atgaaagtct aatattagat | 1200 |
| gggcttttta tggaaattct caatgactgt tctgatgtag atgagatcaa attccaagaa | 1260 |
| gatggttctt ggtgtccaat gagaccgaag aaagaagcta tgaaagtatc cagccaaccg | 1320 |
| tgtacaaaaa tagaaagttc aagcgtcctc agtaagcctt gttcagtgac tgtagccagt | 1380 |
| gaggcaagca agaagaaagt agatgttatt gatcttacaa tagaaagctc ttctgacgaa | 1440 |
| gaggaagacc ctcctgccaa aaggaaatgc atctttatgt cagaaacaca aagcagccca | 1500 |
| accaaagggg ttctcatgta tcagccatct tctgtaaggg tgcccagtgt gacttcggtt | 1560 |
| gatcctgctg ctattccgcc ttcattaaca gactactcag taccattcca ccatacgcca | 1620 |
| atatcaagca tgtcatcaga tttgccaggt ttggattttc tttcccttat tccagttgat | 1680 |
| ccccagtact gtcctcctat gtttttggat agtctcacct caccttaac agcaagcagt | 1740 |
| acgtctgtca ccaccaccag ctcccatgaa agcagtactc atgttagttc atccagcagc | 1800 |
| aggagtgaga caggggtcat aaccagcagt ggaagtaaca ttcctgaaat catctcattg | 1860 |
| gactaa | 1866 |

<210> SEQ ID NO 24
<211> LENGTH: 2972
<212> TYPE: DNA
<213> ORGANISM: homo sapiens

<400> SEQUENCE: 24

| | |
|---|---|
| gcgcgcggct ccgatgggaa gcatgacccg ggtggcggga caagacttgc ttcccggcca | 60 |
| cgcgcgctcg gccggccgtg gggcggggca taggcgtgac gtggtgtcgc gtatcgagtc | 120 |
| tccgcccccct tccgcctcc ccgtatataa gacttcgccg agcactctca ctcgcacaag | 180 |
| tggaccgggg tgttgggtgc tagtcggcac cagaggcaag ggtgcgagga ccacggccgg | 240 |
| ctcggacgtg tgaccgcgcc taggggtgg cagcggggcag tgcggggcgg caaggcgacc | 300 |
| atggarcttt tgcggactat cacctaccag ccagccgcca gcaccaaaat gtgcgagcag | 360 |
| gcgctgggca agggttgcgg aggggactcg aagaagaagc ggccgccgca gccccccgag | 420 |
| gaatcgcagc cacctcagtc ccaggcgcaa gtgccccgg cggcccctca ccaccatcac | 480 |
| caccattcgc actcggggcc ggagatctcg cggattatcg tcgacccac gactgggaag | 540 |
| cgctactgcc ggggcaaagt gctgggaaag ggtggctttg caaaatgtta cgagatgaca | 600 |
| gatttgacaa ataacaaagt ctacgccgca aaaattattc ctcacagcag agtagctaaa | 660 |
| cctcatcaaa gggaaaagat tgacaaagaa atagagcttc acagaattct tcatcataag | 720 |

```
catgtagtgc agttttacca ctacttcgag gacaaagaaa acatttacat tctcttggaa    780
tactgcagta gaaggtcaat ggctcatatt ttgaaagcaa gaaaggtgtt gacagagcca    840
gaagttcgat actacctcag gcagattgtg tctggactga aataccttca tgaacaagaa    900
atcttgcaca gagatctcaa actagggaac tttttttatta atgaagccat ggaactaaaa   960
gttggggact tcggtctggc agccaggcta gaacccytgg aacacagaag gagaacgata   1020
tgtggtaccc caaattatct ctctcctgaa gtcctcaaca aacaaggaca tggctgtgaa   1080
tcagacattt gggccctggg ctgtgtaatg tatacaatgt tactagggag ccccccattt   1140
gaaactacaa atctcaaaga aacttatagg tgcataaggg aagcaaggta tacaatgccg   1200
tcctcattgc tggctcctgc caagcactta attgctagta tgttgtccaa aaacccagag   1260
gatcgtccca gtttggatga catcattcga catgactttt ttttgcaggg cttcactccg   1320
gacagactgt cttctagctg ttgtcataca gttccagatt tccacttatc aagcccagct   1380
aagaatttct ttaagaaagc agctgctgct ctttttggtg gcaaaaaaga caaagcaaga   1440
tatattgaca cacataatag agtgtctaaa gaagatgaag acatctacaa gcttaggcat   1500
gatttgaaaa agacttcaat aactcagcaa cccagcaaac acaggacaga tgaggagctc   1560
cagccaccta ccaccacagt tgccaggtct ggaacacccg cagtagaaaa caagcagcag   1620
attggggatg ctattcggat gatagtcaga gggactcttg gcagctgtag cagcagcagt   1680
gaatgccttg aagacagtac catgggaagt gttgcagaca cagtggcaag ggttcttcgg   1740
ggatgtctgg aaaacatgcc ggaagctgat tgcattccca aagagcagct gagcacatca   1800
tttcagtggg tcaccaaatg ggttgattac tctaacaaat atggctttgg gtaccagctc   1860
tcagaccaca ccgtcggtgt cctttttcaac aatggtgctc acatgagcct ccttccagac   1920
aaaaaaacag ttcactatta cgcagagctt ggccaatgct cagttttccc agcaacagat   1980
gctcctgagc aatttattag tcaagtgacg gtgctgaaat acttttctca ttacatggag   2040
gagaacctca tggatggtgg agatctgcct agtgttactg atattcgaag acctcggctc   2100
tacctccttc agtggctaaa atctgataag gccctaatga tgctctttaa tgatggcacc   2160
tttcaggtga atttctacca tgatcataca aaaatcatca tctgtagcca aaatgaagaa   2220
taccttctca cctacatcaa tgaggatagg atatctacaa cttttcaggct gacaactctg   2280
ctgatgtctg ctgttcatc agaattaaaa aatcgaatgg aatatgccct gaacatgctc   2340
ttacaaagat gtaactgaaa gacttttcga atggacccta tgggactcct ctttttccact  2400
gtgagatcta cagggaagcc aaaagaatga tctagagtat gttgaagaag atggacatgt   2460
ggtggtacga aaacaattcc cctgtggcct gctggactgg gtggaaccca gaaccaggct   2520
aaggcataca gttcttgact ttggacaatc ccaagagtga accagaatgc agttttcctt   2580
gagataccctg tttttaaaagg ttttttcagac aattttgcag aaaggtgcat tgattcttaa  2640
attctctctg ttgagagcat ttcagccaga ggactttgga actgtgaata tacttcctga   2700
aggggaggga gaagggagga agctcccatg ttgtttaaag gctgtaattg gagcagcttt   2760
tggctgcgta actgtgaact atggccatat ataatttttt tcattaatt tttgaagata    2820
cttgtggctg gaaaagtgca ttccttgtta ataaactttt tatttattac agcccaaaga   2880
gcagtattta ttatcaaaat gtctttttttt ttatgttgac catttttaaac cgttggcaat   2940
aaagagtatg aaaacgcaaa aaaaaaaaaa aa                                  2972
```

<210> SEQ ID NO 25
<211> LENGTH: 2805
<212> TYPE: DNA

<213> ORGANISM: homo sapiens

<400> SEQUENCE: 25

```
gctgagctgg acttggcggt gggagccgga gcctgcttgt tgcagctgtg ggtgaggacg      60
gctctagcta ggtgagcggc tccggccagt tcccttttag actatggcga catacctgga     120
gttcatccag cagaatgaag aacgggatgg tgtgcgtttt agttggaacg tgtggccttc     180
cagccggctg gaggctacaa gaatggttgt accccctggct tgtctcctta ctcctttgaa    240
agaacgtcca gacctacctc ctgtacaata tgaacctgtg ctttgcagca ggccaacttg     300
taaagctgtt ctcaacccac tttgtcaggt tgattatcga gcaaaacttt gggcctgtaa     360
tttctgtttt caaagaaatc agtttcctcc agcttatgga ggcatatctg aggtgaatca     420
acctgccgaa ttgatgcccc agttttctac aattgagtac gtgatacagc gaggtgctca     480
gtcccctctg atctttctct atgtggttga cacatgcctg gaggaagatg accttcaagc     540
actcaaagag tccctgcaga tgtccctgag tcttcttcct ccagatgctc tggtgggtct     600
gatcacattt ggaaggatgg tgcaggttca tgagctaagc tgtgaaggaa tctccaaaag     660
ttatgtcttc cgagggacca aggatttaac tgcaaagcaa atacaggata tgtgggcct      720
gaccaagcca gccatgccca tgcagcaagc acgacctgca caaccacagg agcacccttt     780
tgcttcaagc agatttctgc agcctgttca caagattgat atgaacctca ctgatcttct     840
tggggagcta cagagggacc catggccagt aactcagggg aagagacctt tgcgatccac     900
tggtgtggct ttgtccattg ctgttggctt gctggagggc acttttccaa acacaggagc     960
caggatcatg ctgtttactg gaggtccccc tacccaaggg cctggcatgg tggttggaga    1020
tgaattaaag attcctattc gttcttggca tgatattgag aaagataatg cacgattcat    1080
gaaaaaggca accaagcact atgagatgct tgctaatcga acagctgcaa atggtcactg    1140
cattgatatt tatgcttgtg cccttgatca aactggactt ttggagatga agtgttgtgc    1200
aaatcttact ggaggctaca tggtaatggg agattctttc aacacttctc tcttcaagca    1260
gacattccaa agaatcttta ctaaagattt taatggagat ttccgaatgg catttggtgc    1320
tactttggac gtaaagacct ctcgggaact gaagattgca ggagccattg gtccatgcgt    1380
atctctgaat gtgaaggac cgtgtgtgtc agaaaatgag cttggtgttg gtggcacgag    1440
tcagtggaaa atctgtggcc tagatcctac atctacactt ggcatctatt ttgaagttgt    1500
caatcagcac aacaccccga tcccccaagg aggcagagga gccatccagt tgtcacgca    1560
ttatcagcac tccagcaccc agagacgcat ccgcgtgacc accatcgccc gaaattgggc    1620
agatgtacag agtcagctca ggcacataga agcagcattt gaccaggagg ctgcggcagt    1680
gttgatggca cggcttgggg tgttccgagc ggagtcagag gaggggcccg atgtgctccg    1740
gtggctggac cgacaactca tccgactgtg tcaaaagttt ggacagtata caaagaaga    1800
ccccacttct tttaggttat cagattcctt ttctctatat cctcagttta tgttccatct    1860
gagaagatct ccatttcttc aagtgtttaa caacagtcct gatgagtcgt catattacag    1920
acatcatttt gccggcagg acctgaccca gtccctcatc atgatccagc ccattctcta    1980
ctcttactcc tttcatgggc caccagagcc agtactcttg atagcagca gcattctagc    2040
tgacagaatt ttgctgatgg atactttctt caaattgtc atttatcttg gtgagaccat    2100
agcccagtgg cgtaaagctg gctaccagga catgcccgag tatgaaaact tcaagcacct    2160
tctgcaggca ccactggatg atgctcaaga aattctgcaa gcacgcttcc cgatgccacg    2220
ttacatcaac acggagcatg gaggcagtca ggctcgattc cttttgtcca aagtgaaccc    2280
```

```
atctcagaca cacaataacc tgtatgcttg gggacaggaa actggagcac ccatcctaac    2340
tgatgatgtt agcctgcagg tgttcatgga ccatttgaag aagctggctg tctccagtgc    2400
ctgttaagct gaggatacaa ccaggaaatg caacggtgtc agattgtgtt caaaatgtct    2460
agaaaggctt gataacattc tgttactttt tctagcagat tttaacaaat aatcaaggac    2520
attttatatg taactcttta gattataatt tatttgtatt cctgtctttg tcctttttct    2580
tgcactataa aattataagg tcataaatgt tttggtactt gtagatgttt atgtgctttt    2640
tgtatcctaa cttttagaat ctaaataaaa tcagaggtaa tgtattttgg cagcttgttt    2700
aggtgagaat cttaatgatc ataaaaggaa ataaatctag atgcagaaag tactggctaa    2760
aatattgcta atacaaatgt gatttcctga aaaaaaaaaa aaaaa                    2805
```

<210> SEQ ID NO 26
<211> LENGTH: 766
<212> TYPE: DNA
<213> ORGANISM: homo sapiens

<400> SEQUENCE: 26

```
cactttgtca ccaactgctg ccaactcgcc accactgctg ccgcaatcgc aaccactgct     60
ttgtctctga agtgagactg ctcctggtgc catgaacgga gacgacacct ttgcaaagag    120
acccagggat gatgctaaag catcagagaa gagaagcaag gcctttgatg atattgccac    180
atacttctct aagaaagagt ggaaaaagat gaaatactcg gagaaaatca gctatgtgta    240
tatgaagaga aactataagg ccatgactaa actaggtttc aaagtcaccc tcccacccttt    300 catgtgtaat aaacaggcca cagacttcca ggggaatgat tttgataatg accataaccg    360
caggattcag gttgaacatc ctcagatgac tttcggcagg ctccacagaa tcatcccgaa    420
gatcatgccc aagaagccag cagaggacga aaatgattcg aagggagtgt cagaagcatc    480
tggcccacaa aacgatggga aacaactgca ccccccagga aaagcaaata tttctgagaa    540
gattaataag agatctggac ccaaaagggg gaaacatgcc tggacccaca gactgcgtga    600
gagaaagcag ctggtgattt atgaagagat cagtgaccct gaggaagatg acgagtaact    660
cccctggggg atacgacaca tgcccttgat gagaagcaga acgtggtgac ctttcacgaa    720
catgggcatg gctgcggctc cctcgtcatc aggtgcatag caagtg                  766
```

<210> SEQ ID NO 27
<211> LENGTH: 3432
<212> TYPE: DNA
<213> ORGANISM: homo sapiens
<220> FEATURE:
<221> NAME/KEY: misc_feature
<222> LOCATION: (2741)..(2741)
<223> OTHER INFORMATION: n = a, c, g or t/u

<400> SEQUENCE: 27

```
ctcgtcatgc gcaatgtggc gctgcggcgg gcggcagggc ctgtgtgtgc tgaggcggct     60
gagcggcgga catgcacacc acagagcgtg gcgatggaac agtaaccggg cttgtgagag    120
ggctctgcag tataaactag gagacaagat ccatggattc accgtaaacc aggtgacatc    180
tgttcccgag ctgttcctga ctgcagtgaa gctcacccat gatgacacag gagccaggta    240
tttacacctg gccagagaag acacgaataa tctgttcagc gtgcagttcc gtaccactcc    300
catggacagt actggtgttc ctcacattct tgagcatacc gtcctttgtg ggtctcaaaa    360
atatccgtgc agaaaccctt tcttcaaaat gttgaaccgg tccctctcca cgttcatgaa    420
cgccttcaca gctagtgatt atactctgta tccatttttcc acacaaaatc ccaaggactt    480
```

```
tcagaatctc ctctcggtgt atttggatgc cacctttcc ccatgtttac gcgagctgga    540
tttctggcag gaaggatggc ggctggaaca tgagaatccg agcgaccccc agacgccctt    600
ggtctttaaa ggagtcgtct ttaatgagat gaagggagcg tttacagaca atgagaggat    660
attctcccag caccttcaga acagacttct tcccgaccac acgtactcag tggtctccgg    720
gggtgaccca ctgtgcatcc cggagcttac atgggagcag cttaagcagt tcatgccac     780
tcactatcac ccaagcaatg ctaggttctt cacgtacggt aattttccat tagaacagca    840
tctgaaacaa attcacgagg aagcactgag caaattccag aaaattgaac caagcaccgt    900
ggtgccagct cagacaccct gggacaagcc tagggaattc cagataacat gtggcccgga    960
ttcatttgct acagatccct ctaaacaaac aaccgtcagc gttagcttcc tcttaccgga   1020
catcaccgac acatttgaag ccttcacatt aagtcttctg tcttcactct tgacttctgg   1080
gcccaattct cccttttaca aagccttgat tgaatctggc cttggcacag aatttttctcc  1140
tgatgttgga tataatggct acacgaggga ggcctacttt agtgtcggcc tccaagggat   1200
tgtggagaaa gacattgaga ccgtcagaag cctcatagac agaacgattg atgaagtagt   1260
tgagacaagg attgaagatg atcgaattga ggctttactt cataaaattg aaatacagat   1320
gaaacatcag tctaccagct ttgggctgat gctgacatca tacatagctt cttgctggaa   1380
ccatgatggg gaccctgtgg agctcttgaa gttgggaaat cagttagcta aattcagaca   1440
gtgcctgcag gaaaatccaa aattttgca agaaaaagta aaacagtatt ttaagaataa    1500
ccagcataag ctgactttat cgatgaggcc agatgacaag tatcacgaga gcaggcaca    1560
ggtggaagcc acgaagctca agcagaaggt cgaggctctg tcccccggag acaggcagca   1620
gatctacgag aaaggtctag aattacggag tcaacaaagc aaacctcaag atgcctcttg   1680
tctgccagcg ttgaaagttt ccgatattga acccaccata cctgtcacag agttggacgt   1740
ggtcctgaca gctggagata tccctgttca gtactgcgcc cagcccacca atggcatggt   1800
gtatttccgg gccttctcca gcctgaacac actccccgag gagctgaggc cctatgtgcc   1860
cctcttctgc agcatcctca ccaagctggg ctgcggcctt cttgactacc gggagcaggc   1920
tcagcagata gaattgaaga ccggagggat gagtgcttct ccccacgtgc tccccgacga   1980
ctcacacatg gacacctacg agcaggtagg tgtgcttttc tcctctctct gcctggatcg   2040
aaacctgcca gacatgatgc agctatggag tgaaatattt aacaacccgt gctttgaaga   2100
agaggagcac ttcaaggtgc tggtgaagat gaccgcccag gagctcgcca atggaattcc   2160
tgactctggg cacctgtacg catccatcag ggcaggccgg accctcacgc ccgcagggga   2220
cctgcaggag accttcagcg ggatggatca ggtgcggctg atgaagagga ttgcagaaat   2280
gacagatatc aaacccatcc tgaggaagct cccgcgtatc aagaaacact tgttaaatgg   2340
tgataatatg aggtgttcag tgaatgcgac tcctcagcag atgcctcaga cagaaaaagc   2400
ggtcgaagac ttccttagaa gcatcggtcg gagtaaaaag gaacggaggc ctgtgcgccc   2460
acacacggtc gagaaacctg tgcccagcag ctctggtgga gatgcccacg ttccccatgg   2520
ctcccaggtc attaggaagc tggtcatgga acccaccttc aagccctggc agatgaagac   2580
tcacttcctg atgcccttcc cggtgaatta cgtgggtgaa tgcatccgaa ctgtccccta   2640
cacggaccca gatcatgcca gtcttaaaat ccttgcacgt ttgatgactg ccaaattctt   2700
gcatacagaa attcgagaaa aaggcggtgc ttatggtgga ngcgcaaaac tcagccacaa   2760
tgggattttc accctttact cttacaggga cccaaataca atagagacgc tccagtcttt   2820
tgggaaggct gtcgactggg ctaagtctgg aaaaattcaca cagcaagaca tcgacgaagc   2880
```

| caaactttct gtcttctcaa ccgtagatgc tcctgtcgct ccttcagaca aggaatgga | 2940 |
| ccacttcttg tacggcctct cggatgagat gaagcaggcc cacagagagc agctctttgc | 3000 |
| tgtcagccac gacaagctcc tggccgtgag cgataggtac ctcggcactg ggaagagcac | 3060 |
| acacggcctg gccatcctcg gacccgagaa cccgaaaatt gccaaggacc atcctggat | 3120 |
| catccgatga gcagccgtgg cgctcgactg cacaggagcc cgagacaata cacctccaag | 3180 |
| ctgaatatga aaagtcagaa atgctactgc ttttccaag aatattatgt cattgagtgt | 3240 |
| cgccaaagcc cttgactggc gagtcaaaaa ctcagatcta tcttaagagt gaccaggaag | 3300 |
| aggttcattg aaataatcat gcatgaagcg ccaaagatgc accatgtaga attttcactt | 3360 |
| tgtactggca ggctcgtttt acctgattct agaatattta agaatctaaa aataaagggc | 3420 |
| aactctgact ta | 3432 |

<210> SEQ ID NO 28
<211> LENGTH: 1232
<212> TYPE: DNA
<213> ORGANISM: homo sapiens

<400> SEQUENCE: 28

| tttcccgaga tcaccaagat gctgggcgcc gagtggagca agctgcagcc aacggaaaag | 60 |
| cagcggtacc tggatgaggc cgagagagag aagcagcagt acatgaagga gctgcgggcg | 120 |
| taccagcagt ctgaagccta aagatgtgc acggagaaga tccaggagaa gaagatcaag | 180 |
| aaagaagact cgagctctgg gctcatgaac actctcctga atggacacaa gggtgggggac | 240 |
| tgcgatggct tctccacctt cgatgttccc atcttcactg aagagttctt ggaccaaaac | 300 |
| aaagcgcgtg aggcggagct tcggcgcttg cggaagatga atgtggcctt cgaggagcag | 360 |
| aacgcggtac tgcagaggca aaacgcagag catgagcagc gcgcgcgagc gtctggagca | 420 |
| ggagctggcg ctggaggagc ggaggacgct ggcgctgcag cagcagctcc aggccgtgcg | 480 |
| ccaggcgctc accgccagct tcgcctcact gccggtgccg ggcacgggcg aaacgcccac | 540 |
| gctgggcact ctggacttct acatggcccg gcttcacgga gccatcgagc gcgaccccgc | 600 |
| ccagcacgag aagctcatcg tccgcatcaa ggaaatcctg gcccaggtcg ccagcgagca | 660 |
| cctgtgagga gtgggcgggc ccacgatgca gaggagaagc tgtgggcgcg gccctgccac | 720 |
| accccacccc gtgacgagag ggctggggt ccacccttg gggcctggtc ccatcctgca | 780 |
| cctttggggg ctccagcccc cctaaaatta aatttctgca gcatcccttt agctttcaat | 840 |
| ctccccagcc cctgaaccc ggaaaaagca ctcgctgcgc gatacaccca gaagaacctc | 900 |
| acagccgagg gtgcccctcc tcggaggaca gccacgcgct acactggctc tccgggccac | 960 |
| ccccaggaca cagggcagac gaaacccacc ccagcacac ggcaggaccc cccaaattac | 1020 |
| tcactacggg gggctgtgcc ataggccaca caggaagctg ccttgtgggg acttacctgg | 1080 |
| ggtgtccccc gcatgcctgt acccccagatg ggtgggggcc ggctttgccc atcctgctct | 1140 |
| cctccagccg agggaccctg gtgggggtgg ctccttctca ctgctggatc cggacttttt | 1200 |
| aaataaaaac aagtaaaatt tgtgttttaa aa | 1232 |

<210> SEQ ID NO 29
<211> LENGTH: 1313
<212> TYPE: DNA
<213> ORGANISM: homo sapiens

<400> SEQUENCE: 29

| aattggagga gttgttgtta ggccgtcccg gagacccggt cgggagggag gaaggtggca | 60 |

```
agatggtgtt ggaaagcact atggtgtgtg tggacaacag tgagtatatg cggaatggag      120
acttcttacc caccaggctg caggcccagc aggatgctgt caacatagtt tgtcattcaa      180
agacccgcag caaccctgag aacaacgtgg gccttatcac actggctaat gactgtgaag      240
tgctgaccac actcacccca gacactggcc gtatcctgtc caagctacat actgtccaac      300
ccaagggcaa gatcaccttc tgcacgggca tccgcgtggc ccatctggct ctgaagcacc      360
gacaaggcaa gaatcacaag atgcgcatca ttgcctttgt gggaagccca gtggaggaca      420
atgagaagga tctggtgaaa ctggctaaac gcctcaagaa ggagaaagta aatgttgaca      480
ttatcaattt tggggaagag gaggtgaaca cagaaaagct gacagccttt gtaaacacgt      540
tgaatggcaa agatggaacc ggttctcatc tggtgacagt gcctcctggg cccagtttgg      600
ctgatgctct catcagttct ccgatttggg ctggtgaagg tggtgccatg ctgggtcttg      660
gtgccagtga ctttgaattt ggagtagatc ccagtgctga tcctgagctg gccttggccc      720
ttcgtgtatc tatggaagag cagcggcagc ggcaggagga ggaggcccgg cgggcagctg      780
cagcttctgc tgctgaggcc gggattgcta cgactgggac tgaagactca gacgatgccc      840
tgctgaagat gaccatcagc cagcaagagt ttggccgcac tgggcttcct gacctaagca      900
gtatgactga ggaagagcag attgcttatg ccatgcagat gtccctgcag ggagcagagt      960
ttggccaggc ggaatcagca gacattgatg ccagctcagc tatggacaca tctgagccag     1020
ccaaggagga ggatgattac gacgtgatgc aggaccccga gttccttcag agtgtcctag     1080
agaacctccc caggtgtggat cccaacaatg aagccattcg aaatgctatg ggctccctgg     1140
cctcccaggc caccaaggac ggcaagaagg acaagaagga ggaagacaag aagtgagact     1200
ggagggaaag ggtagctgag tctgcttagg ggactgcatg ggaagcacgg aatatagggt     1260
tagatgtgtg ttatctgtaa ccattacagc ctaaataaag cttggcaact ttt           1313

<210> SEQ ID NO 30
<211> LENGTH: 1682
<212> TYPE: DNA
<213> ORGANISM: homo sapiens

<400> SEQUENCE: 30
cctgctgagg ccaagctcgg atccggtgcc gagccaagcg gggccgtgcg tcgccggcct       60
tcgctcgcgt gacctccgcc gtcctcccca accctcgtcc tctgcgcctg cggccgcagc      120
cccagcgccc ctcgcctaac ctcccgccgg gccgcgcctc ctcctcctcc tgctccccgc      180
cgcttccgtt tctcgaggga aaggctgctg cctcctgctc tgtcctcatc cccggcttag      240
ctgacggccc agaggtgggt gccaattcca ccagcagctg caactgaaaa gcaaggttca      300
gaaatgtcag atatcctccg ggagctgctc tgtgtctctg agaaggctgc taacattgcc      360
cgggcgtgca gacagcagga agccctcttc cagctgctga tcgaagaaaa gaaagaggga      420
gaaaagaaca gaagtttgc agttgacttc aagactctgg ctgatgtact ggtacaggaa      480
gttataaaac agaatatgga gaacaagttt ccaggcttgg aaaaaaatat ttttggagaa      540
gaatccaatg agtttactaa tgactggggg gaaaagatta ccttgaggtt gtgttcaaca      600
gaggaagaaa cagcagagct tcttagcaaa gtcctcaatg gtaacaaggt agcatctgaa      660
gcattagcca gggttgttca tcaggatgtt gcctttactg acccaactct ggattccaca      720
gagatcaatg ttccacagga cattttggga atttgggtgg accccataga ttcaacttat      780
cagtatataa aaggttctgc tgacattaaa tccaaccagg gaatcttccc ctgtggactt      840
cagtgtgtca ccatttttaat tggtgtctat gacatacaga caggggttcc cctgatggga      900
```

| | |
|---|---|
| gtcatcaatc aaccttttgt gtcacgagat ccaaacaccc tcaggtggaa aggacagtgc | 960 |
| tattggggcc tttcttacat ggggaccaac atgcattcac tacagctcac catctctaga | 1020 |
| agaaacggca gtgaaacaca cactggaaac accggctctg aggcagcatt ctcccccagt | 1080 |
| tttttcagccg taattagtac aagtgaaaag gagactatca aagctgcatt gtcacgtgtg | 1140 |
| tgtggagatc gcatatttgg ggcagctggg gctggttata agagcctatg tgttgtccaa | 1200 |
| ggcctcgttg acatttacat cttttcagaa gataccacat tcaaatggga ctcttgtgct | 1260 |
| gctcatgcca tactgcgggc catgggtggg ggaatagtag acttgaaaga atgcttagaa | 1320 |
| agaaatccag aaacagggct tgatttgcca cagttggtgt accacgtgga aaatgagggt | 1380 |
| gctgctgggg tggatcggtg ggccaacaag ggaggactca ttgcatacag atccaggaag | 1440 |
| cggctggaga cattcctgag cctcctggtc caaaacctgg cacctgcaga gacgcatacc | 1500 |
| tagaggaact ctaaccccgg tgtacctgta taaactgaac tgtgaaactg tttcggttat | 1560 |
| ctctgtcttt tgaggatggc tttgtcctgt tgctggttaa cattcacctt cctcttttga | 1620 |
| ggagtatttt tccattatgt attcataata atgttaattt caataaatga cattcatgca | 1680 |
| gc | 1682 |

<210> SEQ ID NO 31
<211> LENGTH: 1511
<212> TYPE: DNA
<213> ORGANISM: homo sapiens

<400> SEQUENCE: 31

| | |
|---|---|
| cgacgcggga gccgcacgcg ccggacgagg ctcgctgcgc tccctgttgc ccagcgcggg | 60 |
| cccgttgagg cggagccctc agttcccggc caggacacgg tctgggccgc cgaatctccg | 120 |
| gccgaagagc ggcggcggca gcggcgggaa aaaaatgaag aatgaaattg ctgccgttgt | 180 |
| cttctttttc acaaggctag ttcgaaaaca tgataagttg aaaaaagagg cagttgagag | 240 |
| gtttgctgag aaattgaccc taatacttca agaaaaatat aaaaatcact ggtatccaga | 300 |
| aaaaccatcg aaaggacagg cctacagatg tattcgtgtc aataaatttc agagagttga | 360 |
| tcctgatgtc ctgaaagcct gtgaaaacag ctgcatcttg tatagtgacc tgggcttgcc | 420 |
| aaaggagctc actctctggg tggacccatg tgaggtgtgc tgtcgtagag atggggtttc | 480 |
| accatgttgg ccagactgct ctcaaactcc tgacctcgtg atccgcccgc cttggcctcc | 540 |
| caaagcgctg gattacaggc gtgagccact gcgcccggcc tcctcctttt tgattatgta | 600 |
| tggagagaaa acaatgcat tcattgttgc cagctttgaa aataaagatg agaacaagga | 660 |
| tgagatctcc aggaaagtta ccagggccct tgataaggtt acctctgatt atcattcagg | 720 |
| atcctcttct tcagatgaag aaacaagtaa ggaaatggaa gtgaaaccca gttcggtgac | 780 |
| tgcagccgca agtcctgtgt accagatttc agaacttata tttccacctc ttccaatgtg | 840 |
| gcacccttg cccagaaaaa agccaggaat gtatcgaggg aatggccatc agaatcacta | 900 |
| tcctcctcct gttccatttg ttatccaaa tcagggaaga aaaaataaac catatcgccc | 960 |
| aattccagtg acatgggtac ctcctcctgg aatgcattgt gaccggaatc actggattaa | 1020 |
| tcctcacatg ttagcacctc actaacttcg ttttgattg tgttggtgtc atgttgagaa | 1080 |
| aaaggtagaa taaccttac tacacattaa aagtaaaag ttcttactaa tagtagtgaa | 1140 |
| gttagatggg ccaaaccatc aaacttattt ttatagaagt tattgagaat aatctttctt | 1200 |
| aaaaaatata tgcactttag atattgatat agtttgagaa attttattaa agttagtcaa | 1260 |
| gtgcctaagt ttttaatatt ggacttgagt atttatatat tgtgcatcaa ctctgttgga | 1320 |

```
tacgagaacc ctgtagaagt ggacgatttg tttagcccc tttgagaatt tactttatgg    1380
agcgtatgta agttatttat atacaaggaa atctatttta tgtcgttgtt taagagaatt    1440
gtgtgaaatc atgtagttgc aaataaaaaa tagtttgagg caaaaaaaaa aaaaaaaaa     1500 aaaaaaaaaa a                                                         1511

<210> SEQ ID NO 32
<211> LENGTH: 1250
<212> TYPE: DNA
<213> ORGANISM: homo sapiens

<400> SEQUENCE: 32
acacgccgat tgcccttttt gattcttcca caatcagggt gagactgctc ccagtgccat      60
gaacggagac gacgcctttg caaggagacc cagggatgat gctcaaatat cagagaagtt    120
acgaaaggcc ttcgatgata ttgccaaata cttctctaag aaagagtggg aaaagatgaa    180
atcctcggag aaaatcgtct atgtgtatat gaagctaaac tatgaggtca tgactaaact    240
aggtttcaag gtcacccctcc cacctttcat gcgtagtaaa cgggctgcag acttccacgg    300
gaatgatttt ggtaacgatc gaaccacag gaatcaggtt gaacgtcctc agatgacttt     360
cggcagcctc cagagaatct tcccgaagat catgcccaag aagccagcag aggaagaaaa    420
tggtttgaag gaagtgccag aggcatctgg cccacaaaat gatgggaaac agctgtgccc    480
cccgggaaat ccaagtacct tggagaagat caacaagaca tctggaccca aaggggggaa    540
acatgcctgg acccacagac tgcgtgagag aaagcagctg gtggtttatg aagagatcag    600
cgaccctgag gaagatgacg agtaactccc ctcgggata tgacacatgc ccatgatgag     660
aagcagaacg tggtgacctt tcacgaacat gggcatggct gcggacccct cgtcatcagg    720
tgcatagcaa gtgaaagcaa gtgttcacaa cagtgaaaag ttgagcgtca tttttcttag    780
tgtgccaaga gttcgatgtt ggcgtttccg ctgtattttc ttgcagtgtg ccattctgtt    840
agacattagc gttttcgctg atgagcaaga catgcttaat gcatatttcg gcttgtgtat    900
ccatgcacct acctcagaaa caagtattg tcaggtattc tctccataga acagcactac     960
cctcctctct ccccagatgt gactactgag gggaggtctg agtgtttaat ttccgattt    1020 ttcctctgca tttacacaca caccacacac gcacacacac acaccaagta ccagtataag   1080
catctcccat ctgctttttct ccattgccat gcgtcctggt caagccccccc tcactctgtt   1140 tcctgttcag catgtactcc cctcatccga ttccgttgta tcagtcactg acagttaata   1200
aacctttgca aacgttcaac aaaaaaaaaa aaaaaaaaaa aaaaaaaaaa              1250

<210> SEQ ID NO 33
<211> LENGTH: 6792
<212> TYPE: DNA
<213> ORGANISM: homo sapiens

<400> SEQUENCE: 33
ctccagtccg catgctcagt agctgctgcc ggccgggctg cggggcggcg tccgctgcgc     60
gcctacgggc tgcggtggcg gccgccgcgg caccccggcag ggcccgccag tccccgcttc   120
cctgctccag agccgccgcc tgggccgggg cagggcgggc ccggggctcc tccatgctgc   180
cagccgccgg gctgcggagc cgaccaagtg gctcctgcga tggcggcgga agaggaggct   240
gcggcgggag gtaaagtgtt gagagaggag aaccagtgca ttgctcctgt ggtttccagc   300
cgcgtgagtc cagggacaag accaacagct atggggtctt tcagctcaca catgacagag   360
tttccacgaa aacgcaaagg aagtgattca gacccatccc aagtggaaga tggtgaacac   420
```

```
caagttaaaa tgaaggcctt cagagaagct catagccaaa ctgaaaagcg gaggagagat      480
aaaatgaata acctgattga agaactgtct gcaatgatcc ctcagtgcaa ccccatggcg      540
cgtaaactgg acaaacttac agttttaaga atggctgttc aacacttgag atctttaaaa      600
ggcttgacaa attcttatgt gggaagtaat tatagaccat catttcttca ggataatgag      660
ctcagacatt taatccttaa gactgcagaa ggcttcttat ttgtggttgg atgtgaaaga      720
ggaaaaattc tcttcgtttc taagtcagtc tccaaaatac ttaattatga tcaggctagt      780
ttgactggac aaagcttatt tgacttctta catccaaaag atgttgccaa agtaaaggaa      840
caactttctt cttttgatat ttcaccaaga gaaaagctaa tagatgccaa aactggtttg      900
caagttcaca gtaatctcca cgctggaagg acacgtgtgt attctggctc aagacgatct      960
tttttctgtc ggataaagag ttgtaaaatc tctgtcaaag aagagcatgg atgcttaccc     1020
aactcaaaga agaaagagca cagaaaattc tatactatcc attgcactgg ttacttgaga     1080
agctggcctc caaatattgt tggaatggaa gagaaaagga acagtaagaa agacaacagt     1140
aattttacct gccttgtggc cattggaaga ttacagccat atattgttcc acagaacagt     1200
ggagagatta atgtgaaacc aactgaattt ataacccggt ttgcagtgaa tggaaaattt     1260
gtctatgtag atcaaagggc aacagcgatt ttaggatatc tgcctcagga acttttggga     1320
acttcttgtt atgaatattt tcatcaagat gaccacaata atttgactga caagcacaaa     1380
gcagttctac agagtaagga gaaaatactt acagattcct acaaattcag agcaaaagat     1440
ggctcttttg taactttaaa aagccaatgg tttagtttca caaatccttg gacaaaagaa     1500
ctggaatata ttgtatctgt caacactttg gttttgggac atagtgagcc tggagaagca     1560
tcatttttac cttgtagctc tcaatcatca gaagaatcct ctagacagtc ctgtatgagt     1620
gtacctggaa tgtctactgg aacagtactt ggtgctggta gtattggaac agatattgca     1680
aatgaaattc tggatttaca gaggttacag tcttcttcat accttgatga ttcgagtcca     1740
acaggtttaa tgaaagatac tcatactgta aactgcagga gtatgtcaaa taaggagttg     1800
tttccaccaa gtccttctga atgggggag ctagaggcta ccaggcaaaa ccagagtact     1860
gttgctgtcc acagccatga gccactcctc agtgatggtg cacagttgga tttcgatgcc     1920
ctatgtgaca atgatgacac agccatggct gcatttatga attacttaga agcagagggg     1980
ggcctgggag accctgggga cttcagtgac atccagtgga ccctctagcc tttgattttt     2040
aactccaaaa atgagaaaca ttttaaagca ttatttacga aaaaactgtc tcaactattc     2100
ttaagtactg tattgatatt gtttgtatct tttattaatg ttctaccact ttttatagat     2160
ttgcatcttc ctgtcacagg gatgtgggga aatacgtttt cctcccaaga gaaccaagtt     2220
tattatagac tcctttattc agtgaaatgg cttataatcc actagttgcc atattttgc      2280 taaaatattt ctaaccaaga atactactta catattgttt tggctttgtt ttattttga      2340 tgcagttttt tttagttgag gtaatgtaat atattgatgt tttcctttgt gtctaagatt     2400
gatttataat agtaggtttg tataatttgg aacattttcc atgccttgcg aatttcctta     2460
attgaggata gggcttacac actttaagaa aacagtgagt acttgaacat ttaaagggac     2520
agtgcaattt atagtcataa tcacattgaa tactgtattt gatctttgga gacttaggca     2580
agcacagagc tgggatattt atgctcagtt gagcacttta agatgaattt taagtgagat     2640
gatttcttgc ttaaaactca gaaagtcaaa agagtttcag ctttccttac agaaaaggaa     2700
ggatcttggg ccctagatct tggggattaa cctctgcata taagatttac tcttaatagg     2760
ccagacgtgg tgctcacgcc tgtaatccca gtactttggg aggctgagac gggcagatca     2820
```

```
cttgaggtca ggagttcaag accagcctgg ccaatatggt gaaacccgt ttctactaaa      2880 aatacaaaaa aaattaccca ggcactcact cttgaggtaa ctaaccaact cccacgataa      2940
tgacagtcca ttcatgagcg caaaggcctc atgacctaat ggcacacacc tgtaatccca      3000
actgcttggg aggctgaggc gagaggattg cttgaacctg ggaggcagag gttgcagtga      3060
gccgagatcg caccactgca ctccagtctg gcaacagag tgagacttca tctcaaaaaa      3120
agtaaaaaaa aagatttaat ataatcactg aagatctcta ttatagatag attaggtttt      3180
tgacattgga aacatactta gggatagatt tgtcctaaag gaaaaaagta ggcccgggca      3240
gattaaatgt cttgtgtaaa gtcacacatt aaattcagtc acacattaaa ttcatagagt      3300
tttaaatgtt taatgtatat aaaccagttt ctttatacac atttgggaaa acattggtct      3360
cacagattaa atgattaact aactgaccca ggaactagtt gtagctttct aagtaattag      3420
gcaattacag ttattgcctg taaccaaagg taataaaaca aaatgacaag tacatgttta      3480
aaattatgag gcaatgagaa ataatttaaa aaccaatttt ctagttataa tttaaaattt      3540
ggagagcatt tttaacagta attaatccag aggtggctca aattgagtat aagaattaag      3600
attatttaaa atactgcatg tctaccttct cggggatcat actttataac actttctgct      3660
tcagtagctc ttcatagctt gccaagtatg ctcccatatt ttctctctcg tgcctcgcaa      3720
atgaaagtca gataggctgg gaactcatgg ggcagccctc agacttcaat gtgggcttca      3780
aatccagttt cctgttctat atggtgctac atctttccag aaaatttccc tcagagcccc      3840
tcgccaaaac aaagcattat tttgacccctg catgctattt ctttagctgt aggtgataga      3900
ttagaacttc tgtcagacat gttaatgaca aacataccaa cagacaataa ccaaagcaaa      3960
tgtttccttc aagtgtgaaa tgtgcagggg ctcgtgggca aggatgtatt ggcacactgt      4020
cctcttgaac tgatagtgtc ccagcaatgt tggaggttgg caccattcct ggtccgacac      4080
ttgaggacct gagagacatc aggtttagaa tgagccaaag aaatcctaca agatggggag      4140
aattggtgtg cagcagccta agtgttatag ttaagtctaa agaagtatga aagatccct      4200 gtgttctcta aattgagcag aggggcctgc ctaccaatat cacttttag gggactgaac      4260 cattgcaggt tagacttggc ttccaaagag tctgcctaag ccaggggtgg cagggtaggc      4320
catcatagct ggatggcctc aaaagcagat ggggcagac ttgccctcgt gatgccagga      4380
tttgagaggc agagtttcta gagggagacc agtgctgcct ctcacagtgg cagttttttc      4440
tctttgcaag aggagggggct gttcaattcc atagaccagt gggcagatag ccagttgaat      4500
actctgtgca tggtttgatc ctttattagt tcgctctaat attttctgt agatcctttt      4560 gtcctggact caaaatctaa tccatgcatt gtatgatacc gtagctctcc taaggtttgt      4620
gtttccttca aaatgtttta gttttcttca actaaatttg attttttgctg ttagaagtga      4680 catatttta tggtatacac tatgttcctt ttttctactg cgagtcaatt ttttgaattt      4740
tcgtgagaaa gaatatatct acaaattgca cgaaagtatc ataaaaacag tactctagag      4800
cagcgctgtc aatagaaat ataatctgag ccacatgtat aatttatttt tcttctagcc      4860
acattaaaga agtaaaaaga tacaagtaga actaattttta atgttttaat tcagtatatc      4920
caaaatatca tttgaacatg taattaatat aaaattatta atgtgatatt ttacattctt      4980
ttggtaatac tagtccttcaa aatctggtat gtatcttaca ttgatagcac atctcacttt      5040
gtactagcca cattgcaagt gctcagtagc cacatgtggc tagtggctac tgcactggac      5100
agcacagttc taggttccac cctaacaccc aagtcctgtg gattagaatc ccagaatcag      5160
agctggaagt aaacatagag atcaaacctc ctttttaaaaa tgaggacgct gaggcacaga      5220
```

```
gtttaaatgg cttgcatgag gtcatacagc taaattcagc ctcaacaggg tcttctgatt    5280
ccaggcactc ttcccactcc actacattac tgtagtggta attcttaggg ttaaaaaaag    5340
tgtagagtag gccgggcgca gtggctcatg cctgtaatcc cagcactttg ggaggccgaa    5400
gtgggcggat cacgaggtca ggagatcgag accatcctgg ccaacatggt gaaacccgt     5460 ctctactgaa aatacaaagc aaaattagcc aggtgtggtg gcgggcgcct gtggtcccag    5520
ctgctctgga ggctgaggca gaatggcgtg aacccaggag gcagagatgg cagtgagcca    5580
agatcgcgcc actgcacccc agcctgggcg acagagcgag actccatctc aaaaaaaaaa    5640
aaaaaaaaaa aagaaaagaa aagaaaagtc tagagaacat tatattaagt ggttattatt    5700
gaagtagacc aaagtttata ccataaggat attttccctt aaataccatg tttgaagaac    5760
aattatttat tgatccttga atctgtaaga tcaaataaca agtctctatc catgttacca    5820
aatttaacct tttgaaaata ataaacttta aaatatcaga tgtgttatta caggatgata    5880
cttggaatca agtgaaatga gttatatggt catcactaaa tttagaaatc tattgtgaaa    5940
caaagacaaa caggaaagta cagaatagag acttttagta aataaatgga atttaaaaga    6000
aagtgtttat ttacagtgtc acgacagaaa aggatgtctt tgttgtcata gtctttgagg    6060
gatctccgta aaatctgggg cacaggtaca agaaatagcc aatatttagt tcccagacca    6120
tgtttagtag tgtccagttt cagatcatgc tgccaagagg tatctccccc tcaggtgggt    6180
catcactgag ccctggaatt ggagactcat acttgcccag cacaatgtta cgggcagaca    6240
ggccgacatc tatgattagc tagaagccat aaagaaaagc tgctaagtgg ccactaggtg    6300
ccactttcct gtttttgtaa tgctttcatt agcagatctt ttttttccaa gctccatggg    6360
gcctatgaga ggcatttatg attttttgtgc ctacaataag tcagcctgtc tggtgtgagt    6420
tgttttatga gaaatgcttt ccaagggagg tctaggaaga tcctgacaca taagaacttt    6480
ggcttagaga gctttccagg tgtagtgcca ataaaaactg acctggaaag aaaacctgcc    6540
cagcacggaa catgctttct gaactcactt gagagtgtat ggtgtatgtc acttctcata    6600
tattcttgag tttagatttg tctttttatac aattttttagc tcttttccag ttcacttgtg    6660
ctcgtctgta tattggtatt tttaaatttt tgtggtaaat aatgaaaaga gtgaaattat    6720
attttataat tactcatttg tagtttttttt ttttaattta ataaacttcc tccaaaaagt    6780
gctcccttaa aa                                                        6792
```

<210> SEQ ID NO 34
<211> LENGTH: 2946
<212> TYPE: DNA
<213> ORGANISM: homo sapiens

<400> SEQUENCE: 34

```
tcctggaatt gcacgcgctt cctgaccacc aggctctggc ccttgagaag ccagcggggc      60
tttgtccctg ttgctctcct tgccaaaccc agtctctctg ctagtggtgg tttcggttgc     120
gacaccgtcc aggttcccag gcaggaaccg ctcggcctgg ctgcttagct acttttcact     180
gaggaggtgg tggaaggtgt cgcctgctct ggctgagtaa gggtggctgg ctgagccggc     240
agcccccgcc ctaggcctgg ctcttcccgg cctctgtact ttgccctcgc tgcctgacag     300
gttctgctgt gggctctgct gaatggaagt cgctggtagt ccttttccct ttctccagtc     360
ggcccacctt gggacacctt gactccaagc ccagcagtaa gtccaacatg attcggggcc     420
gcaactcagc cacctctgct gatgagcagc cccacattgg aaactaccgg ctcctcaaga     480
ccattggcaa gggtaatttt gccaaggtga agttggcccg acacatcctg actgggaaag     540
```

```
aggtagctgt gaagatcatt gacaagactc aactgaactc ctccagcctc cagaaactat    600
tccgcgaagt aagaataatg aaggttttga atcatcccaa catagttaaa ttatttgaag    660
tgattgagac tgagaaaacg ctctaccttg tcatggagta cgctagtggc ggagaggtat    720
ttgattacct agtggctcat ggcaggatga aagaaaaaga ggctcgagcc aaattccgcc    780
agatagtgtc tgctgtgcag tactgtcacc agaagtttat tgtccataga gacttaaagg    840
cagaaaacct gctcttggat gctgatatga acatcaagat tgcagacttt ggcttcagca    900
atgaattcac ctttgggaac aagctggaca ccttctgtgg cagtccccct tatgctgccc    960
cagaactctt ccagggcaaa aaatatgatg gacccgaggt ggatgtgtgg agcctaggag   1020
ttatcctcta tacactggtc agcggatccc tgccttttga tggacagaac ctcaaggagc   1080
tgcgggaacg ggtactgagg gggaaatacc gtattccatt ctacatgtcc acggactgtg   1140
aaaacctgct taagaaattt ctcatcctta atcccagcaa gagaggcact ttagagcaaa   1200
tcatgaaaga tcgatggatg aatgtgggtc acgaagatga tgaactaaag ccttacgtgg   1260
agccactccc tgactacaag gaccccggc ggacagagct gatggtgtcc atgggttata   1320
cacgggaaga gatccaggac tcgctggtgg gccagagata caacgaggtg atggccacct   1380
atctgctcct gggctacaag agctccgagc tggaaggcga caccatcacc ctgaaacccc   1440
ggccttcagc tgatctaacc aatagcagcg cccaattccc atcccacaag gtacagcgaa   1500
gcgtgtcggc caatcccaag cagcggcgct tcagcgacca ggctggtcct gccattccca   1560
cctctaattc ttactctaag aagactcaga gtaacaacgc agaaaataag cggcctgagg   1620
aggaccggga gtcagggcgg aaagccagca gcacagccaa ggtgcctgcc agcccctgc    1680 ccggtctgga gaggaagaag accaccccaa ccccctccac gaacagcgtc ctctccacca   1740
gcacaaatcg aagcaggaat tccccacttt tggagcgggc cagcctcggc caggcctcca   1800
tccagaatgg caaagacagc ctaaccatgc cagggtcccg ggcctccacg gcttctgctt   1860
ctgccgcagt ctctgcggcc cggccccgcc agcaccagaa atccatgtcg gcctccgtgc   1920
accccaacaa ggcctctggg ctgccccca cggagagtaa ctgtgaggtg ccgcggccca   1980
gcacagcccc ccagcgtgtc cctgttgcct ccccatccgc ccacaacatc agcagcagtg   2040
gtggagcccc agaccgaact aacttccccc ggggtgtgtc cagccgaagc accttccatg   2100
ctgggcagct ccgacaggtg cgggaccagc agaatttgcc ctacggtgtg accccagcct   2160
ctccctctgg ccacagccag ggccggcggg gggcctctgg gagcatcttc agcaagttca   2220
cctccaagtt tgtacgcagg aacctgaatg aacctgaaag caaagaccga gtggagacgc   2280
tcagacctca cgtggtgggc agtggcggca acgacaaaga aaaggaagaa tttcgggagg   2340
ccaagccccg ctccctccgc ttcacgtgga gtatgaagac cacgagctcc atggagccca   2400
acgagatgat gcgggagatc cgcaaggtgc tggacgcgaa cagctgccag agcgagctgc   2460
atgagaagta catgctgctg tgcatgcacg gcacgccggg ccacgaggac ttcgtgcagt   2520
gggagatgga ggtgtgcaaa ctgccgcggc tctctctcaa cggggttcga tttaagcgga   2580
tatcgggcac ctccatggcc ttcaaaaaca ttgcctccaa aatagccaac gagctgaagc   2640
tttaacaggc tgccaggagc gggggcggcg ggggcgggcc agctggacgg gctgccggcc   2700
gtgcgccgcc ccacctgggc gagactgcag cgatggattg tgtgtctccc ctgctggcac   2760
ttctcccctc cctggccctt tcagtttttc tcccacattc accctgccc agagattccc   2820 ccttctcctc tccctactg gaggcaaagg aaggggaggg tggatggggg ggcagggctc   2880
cccctcggta ctgcggttgc acagagtatt tcgcctaaac caagaaattt tttattacca   2940
```

```
aaaaga                                                               2946

<210> SEQ ID NO 35
<211> LENGTH: 1792
<212> TYPE: DNA
<213> ORGANISM: homo sapiens

<400> SEQUENCE: 35
ctccggacag catgagcgtg ggcttcatcg gcgctggcca gctggctttt gccctggcca     60
agggcttcac agcagcaggc gtcttggctg cccacaagat aatggctagc tccccagaca    120
tggacctggc cacagtttct gctctcagga agatgggggt gaagttgaca ccccacaaca    180
aggagacggt gcagcacagt gatgtgctct tcctggctgt gaagccacac atcatcccct    240
tcatcctgga tgaaataggc gccgacattg aggacagaca cattgtgtg tcctgcgcgg    300 ccggcgtcac catcagctcc attgagaaga agctgtcagc gtttcggcca gcccccaggg    360
tcatccgctg catgaccaac actccagtcg tggtgcggga gggggccacc gtgtatgcca    420
caggcacgca cgcccaggtg gaggacggga ggctcatgga gcagctgctg agcacggtgg    480
gcttctgcac ggaggtggaa gaggacctga ttgatgccgt cacggggctc agtggcagcg    540
gccccgccta cgcattcaca gccctggatg ccctggctga tggggtgtg aagatgggac    600 ttccaaggcg cctggcagtc cgcctcgggg cccaggccct cctgggggct gccaagatgc    660
tgctgcactc agaacagcac ccaggccagc tcaaggacaa cgtcagctct cctggtgggg    720
ccaccatcca tgccttgcat gtgctggaga gtggggggctt ccgctccctg ctcatcaacg    780
ctgtggaggc ctcctgcatc cgcacacggg agctgcagtc catggctgac caggagcagg    840
tgtcaccagc cgccatcaag aagaccatcc tggacaaggt gaagctggac tcccctgcag    900
ggaccgctct gtcgccttct ggccacacca agctgctccc ccgcagcctg gccccagcgg    960
gcaaggattg acacgtcctg cctgaccacc atcctgccac acccttctct tctcttgtca   1020 ctaggggac taggggtcc ccaaagtggc ccactttctg tggctctgat cagcgcaggg    1080
gccagccagg gacatagcca gggaggggcc acatcacttc ccactggaaa tctctgtggt   1140
ctgcaagtgc ttcccagccc agaacagggg tggattcccc aacctcaacc tcctttcttc   1200
tctgctccca aaccatgtca ggaccacctt cctctagagc tcgggagccc ggagggtctt   1260
cacccactcc tactccagta tcagctggca cgggctcctt cctgagagca aggtcaagg    1320 accccctctg tgaaggctca gcagaggtgg gatcccacgc cccctcccgg cccctccctg   1380
ccctccattc agggagaaac ctctccttcc cgtgtgagaa gggccagagg gtccaggcat   1440
cccaagtcca gcgtgaaggg ccacagcccc tcttggctgc aagcacgca gatcccatgg    1500 acatttgggg aaagggctcc ttgggctgct ggtgaacttc tgtggccacc acctcctgct   1560
cctgacctcc ctgggagggt gctatcagtt ctgtcctggc cctttcagtt ttataagttg   1620
gtttccagcc cccagtgtcc tgacttctgt ctgccacatg aggagggagg ccctgcctgt   1680
gtgggagggt ggttactgtg gtggaatag tggaggcctt caactgatta gacaaggccc    1740
gcccacatct tggagggcat ctgccttact gattaaaatg tcaatgtaat ct           1792

<210> SEQ ID NO 36
<211> LENGTH: 639
<212> TYPE: DNA
<213> ORGANISM: homo sapiens

<400> SEQUENCE: 36
ccggacggac gctcgtcttc gcccgccatg gccgagagcg actgggacac ggtgacggtg     60
```

| | |
|---|---|
| ctgcgcaaga agggccctac ggccgcccag gccaaatcca agcaggctat cttagcggca | 120 |
| cagagacgag gagaagatgt ggagacttcc aagaaatggg ctgctggcca gaacaaacaa | 180 |
| cattctatta ccaagaacac ggccaagctg gaccgggaga cagaggagct gcaccatgac | 240 |
| agggtgaccc tggaggtggg caaggtgatc cagcaaggtc ggcagagcaa ggggcttacg | 300 |
| cagaaggacc tggccacgaa aatcaatgag aagccacagg tgatcgcgga ctatgagagc | 360 |
| ggacgggcca tacccaataa ccaggtgctt ggcaaaatcg agcgggccat ggcctcaag | 420 |
| ctccggggaa aggacattgg aaagcccatc gagaaggggc ctagggcgaa atgaacacaa | 480 |
| agcctcgaaa tcagtgcgct ccagctgatc tcgttccgcc ggttccccttt ggccgccagt | 540 |
| tccgttctcc tcacgggccg aacggaacaa ggggtccagc ttgcggggga ccctccccag | 600 |
| cccattcctg ctgtcaaaca aacaaaacct tgcaaagcg | 639 |

<210> SEQ ID NO 37
<211> LENGTH: 1793
<212> TYPE: DNA
<213> ORGANISM: homo sapiens

<400> SEQUENCE: 37

| | |
|---|---|
| cgcgtccgcc ccgcgagcac agagcctcgc ctttgccgat ccgccgcccg tccacacccg | 60 |
| ccgccagctc accatggatg atgatatcgc cgcgctcgtc gtcgacaacg gctccggcat | 120 |
| gtgcaaggcc ggcttcgcgg gcgacgatgc cccccgggcc gtcttcccct ccatcgtggg | 180 |
| gcgccccagg caccagggcg tgatggtggg catgggtcag aaggattcct atgtgggcga | 240 |
| cgaggcccag agcaagagag gcatcctcac cctgaagtac cccatcgagc acggcatcgt | 300 |
| caccaactgg gacgacatgg agaaaatctg gcaccacacc ttctacaatg agctgcgtgt | 360 |
| ggctcccgag gagcaccccg tgctgctgac cgaggccccc ctgaacccca aggccaaccg | 420 |
| cgagaagatg acccagatca tgtttgagac cttcaacacc ccagccatgt acgttgctat | 480 |
| ccaggctgtg ctatccctgt acgcctctgg ccgtaccact ggcatcgtga tggactccgg | 540 |
| tgacggggtc acccacactg tgcccatcta cgaggggtat gccctccccc atgccatcct | 600 |
| gcgtctggac ctggctggcc gggacctgac tgactacctc atgaagatcc tcaccgagcg | 660 |
| cggctacagc ttcaccacca cggccgagcg ggaaatcgtg cgtgacatta aggagaagct | 720 |
| gtgctacgtc gccctggact cgagcaagaa gatggcacg gctgcttcca gctcctccct | 780 |
| ggagaagagc tacgagctgc ctgacggcca ggtcatcacc attggcaatg agcggttccg | 840 |
| ctgccctgag gcactcttcc agccttcctt cctgggcatg gagtcctgtg catccacga | 900 |
| aactaccttc aactccatca tgaagtgtga cgtggacatc cgcaaagacc tgtacgccaa | 960 |
| cacagtgctg tctggcggca ccaccatgta ccctggcatt gccgacagga tgcagaagga | 1020 |
| gatcactgcc ctggcaccca gcacaatgaa gatcaagatc attgctcctc ctgagcgcaa | 1080 |
| gtactccgtg tggatcggcg gctccatcct ggcctcgctg tccaccttcc agcagatgtg | 1140 |
| gatcagcaag caggagtatg acgagtccgg cccctccatc gtccaccgca aatgcttcta | 1200 |
| ggcggactat gacttagttg cgttacaccc tttcttgaca aaacctaact tgcgcagaaa | 1260 |
| acaagatgag attggcatgg ctttattttgt ttttttttgtt ttgttttggt tttttttttt | 1320 |
| tttttggctt gactcaggat ttaaaaactg gaacggtgaa ggtgacagca gtcggttgga | 1380 |
| gcgagcatcc cccaaagttc acaatgtggc cgaggacttt gattgcacat tgttgttttt | 1440 |
| ttaatagtca ttccaaatat gagatgcatt gttacaggaa gtcccttgcc atcctaaaag | 1500 |
| ccaccccact tctctctaag gagaatggcc cagtcctctc ccaagtccac acaggggagg | 1560 |

```
tgatagcatt gctttcgtgt aaattatgta atgcaaaatt tttttaatct tcgccttaat    1620
acttttttat tttgttttat tttgaatgat gagccttcgt gccccccctt cccccttttt    1680
gtcccccaac ttgagatgta tgaaggcttt tggtctccct gggagtgggt ggaggcagcc    1740
agggcttacc tgtacactga cttgagacca gttgaataaa agtgcacacc tta           1793

<210> SEQ ID NO 38
<211> LENGTH: 1116
<212> TYPE: DNA
<213> ORGANISM: homo sapiens

<400> SEQUENCE: 38
gttatgtgtt cccgtccgta ctggaggcta gctcttgtcg cggccgcggc gagttaacat      60
cgttttccca atctgtccgc ggctgccgcc acccaagaca gagccagaat gttcaggatg     120
ctgaacagca gttttgagga tgaccccttc ttctctgagt ccattcttgc acaccgagaa     180
aatatgcgac agatgataag aagttttttct gaacccttttg aagagactt gctcagtatc    240 tctgatggta gagggagagc tcataatcgt agaggacata atgatggtga agattctttg     300
actcatacag atgtcagctc tttccagacc atggaccaaa tggtgtcaaa tatgagaaac     360
tatatgcaga aattagaaag aaacttcggt caactttcag tggatccaaa tggacattca     420
ttttgttctt cctcagttat gacttattcc aaaataggag atgaaccgcc aaaggttttt     480
caggcctcaa ctcaaactcg tcgagctcca ggaggaataa aggaaaccag gaaagcaatg     540
agagattctg acagtggact agaaaaaatg gctattggtc atcatatcca tgaccgagct     600
catgtcatta aaagtcaaa gaacaagaag actggagatg aagaggtcaa ccaggagttc     660
atcaatatga tgaaagcga tgctcatgct tttgatgagg agtggcaaag tgaggttttg     720
aagtacaaac caggacgaca caatctagga aacactagaa tgagaagtgt tggccatgag     780
aatcctggct cccgagaact taaaagaagg gagaaacctc aacaaagtcc agccattgaa     840 catgaagga gatcaaatgt ttgggggac aaactccaca tcaaaggctc atctgtgaaa      900
agcaacaaaa aataaatagc catgcatttg atttgtttag ttttgattgt tttaacagtt    960
agtaatggtg ctgggtaata agcataagac caatctcttg ctgttaaatc agttctgtcc   1020
ttggcaactt tcttctgata tctgaatgtt catgaaggtc ctagctttat attgtccctc   1080
ttttaggaat aaaattttga ttttcaacaa aaaaaa                              1116

<210> SEQ ID NO 39
<211> LENGTH: 3074
<212> TYPE: DNA
<213> ORGANISM: homo sapiens

<400> SEQUENCE: 39
ccgctctccg ctgcggggga ggccatggcg gaaccttccc aggccccgac cccggccccg      60
gctgcgcagc cccggcccct tcagtcccca gccctgccc caactccgac tcctgcaccc     120
agcccggctt cagccccgat tccgactccc accccggcac cagcccctgc cccagctgca     180 gcccagccg gcagcacagg gactgggggg ccggggtag gaagtggggg ggccgggagc      240
gggggggatc cggctcggcc tggcctgagc cagcagcagc gcgccagtca gaggaaggcg    300
caagtccggg ggctgccccg cgccaagaag cttgagaagc taggggtctt ctcggcttgc   360
aaggccaatg gaacctgtaa gtgtaatggc tggaaaaacc ccaagccccc cactgcaccc    420
cgcatagatc tgcagcagcc agctgccaac ctgagtgagc tgtgccgcag ttgtgagcac    480
cccttggctg accacgtatc ccacttggag aatgtgtcag aggatgagat aaaccgactg    540
```

```
ctggggatgg tggtggatgt ggagaatctc ttcatgtctg ttcacaagga agaggacaca    600
gacaccaagc aggtctattt ctacctcttc aagctactgc ggaaatgcat cctgcagatg    660
acccggcctg tggtggaggg gtccctgggc agccctccat ttgagaaacc taatattgag    720
cagggtgtgc tgaactttgt gcagtacaag tttagtcacc tggctccccg ggagcggcag    780
acgatgttcg agctctcaaa gatgttcttg ctctgcctta actactggga gcttgagaca    840
cctgcccagt tcggcagag gtctcaggct gaggacgtgg ctacctacaa ggtcaattac    900
accagatggc tctgttactg ccacgtgccc cagagctgtg atagcctccc ccgctacgaa    960
accactcatg tctttgggcg aagccttctc cggtccattt tcaccgttac ccgccggcag   1020
ctgctggaaa agttccgagt ggagaaggac aaattggtgc ccgagaagag gaccctcatc   1080
ctcactcact tccccaaatt cctgtccatg ctggaggagg agatctatgg ggcaaactct   1140
ccaatctggg agtcaggctt caccatgcca ccctcagagg ggacacagct ggttccccgg   1200
ccagcttcag tcagtgcagc ggttgttccc agcacccca tcttcagccc cagcatgggt   1260
gggggcagca acagctccct gagtctggat tctgcagggg ccgagcctat gccaggcgag   1320
aagaggacgc tcccagagaa cctgaccctg gaggatgcca gcggctccg tgtgatgggt   1380 gacatcccca tggagctggt caatgaggtc atgctgacca tcactgaccc tgctgccatg   1440
ctggggcctg agacgagcct gctttcggcc aatgcggccc gggatgagac agcccgcctg   1500
gaggagcgcc gcggcatcat cgagttccat gtcatcggca actcactgac gcccaaggcc   1560
aaccggcggg tgttgctgtg gctcgtgggg ctgcagaatg tcttttccca ccagctgccg   1620
cgcatgccta aggagtatat cgcccgcctc gtctttgacc cgaagcacaa gactctggcc   1680
ttgatcaagg atgggcgggt catcggtggc atctgcttcc gcatgtttcc cacccagggc   1740
ttcacggaga ttgtcttctg tgctgtcacc tcgaatgagc aggtcaaggg ttatgggacc   1800
cacctgatga accacctgaa ggagtatcac atcaagcaca acattctcta cttcctcacc   1860
tacgccgacg agtacgccat cggctacttc aaaaagcagg gtttctccaa ggacatcaag   1920
gtgcccaaga gccgctacct gggctacatc aaggactacg agggagcgac gctgatggag   1980
tgtgagctga atccccgcat cccctacacg gagctgtccc acatcatcaa gaagcagaaa   2040
gagatcatca gaagctgat tgagcgcaaa caggcccaga tccgcaaggt ctacccgggg   2100
ctcagctgct tcaaggaggg cgtgaggcag atccctgtgg agagcgttcc tggcattcga   2160
gagacaggct ggaagccatt ggggaaggag aaggggaagg agctgaagga ccccgaccag   2220
ctctacacaa ccctcaaaaa cctgctggcc caaatcaagt ctcaccccag tgcctggccc   2280
ttcatggagc ctgtgaagaa gtcggaggcc cctgactact acgaggtcat ccgcttcccc   2340
attgacctga agaccatgac tgagcggctg cgaagccgct actacgtgac ccggaagctc   2400
tttgtggccg acctgcagcg ggtcatcgcc aactgtcgcg agtacaaccc cccggacagc   2460
gagtactgcc gctgtgccag cgccctggag aagttcttct acttcaagct caaggaggga   2520
ggcctcattg acaagtaggc ccatctttgg gccgcagccc tgacctggaa tgtctccacc   2580
tcggattctg atctgatcct taggggtgc cctggcccca cggacccgac tcagcttgag   2640
acactccagc caagggtcct ccggacccga tcctgcagct ctttctggac cttcaggcac   2700
ccccaagcgt gcagctctgt cccagccttc actgtgtgtg agaggtctcc tgggttgggg   2760
cccagcccct ctagagtagc tggtggccag ggatgaacct tgcccagccg tggtggcccc   2820
caggcctggt cccaagagc tttgaggct tggattcctg ggcctggccc aggtggctgt   2880
ttccctgagg accagaactg ctcattttag cttgagtgat ggcttcaggg gttggaagtt   2940
```

| | |
|---|---:|
| cagcccaaac tgaagggggc catgccttgt ccagcactgt tctgtcagtc tcccccaggg | 3000 |
| gtgggggta tggggaccat tcattccctg gcattaatcc cttagaggga ataataaagc | 3060 |
| tttttatttc tctg | 3074 |

<210> SEQ ID NO 40
<211> LENGTH: 2381
<212> TYPE: DNA
<213> ORGANISM: homo sapiens

<400> SEQUENCE: 40

| | |
|---|---:|
| gacgggagct cccgggagc cgtttgtgcc cggggtaacc ccgttccggc caagccgctt | 60 |
| cagcggggga cgtagccatg aaggaagaga aggagcacag gcctaaggag aagcgagtaa | 120 |
| ccctgttaac ccccgccggg gccacaggca gcggtggtgg gacctcgggg acagctcca | 180 |
| aggggggaaga taagcaggat cgcaacaagg agaagaaaga agcgctgagc aaggtggtaa | 240 |
| ttcgaagatt acctcccact ttgaccaagg agcagcttca ggaacatctt caacctatgc | 300 |
| ctgagcatga ttattttgag ttttttttcta atgatacgag tttgtatcct catatgtatg | 360 |
| ccagagcata catcaacttt aaaaaccaag aggacattat tttgttcagg gatcgctttg | 420 |
| atggttatgt attccttgac aataaaggtc aggaatatcc cgctatagta gaatttgcac | 480 |
| cttttcaaaa agctgcaaaa aagaagacta agaaaagaga taccaaagtc gggactatcg | 540 |
| atgatgatcc agaatataga aagttttttgg aaagttatgc cacagataat gagaaaatga | 600 |
| catctactcc agagacactg ctagaggaaa tagaagcaaa aaatagagaa ttaatagcta | 660 |
| aaaagacaac cccacttttg agcttcctga aaaacaagca gagaatgaga gaagaaaaga | 720 |
| gagaagaaag gaggaggaga gaaatagaaa gaaaaagaca agagaagaa gagaggagga | 780 |
| aatggaaaga agaagagaaa cgaaaaagga agatatataga aaagctaaag aagatagaca | 840 |
| gaattccaga aagggacaaa ttaaaggatg aaccaaagat taaggtacac aggttttctgt | 900 |
| tacaagctgt gaatcagaaa aatctgctca agaagccaga aaaaggagat gaaaagaat | 960 |
| tggacaaaag agaaaaagcc aagaaattgg acaaagagaa tctcagtgat gaaagagcca | 1020 |
| gtgggcaaag ttgtacattg cccaagcgtt ctgatagcga acttaaagat gaaaaaccaa | 1080 |
| agagacctga agatgagagc ggcagagact atagggagag ggaacgggaa tatgaacgag | 1140 |
| atcaggagcg catacttcga gaagagaga ggctgaagcg gcaagaagaa gagcgccgta | 1200 |
| ggcagaagga gcgctatgag aaagagaaga cttttaagag aaaagaagaa gaaatgaaaa | 1260 |
| aagagaaaga cacacttcgg gataaaggaa agaaggctga agtacagaa tcaataggca | 1320 |
| gctcagaaaa aactgaaaag aagaagaag tggtcaagag agatcgaata agaaacaagg | 1380 |
| atcgtccagc gatgcagctt taccaaccag gagctcgaag ccgaaatcga ctctgtcccc | 1440 |
| ctgatgacag caccaagtct ggagattcag cagcagaaag gaagcaggaa agtggtatta | 1500 |
| gccatagaaa agaaggagga gaggagtgat aagtccagat ggccttaggt gtcctgactg | 1560 |
| tctaggcagc caaagagcac acgttaagca atccagaggt gccttcaggg caaagaatag | 1620 |
| agagaaaggg agccgctgtg ctggtggggt acactgcaga ggagtaagtc ttgtgtcaaa | 1680 |
| gcaggaatct gatcagaggt tcagaattgg aagtacaatt tcattgctttt tgcaatttct | 1740 |
| acaaattaat tttaaagtgt cagaaaaagg tgacggcaag acatgcatt gcaatttgca | 1800 |
| gggggaattg tcaagtgagg acttcatcac atatgacacg agagaaaagt aagagctggt | 1860 |
| tctaaaatca aaagctgttg ttcatcctga attgaatttt ctgaatttgg gtggagcaga | 1920 |
| gtcgctttga agccttgttc cgatctaatt ctattgtatt gttgatgata agtgttgaca | 1980 |

```
ttgggtagtg tagaagcaac aagcatgtcc ttgtagtaca ggtacagtga aggatagaac   2040
acactttcgt tgatacaaaa atttaaatag ttatgttact tctgtatcca gtgtcctaaa   2100
gttttaggat tagttttagt tttttgtttg cttatatgag cttagcgtaa agaatatttt   2160
taaacttcgt gttttgtcat cagcatcttt tctattaaga ggtaaaatgt agtccttgtt   2220
tgactcttga caatccagtg tgtttgatct taggtctcat gatctgagtg catacgctct   2280
ccaggaagga aactgcacca gtgtctattc ctgttaaata gcaactttta gtctcagctt   2340
gtttcgtttt gatgtcaata atagtaaca gcattcaagt g                        2381

<210> SEQ ID NO 41
<211> LENGTH: 5163
<212> TYPE: DNA
<213> ORGANISM: homo sapiens

<400> SEQUENCE: 41
ttaggggcag aaaaacattt gtaataatta atggctttga gagacacaag gctttgtttg     60
ccccagagta ttagttaacc cacctagtgc tcctaatcat acaatattaa ggattgggag    120
ggacattcat tgcctcactc tctatttgtt tcaccttctg taaaattggt agaataatag    180
tacccacttc atagcattgt atgatgatta aattggttaa tattttaaa atgcttagaa     240 cacagattgg gcacataaca gcaagcacca catgtgttta agataaat tcctttgtgt     300 tgccttccgt taaagtttaa ataagtaaat aaataaataa atacttgcat gacattttga    360
agtctctcta taacatctga gtaagtgcg gctgcgacaa tgctactgga gttccagaat    420
cgtgttggtg acaagattgt tcaccagcat atggtgtggt gaaaactcac taatttggaa   480
ttagttcaga ttattaagcc tgaataggtg aaaatcctga atcaaggat ctttggaact    540 atttgaaatc agtatttat attttcctgt tgtattcatt aaagtgttgc aagtgttcta    600
tttgatggat taagtatatt taggatatac atgttcaatt tgtgattttg tatacttaat   660
tggaacaaga aagctaataa aggttttgat atggacatct attcttttaa gtaaacttca   720
atgaaaatat atgagtagag catatagaga tgtaaataat ttgtggacac accacagact    780
gaaatagcaa atttaaaaga aattgttgga agaatcaagt gtttgtggaa tgagtcctcc    840
tagtaaagtt cctgctcttg tgaataatta agcctcatgt ataattacta tagcaaaagg    900
aagcctaaga agtattagac tctacttgta tttaaattac attttacata atttatgtgt    960
atgaaaaatg ttttaaatgc ttattttcgt aagccatgag atagctcctt tatattttaa   1020
gaatttctga attaatttgc ttggatttta ttagtgcaaa tggcagagct agcaattcct   1080
ttttctgtgt tcccattcca tcctattcat ccctctttta ggaaactctg aactctggat   1140
tgtccttgtt tacatacctg cctcctgcat tggactatgt gtctctgagt gtagtatgac   1200
taattcattt gtttgtcaag gactctcaat gcatttgttg aacagcctaa ttagtaatgt   1260
ctgcaacaat gacattttac tgtatttaat aaagctctgg gaaagtagga tacacataag   1320
acaggtctag gtctaaattc tttacagaaa cttggatttt tagttcggtt tgaaatttga   1380
agatgtgagt atatttatct cagtttccca aaggacaagc taattggaat tatcatcctc   1440
tttcacttga ttggatcccc agaatgccat ttacgcatgc agcaggattt tataacagtt   1500
ttaaattctg tatatttgat gaagaggttt tatattttg gattcaagcc tcttttaaa    1560 cttctacaat atggtttaca ataattcctt atatcctgct tttgaaatac atattacaac   1620
tttttaagtt tggaaggcta tatttcaagg actgaagtta cagtatactc aagtgataca   1680
caagcctagc accccacttt ccacatagtg ttcgataaag attgataaac tcgaaatcac   1740
```

```
agacctttta attcttaaga caaatagcag cagaaagaaa catctttggc ttatttctgg    1800
taaggttttt atgctctgta aaacaaagaa ttgtattcat ccgcgcagca cagattctat    1860
taaaaataaa tgtgagagtc gttaatgtag tactgctcat ttaccatcaa aattcacttt    1920
tcaggaataa tcccatcagt ttaaattgga tattggaatg agcattgatt acatttaact    1980
tggtagccca aaatttcttc atggggtttt gaactcggcg ggatttcaaa ggttttaaaa    2040
atgagttttt gattttttt aaaaccctca aatttcatta cctttaaact aggtcgaaac    2100
ggggcgcaag agattggatt aacaccatag taatacttat tttgttctta accatttcag    2160
ggcttcttga aatagaggct gtatggtgta atggaaaaaa cagccttgga atctgggagc    2220
ctgattcctg gattcagtcc cagttttgcg tgaccttggg caagttactt tacttctctg    2280
aatttccgtt tcctcctctg caaaatgagg atcgcaatag ccaccttgca accttgactg    2340
gagcgagcct cgcacacccc gcgccggcct ggaggaagag cagccatgat tacgccgcct    2400
tcgctccgct acccgcttgc ggctggcgcc ctcctccagc aggtgtaggc gctgccgcgc    2460
tgccccacgc ctttccgccg ctcgcgggcc tgcgcctcgg cgtccccgag gaggccgctg    2520
cgggctgagg tagcgcaccg gcctctcggc gtcccagtcc ggtcccgggc ggagggaaag    2580
cgggcgaccc acctccgagg cagaagccga ggcccggccc cgccgagtgc ggaggagcgc    2640
aggcagcccc cgccctcgg ccctccccc ggccctcccg gccctccctc cgccccctcc    2700
gccctcgcgc gccgcccgcc cgggtcgccg cggggccgtg gtgtacgtgc agagcgcgca    2760
gagcgagtgg cgcccgtatg ccctgcgctc ctccacagcc tgggccgggc cgcccgggac    2820
gctgaggcgg cggcggcggc cgaggggcc ggtcttgcgc tccccaggcc cgcgcgcctg    2880
agcccaggtt gccattcgcc gcacaggccc tattctctca gccctcggcg gcgatgaggc    2940
gctgaggcgg ctgccggcgc tgccgccgag cttaggactc ggaagcggcc gggccgaggg    3000
cgtggggtgc cggcctccct gaggcgaggg tagcgggtgc atggcgcagt aacggcccct    3060
atctctctcc ccgctcccca gcctcgggcg aggccgtccg gccgctaccc ctcctgctcg    3120
gccgccgcag tcgccgtcgc cgccgccgcc gccgccatgg ccaatgacag cggcgggccc    3180
ggcgggccga gcccgagcga gcgagaccgg cagtactgcg agctgtgcgg gaagatggag    3240
aacctgctgc gctgcagccg ctgccgcagc tccttctact gctgcaagga gcaccagcgt    3300
caggactgga agaagcacaa gctcgtgtgc caggcagcg agggcgccct cggccacgga    3360
gtgggcccac accagcattc cggccccgcg ccgccggctg cagtgccgcc gcccagggcc    3420
ggggcccggg agcccaggaa ggcagcggcg cgccgggaca acgcctccgg ggacgcggcc    3480
aagggaaaag taaaggccaa gcccccggcc gacccagcgg cggccgcgtc gccgtgtcgt    3540
gcggccgccg gcgccagggg ctcggcgtg gctgccgaag ccgagcccgg caaggaggag    3600
ccgccggccc gctcatcgct gttccaggag aaggcgaacc tgtacccccc aagcaacacg    3660
cccgggatg cgctgagccc cggcggcggc ctgcggccca cgggcagac gaagcccctg    3720
ccggcgctga gctggcgct cgagtacatc gtgccgtgca tgaacaagca cggcatctgt    3780
gtggtggacg acttcctcgg caaggagacc ggacagcaga tcggcgacga ggtgcgcgcc    3840
ctgcacgaca ccgggaagtt cacggacggg cagctggtca gccagaagag tgactcgtcc    3900
aaggacatcc gaggcgataa gatcacctgg atcgagggca aggagcccgg ctgcgaaacc    3960
attgggctgc tcatgagcag catggacgac ctgatacgcc actgtaacgg gaagctgggc    4020
agctacaaaa tcaatggccg gacgaaagcc atggttgctt gttatccggg caatggaacg    4080
ggttatgtac gtcatgttga taatccaaat ggagatggaa gatgtgtgac atgtatatat    4140
```

```
tatcttaata aagactggga tgccaaggta agtggaggta acttcgaat ttttccagaa    4200 ggcaaagccc agtttgctga cattgaaccc aaatttgata gactgctgtt tttctggtct    4260
gaccgtcgca accctcatga agtacaacca gcatatgcta caaggtacgc aataactgtt    4320
tggtattttg atgcagatga gagcacga gctaaagtaa aatatctaac aggtgaaaaa    4380
ggtgtgaggg ttgaactcaa taaaccttca gattcggtcg gtaaagacgt cttctagagc    4440
ctttgatcca gcataccccc acttcaccta caatattgtt aactatttgt taacttgtga    4500
atacgaataa atgggataaa gaaaaataga caaccagttc gcattttaat aaggaaacag    4560
aaacaacttt ttgtgttgca tcaaacagaa gattttgact gctgtgactt tgtactgcat    4620
gatcaacttc aaatctgtga ttgcttacag gaggaagata agctactaat tgaaaatggt    4680
ttttacatct ggatatgaaa taagtgccct gtgtagaatt ttttttcattc ttatattttg    4740 ccagatctgt tatctagctg agttcatttc atctctccct tttttatatc aagtttgaat    4800
ttgggataat ttttctatat taggtacaat ttatctaaac tgaattgaga aaaaattaca    4860
gtattattcc tcaaaataac atcaatctat tttgtaaac ctgttcatac tattaaattt    4920
tgccctaaaa gacctcttaa taatgattgt tgccagtgac tgatgattaa ttttatttta    4980
cttaaaataa gaaaaggagc actttaatta caactgaaaa atcagattgt tttgcagtcc    5040
ttccttacac taatttgaac tcttaaagat tgctgcttttt tttttgacat tgtcaataac    5100
gaaacctaat tgtaaaacag tcaccattta ctaccaataa cttttagtta atgttttaca    5160
agg                                                                  5163
```

<210> SEQ ID NO 42
<211> LENGTH: 4506
<212> TYPE: DNA
<213> ORGANISM: homo sapiens

<400> SEQUENCE: 42

```
ggcggtggcg gcggcgccgg gacggggag gggcgcgccg aaccggaac cgacctgcgc      60 cggaaccgga acggagagcg ggttgccagg gcccgaagag ggctggctgc ggcggtctcg    120
ctcggctgtc cgttccttgc tggagaattt ggccacaaag agttgccaag atagctgggc    180
caggaagaaa gcgccgcagc cctgacccag acgctgttgc cgaccccggg gcactctggc    240
tgtcgaccaa gcggctcaag atgtctggcg gggccagtgc cacaggccca aggagagggc    300
ccccaggact ggaggacacc actagtaaga agaagcagaa ggatcgagca accaggaga    360 gcaaggatgg agatcctagg aaagagacag ggtctcgata tgttgcccag gctggtcttg    420
aacctctggc ctcaggtgat ccttctgcct cagcctccca tgcagctggg atcacaggct    480
cacgccaccg tacccggctg ttctttcctt catcgtcagg gtcagcatcc actcctcaag    540
aggagcagac caaagaggga gcttgtgaag accctcatga tctcttggct actcccactc    600
cagagttgtt gctcgattgg aggcagagtg cagaagaggt gattgtcaag cttcgtgtgg    660
gagtaggtcc cctgcagctg gaggatgtag atgctgcttt cacagataca gactgtgtgg    720 tgcggttttgc aggtggtcag cagtggggtg gtgtcttcta tgctgagata aaagctctt    780 gtgctaaagt gcaaacccgc aagggcagtc tcctgcacct gacactgccc aaaaaggtgc    840
ctatgctcac gtgccctcc ctcctggttg aggctgatga acagctttgc ataccaccgc    900
tgaactccca aacctgtctc ctgggctcag aggagaattt agccccttg gcaggagaga    960 aagcagtgcc tcccgggaat gacccagtct ctccagccat ggtccggagc agaaaccctg    1020
ggaaagatga ctgtgccaag gaggagatgg cagtggcagc agatgctgca accttggtgg    1080
```

```
atgagcccga gtcgatggtg aacctggcgt ttgtcaagaa tgactcgtat gagaagggcc    1140
cggattcagt ggtggtgcac gtgtacgtga aggagatctg cagggacacc tcaagagtac    1200
ttttccgtga gcaggacttc acgctcatct tccagaccag ggatggaaac ttcctgaggc    1260
tgcacccggg ctgtgggccc cacaccacct tccgttggca ggtgaagctc aggaatctga    1320
ttgagccaga gcagtgcacc ttctgtttca cggcttctcg catcgacatc tgccttcgta    1380
agaggcagag tcagcgctgg gggggcctgg aggccccggc tgcacgaggt gcagtgggtg    1440
gtgcaaaggt tgccgtgccg acaggtccaa cccctctgga ttcaaccccca ccaggaggtg    1500
ctccccaccc cctgacaggc caggaggagg cccgggctgt ggagaaggat aaatccaagg    1560
cacgatctga ggacacaggg ctagacagtg tggcaacccg cacacccatg gagcatgtaa    1620
ccccaaagcc agagacacac ctggcctcgc ccaagcctac atgcatggtg cctcccatgc    1680
cccacagccc agttagtgga gacagcgtgg aggaggagga agaggaagag aagaaggtgt    1740
gtctgccagg cttcactggc cttgtcaatt taggcaacac ctgcttcatg aacagcgtca    1800
ttcagtctct gtccaacact cgggaactcc gggacttctt ccatgaccgc tcctttgagg    1860
ctgagatcaa ctacaacaac ccactaggga ctggtgggcg tctggccatt ggcttttccg    1920
tgctgcttcg ggcgctgtgg aagggcaccc accatgcctt ccagccttcc aagttgaagg    1980
ccattgtggc gagtaaggcc agccagttca caggctatgc acagcatgat gcccaggagt    2040
tcatggcttt cctgctggat gggctgcacg aggacctgaa tcgcattcag aacaagccct    2100
acacagagac cgtggattca gatgggcggc ccgatgaggt ggtagctgag gaagcatggc    2160
agcggcacaa gatgaggaat gactctttca tcgtggacct atttcagggg cagtacaagt    2220
cgaagctggt gtgccctgtg tgtgccaagg tctccatcac ttttgacccg tttctttatc    2280
tgccggtgcc cttgccacaa aagcaaaagg ttctccctgt cttttatttt gcccgagagc    2340
cccacagcaa gcccatcaag ttcctggtga gcgtcagcaa ggagaactcc actgcgagcg    2400
aagtattgga ctccctctct cagagtgttc atgtgaagcc tgagaacctg cgtttggcag    2460
aggtaattaa gaatcgtttt catcgtgtgt tcctacccctc ccactcactg gacactgtgt    2520
ccccatctga tacgctcctc tgctttgagc tgctatcctc agagttggct aaggagcggg    2580
tagtggtgct agaggtgcaa cagcgccccc aggtgcccag cgtccccatc tccaagtgtg    2640
cagcctgcca gcgaagcaa cagtcggagg atgaaaagct gaagcgctgt acccggtgct    2700
accgtgtggg ctactgcaac cagctctgcc agaaaaccca ctggcctgac cacaagggcc    2760
tctgccgacc tgagaacatt ggctacccct tcctggtcag tgtacctgcc tcacgcctca    2820
cttatgcccg cctcgctcag ttgctagagg gctatgcccg gtactctgtg agtgtattcc    2880
agccacccctt tcagccaggc cgcatggcct tggagtctca gagccctggc tgcaccacac    2940
tgctctccac aggttccctg gaggctgggg acagcgagag agaccccatt cagccacctg    3000
agctccagct ggtgacccct atggctgagg gggacacagg gcttccccgg gtgtgggcag    3060
cccctgaccg gggtcctgtg cccagcacca gtggaatttc ttctgagatg ctggccagtg    3120
ggcccattga ggttggctcc ttgccagctg gcgagagggt gtcccgaccc gaagctgctg    3180
tgcctgggta ccagcatcca agtgaagcta tgaatgccca cacccccag ttcttcatct    3240
ataaaattga ttcatccaac cgagagcagc ggctagagga caaaggagac accccactgg    3300
agctgggtga cgactgtagc ctggctctcg tctggcggaa caatgagcgc ttgcaggagt    3360
ttgtgttggt agcctccaag gagctggaat gtgctgagga tccaggctct gccggtgagg    3420
ctgcccgggc cggccacttc accctggacc agtgcctcaa cctcttcaca cggcctgagg    3480
```

```
tgctggcacc cgaggaggcc tggtactgcc cacagtgcaa acagcaccgt gaggcctcca    3540
agcagctgtt gctatggcgc ctgccaaatg ttctcatcgt gcagctcaag cgcttctcct    3600
ttcgtagttt tatctggcgt gacaagatca atgacttggt ggagttccct gttaggaacc    3660
tggacctgag caagttctgc attggtcaga aagaggagca gctgcccagc tacgatctat    3720
atgctgtcat caaccactat ggaggcatga ttggtggcca ctacactgcc tgtgcacgcc    3780
tgcccaatga tcgtagcagt cagcgcagtg acgtgggctg gcgcttgttt gatgacagca    3840
cagtgacaac ggtagacgag agccaggttg tgacgcgtta tgcctatgta ctcttctacc    3900
gccggcggaa ctctcctgtg gagaggcccc ccagggcagg tcactctgag caccacccag    3960
acctaggccc tgcagctgag gctgctgcca gccaggcttc ccggatttgg caggagctgg    4020
aggctgagga ggagccggtg cctgagggg t ctgggcccct gggtccctgg ggccccaag    4080 actgggtggg ccccctacca cgtggcccta ccacaccaga tgagggctgc ctccggtact    4140
ttgtcctggg caccgtggcg gctttggtgg ccctcgtgct caacgtgttc tatcctctgg    4200
tatcccagag tcgctggaga tgagctcgcc tgcaggcagc tgctgtgagc tggcctacct    4260
gcctgcccca ggccatgcct gcctttgttg tggggaacac ctctgggctt tgggcctcag    4320
cttatgcatc tggtgggaga gggtggggag gttgtggccc ctgcaggggc agagtatcct    4380
agggtgtgta tccatctggc tgtctgtcca ttcatcctgc tgctctgacc cttggcctca    4440
ggcttggccc tgcccaagct acttcctgta cttaaaagtg ttaataaaac cagactattc    4500
aggccc                                                              4506

<210> SEQ ID NO 43
<211> LENGTH: 1542
<212> TYPE: DNA
<213> ORGANISM: homo sapiens

<400> SEQUENCE: 43
ccgacgcgac catcgtttgt cgacgccgct gccaccgcct gcctgagaga agtcgtcgcg      60
gccgaccccg tcgcctccgc cggctaccat gtccgcccag gcgcagatgc gggccctgct     120
ggaccagctc atgggcacgg ctcgggacgg agacgaaacc agacagaggg tcaagtttac     180
agatgaccgt gtctgcaaga gtcaccttct ggactgctgc ccccatgaca tcctggctgg     240
gacgcgcatg gatttaggag aatgtaccaa aatccacgac ttggccctcc gagcagatta     300
tgagattgca agtaaagaaa gagacctgtt ttttgaatta gatgcaatgg atcacttgga     360
gtcctttatt gctgaatgtg atcggagaac tgagctcgcc aagaagcggc tggcagaaac     420
acaggaggaa atcagtgcgg aagtttctgc aaaggcagaa aaagtacatg agttaaatga     480
agaaatagga aaactccttg ctaaagccga acagctaggg gctgaaggta atgtggatga     540
atcccagaag attcttatgg aagtggaaaa agttcgtgcg aagaaaaaag aagctgagga     600
agaatacaga aattccatgc ctgcatccag ttttcagcag caaaagctgc gtgtctgcga     660
ggtctgttca gcctaccttg gtctccatga caatgaccgt cgcctggcag accacttcgg     720
tgcaagttta cacttggggt tcattcagat ccgagagaag cttgatcagt tgaggaaaac     780
tgtcgctgaa aagcaggaga agagaaatca ggatcgcttg aggaggagag aggagaggga     840 acggaggag cgtctgagca ggaggtcggg atcaagaacc agagatcgca ggaggtcacg     900
ctcccgggat cggcgtcgga ggcggtcaag atctacctcc cgagagcgac ggaaattgtc     960
ccggtcccgg tccgagata gacatcgcg ccaccgcagc cgttcccgga gccacagccg    1020
gggacatcgt cgggcttccc gggaccgaag tgcgaaatac aagtaactac tctgactcct    1080
```

| | |
|---|---|
| tcggtagctg caaccaggag tgagcccttc tctgtgttcc cagggtctgc tgagggccgt | 1140 |
| gtctggtggg gatggggctg ggctcaccct caggagtagg gctggggagt cgtgaacggg | 1200 |
| actcaggtgt gggaagaggc gagagggctg tggaggagct cgcacggcgc caggtgatgg | 1260 |
| gctgcacagg cactgtcccc tgcctgcgtc ctggggcctg tgcactgttg cgtccatgct | 1320 |
| cagagtggct gagacttgtg tcctgaccag gccctgctta cctctgtttt ggttttttgtt | 1380 |
| tttgatattt ttttttccat tgtgttttta cgtagtgtca tgttctgtgc atatagtgtt | 1440 |
| gtattctcct ttgcactgtt tatgttacag tgaaggctct ccttattaaa aatcttcgca | 1500 |
| aaggtcaaaa aaaaaaaaaa aaaaaaaaaa aaaaaaaaaa aa | 1542 |

<210> SEQ ID NO 44
<211> LENGTH: 968
<212> TYPE: DNA
<213> ORGANISM: homo sapiens

<400> SEQUENCE: 44

| | |
|---|---|
| gggggaagtt gctggctgac tgggcttgcg aggaaaccgc ctcggagctg cagcgaaggc | 60 |
| caaggaatca ctgaagatcg gcgagggagg acagggggtt catcatgggt ggcttttttct | 120 |
| caagtatatt ttccagtctg tttggaactc gggaaatgag aattttaatt ttgggattag | 180 |
| atggagcagg aaaaaccaca attttgtaca gattacaagt gggagaagtt gttactacta | 240 |
| tacctaccat tggatttaat gtagagacgg tgacgtacaa aaaccttaaa ttccaagtct | 300 |
| gggatttagg aggacagaca agtatcaggc catactggag atgttactat tcaaacacag | 360 |
| atgcagtcat ttatgtagta gacagttgtg accgagaccg aattggcatt tccaaatcag | 420 |
| agttagttgc catgttggag gaagaagagc tgagaaaagc cattttagtg gtgtttgcaa | 480 |
| ataaacagga catggaacag gccatgactt cctcagagat ggcaaattca cttgggttac | 540 |
| ctgccttgaa ggaccgaaaa tggcagatat tcaaaacgtc agcaaccaaa ggcaccggcc | 600 |
| ttgatgaggc aatggaatgg ttagttgaaa cattaaaaag cagacagtaa ttcagtccat | 660 |
| tcttctcccc tgaaatgaag actacatcac ctctctccct ttggaaacag tcaagtgtac | 720 |
| ttcacactac tagatgttaa aactatatga ttattggcat atactgactg actgcaatat | 780 |
| ttgtagtaaa tagggaaaat aagtatttag ttggagggat aatttgatcg aatcacctga | 840 |
| atgttctatg taatgtaaaa tattcttttc ttgctttctt gtgttaaggt atatattcta | 900 |
| tttgtatgga attcttattc aaatacagtt gtattaaaga gtatactcct attggatgaa | 960 |
| aaaaacct | 968 |

<210> SEQ ID NO 45
<211> LENGTH: 700
<212> TYPE: DNA
<213> ORGANISM: homo sapiens

<400> SEQUENCE: 45

| | |
|---|---|
| gcggcgtgag aagccatgag cagcaaagtc tctcgcgaca ccctgtacga ggcggtgcgg | 60 |
| gaagtcctgc acgggaacca gcgcaagcgc cgcaagttcc tggagacggt ggagttgcag | 120 |
| atcagcttga agaactatga tccccagaag acaagcgct tctcgggcac cgtcaggctt | 180 |
| aagtccactc cccgccctaa gttctctgtg tgtgtcctgg gggaccagca gcactgtgac | 240 |
| gaggctaagg ccgtggatat cccccacatg gacatcgagg cgctgaaaaa actcaacaag | 300 |
| aataaaaaac tggtcaagaa gctggccaag aagtatgatg cgttttttggc ctcagagtct | 360 |
| ctgatcaagc agattccacg aatcctcggc ccaggtttaa ataaggcagg aaagttccct | 420 |

```
tccctgctca cacacaacga aaacatggtg gccaaagtgg atgaggtgaa gtccacaatc    480
aagttccaaa tgaagaaggt gttatgtctg gctgtagctg ttggtcacgt gaagatgaca    540
gacgatgagc ttgtgtataa cattcacctg gctgtcaact tcttggtgtc attgctcaag    600
aaaaactggc agaatgtccg ggccttatat atcaagagca ccatgggcaa gccccagcgc    660
ctatattaag gcacatttga ataaattcta ttaccagttc                          700
```

```
<210> SEQ ID NO 46
<211> LENGTH: 145
<212> TYPE: PRT
<213> ORGANISM: homo sapiens
<220> FEATURE:
<221> NAME/KEY: MISC_FEATURE
<222> LOCATION: (65)..(65)
<223> OTHER INFORMATION: Xaa = any amino acid
<220> FEATURE:
<221> NAME/KEY: MISC_FEATURE
<222> LOCATION: (101)..(101)
<223> OTHER INFORMATION: Xaa = any amino acid
<220> FEATURE:
<221> NAME/KEY: MISC_FEATURE
<222> LOCATION: (105)..(105)
<223> OTHER INFORMATION: Xaa = any amino acid
<220> FEATURE:
<221> NAME/KEY: MISC_FEATURE
<222> LOCATION: (108)..(108)
<223> OTHER INFORMATION: Xaa = any amino acid
<220> FEATURE:
<221> NAME/KEY: MISC_FEATURE
<222> LOCATION: (113)..(113)
<223> OTHER INFORMATION: Xaa = any amino acid
<220> FEATURE:
<221> NAME/KEY: MISC_FEATURE
<222> LOCATION: (125)..(128)
<223> OTHER INFORMATION: Xaa = any amino acid
<220> FEATURE:
<221> NAME/KEY: MISC_FEATURE
<222> LOCATION: (132)..(132)
<223> OTHER INFORMATION: Xaa = any amino acid
<220> FEATURE:
<221> NAME/KEY: MISC_FEATURE
<222> LOCATION: (136)..(136)
<223> OTHER INFORMATION: Xaa = any amino acid

<400> SEQUENCE: 46

Arg Arg Lys Trp Ser Leu Asp Arg Leu Arg Asp Thr Val Lys Ala Leu
1               5                   10                  15

Thr Arg Glu Gln Glu Lys Leu Leu Gly Gln Leu Lys Glu Val Gln Ala
            20                  25                  30

Asp Lys Glu Gln Ser Glu Ala Glu Leu Gln Val Ala Gln Gln Glu Asn
        35                  40                  45

His His Leu Asn Leu Asp Leu Lys Glu Ala Lys Ser Trp Gln Glu Glu
    50                  55                  60

Xaa Ser Ala Gln Ala Gln Arg Leu Lys Asp Lys Val Ala Gln Met Lys
65                  70                  75                  80

Asp Thr Leu Cys Gln Ala Gln Gln Arg Val Ala Gln Leu Glu Pro Leu
                85                  90                  95

Lys Glu Gln Leu Xaa Gly Ala Gln Xaa Ala Leu Xaa Ala Ser Ser Gln
            100                 105                 110

Xaa Lys Ala Thr Leu Ser Trp Gly Gly Val Cys Gln Xaa Xaa Xaa Xaa
        115                 120                 125

Pro Gly Thr Xaa Pro Tyr Ala Xaa Leu His Arg Ser Arg Pro Gly Ser
    130                 135                 140

Gly
145
```

```
<210> SEQ ID NO 47
<211> LENGTH: 208
<212> TYPE: PRT
<213> ORGANISM: homosapiens
<220> FEATURE:
<221> NAME/KEY: MISC_FEATURE
<222> LOCATION: (6)..(6)
<223> OTHER INFORMATION: Xaa = any amino acid

<400> SEQUENCE: 47
```

Gly Arg Ala Pro Val Xaa Gln Cys Ser Asp Gly Glu Gly Arg Lys Arg
1               5                   10                  15

Thr Ser Ser Thr Cys Ser Asn Glu Ser Leu Ser Val Gly Gly Thr Ser
            20                  25                  30

Val Thr Pro Arg Arg Ile Ser Trp Arg Gln Arg Ile Phe Leu Arg Val
        35                  40                  45

Ala Ser Pro Met Asn Lys Ser Pro Ser Ala Met Gln Gln Gln Asp Gly
    50                  55                  60

Leu Asp Arg Asn Glu Leu Leu Pro Leu Ser Pro Leu Ser Pro Thr Met
65                  70                  75                  80

Glu Glu Glu Pro Leu Val Val Phe Leu Ser Gly Glu Asp Asp Pro Glu
                85                  90                  95

Lys Ile Glu Glu Arg Lys Lys Ser Lys Glu Leu Arg Ser Leu Trp Arg
            100                 105                 110

Lys Ala Ile His Gln Gln Ile Leu Leu Leu Arg Met Glu Lys Glu Asn
        115                 120                 125

Gln Lys Leu Glu Ala Ser Arg Asp Glu Leu Gln Ser Arg Lys Val Lys
    130                 135                 140

Leu Asp Tyr Glu Glu Val Gly Ala Cys Gln Lys Glu Val Leu Ile Thr
145                 150                 155                 160

Trp Asp Lys Lys Leu Leu Asn Cys Arg Ala Lys Ile Arg Cys Asp Met
                165                 170                 175

Glu Asp Ile His Thr Leu Leu Lys Lys Glu Phe Pro Lys Ser Thr Arg
            180                 185                 190

Arg Ile Trp Gln Phe Leu Ala Tyr Ser Thr Asp Ser Thr Gln Ile Ala
        195                 200                 205

```
<210> SEQ ID NO 48
<211> LENGTH: 256
<212> TYPE: PRT
<213> ORGANISM: homosapiens
<220> FEATURE:
<221> NAME/KEY: MISC_FEATURE
<222> LOCATION: (186)..(186)
<223> OTHER INFORMATION: Xaa = any amino acid
<220> FEATURE:
<221> NAME/KEY: MISC_FEATURE
<222> LOCATION: (219)..(219)
<223> OTHER INFORMATION: Xaa = any amino acid
<220> FEATURE:
<221> NAME/KEY: MISC_FEATURE
<222> LOCATION: (222)..(222)
<223> OTHER INFORMATION: Xaa = any amino acid
<220> FEATURE:
<221> NAME/KEY: MISC_FEATURE
<222> LOCATION: (230)..(230)
<223> OTHER INFORMATION: Xaa = any amino acid
<220> FEATURE:
<221> NAME/KEY: MISC_FEATURE
<222> LOCATION: (243)..(243)
<223> OTHER INFORMATION: Xaa = any amino acid
<220> FEATURE:
<221> NAME/KEY: MISC_FEATURE
<222> LOCATION: (247)..(247)
<223> OTHER INFORMATION: Xaa = any amino acid
```

<220> FEATURE:
<221> NAME/KEY: MISC_FEATURE
<222> LOCATION: (254)..(254)
<223> OTHER INFORMATION: Xaa = any amino acid

<400> SEQUENCE: 48

Met Leu Arg Ser Pro Phe Asp Arg Asn Val Pro Val Asn Leu Glu Leu
1               5                   10                  15

Gln Glu Leu Leu Leu Asp Tyr Ser Phe Gln His Leu Gly Val Ser Ser
            20                  25                  30

Gln Gly Cys Val Asp His Pro Ile Val Leu Thr Glu Ala Val Cys Asn
        35                  40                  45

Pro Leu Tyr Ser Arg Gln Met Met Ser Glu Leu Leu Phe Glu Cys Tyr
    50                  55                  60

Gly Ile Pro Lys Val Ala Tyr Gly Ile Asp Ser Leu Phe Ser Phe Tyr
65                  70                  75                  80

His Asn Lys Pro Lys Asn Ser Met Cys Ser Gly Leu Ile Ile Ser Ser
                85                  90                  95

Gly Tyr Gln Cys Thr His Val Leu Pro Ile Leu Glu Gly Arg Leu Asp
            100                 105                 110

Ala Lys Asn Cys Lys Arg Ile Asn Leu Gly Gly Ser Gln Ala Ala Gly
        115                 120                 125

Tyr Leu Gln Arg Leu Leu Gln Leu Lys Tyr Pro Gly His Leu Ala Ala
    130                 135                 140

Ile Thr Leu Ser Arg Met Glu Glu Ile Leu His Glu His Ser Tyr Ile
145                 150                 155                 160

Ala Glu Asp Tyr Val Glu Glu Leu His Lys Trp Arg Cys Pro Asp Tyr
                165                 170                 175

Tyr Glu Asn Asn Val His Lys Met Gln Xaa Pro Phe Ser Ser Lys Leu
            180                 185                 190

Leu Gly Ser Thr Leu Thr Ser Glu Glu Lys Gln Glu Arg Arg Gln Gln
        195                 200                 205

Gln Leu Arg Arg Leu Gln Glu Leu Asn Ala Xaa Arg Arg Xaa Glu Lys
    210                 215                 220

Leu Gln Leu Gly Ser Xaa Ala Ser Gly Pro Thr Ala Ile Cys Ala Gly
225                 230                 235                 240

Thr Ser Xaa Gly Trp Pro Xaa Gly Ser Val Tyr Lys Ala Xaa Met Ser
                245                 250                 255

<210> SEQ ID NO 49
<211> LENGTH: 205
<212> TYPE: PRT
<213> ORGANISM: homosapiens
<220> FEATURE:
<221> NAME/KEY: MISC_FEATURE
<222> LOCATION: (144)..(144)
<223> OTHER INFORMATION: Xaa = any amino acid
<220> FEATURE:
<221> NAME/KEY: MISC_FEATURE
<222> LOCATION: (157)..(157)
<223> OTHER INFORMATION: Xaa = any amino acid
<220> FEATURE:
<221> NAME/KEY: MISC_FEATURE
<222> LOCATION: (159)..(159)
<223> OTHER INFORMATION: Xaa = any amino acid
<220> FEATURE:
<221> NAME/KEY: MISC_FEATURE
<222> LOCATION: (188)..(188)
<223> OTHER INFORMATION: Xaa = any amino acid
<220> FEATURE:
<221> NAME/KEY: MISC_FEATURE
<222> LOCATION: (194)..(194)
<223> OTHER INFORMATION: Xaa = any amino acid -continued

```
<220> FEATURE:
<221> NAME/KEY: MISC_FEATURE
<222> LOCATION: (197)..(197)
<223> OTHER INFORMATION: Xaa = any amino acid

<400> SEQUENCE: 49
```

Met Asn Asp Ile Ser Gln Lys Ala Glu Ile Leu Leu Ser Ser Ser Lys
1               5                   10                  15

Pro Val Pro Lys Thr Tyr Val Pro Lys Leu Gly Lys Gly Asp Val Lys
            20                  25                  30

Asp Lys Phe Glu Ala Met Gln Arg Ala Arg Glu Glu Arg Asn Gln Arg
        35                  40                  45

Arg Ser Arg Asp Glu Lys Gln Arg Arg Lys Glu Gln Tyr Ile Arg Glu
    50                  55                  60

Arg Glu Trp Asn Arg Arg Lys Gln Glu Ile Lys Glu Met Leu Ala Ser
65                  70                  75                  80

Asp Asp Glu Glu Asp Val Ser Ser Lys Val Glu Lys Ala Tyr Val Pro
                85                  90                  95

Lys Leu Thr Gly Thr Val Lys Gly Arg Phe Ala Glu Met Glu Lys Gln
            100                 105                 110

Arg Gln Glu Glu Gln Arg Lys Arg Thr Glu Glu Glu Arg Lys Arg Arg
        115                 120                 125

Ile Glu Gln Asp Met Leu Glu Lys Arg Lys Ile Gln Arg Glu Leu Xaa
    130                 135                 140

Lys Arg Ala Glu Gln Glu Gly Asp Asp Ser Leu Leu Xaa Thr Xaa Val
145                 150                 155                 160

Pro Val Asn His Ile Asn Ile Trp Lys Met Lys Arg Ile Leu Arg Ser
                165                 170                 175

Arg Lys Arg Arg Glu Glu Lys Lys Asp Pro Val Xaa Glu Ile Lys Ile
            180                 185                 190

Arg Xaa Glu Thr Xaa Pro Leu Ser Gly Ala Arg Ala Ser
        195                 200                 205

```
<210> SEQ ID NO 50
<211> LENGTH: 172
<212> TYPE: PRT
<213> ORGANISM: homosapiens
<220> FEATURE:
<221> NAME/KEY: MISC_FEATURE
<222> LOCATION: (136)..(136)
<223> OTHER INFORMATION: Xaa = any amino acid
<220> FEATURE:
<221> NAME/KEY: MISC_FEATURE
<222> LOCATION: (142)..(142)
<223> OTHER INFORMATION: Xaa = any amino acid
<220> FEATURE:
<221> NAME/KEY: MISC_FEATURE
<222> LOCATION: (146)..(146)
<223> OTHER INFORMATION: Xaa = any amino acid
<220> FEATURE:
<221> NAME/KEY: MISC_FEATURE
<222> LOCATION: (151)..(151)
<223> OTHER INFORMATION: Xaa = any amino acid

<400> SEQUENCE: 50
```

Met Glu Ser Tyr Arg Glu Asn Leu Glu Arg Val Phe Val Arg Met Asp
1               5                   10                  15

Gln Val Leu Pro Asp Ser Cys Leu Leu Val Trp Asn Met Ala Met Pro
            20                  25                  30

Leu Gly Glu Arg Ile Thr Gly Gly Phe Leu Leu Pro Glu Leu Gln Pro
        35                  40                  45

Leu Ala Gly Ser Leu Arg Arg Asp Val Val Glu Gly Asn Phe Tyr Ser

```
                50                  55                  60
Ala Thr Leu Ala Gly Asp His Cys Phe Asp Val Leu Asp Leu His Phe
 65                  70                  75                  80

His Phe Arg His Ala Val Gln His Arg His Arg Asp Gly Val His Trp
                    85                  90                  95

Asp Gln His Ala His Arg His Leu Ser His Leu Leu Leu Thr His Val
                100                 105                 110

Ala Asp Ala Trp Gly Val Glu Leu Pro Lys Arg Gly Tyr Pro Pro Asp
            115                 120                 125

Pro Trp Ile Glu Asp Trp Ala Xaa Met Asn His Pro Phe Xaa Gly Ser
130                 135                 140

His Xaa Gln Thr Gln Thr Xaa Gly Arg Pro Gly Pro Cys Ser Thr Pro
145                 150                 155                 160

Leu Leu Leu Ala Leu His Ala Phe Ser Tyr Arg Phe
                165                 170

<210> SEQ ID NO 51
<211> LENGTH: 159
<212> TYPE: PRT
<213> ORGANISM: homosapiens
<220> FEATURE:
<221> NAME/KEY: MISC_FEATURE
<222> LOCATION: (143)..(143)
<223> OTHER INFORMATION: Xaa = any amino acid
<220> FEATURE:
<221> NAME/KEY: MISC_FEATURE
<222> LOCATION: (153)..(153)
<223> OTHER INFORMATION: Xaa = any amino acid

<400> SEQUENCE: 51

Met Leu Gln Gln Glu Thr Ile Arg Asn Gly Glu Leu Glu Asp Thr Gln
 1               5                  10                  15

Thr Lys Leu Glu Lys Gln Val Ser Lys Leu Glu Gln Glu Leu Gln Lys
                20                  25                  30

Gln Arg Glu Ser Ser Ala Glu Lys Leu Arg Lys Met Glu Glu Lys Cys
            35                  40                  45

Glu Ser Ala Ala His Glu Ala Asp Leu Lys Arg Gln Lys Val Ile Glu
 50                  55                  60

Leu Thr Gly Thr Ala Arg Gln Val Lys Ile Glu Met Asp Gln Tyr Lys
 65                  70                  75                  80

Glu Glu Leu Ser Lys Met Glu Lys Glu Ile Met His Leu Lys Arg Asp
                85                  90                  95

Gly Glu Asn Lys Ala Met His Leu Ser Gln Leu Asp Met Ile Leu Asp
            100                 105                 110

Gln Thr Lys Thr Glu Leu Glu Lys Lys Thr Asn Ala Val Lys Glu Leu
        115                 120                 125

Glu Lys Leu Gln His Ser Thr Glu Thr Glu Leu Thr Glu Ala Xaa Gln
130                 135                 140

Asn Gly Lys Tyr Leu Arg Leu Thr Xaa Lys Cys Ser Trp Glu Ile
145                 150                 155

<210> SEQ ID NO 52
<211> LENGTH: 122
<212> TYPE: PRT
<213> ORGANISM: homosapiens

<400> SEQUENCE: 52

Met Ile Gly Gly Thr Glu Met Thr Lys Glu Ile Pro Arg Lys Arg Lys
 1               5                  10                  15
```

```
Asn Thr Val Glu Ala Glu Ala Glu Lys Gly Asn Thr Glu Val Gly Val
            20                  25                  30

Glu Val Glu Met Gln Gly Asn Glu Val Val Glu Ala Lys Arg Asn
        35                  40                  45

Gln Val Asn Ile Lys Met Lys Val Lys Asn Gln Ile Asn Glu Val
 50                  55                  60

Glu Val Ala Val Lys Glu Glu Leu Thr Val Leu Lys Asn Gln Lys Asn
 65                  70                  75                  80

Gly Asn Ile Val Pro Ala Lys Lys Asn Leu Glu Ser Val Val Glu Ala
                85                  90                  95

Lys Asn Val Pro Thr Asn Glu Ile Thr Val Ile Val Arg Thr Ser Gln
            100                 105                 110

Thr Asn Met Ile Val Glu Gly Ala Lys Val
        115                 120
```

<210> SEQ ID NO 53
<211> LENGTH: 127
<212> TYPE: PRT
<213> ORGANISM: homosapiens

<400> SEQUENCE: 53

```
Met Ser Arg Pro Lys Thr Gln Asn Gln Val Thr His Thr Gln Val Lys
 1               5                  10                  15

Asn Thr Arg Arg Lys Pro Ile Thr Val Leu Lys Arg Lys Lys Met Arg
            20                  25                  30

Thr Thr Cys Gln Ser Lys Ile Leu Ile Arg Ile Ser Ile Glu Lys Trp
        35                  40                  45

Gly Leu Val Thr Met Lys Lys Lys Ala Val Gly Arg Asn Lys Arg
 50                  55                  60

Val Lys Arg Glu Thr Glu Leu Arg Thr Glu Val Val Ala Asp Leu Glu
 65                  70                  75                  80

Arg Gly Met Ala Ile Ile Val Ile Val Ile Asn Gln Asn Thr Lys Gln
                85                  90                  95

Ile Phe Met Lys Glu Lys Gly Val Lys Arg Glu Thr Glu Ala Glu Val
            100                 105                 110

Gln Arg Ser Pro Lys Ile Lys Lys Asn Leu Ser Ile Asp Glu Arg
        115                 120                 125
```

<210> SEQ ID NO 54
<211> LENGTH: 175
<212> TYPE: PRT
<213> ORGANISM: homosapiens
<220> FEATURE:
<221> NAME/KEY: MISC_FEATURE
<222> LOCATION: (132)..(132)
<223> OTHER INFORMATION: Xaa = any amino acid
<220> FEATURE:
<221> NAME/KEY: MISC_FEATURE
<222> LOCATION: (146)..(146)
<223> OTHER INFORMATION: Xaa = any amino acid

<400> SEQUENCE: 54

```
Met Gly Lys Lys His Lys Lys His Lys Ala Glu Trp Arg Ser Ser Tyr
 1               5                  10                  15

Glu Asp Tyr Ala Asp Lys Pro Leu Glu Lys Pro Leu Lys Leu Val Leu
            20                  25                  30

Lys Val Gly Gly Ser Glu Val Thr Glu Leu Ser Gly Ser Gly His Asp
        35                  40                  45

Ser Ser Tyr Tyr Asp Asp Arg Ser Asp His Glu Arg Glu Arg His Lys
 50                  55                  60
```

-continued

Glu Lys Lys Lys Lys Lys Lys Lys Ser Glu Lys Glu Lys His Leu
65                  70                  75                  80

Asp Asp Glu Glu Arg Arg Lys Arg Lys Glu Glu Lys Lys Arg Lys Arg
            85                  90                  95

Glu Arg Glu His Cys Asp Thr Glu Gly Glu Ala Asp Asp Phe Asp Pro
                100                 105                 110

Gly Lys Lys Val Glu Val Glu Pro Pro Pro Asp Arg Pro Val Arg Ala
            115                 120                 125

Cys Arg Thr Xaa Pro Ala Glu Asn Glu Ser Thr Pro Ile Gln Gln Leu
        130                 135                 140

Leu Xaa Thr Leu Pro Pro Pro Ala Ser Glu Lys Arg Ser Pro Trp Ile
145                 150                 155                 160

Phe Cys Phe Ser Cys His Gly Cys Asn Cys Ser Trp Asp Ile Pro
                165                 170                 175

<210> SEQ ID NO 55
<211> LENGTH: 255
<212> TYPE: PRT
<213> ORGANISM: Homo sapiens

<400> SEQUENCE: 55

Met Ser Ser His Arg Arg Lys Ala Lys Gly Arg Asn Arg Arg Ser His
1               5                   10                  15

Arg Ala Met Arg Val Ala His Leu Glu Leu Ala Thr Tyr Glu Leu Ala
            20                  25                  30

Ala Thr Glu Ser Asn Pro Glu Ser Ser His Pro Gly Tyr Glu Ala Ala
        35                  40                  45

Met Ala Asp Arg Pro Gln Pro Gly Trp Arg Glu Ser Leu Lys Met Arg
    50                  55                  60

Val Ser Lys Pro Phe Gly Met Leu Met Leu Ser Ile Trp Ile Leu Leu
65                  70                  75                  80

Phe Val Cys Tyr Tyr Leu Ser Tyr Tyr Leu Cys Ser Gly Ser Ser Tyr
                85                  90                  95

Phe Val Leu Ala Asn Gly His Ile Leu Pro Asn Ser Glu Asn Ala His
            100                 105                 110

Gly Gln Ser Leu Glu Glu Asp Ser Ala Leu Glu Ala Leu Leu Asn Phe
        115                 120                 125

Phe Phe Pro Thr Thr Cys Asn Leu Arg Glu Asn Gln Val Ala Lys Pro
    130                 135                 140

Cys Asn Glu Leu Gln Asp Leu Ser Glu Ser Glu Cys Leu Arg His Lys
145                 150                 155                 160

Cys Cys Phe Ser Ser Ser Gly Thr Thr Ser Phe Lys Cys Phe Ala Pro
                165                 170                 175

Phe Arg Asp Val Pro Lys Gln Met Met Gln Met Phe Gly Leu Gly Ala
            180                 185                 190

Ile Ser Leu Ile Leu Val Cys Leu Pro Ile Tyr Cys Arg Ser Leu Phe
        195                 200                 205

Trp Arg Ser Glu Pro Ala Asp Asp Leu Gln Arg Gln Asp Asn Arg Val
    210                 215                 220

Val Thr Gly Leu Lys Lys Gln Arg Arg Lys Arg Lys Arg Lys Ser Glu
225                 230                 235                 240

Met Leu Gln Lys Ala Ala Arg Gly Arg Glu Glu His Gly Asp Glu
                245                 250                 255

<210> SEQ ID NO 56

```
<211> LENGTH: 239
<212> TYPE: PRT
<213> ORGANISM: homosapiens
<220> FEATURE:
<221> NAME/KEY: MISC_FEATURE
<222> LOCATION: (42)..(42)
<223> OTHER INFORMATION: Xaa = any amino acid
<220> FEATURE:
<221> NAME/KEY: MISC_FEATURE
<222> LOCATION: (225)..(229)
<223> OTHER INFORMATION: Xaa = any amino acid
<220> FEATURE:
<221> NAME/KEY: MISC_FEATURE
<222> LOCATION: (231)..(234)
<223> OTHER INFORMATION: Xaa = any amino acid

<400> SEQUENCE: 56

Met Leu Gln Asn Glu Gln Glu Ile Ser Gln Leu Lys Lys Glu Ile Glu
1               5                   10                  15

Arg Thr Gln Gln Arg Met Lys Glu Met Glu Ser Val Met Lys Glu Gln
            20                  25                  30

Glu Gln Tyr Ile Ala Thr Gln Tyr Lys Xaa Ala Ile Asp Leu Gly Gln
        35                  40                  45

Glu Leu Arg Leu Thr Arg Glu Gln Val Gln Asn Ser His Thr Glu Leu
    50                  55                  60

Ala Glu Ala Arg His Gln Gln Val Gln Ala Gln Arg Glu Ile Glu Arg
65                  70                  75                  80

Leu Ser Ser Glu Leu Glu Asp Met Lys Gln Leu Ser Lys Glu Lys Asp
                85                  90                  95

Ala His Gly Asn His Leu Ala Glu Glu Leu Gly Ala Ser Lys Val Arg
            100                 105                 110

Glu Ala His Leu Glu Ala Arg Met Gln Ala Glu Ile Lys Lys Leu Ser
        115                 120                 125

Ala Glu Val Glu Ser Leu Lys Glu Ala Tyr His Met Glu Met Ile Ser
    130                 135                 140

His Gln Glu Asn His Ala Lys Trp Lys Ile Ser Ala Asp Ser Gln Lys
145                 150                 155                 160

Ser Ser Val Gln Gln Leu Asn Glu Gln Leu Lys Ala Lys Leu Glu
                165                 170                 175

Leu Glu Glu Ala Gln Asp Thr Val Ser Asn Leu His Gln Gln Val Gln
            180                 185                 190

Asp Arg Asn Glu Val Ile Glu Ala Ala Asn Glu Ala Leu Leu Thr Lys
        195                 200                 205

Val Ser Lys His Ile Lys Val Leu Lys His Ile Tyr Glu Asn Lys Thr
    210                 215                 220

Xaa Xaa Xaa Xaa Xaa Pro Xaa Xaa Xaa Xaa Ser Arg Glu Tyr Phe
225                 230                 235

<210> SEQ ID NO 57
<211> LENGTH: 249
<212> TYPE: PRT
<213> ORGANISM: homosapiens
<220> FEATURE:
<221> NAME/KEY: MISC_FEATURE
<222> LOCATION: (226)..(226)
<223> OTHER INFORMATION: Xaa = any amino acid
<220> FEATURE:
<221> NAME/KEY: MISC_FEATURE
<222> LOCATION: (239)..(239)
<223> OTHER INFORMATION: Xaa = any amino acid

<400> SEQUENCE: 57

Met Ala Asp Ser Ser Gly Arg Gly Ala Gly Lys Pro Ala Thr Gly Pro
```

```
                1               5                  10                 15
Thr Asn Ser Ser Ser Ala Lys Lys Asp Lys Arg Val Gln Gly Gly
                        20                  25                  30

Arg Val Ile Glu Ser Arg Tyr Leu Gln Tyr Glu Lys Lys Thr Thr Gln
                        35                  40                  45

Lys Ala Pro Ala Gly Asp Gly Ser Gln Thr Arg Gly Lys Met Ser Glu
            50                  55                  60

Gly Gly Arg Lys Ser Ser Leu Leu Gln Lys Ser Lys Ala Asp Ser Ser
65                      70                  75                      80

Gly Val Gly Lys Gly Asp Leu Gln Ser Thr Leu Leu Glu Gly His Gly
                        85                  90                  95

Thr Ala Pro Pro Asp Leu Asp Leu Ser Ala Ile Asn Asp Lys Ser Ile
                        100                 105                 110

Val Lys Lys Thr Pro Gln Leu Ala Lys Thr Ile Ser Lys Lys Pro Glu
                115                 120                 125

Ser Thr Ser Phe Ser Ala Pro Arg Lys Ser Pro Asp Leu Ser Glu
                130                 135                 140

Ala Met Glu Met Met Glu Ser Gln Thr Leu Leu Leu Thr Leu Leu Ser
145                     150                 155                 160

Val Lys Met Glu Asn Asn Leu Ala Glu Phe Glu Arg Arg Ala Glu Lys
                        165                 170                 175

Asn Leu Leu Ile Met Cys Lys Glu Lys Glu Lys Leu Gln Lys Lys Ala
                    180                 185                 190

His Glu Leu Lys Arg Arg Leu Leu Leu Ser Gln Arg Lys Arg Glu Leu
                    195                 200                 205

Ala Asp Val Leu Asp Ala Gln Ile Glu Met Leu Ser Pro Leu Arg Gly
                    210                 215                 220

Ser Xaa His Thr Leu Gln Gly Ala Ile Gln Asp Ile Arg His Xaa Pro
225                     230                 235                 240

Trp Thr Leu Pro Gly Thr Ser Cys Pro
                        245

<210> SEQ ID NO 58
<211> LENGTH: 116
<212> TYPE: PRT
<213> ORGANISM: homosapiens

<400> SEQUENCE: 58

Met Asp Tyr Arg Arg Leu Leu Met Ser Arg Val Val Pro Gly Gln Phe
1               5                   10                  15

Asp Asp Ala Asp Ser Ser Asp Ser Glu Asn Arg Asp Leu Lys Thr Val
                    20                  25                  30

Lys Glu Lys Asp Asp Ile Leu Phe Glu Asp Leu Gln Asp Asn Val Asn
                35                  40                  45

Glu Asn Gly Glu Gly Glu Ile Glu Asp Glu Glu Glu Gly Tyr Asp
            50                  55                  60

Asp Asp Asp Asp Trp Asp Trp Asp Glu Gly Val Gly Lys Leu Ala
65                  70                  75                  80

Lys Gly Tyr Val Trp Asn Gly Gly Ser Asn Pro Gln Ala Asn Arg Gln
                        85                  90                  95

Thr Ser Asp Ser Ser Ser Ala Lys Met Ser Thr Pro Ala Asp Lys Val
                    100                 105                 110

Leu Arg Lys Ile
            115
```

```
<210> SEQ ID NO 59
<211> LENGTH: 225
<212> TYPE: PRT
<213> ORGANISM: homo sapiens

<400> SEQUENCE: 59

Met Ala His Ala Ala Gln Val Gly Leu Gln Asp Ala Thr Ser Pro Ile
1               5                   10                  15

Met Glu Glu Leu Ile Thr Phe His Asp His Ala Leu Met Ile Ile Phe
            20                  25                  30

Leu Ile Cys Phe Leu Val Leu Tyr Ala Leu Phe Leu Thr Leu Thr Thr
        35                  40                  45

Lys Leu Thr Asn Thr Asn Ile Ser Asp Ala Gln Glu Met Val Trp Thr
50                  55                  60

Ile Leu Pro Ala Ile Ile Leu Val Leu Ile Ala Leu Pro Ser Leu Arg
65                  70                  75                  80

Ile Leu Tyr Met Thr Asp Glu Val Asn Asp Pro Ser Leu Thr Ile Lys
                85                  90                  95

Ser Ile Gly His Gln Trp Tyr Trp Thr Tyr Glu Tyr Thr Asp Tyr Gly
            100                 105                 110

Gly Leu Ile Phe Asn Ser Tyr Met Leu Pro Pro Leu Phe Leu Glu Pro
        115                 120                 125

Gly Asp Leu Arg Leu Leu Asp Val Asp Asn Arg Val Val Leu Pro Ile
130                 135                 140

Glu Ala Pro Ile Arg Met Met Ile Thr Ser Gln Asp Val Leu His Ser
145                 150                 155                 160

Trp Ala Val Pro Thr Leu Gly Leu Lys Thr Asp Ala Ile Pro Gly Arg
                165                 170                 175

Leu Asn Gln Thr Thr Phe Thr Ala Thr Arg Pro Gly Val Tyr Tyr Gly
            180                 185                 190

Gln Cys Ser Glu Ile Cys Gly Ala Asn His Ser Phe Met Pro Ile Val
        195                 200                 205

Leu Glu Leu Ile Pro Leu Lys Ile Phe Glu Met Gly Pro Val Phe Thr
210                 215                 220

Leu
225

<210> SEQ ID NO 60
<211> LENGTH: 384
<212> TYPE: PRT
<213> ORGANISM: homo sapiens

<400> SEQUENCE: 60

Met Asp Ala Val Met Thr Arg Lys Lys Ile Met Lys Gln Lys Glu Met
1               5                   10                  15

Val Trp Asn Asn Asn Lys Lys Leu Ser Asp Leu Glu Glu Val Ala Lys
            20                  25                  30

Glu Arg Ala Gln Asn Leu Leu Gln Arg Ala Asn Lys Leu Arg Met Glu
        35                  40                  45

Gln Glu Glu Glu Leu Lys Asp Met Ser Lys Ile Ile Leu Asn Ala Lys
50                  55                  60

Cys His Ala Ile Arg Asp Ala Gln Ile Leu Glu Lys Gln Gln Ile Gln
65                  70                  75                  80

Lys Glu Leu Asp Thr Glu Glu Lys Arg Leu Asp Gln Met Met Glu Val
                85                  90                  95

Glu Arg Gln Lys Ser Ile Gln Arg Gln Glu Glu Leu Glu Arg Lys Arg
            100                 105                 110
```

```
Arg Glu Glu Arg Ile Arg Gly Arg Arg Gln Ile Val Glu Gln Met Glu
            115                 120                 125

Lys Asn Gln Glu Glu Arg Ser Leu Leu Ala Glu Gln Arg Glu Gln Glu
            130                 135                 140

Lys Glu Gln Met Leu Glu Tyr Met Glu Gln Leu Glu Glu Glu Asp Leu
145                 150                 155                 160

Lys Asp Met Glu Arg Arg Gln Gln Gln Lys Leu Lys Met Gln Ala Glu
                165                 170                 175

Ile Lys Arg Ile Asn Asp Glu Asn Gln Lys Gln Lys Ala Glu Leu Leu
            180                 185                 190

Ala Gln Glu Lys Leu Ala Asp Gln Met Val Met Glu Phe Thr Lys Lys
            195                 200                 205

Lys Met Ala Arg Glu Ala Glu Phe Glu Ala Glu Gln Glu Arg Ile Arg
            210                 215                 220

Arg Glu Lys Glu Lys Glu Ile Ala Arg Leu Arg Ala Met Gln Glu Lys
225                 230                 235                 240

Ala Gln Asp Tyr Gln Ala Glu Gln Asp Ala Leu Arg Ala Lys Arg Asn
                245                 250                 255

Gln Glu Val Ala Asp Arg Glu Trp Arg Arg Lys Glu Lys Glu Asn Ala
            260                 265                 270

Arg Lys Lys Met Glu Ala Glu Leu Arg Lys Ser Arg Leu Glu Gln Val
            275                 280                 285

Ala Phe Lys Glu His Ala Leu Ala Val Gln Val His Gly Thr Gly Met
            290                 295                 300

Ser Ser Arg Gly Phe Phe Gly Leu Arg Glu Asn Arg Leu Arg Arg Ser
305                 310                 315                 320

Gly Trp Arg Arg Arg Lys Arg Pro Gln Gly Ala Tyr Ser Met Pro Met
                325                 330                 335

Ser Ser Gly Ala Arg Cys Ala Arg Thr Ser Arg Arg Lys Cys Arg Thr
            340                 345                 350

Gly Leu Pro Pro Leu Arg Gly Ala Gly Ala Ser Lys Arg Arg Pro Arg
            355                 360                 365

Asn Ala Val Ser Ala Ser Met Arg Ser Arg Gly Lys Ser Leu Lys Ser
            370                 375                 380

<210> SEQ ID NO 61
<211> LENGTH: 510
<212> TYPE: PRT
<213> ORGANISM: homo sapiens

<400> SEQUENCE: 61

Met Tyr Arg Ala Leu Arg Leu Leu Ala Arg Ser Arg Pro Leu Val Arg
1               5                   10                  15

Ala Pro Ala Ala Ala Leu Ala Ser Ala Pro Gly Leu Gly Gly Ala Ala
            20                  25                  30

Val Pro Ser Phe Trp Pro Pro Asn Ala Ala Arg Met Ala Ser Gln Asn
            35                  40                  45

Ser Phe Arg Ile Glu Tyr Asp Thr Phe Gly Glu Leu Lys Val Pro Asn
            50                  55                  60

Asp Lys Tyr Tyr Gly Ala Gln Thr Val Arg Ser Thr Met Asn Phe Lys
65                  70                  75                  80

Ile Gly Gly Val Thr Glu Arg Met Pro Thr Pro Val Ile Lys Ala Phe
                85                  90                  95

Gly Ile Leu Lys Arg Ala Ala Ala Glu Val Asn Gln Asp Tyr Gly Leu
            100                 105                 110
```

Asp Pro Lys Ile Ala Asn Ala Ile Met Lys Ala Ala Asp Glu Val Ala
            115                 120                 125

Glu Gly Lys Leu Asn Asp His Phe Pro Leu Val Val Trp Gln Thr Gly
        130                 135                 140

Ser Gly Thr Gln Thr Asn Met Asn Val Asn Glu Val Ile Ser Asn Arg
145                 150                 155                 160

Ala Ile Glu Met Leu Gly Gly Glu Leu Gly Ser Lys Ile Pro Val His
                165                 170                 175

Pro Asn Asp His Val Asn Lys Ser Gln Ser Ser Asn Asp Thr Phe Pro
            180                 185                 190

Thr Ala Met His Ile Ala Ala Ile Glu Val His Glu Val Leu Leu
        195                 200                 205

Pro Gly Leu Gln Lys Leu His Asp Ala Leu Asp Ala Lys Ser Lys Glu
        210                 215                 220

Phe Ala Gln Ile Ile Lys Ile Gly Arg Thr His Thr Gln Asp Ala Val
225                 230                 235                 240

Pro Leu Thr Leu Gly Gln Glu Phe Ser Gly Tyr Val Gln Gln Val Lys
                245                 250                 255

Tyr Ala Met Thr Arg Ile Lys Ala Ala Met Pro Arg Ile Tyr Glu Leu
            260                 265                 270

Ala Ala Gly Gly Thr Ala Val Gly Thr Gly Leu Asn Thr Arg Ile Gly
        275                 280                 285

Phe Ala Glu Lys Val Ala Ala Lys Val Ala Ala Leu Thr Gly Leu Pro
    290                 295                 300

Phe Val Thr Ala Pro Asn Lys Phe Glu Ala Leu Ala Ala His Asp Ala
305                 310                 315                 320

Leu Val Glu Leu Ser Gly Ala Met Asn Thr Thr Ala Cys Ser Leu Met
                325                 330                 335

Lys Ile Ala Asn Asp Ile Arg Phe Leu Gly Ser Gly Pro Arg Ser Gly
            340                 345                 350

Leu Gly Glu Leu Ile Leu Pro Glu Asn Glu Pro Gly Ser Ser Ile Met
        355                 360                 365

Pro Gly Lys Val Asn Pro Thr Gln Cys Glu Ala Met Thr Met Val Ala
    370                 375                 380

Ala Gln Val Met Gly Asn His Val Ala Val Thr Val Gly Gly Ser Asn
385                 390                 395                 400

Gly His Phe Glu Leu Asn Val Phe Lys Pro Met Met Ile Lys Asn Val
                405                 410                 415

Leu His Ser Ala Arg Leu Leu Gly Asp Ala Ser Val Ser Phe Thr Glu
            420                 425                 430

Asn Cys Val Val Gly Ile Gln Ala Asn Thr Glu Arg Ile Asn Lys Leu
        435                 440                 445

Met Asn Glu Ser Leu Met Leu Val Thr Ala Leu Asn Pro His Ile Gly
    450                 455                 460

Tyr Asp Lys Ala Ala Lys Ile Ala Lys Thr Ala His Lys Asn Gly Ser
465                 470                 475                 480

Thr Leu Lys Glu Thr Ala Ile Glu Leu Gly Tyr Leu Thr Ala Glu Gln
                485                 490                 495

Phe Asp Glu Trp Val Lys Pro Lys Asp Met Leu Gly Pro Lys
            500                 505                 510

<210> SEQ ID NO 62
<211> LENGTH: 937
<212> TYPE: PRT

-continued

<213> ORGANISM: homo sapiens

<400> SEQUENCE: 62

Met Arg Lys Ser Phe Ser Gln Pro Gly Leu Arg Ser Leu Ala Phe Arg
1               5                   10                  15

Lys Glu Leu Gln Asp Gly Gly Leu Arg Ser Ser Gly Phe Phe Ser Ser
            20                  25                  30

Phe Glu Glu Ser Asp Ile Glu Asn His Leu Ile Ser Gly His Asn Ile
        35                  40                  45

Val Gln Pro Thr Asp Ile Glu Asn Arg Thr Met Leu Phe Thr Ile
    50                  55                  60

Gly Gln Ser Glu Val Tyr Leu Ile Ser Pro Asp Thr Lys Lys Ile Ala
65                  70                  75                  80

Leu Glu Lys Asn Phe Lys Glu Ile Ser Phe Cys Ser Gln Gly Ile Arg
                85                  90                  95

His Val Asp His Phe Gly Phe Ile Cys Arg Glu Ser Ser Gly Gly Gly
            100                 105                 110

Gly Phe His Phe Val Cys Tyr Val Phe Gln Cys Thr Asn Glu Ala Leu
        115                 120                 125

Val Asp Glu Ile Met Met Thr Leu Lys Gln Ala Phe Thr Val Ala Ala
    130                 135                 140

Val Gln Gln Thr Ala Lys Ala Pro Ala Gln Leu Cys Glu Gly Cys Pro
145                 150                 155                 160

Leu Gln Ser Leu His Lys Leu Cys Glu Arg Ile Glu Gly Met Asn Ser
                165                 170                 175

Ser Lys Thr Lys Leu Glu Leu Gln Lys His Leu Thr Thr Leu Thr Asn
            180                 185                 190

Gln Glu Gln Ala Thr Ile Phe Glu Glu Val Gln Lys Leu Arg Pro Arg
        195                 200                 205

Asn Glu Gln Arg Glu Asn Glu Leu Ile Ile Ser Phe Leu Arg Cys Leu
    210                 215                 220

Tyr Glu Glu Lys Gln Lys Glu His Ile His Ile Gly Glu Met Lys Gln
225                 230                 235                 240

Thr Ser Gln Met Ala Ala Glu Asn Ile Gly Ser Glu Leu Pro Pro Ser
                245                 250                 255

Ala Thr Arg Phe Arg Leu Asp Met Leu Lys Asn Lys Ala Lys Arg Ser
            260                 265                 270

Leu Thr Glu Ser Leu Glu Ser Ile Leu Ser Arg Gly Asn Lys Ala Arg
        275                 280                 285

Gly Leu Gln Glu His Ser Ile Ser Val Asp Leu Asp Ser Ser Leu Ser
    290                 295                 300

Ser Thr Leu Ser Asn Thr Ser Lys Glu Pro Ser Val Cys Glu Lys Glu
305                 310                 315                 320

Ala Leu Pro Ile Ser Glu Ser Ser Phe Lys Leu Leu Gly Ser Ser Glu
                325                 330                 335

Asp Leu Ser Ser Asp Ser Glu Ser His Leu Pro Glu Glu Pro Ala Pro
            340                 345                 350

Leu Ser Pro Gln Gln Ala Phe Arg Arg Arg Ala Asn Thr Leu Ser His
        355                 360                 365

Phe Pro Ile Glu Cys Gln Glu Pro Pro Gln Pro Ala Arg Gly Ser Pro
    370                 375                 380

Gly Val Ser Gln Arg Lys Leu Met Arg Tyr His Ser Val Ser Thr Glu
385                 390                 395                 400

Thr Pro His Glu Arg Lys Asp Phe Glu Ser Lys Ala Asn His Leu Gly

```
                    405                 410                 415
Asp Ser Gly Gly Thr Pro Val Lys Thr Arg Arg His Ser Trp Arg Gln
            420                 425                 430

Gln Ile Phe Leu Arg Val Ala Thr Pro Gln Lys Ala Cys Asp Ser Ser
        435                 440                 445

Ser Arg Tyr Glu Asp Tyr Ser Glu Leu Gly Glu Leu Pro Pro Arg Ser
    450                 455                 460

Pro Leu Glu Pro Val Cys Glu Asp Gly Pro Phe Gly Pro Pro Glu
465                 470                 475                 480

Glu Lys Lys Arg Thr Ser Arg Glu Leu Arg Glu Leu Trp Gln Lys Ala
                485                 490                 495

Ile Leu Gln Gln Ile Leu Leu Arg Met Glu Lys Glu Asn Gln Lys
            500                 505                 510

Leu Gln Ala Ser Glu Asn Asp Leu Leu Asn Lys Arg Leu Lys Leu Asp
        515                 520                 525

Tyr Glu Glu Ile Thr Pro Cys Leu Lys Glu Val Thr Thr Val Trp Glu
    530                 535                 540

Lys Met Leu Ser Thr Pro Gly Arg Ser Lys Ile Lys Phe Asp Met Glu
545                 550                 555                 560

Lys Met His Ser Ala Val Gly Gln Gly Val Pro Arg His His Arg Gly
                565                 570                 575

Glu Ile Trp Lys Phe Leu Ala Glu Gln Phe His Leu Lys His Gln Phe
            580                 585                 590

Pro Ser Lys Gln Gln Pro Lys Asp Val Pro Tyr Lys Glu Leu Leu Lys
        595                 600                 605

Gln Leu Thr Ser Gln Gln His Ala Ile Leu Ile Asp Leu Gly Arg Thr
    610                 615                 620

Phe Pro Thr His Pro Tyr Phe Ser Ala Gln Leu Gly Ala Gly Gln Leu
625                 630                 635                 640

Ser Leu Tyr Asn Ile Leu Lys Ala Tyr Ser Leu Leu Asp Gln Glu Val
                645                 650                 655

Gly Tyr Cys Gln Gly Leu Ser Phe Val Ala Gly Ile Leu Leu Leu His
            660                 665                 670

Met Ser Glu Glu Glu Ala Phe Lys Met Leu Lys Phe Leu Met Phe Asp
        675                 680                 685

Met Gly Leu Arg Lys Gln Tyr Arg Pro Asp Met Ile Ile Leu Gln Ile
    690                 695                 700

Gln Met Tyr Gln Leu Ser Arg Leu Leu His Asp Tyr His Arg Asp Leu
705                 710                 715                 720

Tyr Asn His Leu Glu Glu His Glu Ile Gly Pro Ser Leu Tyr Ala Ala
                725                 730                 735

Pro Trp Phe Leu Thr Met Phe Ala Ser Gln Phe Pro Leu Gly Phe Val
            740                 745                 750

Ala Arg Val Phe Asp Met Ile Phe Leu Gln Gly Thr Glu Val Ile Phe
        755                 760                 765

Lys Val Ala Leu Ser Leu Leu Gly Ser His Lys Pro Leu Ile Leu Gln
    770                 775                 780

His Glu Asn Leu Glu Thr Ile Val Asp Phe Ile Lys Ser Thr Leu Pro
785                 790                 795                 800

Asn Leu Gly Leu Val Gln Met Glu Lys Thr Ile Asn Gln Val Phe Glu
                805                 810                 815

Met Asp Ile Ala Lys Gln Leu Gln Ala Tyr Glu Val Glu Tyr His Val
            820                 825                 830
```

-continued

Leu Gln Glu Glu Leu Ile Asp Ser Ser Pro Leu Ser Asp Asn Gln Arg
                835                 840                 845

Met Asp Lys Leu Glu Lys Thr Asn Ser Ser Leu Arg Lys Gln Asn Leu
850                 855                 860

Asp Leu Leu Glu Gln Leu Gln Val Ala Asn Gly Arg Ile Gln Ser Leu
865                 870                 875                 880

Glu Ala Thr Ile Glu Lys Leu Leu Ser Glu Ser Lys Leu Lys Gln
                885                 890                 895

Ala Met Leu Thr Leu Glu Leu Glu Arg Ser Ala Leu Leu Gln Thr Val
                900                 905                 910

Glu Glu Leu Arg Arg Arg Ser Ala Glu Pro Ser Asp Arg Glu Pro Glu
                915                 920                 925

Cys Thr Gln Pro Glu Pro Thr Gly Asp
                930                 935

<210> SEQ ID NO 63
<211> LENGTH: 618
<212> TYPE: PRT
<213> ORGANISM: homo sapiens

<400> SEQUENCE: 63

Met His Lys Thr Ala Ser Gln Arg Leu Phe Pro Gly Pro Ser Tyr Gln
1               5                   10                  15

Asn Ile Lys Ser Ile Met Glu Asp Ser Thr Ile Leu Ser Asp Trp Thr
                20                  25                  30

Asn Ser Asn Lys Gln Lys Met Lys Tyr Asp Phe Ser Cys Glu Leu Tyr
                35                  40                  45

Arg Met Ser Thr Tyr Ser Thr Phe Pro Ala Gly Val Pro Val Ser Glu
50                  55                  60

Arg Ser Leu Ala Arg Ala Gly Phe Tyr Tyr Thr Gly Val Asn Asp Lys
65                  70                  75                  80

Val Lys Cys Phe Cys Cys Gly Leu Met Leu Asp Asn Trp Lys Leu Gly
                85                  90                  95

Asp Ser Pro Ile Gln Lys His Lys Gln Leu Tyr Pro Ser Cys Ser Phe
                100                 105                 110

Ile Gln Asn Leu Val Ser Ala Ser Leu Gly Ser Thr Ser Lys Asn Thr
                115                 120                 125

Ser Pro Met Arg Asn Ser Phe Ala His Ser Leu Ser Pro Thr Leu Glu
130                 135                 140

His Ser Ser Leu Phe Ser Gly Ser Tyr Ser Ser Leu Ser Pro Asn Pro
145                 150                 155                 160

Leu Asn Ser Arg Ala Val Glu Asp Ile Ser Ser Ser Arg Thr Asn Pro
                165                 170                 175

Tyr Ser Tyr Ala Met Ser Thr Glu Glu Ala Arg Phe Leu Thr Tyr His
                180                 185                 190

Met Trp Pro Leu Thr Phe Leu Ser Pro Ser Glu Leu Ala Arg Ala Gly
                195                 200                 205

Phe Tyr Tyr Ile Gly Pro Gly Asp Arg Val Ala Cys Phe Ala Cys Gly
210                 215                 220

Gly Lys Leu Ser Asn Trp Glu Pro Lys Asp Asp Ala Met Ser Glu His
225                 230                 235                 240

Arg Arg His Phe Pro Asn Cys Pro Phe Leu Glu Asn Ser Leu Glu Thr
                245                 250                 255

Leu Arg Phe Ser Ile Ser Asn Leu Ser Met Gln Thr His Ala Ala Arg
                260                 265                 270

```
Met Arg Thr Phe Met Tyr Trp Pro Ser Ser Val Pro Val Gln Pro Glu
        275                 280                 285

Gln Leu Ala Ser Ala Gly Phe Tyr Val Gly Arg Asn Asp Asp Val
        290                 295                 300

Lys Cys Phe Cys Cys Asp Gly Gly Leu Arg Cys Trp Glu Ser Gly Asp
305                 310                 315                 320

Asp Pro Trp Val Glu His Ala Lys Trp Phe Pro Arg Cys Glu Phe Leu
                325                 330                 335

Ile Arg Met Lys Gly Gln Glu Phe Val Asp Glu Ile Gln Gly Arg Tyr
                340                 345                 350

Pro His Leu Leu Glu Gln Leu Leu Ser Thr Ser Asp Thr Thr Gly Glu
        355                 360                 365

Glu Asn Ala Asp Pro Pro Ile Ile His Phe Gly Pro Gly Glu Ser Ser
370                 375                 380

Ser Glu Asp Ala Val Met Met Asn Thr Pro Val Val Lys Ser Ala Leu
385                 390                 395                 400

Glu Met Gly Phe Asn Arg Asp Leu Val Lys Gln Thr Val Gln Ser Lys
                405                 410                 415

Ile Leu Thr Thr Gly Glu Asn Tyr Lys Thr Val Asn Asp Ile Val Ser
                420                 425                 430

Ala Leu Leu Asn Ala Glu Asp Glu Lys Arg Glu Glu Lys Glu Lys
                435                 440                 445

Gln Ala Glu Glu Met Ala Ser Asp Asp Leu Ser Leu Ile Arg Lys Asn
        450                 455                 460

Arg Met Ala Leu Phe Gln Gln Leu Thr Cys Val Leu Pro Ile Leu Asp
465                 470                 475                 480

Asn Leu Leu Lys Ala Asn Val Ile Asn Lys Gln Glu His Asp Ile Ile
                485                 490                 495

Lys Gln Lys Thr Gln Ile Pro Leu Gln Ala Arg Glu Leu Ile Asp Thr
                500                 505                 510

Ile Leu Val Lys Gly Asn Ala Ala Ala Asn Ile Phe Lys Asn Cys Leu
        515                 520                 525

Lys Glu Ile Asp Ser Thr Leu Tyr Lys Asn Leu Phe Val Asp Lys Asn
530                 535                 540

Met Lys Tyr Ile Pro Thr Glu Asp Val Ser Gly Leu Ser Leu Glu Glu
545                 550                 555                 560

Gln Leu Arg Arg Leu Gln Glu Arg Thr Cys Lys Val Cys Met Asp
                565                 570                 575

Lys Glu Val Ser Val Val Phe Ile Pro Cys Gly His Leu Val Val Cys
                580                 585                 590

Gln Glu Cys Ala Pro Ser Leu Arg Lys Cys Pro Ile Cys Arg Gly Ile
        595                 600                 605

Ile Lys Gly Thr Val Arg Thr Phe Leu Ser
    610                 615

<210> SEQ ID NO 64
<211> LENGTH: 539
<212> TYPE: PRT
<213> ORGANISM: homo sapiens

<400> SEQUENCE: 64

Met Thr Ser Leu Trp Gly Lys Gly Thr Gly Cys Lys Leu Phe Lys Phe
1               5                   10                  15

Arg Val Ala Ala Pro Ala Ser Gly Ala Leu Arg Arg Leu Thr Pro
            20                  25                  30
```

```
Ser Ala Ser Leu Pro Pro Ala Gln Leu Leu Arg Ala Val Arg Arg
         35                  40                  45
Arg Ser His Pro Val Arg Asp Tyr Ala Ala Gln Thr Ser Pro Ser Pro
 50                  55                  60
Lys Ala Gly Ala Ala Thr Gly Arg Ile Val Ala Val Ile Gly Ala Val
 65                  70                  75                  80
Val Asp Val Gln Phe Asp Glu Gly Leu Pro Pro Ile Leu Asn Ala Leu
                 85                  90                  95
Glu Val Gln Gly Arg Glu Thr Arg Leu Val Leu Glu Val Ala Gln His
                100                 105                 110
Leu Gly Glu Ser Thr Val Arg Thr Ile Ala Met Asp Gly Thr Glu Gly
            115                 120                 125
Leu Val Arg Gly Gln Lys Val Leu Asp Ser Gly Ala Pro Ile Lys Ile
130                 135                 140
Pro Val Gly Pro Glu Thr Leu Gly Arg Ile Met Asn Val Ile Gly Glu
145                 150                 155                 160
Pro Ile Asp Glu Arg Gly Pro Ile Lys Thr Lys Gln Phe Ala Pro Ile
                165                 170                 175
His Ala Glu Ala Pro Glu Phe Met Glu Met Ser Val Glu Gln Glu Ile
                180                 185                 190
Leu Val Thr Gly Ile Lys Val Val Asp Leu Leu Ala Pro Tyr Ala Lys
            195                 200                 205
Gly Gly Lys Ile Gly Leu Phe Gly Gly Ala Gly Val Gly Lys Thr Val
            210                 215                 220
Leu Ile Met Glu Leu Ile Asn Asn Val Ala Lys Ala His Gly Gly Tyr
225                 230                 235                 240
Ser Val Phe Ala Gly Val Gly Glu Arg Thr Arg Glu Gly Asn Asp Leu
                245                 250                 255
Tyr His Glu Met Ile Glu Ser Gly Val Ile Asn Leu Lys Asp Ala Thr
                260                 265                 270
Ser Lys Val Ala Leu Val Tyr Gly Gln Met Asn Glu Pro Pro Gly Ala
            275                 280                 285
Arg Ala Arg Val Ala Leu Thr Gly Leu Thr Val Ala Glu Tyr Phe Arg
290                 295                 300
Asp Gln Glu Gly Gln Asp Val Leu Leu Phe Ile Asp Asn Ile Phe Arg
305                 310                 315                 320
Phe Thr Gln Ala Gly Ser Glu Val Ser Ala Leu Leu Gly Arg Ile Pro
                325                 330                 335
Ser Ala Val Gly Tyr Gln Pro Thr Leu Ala Thr Asp Met Gly Thr Met
                340                 345                 350
Gln Glu Arg Ile Thr Thr Thr Lys Lys Gly Ser Ile Thr Ser Val Gln
            355                 360                 365
Ala Ile Tyr Val Pro Ala Asp Asp Leu Thr Asp Pro Ala Pro Ala Thr
370                 375                 380
Thr Phe Ala His Leu Asp Ala Thr Thr Val Leu Ser Arg Ala Ile Ala
385                 390                 395                 400
Glu Leu Gly Ile Tyr Pro Ala Val Asp Pro Leu Asp Ser Thr Ser Arg
                405                 410                 415
Ile Met Asp Pro Asn Ile Val Gly Ser Glu His Tyr Asp Val Ala Arg
                420                 425                 430
Gly Val Gln Lys Ile Leu Gln Asp Tyr Lys Ser Leu Gln Asp Ile Ile
            435                 440                 445
Ala Ile Leu Gly Met Asp Glu Leu Ser Glu Glu Asp Lys Leu Thr Val
450                 455                 460
```

```
Ser Arg Ala Arg Lys Ile Gln Arg Phe Leu Ser Gln Pro Phe Gln Val
465                 470                 475                 480

Ala Glu Val Phe Thr Gly His Met Gly Lys Leu Val Pro Leu Lys Glu
            485                 490                 495

Thr Ile Lys Gly Phe Gln Gln Ile Leu Ala Gly Glu Tyr Asp His Leu
        500                 505                 510

Pro Glu Gln Ala Phe Tyr Met Val Gly Pro Ile Glu Glu Ala Val Ala
        515                 520                 525

Lys Ala Asp Lys Leu Ala Glu Glu His Ser Ser
        530                 535

<210> SEQ ID NO 65
<211> LENGTH: 772
<212> TYPE: PRT
<213> ORGANISM: homo sapiens

<400> SEQUENCE: 65

Met Ala Ala Glu Ser Ala Leu Gln Val Val Glu Lys Leu Gln Ala Arg
1               5                   10                  15

Leu Ala Ala Asn Pro Asp Pro Lys Lys Leu Leu Lys Tyr Leu Lys Lys
            20                  25                  30

Leu Ser Thr Leu Pro Ile Thr Val Asp Ile Leu Ala Glu Thr Gly Val
        35                  40                  45

Gly Lys Thr Val Asn Ser Leu Arg Lys His Glu His Val Gly Ser Phe
    50                  55                  60

Ala Arg Asp Leu Val Ala Gln Trp Lys Lys Leu Val Pro Val Glu Arg
65                  70                  75                  80

Asn Ala Glu Pro Asp Glu Gln Asp Phe Glu Lys Ser Asn Ser Arg Lys
                85                  90                  95

Arg Pro Arg Asp Ala Leu Gln Lys Glu Glu Met Glu Gly Asp Tyr
            100                 105                 110

Gln Glu Thr Trp Lys Ala Thr Gly Ser Arg Ser Tyr Ser Pro Asp His
        115                 120                 125

Arg Gln Lys Lys His Arg Lys Leu Ser Glu Leu Glu Arg Pro His Lys
    130                 135                 140

Val Ser His Gly His Glu Arg Arg Asp Glu Arg Lys Arg Cys His Arg
145                 150                 155                 160

Met Ser Pro Thr Tyr Ser Ser Asp Pro Glu Ser Ser Asp Tyr Gly His
                165                 170                 175

Val Gln Ser Pro Pro Ser Cys Thr Ser Pro His Gln Met Tyr Val Asp
            180                 185                 190

His Tyr Arg Ser Leu Glu Glu Asp Gln Glu Pro Ile Val Ser His Gln
        195                 200                 205

Lys Pro Gly Lys Gly His Ser Asn Ala Phe Gln Asp Arg Leu Gly Ala
    210                 215                 220

Ser Gln Glu Arg His Leu Gly Glu Pro His Gly Lys Gly Val Val Ser
225                 230                 235                 240

Gln Asn Lys Glu His Lys Ser Ser His Lys Asp Lys Arg Pro Val Asp
                245                 250                 255

Ala Lys Ser Asp Glu Lys Ala Ser Val Val Ser Arg Glu Lys Ser His
            260                 265                 270

Lys Ala Leu Ser Lys Glu Glu Asn Arg Arg Pro Pro Ser Gly Asp Asn
        275                 280                 285

Ala Arg Glu Lys Pro Pro Ser Ser Gly Val Lys Lys Glu Lys Asp Arg
    290                 295                 300
```

```
Glu Gly Ser Ser Leu Lys Lys Lys Cys Leu Pro Pro Ser Glu Ala Ala
305                 310                 315                 320

Ser Asp Asn His Lys Lys Pro Lys His Arg Asp Pro Glu Lys Ala
            325                 330                 335

Lys Leu Asp Lys Ser Lys Gln Gly Leu Asp Ser Phe Asp Thr Gly Lys
            340                 345                 350

Gly Ala Gly Asp Leu Leu Pro Lys Val Lys Glu Lys Gly Ser Asn Asn
            355                 360                 365

Leu Lys Thr Pro Glu Gly Lys Val Lys Thr Asn Leu Asp Arg Lys Ser
        370                 375                 380

Leu Gly Ser Leu Pro Lys Val Glu Glu Thr Asp Met Glu Asp Glu Phe
385                 390                 395                 400

Glu Gln Pro Thr Met Ser Phe Glu Ser Tyr Leu Ser Tyr Asp Gln Pro
                405                 410                 415

Arg Lys Lys Lys Lys Lys Ile Val Lys Thr Ser Ala Thr Ala Leu Gly
                420                 425                 430

Asp Lys Gly Leu Lys Lys Asn Asp Ser Lys Ser Thr Gly Lys Asn Leu
        435                 440                 445

Asp Ser Val Gln Lys Leu Pro Lys Val Asn Lys Thr Lys Ser Glu Lys
    450                 455                 460

Pro Ala Gly Ala Asp Leu Ala Lys Leu Arg Lys Val Pro Asp Val Leu
465                 470                 475                 480

Pro Val Leu Pro Asp Leu Pro Leu Pro Ala Ile Gln Ala Asn Tyr Arg
                485                 490                 495

Pro Leu Pro Ser Leu Glu Leu Ile Ser Ser Phe Gln Pro Lys Arg Lys
                500                 505                 510

Ala Phe Ser Ser Pro Gln Glu Glu Glu Ala Gly Phe Thr Gly Arg
        515                 520                 525

Arg Met Asn Ser Lys Met Gln Val Tyr Ser Gly Ser Lys Cys Ala Tyr
530                 535                 540

Leu Pro Lys Met Met Thr Leu His Gln Gln Cys Ile Arg Val Leu Lys
545                 550                 555                 560

Asn Asn Ile Asp Ser Ile Phe Glu Val Gly Val Pro Tyr Ser Val
                565                 570                 575

Leu Glu Pro Val Leu Glu Arg Cys Thr Pro Asp Gln Leu Tyr Arg Ile
            580                 585                 590

Glu Glu Tyr Asn His Val Leu Ile Glu Glu Thr Asp Gln Leu Trp Lys
        595                 600                 605

Val His Cys His Arg Asp Phe Lys Glu Glu Arg Pro Glu Glu Tyr Glu
    610                 615                 620

Ser Trp Arg Glu Met Tyr Leu Arg Leu Gln Asp Ala Arg Glu Gln Arg
625                 630                 635                 640

Leu Arg Val Leu Thr Lys Asn Ile Gln Phe Ala His Ala Asn Lys Pro
                645                 650                 655

Lys Gly Arg Gln Ala Lys Met Ala Phe Val Asn Ser Val Ala Lys Pro
            660                 665                 670

Pro Arg Asp Val Arg Arg Gln Glu Lys Phe Gly Thr Gly Gly Ala
        675                 680                 685

Ala Val Pro Glu Lys Ile Lys Ile Lys Pro Ala Pro Tyr Pro Met Gly
        690                 695                 700

Ser Ser His Ala Ser Ala Ser Ser Ile Ser Phe Asn Pro Ser Pro Glu
705                 710                 715                 720

Glu Pro Ala Tyr Asp Gly Pro Ser Thr Ser Ser Ala His Leu Ala Pro
```

```
                        725                 730                 735
Val Val Ser Ser Thr Val Ser Tyr Asp Pro Arg Lys Pro Thr Val Lys
                740                 745                 750

Lys Ile Ala Pro Met Met Ala Lys Thr Ile Lys Ala Phe Lys Asn Arg
            755                 760                 765

Phe Ser Arg Arg
        770

<210> SEQ ID NO 66
<211> LENGTH: 886
<212> TYPE: PRT
<213> ORGANISM: homo sapiens

<400> SEQUENCE: 66

Met Ser Gly Phe Ser Pro Glu Leu Ile Asp Tyr Leu Glu Gly Lys Ile
1               5                   10                  15

Ser Phe Glu Glu Phe Glu Arg Arg Glu Glu Arg Lys Thr Arg Glu
            20                  25                  30

Lys Lys Ser Leu Gln Glu Lys Gly Lys Leu Ser Ala Glu Glu Asn Pro
        35                  40                  45

Asp Asp Ser Glu Val Pro Ser Ser Gly Ile Asn Ser Thr Lys Ser
    50                  55                  60

Gln Asp Lys Asp Val Asn Glu Gly Glu Thr Ser Asp Gly Val Arg Lys
65                  70                  75                  80

Ser Val His Lys Val Phe Ala Ser Met Leu Gly Glu Asn Glu Asp Asp
                85                  90                  95

Glu Glu Glu Glu Glu Glu Glu Glu Glu Glu Glu Glu Glu Glu Glu Thr
            100                 105                 110

Pro Glu Gln Pro Thr Ala Gly Asp Val Phe Val Leu Glu Met Val Leu
        115                 120                 125

Asn Arg Glu Thr Lys Lys Met Met Lys Glu Lys Arg Pro Arg Ser Lys
    130                 135                 140

Leu Pro Arg Ala Leu Arg Gly Leu Met Gly Glu Ala Asn Ile Arg Phe
145                 150                 155                 160

Ala Arg Gly Glu Arg Glu Ala Ile Leu Met Cys Met Glu Ile Ile
                165                 170                 175

Arg Gln Ala Pro Leu Ala Tyr Glu Pro Phe Ser Thr Leu Ala Met Ile
            180                 185                 190

Tyr Glu Asp Gln Gly Asp Met Glu Lys Ser Leu Gln Phe Glu Leu Ile
        195                 200                 205

Ala Ala His Leu Asn Pro Ser Asp Thr Glu Glu Trp Val Arg Leu Ala
    210                 215                 220

Glu Met Ser Leu Glu Gln Asp Asn Ile Lys Gln Ala Ile Phe Cys Tyr
225                 230                 235                 240

Thr Lys Ala Leu Lys Tyr Glu Pro Thr Asn Val Arg Tyr Leu Trp Glu
                245                 250                 255

Arg Ser Ser Leu Tyr Glu Gln Met Gly Asp His Lys Met Ala Met Asp
            260                 265                 270

Gly Tyr Arg Arg Ile Leu Asn Leu Leu Ser Pro Ser Asp Gly Glu Arg
        275                 280                 285

Phe Met Gln Leu Ala Arg Asp Met Ala Lys Ser Tyr Tyr Glu Ala Asn
    290                 295                 300

Asp Val Thr Ser Ala Ile Asn Ile Ile Asp Glu Ala Phe Ser Lys His
305                 310                 315                 320

Gln Gly Leu Val Ser Met Glu Asp Val Asn Ile Ala Ala Glu Leu Tyr
```

```
            325                 330                 335
Ile Ser Asn Lys Gln Tyr Asp Lys Ala Leu Glu Ile Ile Thr Asp Phe
            340                 345                 350
Ser Gly Ile Val Leu Glu Lys Lys Thr Ser Glu Glu Gly Thr Ser Glu
            355                 360                 365
Glu Asn Lys Ala Pro Glu Asn Val Thr Cys Thr Ile Pro Asp Gly Val
            370                 375                 380
Pro Ile Asp Ile Thr Val Lys Leu Met Val Cys Leu Val His Leu Asn
385                 390                 395                 400
Ile Leu Glu Pro Leu Asn Pro Leu Leu Thr Thr Leu Val Glu Gln Asn
            405                 410                 415
Pro Glu Asp Met Gly Asp Leu Tyr Leu Asp Val Ala Glu Ala Phe Leu
            420                 425                 430
Asp Val Gly Glu Tyr Asn Ser Ala Leu Pro Leu Leu Ser Ala Leu Val
            435                 440                 445
Cys Ser Glu Arg Tyr Asn Leu Ala Val Val Trp Leu Arg His Ala Glu
            450                 455                 460
Cys Leu Lys Ala Leu Gly Tyr Met Glu Arg Ala Ala Glu Ser Tyr Gly
465                 470                 475                 480
Lys Val Val Asp Leu Ala Pro Leu His Leu Asp Ala Arg Ile Ser Leu
            485                 490                 495
Ser Thr Leu Gln Gln Leu Gly Gln Pro Glu Lys Ala Leu Glu Ala
            500                 505                 510
Leu Glu Pro Met Tyr Asp Pro Asp Thr Leu Ala Gln Asp Ala Asn Ala
            515                 520                 525
Ala Gln Gln Glu Leu Lys Leu Leu His Arg Ser Thr Leu Leu Phe
            530                 535                 540
Ser Gln Gly Lys Met Tyr Gly Tyr Val Asp Thr Leu Leu Thr Met Leu
545                 550                 555                 560
Ala Met Leu Leu Lys Val Ala Met Asn Arg Ala Gln Val Cys Leu Ile
            565                 570                 575
Ser Ser Ser Lys Ser Gly Glu Arg His Leu Tyr Leu Ile Lys Val Ser
            580                 585                 590
Arg Asp Lys Ile Ser Asp Ser Asn Asp Gln Glu Ser Ala Asn Cys Asp
            595                 600                 605
Ala Lys Ala Ile Phe Ala Val Leu Thr Ser Val Leu Thr Lys Asp Asp
            610                 615                 620
Trp Trp Asn Leu Leu Lys Ala Ile Tyr Ser Leu Cys Asp Leu Ser
625                 630                 635                 640
Arg Phe Gln Glu Ala Glu Leu Leu Val Asp Ser Ser Leu Glu Tyr Tyr
            645                 650                 655
Ser Phe Tyr Asp Asp Arg Gln Lys Arg Lys Glu Leu Glu Tyr Phe Gly
            660                 665                 670
Leu Ser Ala Ala Ile Leu Asp Lys Asn Phe Arg Lys Ala Tyr Asn Tyr
            675                 680                 685
Ile Arg Ile Met Val Met Glu Asn Val Asn Lys Pro Gln Leu Trp Asn
            690                 695                 700
Ile Phe Asn Gln Val Thr Met His Ser Gln Asp Val Arg His His Arg
705                 710                 715                 720
Phe Cys Leu Arg Leu Met Leu Lys Asn Pro Glu Asn His Ala Leu Cys
            725                 730                 735
Val Leu Asn Gly His Asn Ala Phe Val Ser Gly Ser Phe Lys His Ala
            740                 745                 750
```

-continued

```
Leu Gly Gln Tyr Val Gln Ala Phe Arg Thr His Pro Asp Glu Pro Leu
            755                 760                 765

Tyr Ser Phe Cys Ile Gly Leu Thr Phe Ile His Met Ala Ser Gln Lys
    770                 775                 780

Tyr Val Leu Arg Arg His Ala Leu Ile Val Gln Gly Phe Ser Phe Leu
785                 790                 795                 800

Asn Arg Tyr Leu Ser Leu Arg Gly Pro Cys Gln Glu Ser Phe Tyr Asn
                805                 810                 815

Leu Gly Arg Gly Leu His Gln Leu Gly Leu Ile His Leu Ala Ile His
                820                 825                 830

Tyr Tyr Gln Lys Ala Leu Glu Leu Pro Pro Leu Val Val Glu Gly Ile
                835                 840                 845

Glu Leu Asp Gln Leu Asp Leu Arg Arg Asp Ile Ala Tyr Asn Leu Ser
850                 855                 860

Leu Ile Tyr Gln Ser Ser Gly Asn Thr Gly Met Ala Gln Thr Leu Leu
865                 870                 875                 880

Tyr Thr Tyr Cys Ser Ile
                885

<210> SEQ ID NO 67
<211> LENGTH: 1130
<212> TYPE: PRT
<213> ORGANISM: homo sapiens

<400> SEQUENCE: 67

Met Lys Glu Ile Cys Arg Ile Cys Ala Arg Glu Leu Cys Gly Asn Gln
1               5                   10                  15

Arg Arg Trp Ile Phe His Thr Ala Ser Lys Leu Asn Leu Gln Val Leu
                20                  25                  30

Leu Ser His Val Leu Gly Lys Asp Val Pro Arg Asp Gly Lys Ala Glu
            35                  40                  45

Phe Ala Cys Ser Lys Cys Ala Phe Met Leu Asp Arg Ile Tyr Arg Phe
    50                  55                  60

Asp Thr Val Ile Ala Arg Ile Glu Ala Leu Ser Ile Glu Arg Leu Gln
65                  70                  75                  80

Lys Leu Leu Leu Glu Lys Asp Arg Leu Lys Phe Cys Ile Ala Ser Met
                85                  90                  95

Tyr Arg Lys Asn Asn Asp Asp Ser Gly Ala Glu Ile Lys Ala Gly Asn
                100                 105                 110

Gly Thr Val Asp Met Ser Val Leu Pro Asp Ala Arg Tyr Ser Ala Leu
            115                 120                 125

Leu Gln Glu Asp Phe Ala Tyr Ser Gly Phe Glu Cys Trp Val Glu Asn
    130                 135                 140

Glu Asp Gln Ile Gln Glu Pro His Ser Cys His Gly Ser Glu Gly Pro
145                 150                 155                 160

Gly Asn Arg Pro Arg Arg Cys Arg Cys Ala Ala Leu Arg Val Ala
                165                 170                 175

Asp Ser Asp Tyr Glu Ala Ile Cys Lys Val Pro Arg Lys Val Ala Arg
            180                 185                 190

Ser Ile Ser Cys Gly Pro Ser Ser Arg Trp Ser Thr Ser Ile Cys Thr
    195                 200                 205

Glu Glu Pro Ala Leu Ser Glu Val Gly Pro Asp Leu Ala Ser Thr
    210                 215                 220

Lys Val Pro Pro Asp Gly Glu Ser Met Glu Glu Thr Pro Gly Ser
225                 230                 235                 240
```

```
Ser Val Glu Ser Leu Asp Ala Ser Val Gln Ala Ser Pro Pro Gln
            245                 250                 255

Lys Asp Glu Glu Thr Glu Arg Ser Ala Lys Glu Leu Gly Lys Cys Asp
                260                 265                 270

Cys Cys Ser Asp Asp Gln Ala Pro Gln His Gly Cys Asn His Lys Leu
        275                 280                 285

Glu Leu Ala Leu Ser Met Ile Lys Gly Leu Asp Tyr Lys Pro Ile Gln
    290                 295                 300

Ser Pro Arg Gly Ser Arg Leu Pro Ile Pro Val Lys Ser Ser Leu Pro
305                 310                 315                 320

Gly Ala Lys Pro Gly Pro Ser Met Thr Asp Gly Val Ser Gly Phe
                325                 330                 335

Leu Asn Arg Ser Leu Lys Pro Leu Tyr Lys Thr Pro Val Ser Tyr Pro
                340                 345                 350

Leu Glu Leu Ser Asp Leu Gln Glu Leu Trp Asp Asp Leu Cys Glu Asp
            355                 360                 365

Tyr Leu Pro Leu Arg Val Gln Pro Met Thr Glu Glu Leu Leu Lys Gln
    370                 375                 380

Gln Lys Leu Asn Ser His Glu Thr Thr Ile Thr Gln Gln Ser Val Ser
385                 390                 395                 400

Asp Ser His Leu Ala Glu Leu Gln Glu Lys Ile Gln Gln Thr Glu Ala
                405                 410                 415

Thr Asn Lys Ile Leu Gln Glu Lys Leu Asn Glu Met Ser Tyr Glu Leu
                420                 425                 430

Lys Cys Ala Gln Glu Ser Ser Gln Lys Gln Asp Gly Thr Ile Gln Asn
            435                 440                 445

Leu Lys Glu Thr Leu Lys Ser Arg Glu Arg Glu Thr Glu Glu Leu Tyr
    450                 455                 460

Gln Val Ile Glu Gly Gln Asn Asp Thr Met Ala Lys Leu Arg Glu Met
465                 470                 475                 480

Leu His Gln Ser Gln Leu Gly Gln Leu His Ser Ser Glu Gly Thr Ser
                485                 490                 495

Pro Ala Gln Gln Gln Val Ala Leu Leu Asp Leu Gln Ser Ala Leu Phe
                500                 505                 510

Cys Ser Gln Leu Glu Ile Gln Lys Leu Gln Arg Val Val Arg Gln Lys
            515                 520                 525

Glu Arg Gln Leu Ala Asp Ala Lys Gln Cys Val Gln Phe Val Glu Ala
    530                 535                 540

Ala Ala His Glu Ser Glu Gln Gln Lys Glu Ala Ser Trp Lys His Asn
545                 550                 555                 560

Gln Glu Leu Arg Lys Ala Leu Gln Gln Leu Gln Glu Glu Leu Gln Asn
                565                 570                 575

Lys Ser Gln Gln Leu Arg Ala Trp Glu Ala Glu Lys Tyr Asn Glu Ile
                580                 585                 590

Arg Thr Gln Glu Gln Asn Ile Gln His Leu Asn His Ser Leu Ser His
            595                 600                 605

Lys Glu Gln Leu Leu Gln Glu Phe Arg Glu Leu Leu Gln Tyr Arg Asp
    610                 615                 620

Asn Ser Asp Lys Thr Leu Glu Ala Asn Glu Met Leu Leu Glu Lys Leu
625                 630                 635                 640

Arg Gln Arg Ile His Asp Lys Ala Val Ala Leu Glu Arg Ala Ile Asp
                645                 650                 655

Glu Lys Phe Ser Ala Leu Glu Glu Lys Glu Lys Glu Leu Arg Gln Leu
                660                 665                 670
```

```
Arg Leu Ala Val Arg Glu Arg Asp His Asp Leu Glu Arg Leu Arg Asp
            675                 680                 685

Val Leu Ser Ser Asn Glu Ala Thr Met Gln Ser Met Glu Ser Leu Leu
            690                 695                 700

Arg Ala Lys Gly Leu Glu Val Glu Gln Leu Ser Thr Thr Cys Gln Asn
705                 710                 715                 720

Leu Gln Trp Leu Lys Glu Met Lys Phe Ser Arg Trp Gln Lys Glu
                725                 730                 735

Gln Glu Ser Ile Ile Gln Gln Leu Gln Thr Ser Leu His Asp Arg Asn
            740                 745                 750

Lys Glu Val Glu Asp Leu Ser Ala Thr Leu Leu Cys Lys Leu Gly Pro
            755                 760                 765

Gly Gln Ser Glu Ile Ala Glu Glu Leu Cys Arg Leu Gln Arg Lys
            770                 775                 780

Glu Arg Met Leu Gln Asp Leu Leu Ser Asp Arg Asn Lys Gln Val Leu
785                 790                 795                 800

Glu His Glu Met Glu Ile Gln Gly Leu Leu Gln Ser Val Ser Thr Arg
                805                 810                 815

Glu Gln Glu Ser Gln Ala Ala Ala Glu Lys Leu Val Gln Ala Leu Met
            820                 825                 830

Glu Arg Asn Ser Glu Leu Gln Ala Leu Arg Gln Tyr Leu Gly Gly Arg
            835                 840                 845

Asp Ser Leu Met Ser Gln Ala Pro Ile Ser Asn Gln Gln Ala Glu Val
850                 855                 860

Thr Pro Thr Gly Arg Leu Gly Lys Gln Thr Asp Gln Gly Ser Met Gln
865                 870                 875                 880

Ile Pro Ser Arg Asp Asp Ser Thr Ser Leu Thr Ala Lys Glu Asp Val
            885                 890                 895

Ser Ile Pro Arg Ser Thr Leu Gly Asp Leu Asp Thr Val Ala Gly Leu
            900                 905                 910

Glu Lys Glu Leu Ser Asn Ala Lys Glu Glu Leu Glu Leu Met Ala Lys
            915                 920                 925

Lys Glu Arg Glu Ser Gln Met Glu Leu Ser Ala Leu Gln Ser Met Met
930                 935                 940

Ala Val Gln Glu Glu Leu Gln Val Gln Ala Ala Asp Met Glu Ser
945                 950                 955                 960

Leu Thr Arg Asn Ile Gln Ile Lys Glu Asp Leu Ile Lys Asp Leu Gln
            965                 970                 975

Met Gln Leu Val Asp Pro Glu Asp Ile Pro Ala Met Glu Arg Leu Thr
            980                 985                 990

Gln Glu Val Leu Leu Arg Glu Lys Val Ala Ser Val Glu Ser Gln
            995                 1000                1005

Gly Gln Glu Ile Ser Gly Asn Arg Arg Gln Gln Leu Leu Leu Met
    1010                1015                1020

Leu Glu Gly Leu Val Asp Glu Arg Ser Arg Leu Asn Glu Ala Leu
    1025                1030                1035

Gln Ala Glu Arg Gln Leu Tyr Ser Ser Leu Val Lys Phe His Ala
    1040                1045                1050

His Pro Glu Ser Ser Glu Arg Asp Arg Thr Leu Gln Val Glu Leu
    1055                1060                1065

Glu Gly Ala Gln Val Leu Arg Ser Arg Leu Glu Glu Val Leu Gly
    1070                1075                1080

Arg Ser Leu Glu Arg Leu Asn Arg Leu Glu Thr Leu Ala Ala Ile
```

-continued

```
            1085                1090                1095
Gly Gly Ala Ala Ala Gly Asp Asp Thr Glu Asp Thr Ser Thr Glu
        1100                1105                1110

Phe Thr Asp Ser Ile Glu Glu Glu Ala Ala His His Ser His Gln
    1115                1120                1125

Gln Leu
    1130

<210> SEQ ID NO 68
<211> LENGTH: 621
<212> TYPE: PRT
<213> ORGANISM: homo sapiens

<400> SEQUENCE: 68

Met Ala Asp Phe Glu Glu Leu Arg Asn Met Val Ser Phe Arg Val
1               5                   10                  15

Ser Glu Leu Gln Val Leu Leu Gly Phe Ala Gly Arg Asn Lys Ser Gly
                20                  25                  30

Arg Lys His Asp Leu Leu Met Arg Ala Leu His Leu Leu Lys Ser Gly
            35                  40                  45

Cys Ser Pro Ala Val Gln Ile Lys Ile Arg Glu Leu Tyr Arg Arg Arg
    50                  55                  60

Tyr Pro Arg Thr Leu Glu Gly Leu Ser Asp Leu Ser Thr Ile Lys Ser
65                  70                  75                  80

Ser Val Phe Ser Leu Asp Gly Gly Ser Ser Pro Val Glu Pro Asp Leu
                85                  90                  95

Ala Val Ala Gly Ile His Ser Leu Pro Ser Thr Ser Val Thr Pro His
            100                 105                 110

Ser Pro Ser Ser Pro Val Gly Ser Val Leu Leu Gln Asp Thr Lys Pro
        115                 120                 125

Thr Phe Glu Met Gln Gln Pro Ser Pro Ile Pro Pro Val His Pro
    130                 135                 140

Asp Val Gln Leu Lys Asn Leu Pro Phe Tyr Asp Val Leu Asp Val Leu
145                 150                 155                 160

Ile Lys Pro Thr Ser Leu Val Gln Ser Ser Ile Gln Arg Phe Gln Glu
                165                 170                 175

Lys Phe Phe Ile Phe Ala Leu Thr Pro Gln Gln Val Arg Glu Ile Cys
            180                 185                 190

Ile Ser Arg Asp Phe Leu Pro Gly Gly Arg Arg Asp Tyr Thr Val Gln
        195                 200                 205

Val Gln Leu Arg Leu Cys Leu Ala Glu Thr Ser Cys Pro Gln Glu Asp
    210                 215                 220

Asn Tyr Pro Asn Ser Leu Cys Ile Lys Val Asn Gly Lys Leu Phe Pro
225                 230                 235                 240

Leu Pro Gly Tyr Ala Pro Pro Lys Asn Gly Ile Glu Gln Lys Arg
                245                 250                 255

Pro Gly Arg Pro Leu Asn Ile Thr Ser Leu Val Arg Leu Ser Ser Ala
            260                 265                 270

Val Pro Asn Gln Ile Ser Ile Ser Trp Ala Ser Glu Ile Gly Lys Asn
        275                 280                 285

Tyr Ser Met Ser Val Tyr Leu Val Arg Gln Leu Thr Ser Ala Met Leu
    290                 295                 300

Leu Gln Arg Leu Lys Met Lys Gly Ile Arg Asn Pro Asp His Ser Arg
305                 310                 315                 320

Ala Leu Ile Lys Glu Lys Leu Thr Ala Asp Pro Asp Ser Glu Ile Ala
```

```
                          325                 330                 335
Thr Thr Ser Leu Arg Val Ser Leu Met Cys Pro Leu Gly Lys Met Arg
            340                 345                 350

Leu Thr Ile Pro Cys Arg Ala Val Thr Cys Thr His Leu Gln Cys Phe
            355                 360                 365

Asp Ala Ala Leu Tyr Leu Gln Met Asn Glu Lys Lys Pro Thr Trp Ile
    370                 375                 380

Cys Pro Val Cys Asp Lys Lys Ala Ala Tyr Glu Ser Leu Ile Leu Asp
385                 390                 395                 400

Gly Leu Phe Met Glu Ile Leu Asn Asp Cys Ser Asp Val Asp Glu Ile
                405                 410                 415

Lys Phe Gln Glu Asp Gly Ser Trp Cys Pro Met Arg Pro Lys Lys Glu
            420                 425                 430

Ala Met Lys Val Ser Ser Gln Pro Cys Thr Lys Ile Glu Ser Ser Ser
            435                 440                 445

Val Leu Ser Lys Pro Cys Ser Val Thr Val Ala Ser Glu Ala Ser Lys
            450                 455                 460

Lys Lys Val Asp Val Ile Asp Leu Thr Ile Glu Ser Ser Ser Asp Glu
465                 470                 475                 480

Glu Glu Asp Pro Pro Ala Lys Arg Lys Cys Ile Phe Met Ser Glu Thr
                485                 490                 495

Gln Ser Ser Pro Thr Lys Gly Val Leu Met Tyr Gln Pro Ser Ser Val
            500                 505                 510

Arg Val Pro Ser Val Thr Ser Val Asp Pro Ala Ala Ile Pro Pro Ser
            515                 520                 525

Leu Thr Asp Tyr Ser Val Pro Phe His His Thr Pro Ile Ser Ser Met
    530                 535                 540

Ser Ser Asp Leu Pro Gly Leu Asp Phe Leu Ser Leu Ile Pro Val Asp
545                 550                 555                 560

Pro Gln Tyr Cys Pro Pro Met Phe Leu Asp Ser Leu Thr Ser Pro Leu
                565                 570                 575

Thr Ala Ser Ser Thr Ser Val Thr Thr Thr Ser Ser His Glu Ser Ser
            580                 585                 590

Thr His Val Ser Ser Ser Ser Arg Ser Glu Thr Gly Val Ile Thr
            595                 600                 605

Ser Ser Gly Ser Asn Ile Pro Glu Ile Ile Ser Leu Asp
        610                 615                 620

<210> SEQ ID NO 69
<211> LENGTH: 685
<212> TYPE: PRT
<213> ORGANISM: homo sapiens

<400> SEQUENCE: 69

Met Glu Leu Leu Arg Thr Ile Thr Tyr Gln Pro Ala Ala Ser Thr Lys
1               5                   10                  15

Met Cys Glu Gln Ala Leu Gly Lys Gly Cys Gly Gly Asp Ser Lys Lys
            20                  25                  30

Lys Arg Pro Pro Gln Pro Glu Glu Ser Gln Pro Gln Ser Gln
            35                  40                  45

Ala Gln Val Pro Pro Ala Ala Pro His His His His Ser His
    50                  55                  60

Ser Gly Pro Glu Ile Ser Arg Ile Ile Val Asp Pro Thr Thr Gly Lys
65                  70                  75                  80

Arg Tyr Cys Arg Gly Lys Val Leu Gly Lys Gly Gly Phe Ala Lys Cys
```

-continued

```
                85                  90                  95
Tyr Glu Met Thr Asp Leu Thr Asn Asn Lys Val Tyr Ala Ala Lys Ile
            100                 105                 110

Ile Pro His Ser Arg Val Ala Lys Pro His Gln Arg Glu Lys Ile Asp
            115                 120                 125

Lys Glu Ile Glu Leu His Arg Ile Leu His His Lys His Val Val Gln
            130                 135                 140

Phe Tyr His Tyr Phe Glu Asp Lys Glu Asn Ile Tyr Ile Leu Leu Glu
145                 150                 155                 160

Tyr Cys Ser Arg Arg Ser Met Ala His Ile Leu Lys Ala Arg Lys Val
                165                 170                 175

Leu Thr Glu Pro Glu Val Arg Tyr Tyr Leu Arg Gln Ile Val Ser Gly
            180                 185                 190

Leu Lys Tyr Leu His Glu Gln Glu Ile Leu His Arg Asp Leu Lys Leu
            195                 200                 205

Gly Asn Phe Phe Ile Asn Glu Ala Met Glu Leu Lys Val Gly Asp Phe
            210                 215                 220

Gly Leu Ala Ala Arg Leu Glu Pro Leu Glu His Arg Arg Thr Ile
225                 230                 235                 240

Cys Gly Thr Pro Asn Tyr Leu Ser Pro Glu Val Leu Asn Lys Gln Gly
                245                 250                 255

His Gly Cys Glu Ser Asp Ile Trp Ala Leu Gly Cys Val Met Tyr Thr
            260                 265                 270

Met Leu Leu Gly Arg Pro Pro Phe Glu Thr Thr Asn Leu Lys Glu Thr
            275                 280                 285

Tyr Arg Cys Ile Arg Glu Ala Arg Tyr Thr Met Pro Ser Ser Leu Leu
            290                 295                 300

Ala Pro Ala Lys His Leu Ile Ala Ser Met Leu Ser Lys Asn Pro Glu
305                 310                 315                 320

Asp Arg Pro Ser Leu Asp Asp Ile Ile Arg His Asp Phe Phe Leu Gln
                325                 330                 335

Gly Phe Thr Pro Asp Arg Leu Ser Ser Ser Cys Cys His Thr Val Pro
            340                 345                 350

Asp Phe His Leu Ser Ser Pro Ala Lys Asn Phe Phe Lys Lys Ala Ala
            355                 360                 365

Ala Ala Leu Phe Gly Gly Lys Lys Asp Lys Ala Arg Tyr Ile Asp Thr
            370                 375                 380

His Asn Arg Val Ser Lys Glu Asp Glu Asp Ile Tyr Lys Leu Arg His
385                 390                 395                 400

Asp Leu Lys Lys Thr Ser Ile Thr Gln Gln Pro Ser Lys His Arg Thr
                405                 410                 415

Asp Glu Glu Leu Gln Pro Pro Thr Thr Val Ala Arg Ser Gly Thr
            420                 425                 430

Pro Ala Val Glu Asn Lys Gln Gln Ile Gly Asp Ala Ile Arg Met Ile
            435                 440                 445

Val Arg Gly Thr Leu Gly Ser Cys Ser Ser Ser Glu Cys Leu Glu
            450                 455                 460

Asp Ser Thr Met Gly Ser Val Ala Asp Thr Val Ala Arg Val Leu Arg
465                 470                 475                 480

Gly Cys Leu Glu Asn Met Pro Glu Ala Asp Cys Ile Pro Lys Glu Gln
                485                 490                 495

Leu Ser Ser Phe Gln Trp Val Thr Lys Trp Val Asp Tyr Ser Asn
            500                 505                 510
```

```
Lys Tyr Gly Phe Gly Tyr Gln Leu Ser Asp His Thr Val Gly Val Leu
            515                 520                 525

Phe Asn Asn Gly Ala His Met Ser Leu Leu Pro Asp Lys Lys Thr Val
        530                 535                 540

His Tyr Ala Glu Leu Gly Gln Cys Ser Val Phe Pro Ala Thr Asp
545                 550                 555                 560

Ala Pro Glu Gln Phe Ile Ser Gln Val Thr Val Leu Lys Tyr Phe Ser
                565                 570                 575

His Tyr Met Glu Glu Asn Leu Met Asp Gly Asp Leu Pro Ser Val
            580                 585                 590

Thr Asp Ile Arg Arg Pro Arg Leu Tyr Leu Leu Gln Trp Leu Lys Ser
                595                 600                 605

Asp Lys Ala Leu Met Met Leu Phe Asn Asp Gly Thr Phe Gln Val Asn
        610                 615                 620

Phe Tyr His Asp His Thr Lys Ile Ile Ile Cys Ser Gln Asn Glu Glu
625                 630                 635                 640

Tyr Leu Leu Thr Tyr Ile Asn Glu Asp Arg Ile Ser Thr Thr Phe Arg
                645                 650                 655

Leu Thr Thr Leu Leu Met Ser Gly Cys Ser Ser Glu Leu Lys Asn Arg
            660                 665                 670

Met Glu Tyr Ala Leu Asn Met Leu Leu Gln Arg Cys Asn
            675                 680                 685

<210> SEQ ID NO 70
<211> LENGTH: 767
<212> TYPE: PRT
<213> ORGANISM: homo sapiens

<400> SEQUENCE: 70

Met Ala Thr Tyr Leu Glu Phe Ile Gln Gln Asn Glu Glu Arg Asp Gly
1               5                   10                  15

Val Arg Phe Ser Trp Asn Val Trp Pro Ser Ser Arg Leu Glu Ala Thr
            20                  25                  30

Arg Met Val Val Pro Leu Ala Cys Leu Leu Thr Pro Leu Lys Glu Arg
        35                  40                  45

Pro Asp Leu Pro Pro Val Gln Tyr Glu Pro Val Leu Cys Ser Arg Pro
    50                  55                  60

Thr Cys Lys Ala Val Leu Asn Pro Leu Cys Gln Val Asp Tyr Arg Ala
65                  70                  75                  80

Lys Leu Trp Ala Cys Asn Phe Cys Phe Gln Arg Asn Gln Phe Pro Pro
                85                  90                  95

Ala Tyr Gly Gly Ile Ser Glu Val Asn Gln Pro Ala Glu Leu Met Pro
            100                 105                 110

Gln Phe Ser Thr Ile Glu Tyr Val Ile Gln Arg Gly Ala Gln Ser Pro
        115                 120                 125

Leu Ile Phe Leu Tyr Val Val Asp Thr Cys Leu Glu Glu Asp Asp Leu
    130                 135                 140

Gln Ala Leu Lys Glu Ser Leu Gln Met Ser Leu Ser Leu Leu Pro Pro
145                 150                 155                 160

Asp Ala Leu Val Gly Leu Ile Thr Phe Gly Arg Met Val Gln Val His
                165                 170                 175

Glu Leu Ser Cys Glu Gly Ile Ser Lys Ser Tyr Val Phe Arg Gly Thr
            180                 185                 190

Lys Asp Leu Thr Ala Lys Gln Ile Gln Asp Met Leu Gly Leu Thr Lys
        195                 200                 205
```

-continued

```
Pro Ala Met Pro Met Gln Gln Ala Arg Pro Ala Gln Pro Gln Glu His
    210                 215                 220
Pro Phe Ala Ser Ser Arg Phe Leu Gln Pro Val His Lys Ile Asp Met
225                 230                 235                 240
Asn Leu Thr Asp Leu Leu Gly Glu Leu Gln Arg Asp Pro Trp Pro Val
                245                 250                 255
Thr Gln Gly Lys Arg Pro Leu Arg Ser Thr Gly Val Ala Leu Ser Ile
            260                 265                 270
Ala Val Gly Leu Leu Glu Gly Thr Phe Pro Asn Thr Gly Ala Arg Ile
        275                 280                 285
Met Leu Phe Thr Gly Gly Pro Thr Gln Gly Pro Gly Met Val Val
    290                 295                 300
Gly Asp Glu Leu Lys Ile Pro Ile Arg Ser Trp His Asp Ile Glu Lys
305                 310                 315                 320
Asp Asn Ala Arg Phe Met Lys Lys Ala Thr Lys His Tyr Glu Met Leu
                325                 330                 335
Ala Asn Arg Thr Ala Ala Asn Gly His Cys Ile Asp Ile Tyr Ala Cys
            340                 345                 350
Ala Leu Asp Gln Thr Gly Leu Leu Glu Met Lys Cys Cys Ala Asn Leu
        355                 360                 365
Thr Gly Gly Tyr Met Val Met Gly Asp Ser Phe Asn Thr Ser Leu Phe
    370                 375                 380
Lys Gln Thr Phe Gln Arg Ile Phe Thr Lys Asp Phe Asn Gly Asp Phe
385                 390                 395                 400
Arg Met Ala Phe Gly Ala Thr Leu Asp Val Lys Thr Ser Arg Glu Leu
                405                 410                 415
Lys Ile Ala Gly Ala Ile Gly Pro Cys Val Ser Leu Asn Val Lys Gly
            420                 425                 430
Pro Cys Val Ser Glu Asn Glu Leu Gly Val Gly Gly Thr Ser Gln Trp
        435                 440                 445
Lys Ile Cys Gly Leu Asp Pro Thr Ser Thr Leu Gly Ile Tyr Phe Glu
    450                 455                 460
Val Val Asn Gln His Asn Thr Pro Ile Pro Gln Gly Gly Arg Gly Ala
465                 470                 475                 480
Ile Gln Phe Val Thr His Tyr Gln His Ser Ser Thr Gln Arg Arg Ile
                485                 490                 495
Arg Val Thr Thr Ile Ala Arg Asn Trp Ala Asp Val Gln Ser Gln Leu
            500                 505                 510
Arg His Ile Glu Ala Ala Phe Asp Gln Glu Ala Ala Val Leu Met
        515                 520                 525
Ala Arg Leu Gly Val Phe Arg Ala Glu Ser Glu Gly Pro Asp Val
    530                 535                 540
Leu Arg Trp Leu Asp Arg Gln Leu Ile Arg Leu Cys Gln Lys Phe Gly
545                 550                 555                 560
Gln Tyr Asn Lys Glu Asp Pro Thr Ser Phe Arg Leu Ser Asp Ser Phe
                565                 570                 575
Ser Leu Tyr Pro Gln Phe Met Phe His Leu Arg Arg Ser Pro Phe Leu
            580                 585                 590
Gln Val Phe Asn Asn Ser Pro Asp Glu Ser Ser Tyr Tyr Arg His His
        595                 600                 605
Phe Ala Arg Gln Asp Leu Thr Gln Ser Leu Ile Met Ile Gln Pro Ile
    610                 615                 620
Leu Tyr Ser Tyr Ser Phe His Gly Pro Pro Glu Pro Val Leu Leu Asp
625                 630                 635                 640
```

```
Ser Ser Ser Ile Leu Ala Asp Arg Ile Leu Leu Met Asp Thr Phe Phe
            645                 650                 655

Gln Ile Val Ile Tyr Leu Gly Glu Thr Ile Ala Gln Trp Arg Lys Ala
            660                 665                 670

Gly Tyr Gln Asp Met Pro Glu Tyr Glu Asn Phe Lys His Leu Leu Gln
            675                 680                 685

Ala Pro Leu Asp Asp Ala Gln Glu Ile Leu Gln Ala Arg Phe Pro Met
            690                 695                 700

Pro Arg Tyr Ile Asn Thr Glu His Gly Gly Ser Gln Ala Arg Phe Leu
705                 710                 715                 720

Leu Ser Lys Val Asn Pro Ser Gln Thr His Asn Asn Leu Tyr Ala Trp
            725                 730                 735

Gly Gln Glu Thr Gly Ala Pro Ile Leu Thr Asp Val Ser Leu Gln
            740                 745                 750

Val Phe Met Asp His Leu Lys Lys Leu Ala Val Ser Ser Ala Cys
            755                 760                 765

<210> SEQ ID NO 71
<211> LENGTH: 188
<212> TYPE: PRT
<213> ORGANISM: homo sapiens

<400> SEQUENCE: 71

Met Asn Gly Asp Asp Thr Phe Ala Lys Arg Pro Arg Asp Asp Ala Lys
1               5                   10                  15

Ala Ser Glu Lys Arg Ser Lys Ala Phe Asp Ile Ala Thr Tyr Phe
            20                  25                  30

Ser Lys Lys Glu Trp Lys Lys Met Lys Tyr Ser Glu Lys Ile Ser Tyr
            35                  40                  45

Val Tyr Met Lys Arg Asn Tyr Lys Ala Met Thr Lys Leu Gly Phe Lys
        50                  55                  60

Val Thr Leu Pro Pro Phe Met Cys Asn Lys Gln Ala Thr Asp Phe Gln
65              70                  75                  80

Gly Asn Asp Phe Asp Asn Asp His Asn Arg Arg Ile Gln Val Glu His
            85                  90                  95

Pro Gln Met Thr Phe Gly Arg Leu His Arg Ile Ile Pro Lys Ile Met
            100                 105                 110

Pro Lys Lys Pro Ala Glu Asp Glu Asn Asp Ser Lys Gly Val Ser Glu
            115                 120                 125

Ala Ser Gly Pro Gln Asn Asp Gly Lys Gln Leu His Pro Pro Gly Lys
        130                 135                 140

Ala Asn Ile Ser Glu Lys Ile Asn Lys Arg Ser Gly Pro Lys Arg Gly
145                 150                 155                 160

Lys His Ala Trp Thr His Arg Leu Arg Glu Arg Lys Gln Leu Val Ile
            165                 170                 175

Tyr Glu Glu Ile Ser Asp Pro Glu Glu Asp Asp Glu
            180                 185

<210> SEQ ID NO 72
<211> LENGTH: 1038
<212> TYPE: PRT
<213> ORGANISM: homo sapiens
<220> FEATURE:
<221> NAME/KEY: MISC_FEATURE
<222> LOCATION: (910)..(910)
<223> OTHER INFORMATION: Xaa = any amino acid

<400> SEQUENCE: 72
```

```
Met Trp Arg Cys Gly Gly Arg Gln Gly Leu Cys Val Leu Arg Arg Leu
1               5                   10                  15

Ser Gly Gly His Ala His His Arg Ala Trp Arg Trp Asn Ser Asn Arg
            20                  25                  30

Ala Cys Glu Arg Ala Leu Gln Tyr Lys Leu Gly Asp Lys Ile His Gly
        35                  40                  45

Phe Thr Val Asn Gln Val Thr Ser Val Pro Glu Leu Phe Leu Thr Ala
    50                  55                  60

Val Lys Leu Thr His Asp Asp Thr Gly Ala Arg Tyr Leu His Leu Ala
65                  70                  75                  80

Arg Glu Asp Thr Asn Asn Leu Phe Ser Val Gln Phe Arg Thr Thr Pro
                85                  90                  95

Met Asp Ser Thr Gly Val Pro His Ile Leu Glu His Thr Val Leu Cys
            100                 105                 110

Gly Ser Gln Lys Tyr Pro Cys Arg Asn Pro Phe Phe Lys Met Leu Asn
        115                 120                 125

Arg Ser Leu Ser Thr Phe Met Asn Ala Phe Thr Ala Ser Asp Tyr Thr
    130                 135                 140

Leu Tyr Pro Phe Ser Thr Gln Asn Pro Lys Asp Phe Gln Asn Leu Leu
145                 150                 155                 160

Ser Val Tyr Leu Asp Ala Thr Phe Ser Pro Cys Leu Arg Glu Leu Asp
                165                 170                 175

Phe Trp Gln Glu Gly Trp Arg Leu Glu His Glu Asn Pro Ser Asp Pro
            180                 185                 190

Gln Thr Pro Leu Val Phe Lys Gly Val Val Phe Asn Glu Met Lys Gly
        195                 200                 205

Ala Phe Thr Asp Asn Glu Arg Ile Phe Ser Gln His Leu Gln Asn Arg
    210                 215                 220

Leu Leu Pro Asp His Thr Tyr Ser Val Val Ser Gly Gly Asp Pro Leu
225                 230                 235                 240

Cys Ile Pro Glu Leu Thr Trp Glu Gln Leu Lys Gln Phe His Ala Thr
                245                 250                 255

His Tyr His Pro Ser Asn Ala Arg Phe Phe Thr Tyr Gly Asn Phe Pro
            260                 265                 270

Leu Glu Gln His Leu Lys Gln Ile His Glu Glu Ala Leu Ser Lys Phe
        275                 280                 285

Gln Lys Ile Glu Pro Ser Thr Val Pro Ala Gln Thr Pro Trp Asp
    290                 295                 300

Lys Pro Arg Glu Phe Gln Ile Thr Cys Gly Pro Asp Ser Phe Ala Thr
305                 310                 315                 320

Asp Pro Ser Lys Gln Thr Thr Val Ser Val Ser Phe Leu Leu Pro Asp
                325                 330                 335

Ile Thr Asp Thr Phe Glu Ala Phe Thr Leu Ser Leu Leu Ser Ser Leu
            340                 345                 350

Leu Thr Ser Gly Pro Asn Ser Pro Phe Tyr Lys Ala Leu Ile Glu Ser
        355                 360                 365

Gly Leu Gly Thr Glu Phe Ser Pro Asp Val Gly Tyr Asn Gly Tyr Thr
    370                 375                 380

Arg Glu Ala Tyr Phe Ser Val Gly Leu Gln Gly Ile Val Glu Lys Asp
385                 390                 395                 400

Ile Glu Thr Val Arg Ser Leu Ile Asp Arg Thr Ile Asp Glu Val Val
                405                 410                 415

Glu Thr Arg Ile Glu Asp Asp Arg Ile Glu Ala Leu Leu His Lys Ile
```

```
                420             425             430
Glu Ile Gln Met Lys His Gln Ser Thr Ser Phe Gly Leu Met Leu Thr
            435                 440             445
Ser Tyr Ile Ala Ser Cys Trp Asn His Asp Gly Asp Pro Val Glu Leu
            450                 455             460
Leu Lys Leu Gly Asn Gln Leu Ala Lys Phe Arg Gln Cys Leu Gln Glu
465             470                  475                 480
Asn Pro Lys Phe Leu Gln Glu Lys Val Lys Gln Tyr Phe Lys Asn Asn
                485                 490                 495
Gln His Lys Leu Thr Leu Ser Met Arg Pro Asp Asp Lys Tyr His Glu
                500                 505             510
Lys Gln Ala Gln Val Glu Ala Thr Lys Leu Lys Gln Lys Val Glu Ala
            515                 520             525
Leu Ser Pro Gly Asp Arg Gln Gln Ile Tyr Glu Lys Gly Leu Glu Leu
            530                 535             540
Arg Ser Gln Gln Ser Lys Pro Gln Asp Ala Ser Cys Leu Pro Ala Leu
545             550                 555                 560
Lys Val Ser Asp Ile Glu Pro Thr Ile Pro Val Thr Glu Leu Asp Val
                565                 570                 575
Val Leu Thr Ala Gly Asp Ile Pro Val Gln Tyr Cys Ala Gln Pro Thr
            580                 585             590
Asn Gly Met Val Tyr Phe Arg Ala Phe Ser Ser Leu Asn Thr Leu Pro
            595                 600             605
Glu Glu Leu Arg Pro Tyr Val Pro Leu Phe Cys Ser Ile Leu Thr Lys
            610                 615             620
Leu Gly Cys Gly Leu Leu Asp Tyr Arg Glu Gln Ala Gln Gln Ile Glu
625             630                 635                 640
Leu Lys Thr Gly Gly Met Ser Ala Ser Pro His Val Leu Pro Asp Asp
                645                 650                 655
Ser His Met Asp Thr Tyr Glu Gln Val Gly Val Leu Phe Ser Ser Leu
                660                 665             670
Cys Leu Asp Arg Asn Leu Pro Asp Met Met Gln Leu Trp Ser Glu Ile
            675                 680             685
Phe Asn Asn Pro Cys Phe Glu Glu Glu His Phe Lys Val Leu Val
            690                 695             700
Lys Met Thr Ala Gln Glu Leu Ala Asn Gly Ile Pro Asp Ser Gly His
705             710                 715                 720
Leu Tyr Ala Ser Ile Arg Ala Gly Arg Thr Leu Thr Pro Ala Gly Asp
                725                 730             735
Leu Gln Glu Thr Phe Ser Gly Met Asp Gln Val Arg Leu Met Lys Arg
                740                 745             750
Ile Ala Glu Met Thr Asp Ile Lys Pro Ile Leu Arg Lys Leu Pro Arg
            755                 760             765
Ile Lys Lys His Leu Leu Asn Gly Asp Asn Met Arg Cys Ser Val Asn
            770                 775             780
Ala Thr Pro Gln Gln Met Pro Gln Thr Glu Lys Ala Val Glu Asp Phe
785             790                 795                 800
Leu Arg Ser Ile Gly Arg Ser Lys Lys Glu Arg Arg Pro Val Arg Pro
                805                 810                 815
His Thr Val Glu Lys Pro Val Pro Ser Ser Gly Gly Asp Ala His
                820                 825             830
Val Pro His Gly Ser Gln Val Ile Arg Lys Leu Val Met Glu Pro Thr
            835                 840             845
```

Phe Lys Pro Trp Gln Met Lys Thr His Phe Leu Met Pro Phe Pro Val
                850                 855                 860

Asn Tyr Val Gly Glu Cys Ile Arg Thr Val Pro Tyr Thr Asp Pro Asp
865                 870                 875                 880

His Ala Ser Leu Lys Ile Leu Ala Arg Leu Met Thr Ala Lys Phe Leu
                885                 890                 895

His Thr Glu Ile Arg Glu Lys Gly Gly Ala Tyr Gly Gly Xaa Ala Lys
                900                 905                 910

Leu Ser His Asn Gly Ile Phe Thr Leu Tyr Ser Tyr Arg Asp Pro Asn
                915                 920                 925

Thr Ile Glu Thr Leu Gln Ser Phe Gly Lys Ala Val Asp Trp Ala Lys
                930                 935                 940

Ser Gly Lys Phe Thr Gln Gln Asp Ile Asp Glu Ala Lys Leu Ser Val
945                 950                 955                 960

Phe Ser Thr Val Asp Ala Pro Val Ala Pro Ser Asp Lys Gly Met Asp
                965                 970                 975

His Phe Leu Tyr Gly Leu Ser Asp Glu Met Lys Gln Ala His Arg Glu
                980                 985                 990

Gln Leu Phe Ala Val Ser His Asp Lys Leu Leu Ala Val Ser Asp Arg
                995                 1000                1005

Tyr Leu Gly Thr Gly Lys Ser Thr His Gly Leu Ala Ile Leu Gly
            1010                1015                1020

Pro Glu Asn Pro Lys Ile Ala Lys Asp Pro Ser Trp Ile Ile Arg
            1025                1030                1035

<210> SEQ ID NO 73
<211> LENGTH: 341
<212> TYPE: PRT
<213> ORGANISM: homo sapiens

<400> SEQUENCE: 73

Met Leu Gly Ala Glu Trp Ser Lys Leu Gln Pro Thr Glu Lys Gln Arg
1               5                   10                  15

Tyr Leu Asp Glu Ala Glu Arg Glu Lys Gln Gln Tyr Met Lys Glu Leu
                20                  25                  30

Arg Ala Tyr Gln Gln Ser Glu Ala Tyr Lys Met Cys Thr Glu Lys Ile
            35                  40                  45

Gln Glu Lys Lys Ile Lys Lys Glu Asp Ser Ser Gly Leu Met Asn
    50                  55                  60

Thr Leu Leu Asn Gly His Lys Gly Gly Asp Cys Asp Gly Phe Ser Thr
65                  70                  75                  80

Phe Asp Val Pro Ile Phe Thr Glu Glu Phe Leu Asp Gln Asn Lys Ala
                85                  90                  95

Arg Glu Ala Glu Leu Arg Arg Leu Arg Lys Met Asn Val Ala Phe Glu
            100                 105                 110

Glu Gln Asn Ala Val Leu Gln Arg Gln Asn Ala Glu His Glu Gln Arg
        115                 120                 125

Ala Arg Ala Ser Gly Ala Gly Ala Gly Ala Gly Ala Glu Asp Ala
    130                 135                 140

Gly Ala Ala Ala Ala Pro Gly Arg Ala Pro Gly Ala His Arg Gln
145                 150                 155                 160

Leu Arg Leu Thr Ala Gly Ala Gly His Gly Arg Asn Ala His Ala Gly
                165                 170                 175

His Ser Gly Leu Leu His Gly Pro Ala Ser Arg Ser His Arg Ala Arg
            180                 185                 190

-continued

```
Pro Arg Pro Ala Arg Glu Ala His Arg Pro His Gln Gly Asn Pro Gly
        195                 200                 205

Pro Gly Arg Gln Arg Ala Pro Val Arg Ser Gly Arg Ala His Asp Ala
210                 215                 220

Glu Glu Lys Leu Trp Ala Arg Pro Cys His Thr Pro Pro Arg Gly Arg
225                 230                 235                 240

Glu Ala Gly Gly Pro Pro Phe Gly Ala Trp Ser His Pro Ala Pro Leu
                245                 250                 255

Gly Ala Pro Ala Pro Leu Lys Leu Asn Phe Cys Ser Ile Pro Leu Ala
                260                 265                 270

Phe Asn Leu Pro Ser Pro Leu Asn Pro Glu Lys Ala Leu Ala Ala Arg
        275                 280                 285

Tyr Thr Gln Lys Asn Leu Thr Ala Glu Gly Ala Pro Pro Arg Arg Thr
        290                 295                 300

Ala Thr Arg Tyr Thr Gly Ser Pro Gly His Pro Gln Asp Thr Gly Gln
305                 310                 315                 320

Thr Lys Pro Thr Pro Ser Thr Arg Gln Asp Pro Pro Asn Tyr Ser Leu
                325                 330                 335

Arg Gly Ala Val Pro
            340

<210> SEQ ID NO 74
<211> LENGTH: 377
<212> TYPE: PRT
<213> ORGANISM: homo sapiens

<400> SEQUENCE: 74

Met Val Leu Glu Ser Thr Met Val Cys Val Asp Asn Ser Glu Tyr Met
1               5                   10                  15

Arg Asn Gly Asp Phe Leu Pro Thr Arg Leu Gln Ala Gln Gln Asp Ala
                20                  25                  30

Val Asn Ile Val Cys His Ser Lys Thr Arg Ser Asn Pro Glu Asn Asn
            35                  40                  45

Val Gly Leu Ile Thr Leu Ala Asn Asp Cys Glu Val Leu Thr Thr Leu
    50                  55                  60

Thr Pro Asp Thr Gly Arg Ile Leu Ser Lys Leu His Thr Val Gln Pro
65                  70                  75                  80

Lys Gly Lys Ile Thr Phe Cys Thr Gly Ile Arg Val Ala His Leu Ala
                85                  90                  95

Leu Lys His Arg Gln Gly Lys Asn His Lys Met Arg Ile Ile Ala Phe
            100                 105                 110

Val Gly Ser Pro Val Glu Asp Asn Glu Lys Asp Leu Val Lys Leu Ala
        115                 120                 125

Lys Arg Leu Lys Lys Glu Lys Val Asn Val Asp Ile Ile Asn Phe Gly
130                 135                 140

Glu Glu Glu Val Asn Thr Glu Lys Leu Thr Ala Phe Val Asn Thr Leu
145                 150                 155                 160

Asn Gly Lys Asp Gly Thr Gly Ser His Leu Val Thr Val Pro Pro Gly
                165                 170                 175

Pro Ser Leu Ala Asp Ala Leu Ile Ser Ser Pro Ile Leu Ala Gly Glu
            180                 185                 190

Gly Gly Ala Met Leu Gly Leu Gly Ala Ser Asp Phe Glu Phe Gly Val
        195                 200                 205

Asp Pro Ser Ala Asp Pro Glu Leu Ala Leu Ala Leu Arg Val Ser Met
210                 215                 220
```

```
Glu Glu Gln Arg Gln Arg Gln Glu Glu Ala Arg Ala Ala Ala
225                 230                 235                 240

Ala Ser Ala Ala Glu Ala Gly Ile Ala Thr Thr Gly Thr Glu Asp Ser
            245                 250                 255

Asp Asp Ala Leu Leu Lys Met Thr Ile Ser Gln Gln Glu Phe Gly Arg
            260                 265                 270

Thr Gly Leu Pro Asp Leu Ser Ser Met Thr Glu Glu Glu Gln Ile Ala
            275                 280                 285

Tyr Ala Met Gln Met Ser Leu Gln Gly Ala Glu Phe Gly Gln Ala Glu
            290                 295                 300

Ser Ala Asp Ile Asp Ala Ser Ser Ala Met Asp Thr Ser Glu Pro Ala
305                 310                 315                 320

Lys Glu Glu Asp Asp Tyr Asp Val Met Gln Asp Pro Glu Phe Leu Gln
                325                 330                 335

Ser Val Leu Glu Asn Leu Pro Gly Val Asp Pro Asn Asn Glu Ala Ile
            340                 345                 350

Arg Asn Ala Met Gly Ser Leu Ala Ser Gln Ala Thr Lys Asp Gly Lys
            355                 360                 365

Lys Asp Lys Lys Glu Glu Asp Lys Lys
            370                 375

<210> SEQ ID NO 75
<211> LENGTH: 399
<212> TYPE: PRT
<213> ORGANISM: homo sapiens

<400> SEQUENCE: 75

Met Ser Asp Ile Leu Arg Glu Leu Leu Cys Val Ser Glu Lys Ala Ala
1               5                   10                  15

Asn Ile Ala Arg Ala Cys Arg Gln Gln Glu Ala Leu Phe Gln Leu Leu
            20                  25                  30

Ile Glu Glu Lys Lys Gly Gly Lys Asn Lys Lys Phe Ala Val Asp
            35                  40                  45

Phe Lys Thr Leu Ala Asp Val Leu Val Gln Glu Val Ile Lys Gln Asn
50                  55                  60

Met Glu Asn Lys Phe Pro Gly Leu Lys Asn Ile Phe Gly Glu Glu
65                  70                  75                  80

Ser Asn Glu Phe Thr Asn Asp Trp Gly Glu Lys Ile Thr Leu Arg Leu
            85                  90                  95

Cys Ser Thr Glu Glu Thr Ala Glu Leu Leu Ser Lys Val Leu Asn
            100                 105                 110

Gly Asn Lys Val Ala Ser Glu Ala Leu Ala Arg Val Val His Gln Asp
            115                 120                 125

Val Ala Phe Thr Asp Pro Thr Leu Asp Ser Thr Glu Ile Asn Val Pro
            130                 135                 140

Gln Asp Ile Leu Gly Ile Trp Val Asp Pro Ile Asp Ser Thr Tyr Gln
145                 150                 155                 160

Tyr Ile Lys Gly Ser Ala Asp Ile Lys Ser Asn Gln Gly Ile Phe Pro
                165                 170                 175

Cys Gly Leu Gln Cys Val Thr Ile Leu Ile Gly Val Tyr Asp Ile Gln
            180                 185                 190

Thr Gly Val Pro Leu Met Gly Val Ile Asn Gln Pro Phe Val Ser Arg
            195                 200                 205

Asp Pro Asn Thr Leu Arg Trp Lys Gly Gln Cys Tyr Trp Gly Leu Ser
            210                 215                 220
```

```
Tyr Met Gly Thr Asn Met His Ser Leu Gln Leu Thr Ile Ser Arg Arg
225                 230                 235                 240

Asn Gly Ser Glu Thr His Thr Gly Asn Thr Gly Ser Glu Ala Ala Phe
            245                 250                 255

Ser Pro Ser Phe Ser Ala Val Ile Ser Thr Ser Glu Lys Glu Thr Ile
            260                 265                 270

Lys Ala Ala Leu Ser Arg Val Cys Gly Asp Arg Ile Phe Gly Ala Ala
            275                 280                 285

Gly Ala Gly Tyr Lys Ser Leu Cys Val Val Gln Gly Leu Val Asp Ile
290                 295                 300

Tyr Ile Phe Ser Glu Asp Thr Thr Phe Lys Trp Asp Ser Cys Ala Ala
305                 310                 315                 320

His Ala Ile Leu Arg Ala Met Gly Gly Gly Ile Val Asp Leu Lys Glu
                325                 330                 335

Cys Leu Glu Arg Asn Pro Glu Thr Gly Leu Asp Leu Pro Gln Leu Val
                340                 345                 350

Tyr His Val Glu Asn Glu Gly Ala Ala Gly Val Asp Arg Trp Ala Asn
                355                 360                 365

Lys Gly Gly Leu Ile Ala Tyr Arg Ser Arg Lys Arg Leu Glu Thr Phe
370                 375                 380

Leu Ser Leu Leu Val Gln Asn Leu Ala Pro Ala Glu Thr His Thr
385                 390                 395

<210> SEQ ID NO 76
<211> LENGTH: 296
<212> TYPE: PRT
<213> ORGANISM: homo sapiens

<400> SEQUENCE: 76

Met Lys Asn Glu Ile Ala Ala Val Val Phe Phe Thr Arg Leu Val
1               5                   10                  15

Arg Lys His Asp Lys Leu Lys Lys Glu Ala Val Glu Arg Phe Ala Glu
                20                  25                  30

Lys Leu Thr Leu Ile Leu Gln Glu Lys Tyr Lys Asn His Trp Tyr Pro
            35                  40                  45

Glu Lys Pro Ser Lys Gly Gln Ala Tyr Arg Cys Ile Arg Val Asn Lys
50                  55                  60

Phe Gln Arg Val Asp Pro Asp Val Leu Lys Ala Cys Glu Asn Ser Cys
65                  70                  75                  80

Ile Leu Tyr Ser Asp Leu Gly Leu Pro Lys Glu Leu Thr Leu Trp Val
                85                  90                  95

Asp Pro Cys Glu Val Cys Cys Arg Arg Asp Gly Val Ser Pro Cys Trp
            100                 105                 110

Pro Asp Cys Ser Gln Thr Pro Asp Leu Val Ile Arg Pro Pro Trp Pro
            115                 120                 125

Pro Lys Ala Leu Asp Tyr Arg Glu Pro Leu Arg Pro Ala Ser Ser
            130                 135                 140

Phe Leu Ile Met Tyr Gly Glu Lys Asn Asn Ala Phe Ile Val Ala Ser
145                 150                 155                 160

Phe Glu Asn Lys Asp Glu Asn Lys Asp Glu Ile Ser Arg Lys Val Thr
                165                 170                 175

Arg Ala Leu Asp Lys Val Thr Ser Asp Tyr His Ser Gly Ser Ser Ser
            180                 185                 190

Ser Asp Glu Glu Thr Ser Lys Glu Met Glu Val Lys Pro Ser Ser Val
            195                 200                 205
```

```
Thr Ala Ala Ala Ser Pro Val Tyr Gln Ile Ser Glu Leu Ile Phe Pro
    210                 215                 220
Pro Leu Pro Met Trp His Pro Leu Pro Arg Lys Lys Pro Gly Met Tyr
225                 230                 235                 240
Arg Gly Asn Gly His Gln Asn His Tyr Pro Pro Val Pro Phe Gly
                245                 250                 255
Tyr Pro Asn Gln Gly Arg Lys Asn Lys Pro Tyr Arg Pro Ile Pro Val
            260                 265                 270
Thr Trp Val Pro Pro Gly Met His Cys Asp Arg Asn His Trp Ile
        275                 280                 285
Asn Pro His Met Leu Ala Pro His
    290                 295
```

<210> SEQ ID NO 77
<211> LENGTH: 188
<212> TYPE: PRT
<213> ORGANISM: homo sapiens

<400> SEQUENCE: 77

```
Met Asn Gly Asp Asp Ala Phe Ala Arg Arg Pro Arg Asp Asp Ala Gln
1               5                   10                  15
Ile Ser Glu Lys Leu Arg Lys Ala Phe Asp Asp Ile Ala Lys Tyr Phe
            20                  25                  30
Ser Lys Lys Glu Trp Glu Lys Met Lys Ser Ser Glu Lys Ile Val Tyr
        35                  40                  45
Val Tyr Met Lys Leu Asn Tyr Glu Val Met Thr Lys Leu Gly Phe Lys
    50                  55                  60
Val Thr Leu Pro Pro Phe Met Arg Ser Lys Arg Ala Ala Asp Phe His
65                  70                  75                  80
Gly Asn Asp Phe Gly Asn Asp Arg Asn His Arg Asn Gln Val Glu Arg
                85                  90                  95
Pro Gln Met Thr Phe Gly Ser Leu Gln Arg Ile Phe Pro Lys Ile Met
            100                 105                 110
Pro Lys Lys Pro Ala Glu Glu Glu Asn Gly Leu Lys Glu Val Pro Glu
        115                 120                 125
Ala Ser Gly Pro Gln Asn Asp Gly Lys Gln Leu Cys Pro Pro Gly Asn
    130                 135                 140
Pro Ser Thr Leu Glu Lys Ile Asn Lys Thr Ser Gly Pro Lys Arg Gly
145                 150                 155                 160
Lys His Ala Trp Thr His Arg Leu Arg Glu Arg Lys Gln Leu Val Val
                165                 170                 175
Tyr Glu Glu Ile Ser Asp Pro Glu Glu Asp Glu
            180                 185
```

<210> SEQ ID NO 78
<211> LENGTH: 602
<212> TYPE: PRT
<213> ORGANISM: homo sapiens

<400> SEQUENCE: 78

```
Met Ala Ala Glu Glu Ala Ala Ala Gly Gly Lys Val Leu Arg Glu
1               5                   10                  15
Glu Asn Gln Cys Ile Ala Pro Val Val Ser Ser Arg Val Ser Pro Gly
            20                  25                  30
Thr Arg Pro Thr Ala Met Gly Ser Phe Ser Ser His Met Thr Glu Phe
        35                  40                  45
Pro Arg Lys Arg Lys Gly Ser Asp Ser Asp Pro Ser Gln Val Glu Asp
```

```
            50                  55                  60
Gly Glu His Gln Val Lys Met Lys Ala Phe Arg Glu Ala His Ser Gln
 65                  70                  75                  80

Thr Glu Lys Arg Arg Asp Lys Met Asn Asn Leu Ile Glu Glu Leu
                 85                  90                  95

Ser Ala Met Ile Pro Gln Cys Asn Pro Met Ala Arg Lys Leu Asp Lys
                100                 105                 110

Leu Thr Val Leu Arg Met Ala Val Gln His Leu Arg Ser Leu Lys Gly
                115                 120                 125

Leu Thr Asn Ser Tyr Val Gly Ser Asn Tyr Arg Pro Ser Phe Leu Gln
                130                 135                 140

Asp Asn Glu Leu Arg His Leu Ile Leu Lys Thr Ala Glu Gly Phe Leu
145                 150                 155                 160

Phe Val Val Gly Cys Glu Arg Gly Lys Ile Leu Phe Val Ser Lys Ser
                165                 170                 175

Val Ser Lys Ile Leu Asn Tyr Asp Gln Ala Ser Leu Thr Gly Gln Ser
                180                 185                 190

Leu Phe Asp Phe Leu His Pro Lys Asp Val Ala Lys Val Lys Glu Gln
                195                 200                 205

Leu Ser Ser Phe Asp Ile Ser Pro Arg Glu Lys Leu Ile Asp Ala Lys
                210                 215                 220

Thr Gly Leu Gln Val His Ser Asn Leu His Ala Gly Arg Thr Arg Val
225                 230                 235                 240

Tyr Ser Gly Ser Arg Arg Ser Phe Phe Cys Arg Ile Lys Ser Cys Lys
                245                 250                 255

Ile Ser Val Lys Glu Glu His Gly Cys Leu Pro Asn Ser Lys Lys Lys
                260                 265                 270

Glu His Arg Lys Phe Tyr Thr Ile His Cys Thr Gly Tyr Leu Arg Ser
                275                 280                 285

Trp Pro Pro Asn Ile Val Gly Met Glu Glu Arg Asn Ser Lys Lys
                290                 295                 300

Asp Asn Ser Asn Phe Thr Cys Leu Val Ala Ile Gly Arg Leu Gln Pro
305                 310                 315                 320

Tyr Ile Val Pro Gln Asn Ser Gly Glu Ile Asn Val Lys Pro Thr Glu
                325                 330                 335

Phe Ile Thr Arg Phe Ala Val Asn Gly Lys Phe Val Tyr Val Asp Gln
                340                 345                 350

Arg Ala Thr Ala Ile Leu Gly Tyr Leu Pro Gln Glu Leu Leu Gly Thr
                355                 360                 365

Ser Cys Tyr Glu Tyr Phe His Gln Asp Asp His Asn Asn Leu Thr Asp
370                 375                 380

Lys His Lys Ala Val Leu Gln Ser Lys Glu Lys Ile Leu Thr Asp Ser
385                 390                 395                 400

Tyr Lys Phe Arg Ala Lys Asp Gly Ser Phe Val Thr Leu Lys Ser Gln
                405                 410                 415

Trp Phe Ser Phe Thr Asn Pro Trp Thr Lys Glu Leu Glu Tyr Ile Val
                420                 425                 430

Ser Val Asn Thr Leu Val Leu Gly His Ser Glu Pro Gly Glu Ala Ser
                435                 440                 445

Phe Leu Pro Cys Ser Ser Gln Ser Glu Glu Ser Ser Arg Gln Ser
                450                 455                 460

Cys Met Ser Val Pro Gly Met Ser Thr Gly Thr Val Leu Gly Ala Gly
465                 470                 475                 480
```

```
Ser Ile Gly Thr Asp Ile Ala Asn Glu Ile Leu Asp Leu Gln Arg Leu
                485                 490                 495

Gln Ser Ser Ser Tyr Leu Asp Asp Ser Ser Pro Thr Gly Leu Met Lys
            500                 505                 510

Asp Thr His Thr Val Asn Cys Arg Ser Met Ser Asn Lys Glu Leu Phe
        515                 520                 525

Pro Pro Ser Pro Ser Glu Met Gly Glu Leu Glu Ala Thr Arg Gln Asn
    530                 535                 540

Gln Ser Thr Val Ala Val His Ser His Glu Pro Leu Leu Ser Asp Gly
545                 550                 555                 560

Ala Gln Leu Asp Phe Asp Ala Leu Cys Asp Asn Asp Thr Ala Met
                565                 570                 575

Ala Ala Phe Met Asn Tyr Leu Glu Ala Glu Gly Gly Leu Gly Asp Pro
            580                 585                 590

Gly Asp Phe Ser Asp Ile Gln Trp Thr Leu
            595                 600
```

<210> SEQ ID NO 79
<211> LENGTH: 745
<212> TYPE: PRT
<213> ORGANISM: homo sapiens

<400> SEQUENCE: 79

```
Met Ile Arg Gly Arg Asn Ser Ala Thr Ser Ala Asp Glu Gln Pro His
1               5                   10                  15

Ile Gly Asn Tyr Arg Leu Leu Lys Thr Ile Gly Lys Gly Asn Phe Ala
            20                  25                  30

Lys Val Lys Leu Ala Arg His Ile Leu Thr Gly Lys Glu Val Ala Val
        35                  40                  45

Lys Ile Ile Asp Lys Thr Gln Leu Asn Ser Ser Ser Leu Gln Lys Leu
    50                  55                  60

Phe Arg Glu Val Arg Ile Met Lys Val Leu Asn His Pro Asn Ile Val
65                  70                  75                  80

Lys Leu Phe Glu Val Ile Glu Thr Glu Lys Thr Leu Tyr Leu Val Met
                85                  90                  95

Glu Tyr Ala Ser Gly Gly Glu Val Phe Asp Tyr Leu Val Ala His Gly
            100                 105                 110

Arg Met Lys Glu Lys Glu Ala Arg Ala Lys Phe Arg Gln Ile Val Ser
        115                 120                 125

Ala Val Gln Tyr Cys His Gln Lys Phe Ile Val His Arg Asp Leu Lys
    130                 135                 140

Ala Glu Asn Leu Leu Leu Asp Ala Asp Met Asn Ile Lys Ile Ala Asp
145                 150                 155                 160

Phe Gly Phe Ser Asn Glu Phe Thr Phe Gly Asn Lys Leu Asp Thr Phe
                165                 170                 175

Cys Gly Ser Pro Pro Tyr Ala Ala Pro Glu Leu Phe Gln Gly Lys Lys
            180                 185                 190

Tyr Asp Gly Pro Glu Val Asp Val Trp Ser Leu Gly Val Ile Leu Tyr
        195                 200                 205

Thr Leu Val Ser Gly Ser Leu Pro Phe Asp Gly Gln Asn Leu Lys Glu
    210                 215                 220

Leu Arg Glu Arg Val Leu Arg Gly Lys Tyr Arg Ile Pro Phe Tyr Met
225                 230                 235                 240

Ser Thr Asp Cys Glu Asn Leu Leu Lys Lys Phe Leu Ile Leu Asn Pro
                245                 250                 255
```

```
Ser Lys Arg Gly Thr Leu Glu Gln Ile Met Lys Asp Arg Trp Met Asn
            260                 265                 270

Val Gly His Glu Asp Asp Glu Leu Lys Pro Tyr Val Glu Pro Leu Pro
            275                 280                 285

Asp Tyr Lys Asp Pro Arg Thr Glu Leu Met Val Ser Met Gly Tyr
290                 295                 300

Thr Arg Glu Glu Ile Gln Asp Ser Leu Val Gly Gln Arg Tyr Asn Glu
305                 310                 315                 320

Val Met Ala Thr Tyr Leu Leu Leu Gly Tyr Lys Ser Glu Leu Glu
            325                 330                 335

Gly Asp Thr Ile Thr Leu Lys Pro Arg Pro Ser Ala Asp Leu Thr Asn
            340                 345                 350

Ser Ser Ala Gln Phe Pro Ser His Lys Val Gln Arg Ser Val Ser Ala
            355                 360                 365

Asn Pro Lys Gln Arg Arg Phe Ser Asp Gln Ala Gly Pro Ala Ile Pro
            370                 375                 380

Thr Ser Asn Ser Tyr Ser Lys Lys Thr Gln Ser Asn Asn Ala Glu Asn
385                 390                 395                 400

Lys Arg Pro Glu Glu Asp Arg Glu Ser Gly Arg Lys Ala Ser Ser Thr
                405                 410                 415

Ala Lys Val Pro Ala Ser Pro Leu Pro Gly Leu Glu Arg Lys Lys Thr
            420                 425                 430

Thr Pro Thr Pro Ser Thr Asn Ser Val Leu Ser Thr Ser Thr Asn Arg
            435                 440                 445

Ser Arg Asn Ser Pro Leu Leu Glu Arg Ala Ser Leu Gly Gln Ala Ser
            450                 455                 460

Ile Gln Asn Gly Lys Asp Ser Leu Thr Met Pro Gly Ser Arg Ala Ser
465                 470                 475                 480

Thr Ala Ser Ala Ser Ala Ala Val Ser Ala Ala Arg Pro Arg Gln His
                485                 490                 495

Gln Lys Ser Met Ser Ala Ser Val His Pro Asn Lys Ala Ser Gly Leu
            500                 505                 510

Pro Pro Thr Glu Ser Asn Cys Glu Val Pro Arg Pro Ser Thr Ala Pro
            515                 520                 525

Gln Arg Val Pro Val Ala Ser Pro Ser Ala His Asn Ile Ser Ser Ser
            530                 535                 540

Gly Gly Ala Pro Asp Arg Thr Asn Phe Pro Arg Gly Val Ser Ser Arg
545                 550                 555                 560

Ser Thr Phe His Ala Gly Gln Leu Arg Gln Val Arg Asp Gln Gln Asn
                565                 570                 575

Leu Pro Tyr Gly Val Thr Pro Ala Ser Pro Ser Gly His Ser Gln Gly
            580                 585                 590

Arg Arg Gly Ala Ser Gly Ser Ile Phe Ser Lys Phe Thr Ser Lys Phe
            595                 600                 605

Val Arg Arg Asn Leu Asn Glu Pro Glu Ser Lys Asp Arg Val Glu Thr
            610                 615                 620

Leu Arg Pro His Val Val Gly Ser Gly Gly Asn Asp Lys Glu Lys Glu
625                 630                 635                 640

Glu Phe Arg Glu Ala Lys Pro Arg Ser Leu Arg Phe Thr Trp Ser Met
                645                 650                 655

Lys Thr Thr Ser Ser Met Glu Pro Asn Glu Met Met Arg Glu Ile Arg
            660                 665                 670

Lys Val Leu Asp Ala Asn Ser Cys Gln Ser Glu Leu His Glu Lys Tyr
            675                 680                 685
```

```
Met Leu Leu Cys Met His Gly Thr Pro Gly His Glu Asp Phe Val Gln
    690                 695                 700

Trp Glu Met Glu Val Cys Lys Leu Pro Arg Leu Ser Leu Asn Gly Val
705                 710                 715                 720

Arg Phe Lys Arg Ile Ser Gly Thr Ser Met Ala Phe Lys Asn Ile Ala
                725                 730                 735

Ser Lys Ile Ala Asn Glu Leu Lys Leu
                740                 745

<210> SEQ ID NO 80
<211> LENGTH: 319
<212> TYPE: PRT
<213> ORGANISM: homo sapiens

<400> SEQUENCE: 80

Met Ser Val Gly Phe Ile Gly Ala Gly Gln Leu Ala Phe Ala Leu Ala
1               5                   10                  15

Lys Gly Phe Thr Ala Ala Gly Val Leu Ala Ala His Lys Ile Met Ala
            20                  25                  30

Ser Ser Pro Asp Met Asp Leu Ala Thr Val Ser Ala Leu Arg Lys Met
        35                  40                  45

Gly Val Lys Leu Thr Pro His Asn Lys Glu Thr Val Gln His Ser Asp
50                  55                  60

Val Leu Phe Leu Ala Val Lys Pro His Ile Ile Pro Phe Ile Leu Asp
65                  70                  75                  80

Glu Ile Gly Ala Asp Ile Glu Asp Arg His Ile Val Val Ser Cys Ala
                85                  90                  95

Ala Gly Val Thr Ile Ser Ser Ile Glu Lys Lys Leu Ser Ala Phe Arg
            100                 105                 110

Pro Ala Pro Arg Val Ile Arg Cys Met Thr Asn Thr Pro Val Val Val
        115                 120                 125

Arg Glu Gly Ala Thr Val Tyr Ala Thr Gly Thr His Ala Gln Val Glu
    130                 135                 140

Asp Gly Arg Leu Met Glu Gln Leu Leu Ser Thr Val Gly Phe Cys Thr
145                 150                 155                 160

Glu Val Glu Glu Asp Leu Ile Asp Ala Val Thr Gly Leu Ser Gly Ser
                165                 170                 175

Gly Pro Ala Tyr Ala Phe Thr Ala Leu Asp Ala Leu Ala Asp Gly Gly
            180                 185                 190

Val Lys Met Gly Leu Pro Arg Arg Leu Ala Val Arg Leu Gly Ala Gln
        195                 200                 205

Ala Leu Leu Gly Ala Ala Lys Met Leu Leu His Ser Glu Gln His Pro
    210                 215                 220

Gly Gln Leu Lys Asp Asn Val Ser Ser Pro Gly Gly Ala Thr Ile His
225                 230                 235                 240

Ala Leu His Val Leu Glu Ser Gly Gly Phe Arg Ser Leu Leu Ile Asn
                245                 250                 255

Ala Val Glu Ala Ser Cys Ile Arg Thr Arg Glu Leu Gln Ser Met Ala
            260                 265                 270

Asp Gln Glu Gln Val Ser Pro Ala Ala Ile Lys Lys Thr Ile Leu Asp
        275                 280                 285

Lys Val Lys Leu Asp Ser Pro Ala Gly Thr Ala Leu Ser Pro Ser Gly
    290                 295                 300

His Thr Lys Leu Leu Pro Arg Ser Leu Ala Pro Ala Gly Lys Asp
305                 310                 315
```

```
<210> SEQ ID NO 81
<211> LENGTH: 148
<212> TYPE: PRT
<213> ORGANISM: homo sapiens

<400> SEQUENCE: 81

Met Ala Glu Ser Asp Trp Asp Thr Val Thr Val Leu Arg Lys Lys Gly
1               5                   10                  15

Pro Thr Ala Ala Gln Ala Lys Ser Lys Gln Ala Ile Leu Ala Ala Gln
                20                  25                  30

Arg Arg Gly Glu Asp Val Glu Thr Ser Lys Lys Trp Ala Ala Gly Gln
            35                  40                  45

Asn Lys Gln His Ser Ile Thr Lys Asn Thr Ala Lys Leu Asp Arg Glu
50                  55                  60

Thr Glu Glu Leu His His Asp Arg Val Thr Leu Glu Val Gly Lys Val
65                  70                  75                  80

Ile Gln Gln Gly Arg Gln Ser Lys Gly Leu Thr Gln Lys Asp Leu Ala
                85                  90                  95

Thr Lys Ile Asn Glu Lys Pro Gln Val Ile Ala Asp Tyr Glu Ser Gly
            100                 105                 110

Arg Ala Ile Pro Asn Asn Gln Val Leu Gly Lys Ile Glu Arg Ala Ile
        115                 120                 125

Gly Leu Lys Leu Arg Gly Lys Asp Ile Gly Lys Pro Ile Glu Lys Gly
    130                 135                 140

Pro Arg Ala Lys
145

<210> SEQ ID NO 82
<211> LENGTH: 375
<212> TYPE: PRT
<213> ORGANISM: homo sapiens

<400> SEQUENCE: 82

Met Asp Asp Asp Ile Ala Ala Leu Val Val Asp Asn Gly Ser Gly Met
1               5                   10                  15

Cys Lys Ala Gly Phe Ala Gly Asp Asp Ala Pro Arg Ala Val Phe Pro
                20                  25                  30

Ser Ile Val Gly Arg Pro Arg His Gln Gly Val Met Val Gly Met Gly
            35                  40                  45

Gln Lys Asp Ser Tyr Val Gly Asp Glu Ala Gln Ser Lys Arg Gly Ile
50                  55                  60

Leu Thr Leu Lys Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
                85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
    130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175
```

```
Arg Leu Asp Leu Ala Gly Arg Asp Leu Thr Asp Tyr Leu Met Lys Ile
            180                 185                 190

Leu Thr Glu Arg Gly Tyr Ser Phe Thr Thr Thr Ala Glu Arg Glu Ile
        195                 200                 205

Val Arg Asp Ile Lys Glu Lys Leu Cys Tyr Val Ala Leu Asp Phe Glu
    210                 215                 220

Gln Glu Met Ala Thr Ala Ala Ser Ser Ser Leu Glu Lys Ser Tyr
225                 230                 235                 240

Glu Leu Pro Asp Gly Gln Val Ile Thr Ile Gly Asn Glu Arg Phe Arg
                245                 250                 255

Cys Pro Glu Ala Leu Phe Gln Pro Ser Phe Leu Gly Met Glu Ser Cys
            260                 265                 270

Gly Ile His Glu Thr Thr Phe Asn Ser Ile Met Lys Cys Asp Val Asp
        275                 280                 285

Ile Arg Lys Asp Leu Tyr Ala Asn Thr Val Leu Ser Gly Gly Thr Thr
    290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
                325                 330                 335

Tyr Ser Val Trp Ile Gly Gly Ser Ile Leu Ala Ser Leu Ser Thr Phe
            340                 345                 350

Gln Gln Met Trp Ile Ser Lys Gln Glu Tyr Asp Glu Ser Gly Pro Ser
        355                 360                 365

Ile Val His Arg Lys Cys Phe
    370                 375

<210> SEQ ID NO 83
<211> LENGTH: 268
<212> TYPE: PRT
<213> ORGANISM: homo sapiens

<400> SEQUENCE: 83

Met Phe Arg Met Leu Asn Ser Ser Phe Glu Asp Asp Pro Phe Phe Ser
1               5                   10                  15

Glu Ser Ile Leu Ala His Arg Glu Asn Met Arg Gln Met Ile Arg Ser
            20                  25                  30

Phe Ser Glu Pro Phe Gly Arg Asp Leu Leu Ser Ile Ser Asp Gly Arg
        35                  40                  45

Gly Arg Ala His Asn Arg Arg Gly His Asn Asp Gly Glu Asp Ser Leu
    50                  55                  60

Thr His Thr Asp Val Ser Ser Phe Gln Thr Met Asp Gln Met Val Ser
65                  70                  75                  80

Asn Met Arg Asn Tyr Met Gln Lys Leu Glu Arg Asn Phe Gly Gln Leu
                85                  90                  95

Ser Val Asp Pro Asn Gly His Ser Phe Cys Ser Ser Val Met Thr
            100                 105                 110

Tyr Ser Lys Ile Gly Asp Glu Pro Pro Lys Val Phe Gln Ala Ser Thr
        115                 120                 125

Gln Thr Arg Arg Ala Pro Gly Gly Ile Lys Glu Thr Arg Lys Ala Met
    130                 135                 140

Arg Asp Ser Asp Ser Gly Leu Glu Lys Met Ala Ile Gly His His Ile
145                 150                 155                 160

His Asp Arg Ala His Val Ile Lys Ser Lys Asn Lys Thr Gly
                165                 170                 175
```

```
Asp Glu Glu Val Asn Gln Glu Phe Ile Asn Met Asn Glu Ser Asp Ala
            180                 185                 190

His Ala Phe Asp Glu Glu Trp Gln Ser Glu Val Leu Lys Tyr Lys Pro
            195                 200                 205

Gly Arg His Asn Leu Gly Asn Thr Arg Met Arg Ser Val Gly His Glu
            210                 215                 220

Asn Pro Gly Ser Arg Glu Leu Lys Arg Glu Lys Pro Gln Gln Ser
225                 230                 235                 240

Pro Ala Ile Glu His Gly Arg Arg Ser Asn Val Leu Gly Asp Lys Leu
                245                 250                 255

His Ile Lys Gly Ser Ser Val Lys Ser Asn Lys Lys
            260                 265

<210> SEQ ID NO 84
<211> LENGTH: 837
<212> TYPE: PRT
<213> ORGANISM: homo sapiens

<400> SEQUENCE: 84

Met Ala Glu Pro Ser Gln Ala Pro Thr Pro Ala Pro Ala Ala Gln Pro
1               5                   10                  15

Arg Pro Leu Gln Ser Pro Ala Pro Ala Pro Thr Pro Thr Pro Ala Pro
            20                  25                  30

Ser Pro Ala Ser Ala Pro Ile Pro Thr Pro Thr Pro Ala Pro Ala Pro
            35                  40                  45

Ala Pro Ala Ala Ala Pro Ala Gly Ser Thr Gly Thr Gly Gly Pro Gly
        50                  55                  60

Val Gly Ser Gly Gly Ala Gly Ser Gly Gly Asp Pro Ala Arg Pro Gly
65              70                  75                  80

Leu Ser Gln Gln Gln Arg Ala Ser Gln Arg Lys Ala Gln Val Arg Gly
                85                  90                  95

Leu Pro Arg Ala Lys Lys Leu Glu Lys Leu Gly Val Phe Ser Ala Cys
            100                 105                 110

Lys Ala Asn Gly Thr Cys Lys Cys Asn Gly Trp Lys Asn Pro Lys Pro
            115                 120                 125

Pro Thr Ala Pro Arg Ile Asp Leu Gln Gln Pro Ala Ala Asn Leu Ser
130                 135                 140

Glu Leu Cys Arg Ser Cys Glu His Pro Leu Ala Asp His Val Ser His
145                 150                 155                 160

Leu Glu Asn Val Ser Glu Asp Glu Ile Asn Arg Leu Leu Gly Met Val
                165                 170                 175

Val Asp Val Glu Asn Leu Phe Met Ser Val His Lys Glu Glu Asp Thr
            180                 185                 190

Asp Thr Lys Gln Val Tyr Phe Tyr Leu Phe Lys Leu Leu Arg Lys Cys
            195                 200                 205

Ile Leu Gln Met Thr Arg Pro Val Val Glu Gly Ser Leu Gly Ser Pro
            210                 215                 220

Pro Phe Glu Lys Pro Asn Ile Glu Gln Gly Val Leu Asn Phe Val Gln
225                 230                 235                 240

Tyr Lys Phe Ser His Leu Ala Pro Arg Glu Arg Gln Thr Met Phe Glu
                245                 250                 255

Leu Ser Lys Met Phe Leu Leu Cys Leu Asn Tyr Trp Glu Leu Glu Thr
            260                 265                 270

Pro Ala Gln Phe Arg Gln Arg Ser Gln Ala Glu Asp Val Ala Thr Tyr
            275                 280                 285
```

-continued

```
Lys Val Asn Tyr Thr Arg Trp Leu Cys Tyr Cys His Val Pro Gln Ser
        290                 295                 300
Cys Asp Ser Leu Pro Arg Tyr Glu Thr Thr His Val Phe Gly Arg Ser
305                 310                 315                 320
Leu Leu Arg Ser Ile Phe Thr Val Thr Arg Arg Gln Leu Leu Glu Lys
                325                 330                 335
Phe Arg Val Glu Lys Asp Lys Leu Val Pro Glu Lys Arg Thr Leu Ile
            340                 345                 350
Leu Thr His Phe Pro Lys Phe Leu Ser Met Leu Glu Glu Glu Ile Tyr
        355                 360                 365
Gly Ala Asn Ser Pro Ile Trp Glu Ser Gly Phe Thr Met Pro Pro Ser
370                 375                 380
Glu Gly Thr Gln Leu Val Pro Arg Pro Ala Ser Val Ser Ala Ala Val
385                 390                 395                 400
Val Pro Ser Thr Pro Ile Phe Ser Pro Ser Met Gly Gly Gly Ser Asn
                405                 410                 415
Ser Ser Leu Ser Leu Asp Ser Ala Gly Ala Glu Pro Met Pro Gly Glu
            420                 425                 430
Lys Arg Thr Leu Pro Glu Asn Leu Thr Leu Glu Asp Ala Lys Arg Leu
        435                 440                 445
Arg Val Met Gly Asp Ile Pro Met Glu Leu Val Asn Glu Val Met Leu
450                 455                 460
Thr Ile Thr Asp Pro Ala Ala Met Leu Gly Pro Glu Thr Ser Leu Leu
465                 470                 475                 480
Ser Ala Asn Ala Ala Arg Asp Glu Thr Ala Arg Leu Glu Glu Arg Arg
                485                 490                 495
Gly Ile Ile Glu Phe His Val Ile Gly Asn Ser Leu Thr Pro Lys Ala
            500                 505                 510
Asn Arg Arg Val Leu Leu Trp Leu Val Gly Leu Gln Asn Val Phe Ser
        515                 520                 525
His Gln Leu Pro Arg Met Pro Lys Glu Tyr Ile Ala Arg Leu Val Phe
530                 535                 540
Asp Pro Lys His Lys Thr Leu Ala Leu Ile Lys Asp Gly Arg Val Ile
545                 550                 555                 560
Gly Gly Ile Cys Phe Arg Met Phe Pro Thr Gln Gly Phe Thr Glu Ile
                565                 570                 575
Val Phe Cys Ala Val Thr Ser Asn Glu Gln Val Lys Gly Tyr Gly Thr
            580                 585                 590
His Leu Met Asn His Leu Lys Glu Tyr His Ile Lys His Asn Ile Leu
        595                 600                 605
Tyr Phe Leu Thr Tyr Ala Asp Glu Tyr Ala Ile Gly Tyr Phe Lys Lys
610                 615                 620
Gln Gly Phe Ser Lys Asp Ile Lys Val Pro Lys Ser Arg Tyr Leu Gly
625                 630                 635                 640
Tyr Ile Lys Asp Tyr Glu Gly Ala Thr Leu Met Glu Cys Glu Leu Asn
                645                 650                 655
Pro Arg Ile Pro Tyr Thr Glu Leu Ser His Ile Ile Lys Lys Gln Lys
            660                 665                 670
Glu Ile Ile Lys Lys Leu Ile Glu Arg Lys Gln Ala Gln Ile Arg Lys
        675                 680                 685
Val Tyr Pro Gly Leu Ser Cys Phe Lys Glu Gly Val Arg Gln Ile Pro
690                 695                 700
Val Glu Ser Val Pro Gly Ile Arg Glu Thr Gly Trp Lys Pro Leu Gly
705                 710                 715                 720
```

```
Lys Glu Lys Gly Lys Glu Leu Lys Asp Pro Asp Gln Leu Tyr Thr Thr
                725                 730                 735

Leu Lys Asn Leu Leu Ala Gln Ile Lys Ser His Pro Ser Ala Trp Pro
            740                 745                 750

Phe Met Glu Pro Val Lys Lys Ser Glu Ala Pro Asp Tyr Tyr Glu Val
        755                 760                 765

Ile Arg Phe Pro Ile Asp Leu Lys Thr Met Thr Glu Arg Leu Arg Ser
770                 775                 780

Arg Tyr Tyr Val Thr Arg Lys Leu Phe Val Ala Asp Leu Gln Arg Val
785                 790                 795                 800

Ile Ala Asn Cys Arg Glu Tyr Asn Pro Pro Asp Ser Glu Tyr Cys Arg
                805                 810                 815

Cys Ala Ser Ala Leu Glu Lys Phe Phe Tyr Phe Lys Leu Lys Glu Gly
                820                 825                 830

Gly Leu Ile Asp Lys
            835

<210> SEQ ID NO 85
<211> LENGTH: 483
<212> TYPE: PRT
<213> ORGANISM: homo sapiens

<400> SEQUENCE: 85

Met Lys Glu Glu Lys Glu His Arg Pro Lys Glu Lys Arg Val Thr Leu
1               5                   10                  15

Leu Thr Pro Ala Gly Ala Thr Gly Ser Gly Gly Gly Thr Ser Gly Asp
            20                  25                  30

Ser Ser Lys Gly Glu Asp Lys Gln Asp Arg Asn Lys Glu Lys Lys Glu
        35                  40                  45

Ala Leu Ser Lys Val Val Ile Arg Arg Leu Pro Pro Thr Leu Thr Lys
    50                  55                  60

Glu Gln Leu Gln Glu His Leu Gln Pro Met Pro Glu His Asp Tyr Phe
65                  70                  75                  80

Glu Phe Phe Ser Asn Asp Thr Ser Leu Tyr Pro His Met Tyr Ala Arg
                85                  90                  95

Ala Tyr Ile Asn Phe Lys Asn Gln Glu Asp Ile Ile Leu Phe Arg Asp
                100                 105                 110

Arg Phe Asp Gly Tyr Val Phe Leu Asp Asn Lys Gly Gln Glu Tyr Pro
            115                 120                 125

Ala Ile Val Glu Phe Ala Pro Phe Gln Lys Ala Lys Lys Lys Lys Thr
        130                 135                 140

Lys Lys Arg Asp Thr Lys Val Gly Thr Ile Asp Asp Asp Pro Glu Tyr
145                 150                 155                 160

Arg Lys Phe Leu Glu Ser Tyr Ala Thr Asp Asn Glu Lys Met Thr Ser
                165                 170                 175

Thr Pro Glu Thr Leu Leu Glu Glu Ile Glu Ala Lys Asn Arg Glu Leu
            180                 185                 190

Ile Ala Lys Lys Thr Thr Pro Leu Leu Ser Phe Leu Lys Asn Lys Gln
        195                 200                 205

Arg Met Arg Glu Glu Lys Arg Glu Glu Arg Arg Arg Glu Ile Glu
    210                 215                 220

Arg Lys Arg Gln Arg Glu Glu Arg Arg Lys Trp Lys Glu Glu Glu
225                 230                 235                 240

Lys Arg Lys Arg Lys Asp Ile Glu Lys Leu Lys Lys Ile Asp Arg Ile
                245                 250                 255
```

```
Pro Glu Arg Asp Lys Leu Lys Asp Glu Pro Lys Ile Lys Val His Arg
            260                 265                 270
Phe Leu Leu Gln Ala Val Asn Gln Lys Asn Leu Leu Lys Lys Pro Glu
        275                 280                 285
Lys Gly Asp Glu Lys Glu Leu Asp Lys Arg Glu Lys Ala Lys Lys Leu
    290                 295                 300
Asp Lys Glu Asn Leu Ser Asp Glu Arg Ala Ser Gly Gln Ser Cys Thr
305                 310                 315                 320
Leu Pro Lys Arg Ser Asp Ser Glu Leu Lys Asp Glu Lys Pro Lys Arg
                325                 330                 335
Pro Glu Asp Glu Ser Gly Arg Asp Tyr Arg Glu Arg Glu Arg Glu Tyr
            340                 345                 350
Glu Arg Asp Gln Glu Arg Ile Leu Arg Glu Arg Glu Arg Leu Lys Arg
        355                 360                 365
Gln Glu Glu Glu Arg Arg Gln Lys Glu Arg Tyr Glu Lys Glu Lys
    370                 375                 380
Thr Phe Lys Arg Lys Glu Glu Met Lys Lys Glu Lys Asp Thr Leu
385                 390                 395                 400
Arg Asp Lys Gly Lys Lys Ala Glu Ser Thr Glu Ser Ile Gly Ser Ser
                405                 410                 415
Glu Lys Thr Glu Lys Lys Glu Val Val Lys Arg Asp Arg Ile Arg
            420                 425                 430
Asn Lys Asp Arg Pro Ala Met Gln Leu Tyr Gln Pro Gly Ala Arg Ser
        435                 440                 445
Arg Asn Arg Leu Cys Pro Pro Asp Ser Thr Lys Ser Gly Asp Ser
    450                 455                 460
Ala Ala Glu Arg Lys Gln Glu Ser Gly Ile Ser His Arg Lys Glu Gly
465                 470                 475                 480
Gly Glu Glu

<210> SEQ ID NO 86
<211> LENGTH: 426
<212> TYPE: PRT
<213> ORGANISM: homo sapiens

<400> SEQUENCE: 86

Met Ala Asn Asp Ser Gly Gly Pro Gly Gly Pro Ser Pro Ser Glu Arg
1               5                   10                  15
Asp Arg Gln Tyr Cys Glu Leu Cys Gly Lys Met Glu Asn Leu Leu Arg
            20                  25                  30
Cys Ser Arg Cys Arg Ser Ser Phe Tyr Cys Cys Lys Glu His Gln Arg
        35                  40                  45
Gln Asp Trp Lys Lys His Lys Leu Val Cys Gln Gly Ser Glu Gly Ala
    50                  55                  60
Leu Gly His Gly Val Gly Pro His Gln His Ser Gly Pro Ala Pro Pro
65                  70                  75                  80
Ala Ala Val Pro Pro Pro Arg Ala Gly Ala Arg Glu Pro Arg Lys Ala
                85                  90                  95
Ala Ala Arg Arg Asp Asn Ala Ser Gly Asp Ala Ala Lys Gly Lys Val
            100                 105                 110
Lys Ala Lys Pro Pro Ala Asp Pro Ala Ala Ala Ser Pro Cys Arg
        115                 120                 125
Ala Ala Ala Gly Gly Gln Gly Ser Ala Val Ala Ala Glu Ala Glu Pro
    130                 135                 140
```

Gly Lys Glu Glu Pro Pro Ala Arg Ser Ser Leu Phe Gln Glu Lys Ala
145                 150                 155                 160

Asn Leu Tyr Pro Pro Ser Asn Thr Pro Gly Asp Ala Leu Ser Pro Gly
            165                 170                 175

Gly Gly Leu Arg Pro Asn Gly Gln Thr Lys Pro Leu Pro Ala Leu Lys
            180                 185                 190

Leu Ala Leu Glu Tyr Ile Val Pro Cys Met Asn Lys His Gly Ile Cys
            195                 200                 205

Val Val Asp Asp Phe Leu Gly Lys Glu Thr Gly Gln Gln Ile Gly Asp
            210                 215                 220

Glu Val Arg Ala Leu His Asp Thr Gly Lys Phe Thr Asp Gly Gln Leu
225                 230                 235                 240

Val Ser Gln Lys Ser Asp Ser Ser Lys Asp Ile Arg Gly Asp Lys Ile
            245                 250                 255

Thr Trp Ile Glu Gly Lys Glu Pro Gly Cys Glu Thr Ile Gly Leu Leu
            260                 265                 270

Met Ser Ser Met Asp Asp Leu Ile Arg His Cys Asn Gly Lys Leu Gly
            275                 280                 285

Ser Tyr Lys Ile Asn Gly Arg Thr Lys Ala Met Val Ala Cys Tyr Pro
            290                 295                 300

Gly Asn Gly Thr Gly Tyr Val Arg His Val Asp Asn Pro Asn Gly Asp
305                 310                 315                 320

Gly Arg Cys Val Thr Cys Ile Tyr Tyr Leu Asn Lys Asp Trp Asp Ala
            325                 330                 335

Lys Val Ser Gly Gly Ile Leu Arg Ile Phe Pro Glu Gly Lys Ala Gln
            340                 345                 350

Phe Ala Asp Ile Glu Pro Lys Phe Asp Arg Leu Leu Phe Phe Trp Ser
            355                 360                 365

Asp Arg Arg Asn Pro His Glu Val Gln Pro Ala Tyr Ala Thr Arg Tyr
            370                 375                 380

Ala Ile Thr Val Trp Tyr Phe Asp Ala Asp Glu Arg Ala Arg Ala Lys
385                 390                 395                 400

Val Lys Tyr Leu Thr Gly Glu Lys Gly Val Arg Val Glu Leu Asn Lys
            405                 410                 415

Pro Ser Asp Ser Val Gly Lys Asp Val Phe
            420                 425

<210> SEQ ID NO 87
<211> LENGTH: 1320
<212> TYPE: PRT
<213> ORGANISM: homo sapiens

<400> SEQUENCE: 87

Met Ser Gly Gly Ala Ser Ala Thr Gly Pro Arg Arg Gly Pro Pro Gly
1               5                   10                  15

Leu Glu Asp Thr Thr Ser Lys Lys Gln Lys Asp Arg Ala Asn Gln
            20                  25                  30

Glu Ser Lys Asp Gly Asp Pro Arg Lys Glu Thr Gly Ser Arg Tyr Val
            35                  40                  45

Ala Gln Ala Gly Leu Glu Pro Leu Ala Ser Gly Asp Pro Ser Ala Ser
            50                  55                  60

Ala Ser His Ala Ala Gly Ile Thr Gly Ser Arg His Arg Thr Arg Leu
65                  70                  75                  80

Phe Phe Pro Ser Ser Ser Gly Ala Ser Thr Pro Gln Glu Glu Gln
            85                  90                  95

```
Thr Lys Glu Gly Ala Cys Glu Asp Pro His Asp Leu Leu Ala Thr Pro
                100                 105                 110

Thr Pro Glu Leu Leu Leu Asp Trp Arg Gln Ser Ala Glu Glu Val Ile
            115                 120                 125

Val Lys Leu Arg Val Gly Val Gly Pro Leu Gln Leu Glu Asp Val Asp
130                 135                 140

Ala Ala Phe Thr Asp Thr Asp Cys Val Val Arg Phe Ala Gly Gly Gln
145                 150                 155                 160

Gln Trp Gly Gly Val Phe Tyr Ala Glu Ile Lys Ser Ser Cys Ala Lys
                165                 170                 175

Val Gln Thr Arg Lys Gly Ser Leu Leu His Leu Thr Leu Pro Lys Lys
            180                 185                 190

Val Pro Met Leu Thr Trp Pro Ser Leu Leu Val Glu Ala Asp Glu Gln
        195                 200                 205

Leu Cys Ile Pro Pro Leu Asn Ser Gln Thr Cys Leu Leu Gly Ser Glu
    210                 215                 220

Glu Asn Leu Ala Pro Leu Ala Gly Glu Lys Ala Val Pro Pro Gly Asn
225                 230                 235                 240

Asp Pro Val Ser Pro Ala Met Val Arg Ser Arg Asn Pro Gly Lys Asp
                245                 250                 255

Asp Cys Ala Lys Glu Glu Met Ala Val Ala Asp Ala Ala Thr Leu
            260                 265                 270

Val Asp Glu Pro Glu Ser Met Val Asn Leu Ala Phe Val Lys Asn Asp
        275                 280                 285

Ser Tyr Glu Lys Gly Pro Asp Ser Val Val His Val Tyr Val Lys
    290                 295                 300

Glu Ile Cys Arg Asp Thr Ser Arg Val Leu Phe Arg Glu Gln Asp Phe
305                 310                 315                 320

Thr Leu Ile Phe Gln Thr Arg Asp Gly Asn Phe Leu Arg Leu His Pro
                325                 330                 335

Gly Cys Gly Pro His Thr Thr Phe Arg Trp Gln Val Lys Leu Arg Asn
            340                 345                 350

Leu Ile Glu Pro Glu Gln Cys Thr Phe Cys Phe Thr Ala Ser Arg Ile
        355                 360                 365

Asp Ile Cys Leu Arg Lys Arg Gln Ser Gln Arg Trp Gly Gly Leu Glu
    370                 375                 380

Ala Pro Ala Ala Arg Gly Ala Val Gly Gly Ala Lys Val Ala Val Pro
385                 390                 395                 400

Thr Gly Pro Thr Pro Leu Asp Ser Thr Pro Pro Gly Gly Ala Pro His
                405                 410                 415

Pro Leu Thr Gly Gln Glu Glu Ala Arg Ala Val Glu Lys Asp Lys Ser
            420                 425                 430

Lys Ala Arg Ser Glu Asp Thr Gly Leu Asp Ser Val Ala Thr Arg Thr
        435                 440                 445

Pro Met Glu His Val Thr Pro Lys Pro Glu Thr His Leu Ala Ser Pro
    450                 455                 460

Lys Pro Thr Cys Met Val Pro Met Pro His Ser Pro Val Ser Gly
465                 470                 475                 480

Asp Ser Val Glu Glu Glu Glu Glu Lys Lys Val Cys Leu Pro
                485                 490                 495

Gly Phe Thr Gly Leu Val Asn Leu Gly Asn Thr Cys Phe Met Asn Ser
            500                 505                 510

Val Ile Gln Ser Leu Ser Asn Thr Arg Glu Leu Arg Asp Phe Phe His
        515                 520                 525
```

-continued

Asp Arg Ser Phe Glu Ala Glu Ile Asn Tyr Asn Asn Pro Leu Gly Thr
    530                 535                 540

Gly Gly Arg Leu Ala Ile Gly Phe Ala Val Leu Leu Arg Ala Leu Trp
545                 550                 555                 560

Lys Gly Thr His His Ala Phe Gln Pro Ser Lys Leu Lys Ala Ile Val
                565                 570                 575

Ala Ser Lys Ala Ser Gln Phe Thr Gly Tyr Ala Gln His Asp Ala Gln
            580                 585                 590

Glu Phe Met Ala Phe Leu Leu Asp Gly Leu His Glu Asp Leu Asn Arg
        595                 600                 605

Ile Gln Asn Lys Pro Tyr Thr Glu Thr Val Asp Ser Asp Gly Arg Pro
    610                 615                 620

Asp Glu Val Val Ala Glu Ala Trp Gln Arg His Lys Met Arg Asn
625                 630                 635                 640

Asp Ser Phe Ile Val Asp Leu Phe Gln Gly Gln Tyr Lys Ser Lys Leu
                645                 650                 655

Val Cys Pro Val Cys Ala Lys Val Ser Ile Thr Phe Asp Pro Phe Leu
            660                 665                 670

Tyr Leu Pro Val Pro Leu Pro Gln Lys Gln Lys Val Leu Pro Val Phe
        675                 680                 685

Tyr Phe Ala Arg Glu Pro His Ser Lys Pro Ile Lys Phe Leu Val Ser
    690                 695                 700

Val Ser Lys Glu Asn Ser Thr Ala Ser Glu Val Leu Asp Ser Leu Ser
705                 710                 715                 720

Gln Ser Val His Val Lys Pro Glu Asn Leu Arg Leu Ala Glu Val Ile
                725                 730                 735

Lys Asn Arg Phe His Arg Val Phe Leu Pro Ser His Ser Leu Asp Thr
            740                 745                 750

Val Ser Pro Ser Asp Thr Leu Leu Cys Phe Glu Leu Leu Ser Ser Glu
        755                 760                 765

Leu Ala Lys Glu Arg Val Val Leu Glu Val Gln Gln Arg Pro Gln
    770                 775                 780

Val Pro Ser Val Pro Ile Ser Lys Cys Ala Ala Cys Gln Arg Lys Gln
785                 790                 795                 800

Gln Ser Glu Asp Glu Lys Leu Lys Arg Cys Thr Arg Cys Tyr Arg Val
                805                 810                 815

Gly Tyr Cys Asn Gln Leu Cys Gln Lys Thr His Trp Pro Asp His Lys
            820                 825                 830

Gly Leu Cys Arg Pro Glu Asn Ile Gly Tyr Pro Phe Leu Val Ser Val
        835                 840                 845

Pro Ala Ser Arg Leu Thr Tyr Ala Arg Leu Ala Gln Leu Leu Glu Gly
    850                 855                 860

Tyr Ala Arg Tyr Ser Val Ser Val Phe Gln Pro Pro Phe Gln Pro Gly
865                 870                 875                 880

Arg Met Ala Leu Glu Ser Gln Ser Pro Gly Cys Thr Thr Leu Leu Ser
                885                 890                 895

Thr Gly Ser Leu Glu Ala Gly Asp Ser Glu Arg Asp Pro Ile Gln Pro
            900                 905                 910

Pro Glu Leu Gln Leu Val Thr Pro Met Ala Glu Gly Asp Thr Gly Leu
        915                 920                 925

Pro Arg Val Trp Ala Ala Pro Asp Arg Gly Pro Val Pro Ser Thr Ser
    930                 935                 940

Gly Ile Ser Ser Glu Met Leu Ala Ser Gly Pro Ile Glu Val Gly Ser

```
                    945                 950                 955                 960
Leu Pro Ala Gly Glu Arg Val Ser Arg Pro Glu Ala Ala Val Pro Gly
                965                 970                 975
Tyr Gln His Pro Ser Glu Ala Met Asn Ala His Thr Pro Gln Phe Phe
            980                 985                 990
Ile Tyr Lys Ile Asp Ser Ser Asn Arg Glu Gln Arg Leu Glu Asp Lys
            995                 1000                1005
Gly Asp Thr Pro Leu Glu Leu Gly Asp Asp Cys Ser Leu Ala Leu
        1010                1015                1020
Val Trp Arg Asn Asn Glu Arg Leu Gln Glu Phe Val Leu Val Ala
        1025                1030                1035
Ser Lys Glu Leu Glu Cys Ala Glu Asp Pro Gly Ser Ala Gly Glu
        1040                1045                1050
Ala Ala Arg Ala Gly His Phe Thr Leu Asp Gln Cys Leu Asn Leu
        1055                1060                1065
Phe Thr Arg Pro Glu Val Leu Ala Pro Glu Glu Ala Trp Tyr Cys
        1070                1075                1080
Pro Gln Cys Lys Gln His Arg Glu Ala Ser Lys Gln Leu Leu Leu
        1085                1090                1095
Trp Arg Leu Pro Asn Val Leu Ile Val Gln Leu Lys Arg Phe Ser
        1100                1105                1110
Phe Arg Ser Phe Ile Trp Arg Asp Lys Ile Asn Asp Leu Val Glu
        1115                1120                1125
Phe Pro Val Arg Asn Leu Asp Leu Ser Lys Phe Cys Ile Gly Gln
        1130                1135                1140
Lys Glu Glu Gln Leu Pro Ser Tyr Asp Leu Tyr Ala Val Ile Asn
        1145                1150                1155
His Tyr Gly Gly Met Ile Gly Gly His Tyr Thr Ala Cys Ala Arg
        1160                1165                1170
Leu Pro Asn Asp Arg Ser Ser Gln Arg Ser Asp Val Gly Trp Arg
        1175                1180                1185
Leu Phe Asp Asp Ser Thr Val Thr Thr Val Asp Glu Ser Gln Val
        1190                1195                1200
Val Thr Arg Tyr Ala Tyr Val Leu Phe Tyr Arg Arg Arg Asn Ser
        1205                1210                1215
Pro Val Glu Arg Pro Pro Arg Ala Gly His Ser Glu His His Pro
        1220                1225                1230
Asp Leu Gly Pro Ala Ala Glu Ala Ala Ala Ser Gln Ala Ser Arg
        1235                1240                1245
Ile Trp Gln Glu Leu Glu Ala Glu Glu Glu Pro Val Pro Glu Gly
        1250                1255                1260
Ser Gly Pro Leu Gly Pro Trp Gly Pro Gln Asp Trp Val Gly Pro
        1265                1270                1275
Leu Pro Arg Gly Pro Thr Thr Pro Asp Glu Gly Cys Leu Arg Tyr
        1280                1285                1290
Phe Val Leu Gly Thr Val Ala Ala Leu Val Ala Leu Val Leu Asn
        1295                1300                1305
Val Phe Tyr Pro Leu Val Ser Gln Ser Arg Trp Arg
        1310                1315                1320

<210> SEQ ID NO 88
<211> LENGTH: 325
<212> TYPE: PRT
<213> ORGANISM: homo sapiens
```

<400> SEQUENCE: 88

```
Met Ser Ala Gln Ala Gln Met Arg Ala Leu Leu Asp Gln Leu Met Gly
1               5                   10                  15

Thr Ala Arg Asp Gly Asp Glu Thr Arg Gln Arg Val Lys Phe Thr Asp
                20                  25                  30

Asp Arg Val Cys Lys Ser His Leu Leu Asp Cys Cys Pro His Asp Ile
            35                  40                  45

Leu Ala Gly Thr Arg Met Asp Leu Gly Glu Cys Thr Lys Ile His Asp
        50                  55                  60

Leu Ala Leu Arg Ala Asp Tyr Glu Ile Ala Ser Lys Glu Arg Asp Leu
65                  70                  75                  80

Phe Phe Glu Leu Asp Ala Met Asp His Leu Glu Ser Phe Ile Ala Glu
                85                  90                  95

Cys Asp Arg Arg Thr Glu Leu Ala Lys Lys Arg Leu Ala Glu Thr Gln
            100                 105                 110

Glu Glu Ile Ser Ala Glu Val Ser Ala Lys Ala Glu Lys Val His Glu
        115                 120                 125

Leu Asn Glu Glu Ile Gly Lys Leu Leu Ala Lys Ala Glu Gln Leu Gly
    130                 135                 140

Ala Glu Gly Asn Val Asp Glu Ser Gln Lys Ile Leu Met Glu Val Glu
145                 150                 155                 160

Lys Val Arg Ala Lys Lys Glu Ala Glu Glu Tyr Arg Asn Ser
                165                 170                 175

Met Pro Ala Ser Ser Phe Gln Gln Gln Lys Leu Arg Val Cys Glu Val
                180                 185                 190

Cys Ser Ala Tyr Leu Gly Leu His Asp Asn Asp Arg Arg Leu Ala Asp
            195                 200                 205

His Phe Gly Gly Lys Leu His Leu Gly Phe Ile Gln Ile Arg Glu Lys
        210                 215                 220

Leu Asp Gln Leu Arg Lys Thr Val Ala Glu Lys Gln Glu Lys Arg Asn
225                 230                 235                 240

Gln Asp Arg Leu Arg Arg Arg Glu Glu Arg Glu Arg Glu Arg Glu Arg Leu
                245                 250                 255

Ser Arg Arg Ser Gly Ser Arg Thr Arg Asp Arg Arg Ser Arg Ser
            260                 265                 270

Arg Asp Arg Arg Arg Arg Ser Ser Thr Ser Arg Glu Arg Arg
        275                 280                 285

Lys Leu Ser Arg Ser Arg Ser Arg Asp Arg His Arg Arg His Arg Ser
    290                 295                 300

Arg Ser Arg Ser His Ser Arg Gly His Arg Arg Ala Ser Arg Asp Arg
305                 310                 315                 320

Ser Ala Lys Tyr Lys
                325
```

<210> SEQ ID NO 89
<211> LENGTH: 181
<212> TYPE: PRT
<213> ORGANISM: homo sapiens

<400> SEQUENCE: 89

```
Met Gly Gly Phe Phe Ser Ser Ile Phe Ser Ser Leu Phe Gly Thr Arg
1               5                   10                  15

Glu Met Arg Ile Leu Ile Leu Gly Leu Asp Gly Ala Gly Lys Thr Thr
                20                  25                  30

Ile Leu Tyr Arg Leu Gln Val Gly Glu Val Val Thr Thr Ile Pro Thr
```

```
              35                  40                  45
Ile Gly Phe Asn Val Glu Thr Val Thr Tyr Lys Asn Leu Lys Phe Gln
 50                  55                  60
Val Trp Asp Leu Gly Gly Gln Thr Ser Ile Arg Pro Tyr Trp Arg Cys
 65                  70                  75                  80
Tyr Tyr Ser Asn Thr Asp Ala Val Ile Tyr Val Asp Ser Cys Asp
                 85                  90                  95
Arg Asp Arg Ile Gly Ile Ser Lys Ser Glu Leu Val Ala Met Leu Glu
            100                 105                 110
Glu Glu Glu Leu Arg Lys Ala Ile Leu Val Val Phe Ala Asn Lys Gln
            115                 120                 125
Asp Met Glu Gln Ala Met Thr Ser Ser Glu Met Ala Asn Ser Leu Gly
130                 135                 140
Leu Pro Ala Leu Lys Asp Arg Lys Trp Gln Ile Phe Lys Thr Ser Ala
145                 150                 155                 160
Thr Lys Gly Thr Gly Leu Asp Glu Ala Met Glu Trp Leu Val Glu Thr
                165                 170                 175
Leu Lys Ser Arg Gln
            180

<210> SEQ ID NO 90
<211> LENGTH: 217
<212> TYPE: PRT
<213> ORGANISM: homo sapiens

<400> SEQUENCE: 90

Met Ser Ser Lys Val Ser Arg Asp Thr Leu Tyr Glu Ala Val Arg Glu
 1               5                  10                  15
Val Leu His Gly Asn Gln Arg Lys Arg Arg Lys Phe Leu Glu Thr Val
                20                  25                  30
Glu Leu Gln Ile Ser Leu Lys Asn Tyr Asp Pro Gln Lys Asp Lys Arg
            35                  40                  45
Phe Ser Gly Thr Val Arg Leu Lys Ser Thr Pro Arg Pro Lys Phe Ser
 50                  55                  60
Val Cys Val Leu Gly Asp Gln Gln His Cys Asp Glu Ala Lys Ala Val
 65                  70                  75                  80
Asp Ile Pro His Met Asp Ile Glu Ala Leu Lys Lys Leu Asn Lys Asn
                 85                  90                  95
Lys Lys Leu Val Lys Lys Leu Ala Lys Lys Tyr Asp Ala Phe Leu Ala
            100                 105                 110
Ser Glu Ser Leu Ile Lys Gln Ile Pro Arg Ile Leu Gly Pro Gly Leu
            115                 120                 125
Asn Lys Ala Gly Lys Phe Pro Ser Leu Leu Thr His Asn Glu Asn Met
            130                 135                 140
Val Ala Lys Val Asp Glu Val Lys Ser Thr Ile Lys Phe Gln Met Lys
145                 150                 155                 160
Lys Val Leu Cys Leu Ala Val Ala Val Gly His Val Lys Met Thr Asp
                165                 170                 175
Asp Glu Leu Val Tyr Asn Ile His Leu Ala Val Asn Phe Leu Val Ser
            180                 185                 190
Leu Leu Lys Lys Asn Trp Gln Asn Val Arg Ala Leu Tyr Ile Lys Ser
            195                 200                 205
Thr Met Gly Lys Pro Gln Arg Leu Tyr
210                 215
```

```
<210> SEQ ID NO 91
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 91
tggcgcagaa aggaaaagga aaat                                              24

<210> SEQ ID NO 92
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 92
agaggtagct ggcaggatgt tag                                               23

<210> SEQ ID NO 93
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 93
cttggtgcga tcagccttat                                                   20

<210> SEQ ID NO 94
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 94
ttgatgcatg aaaacagaac tc                                                22

<210> SEQ ID NO 95
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 95
agaattggca gaggctcgtc atca                                              24

<210> SEQ ID NO 96
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 96
ttccaatttt gccttctcta actg                                              24

<210> SEQ ID NO 97
<211> LENGTH: 884
<212> TYPE: DNA
<213> ORGANISM: Homo sapiens
<220> FEATURE:
<221> NAME/KEY: misc_feature
<222> LOCATION: (727)..(727)
<223> OTHER INFORMATION: n is a, c, g, or t
```

<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (868)..(868)
<223> OTHER INFORMATION: n is a, c, g, or t

<400> SEQUENCE: 97

```
cacgaggcaa gggtgtcacc cccgcaggat ttccaaagaa ggccagtaga actgctagaa      60
tagcctccga tgaggaaatt caaggcacaa aggatgctgt tattcaagac ctggaacgaa     120
aacttcgctt caaggaggac ctcctgaaca atggccagcc gaggttaaca tacgaagaaa     180
gaatggctcg tcgactgcta ggtgctgaca gtgcaactgt ctttaatatt caggagccag     240
aagaggaaac agctaatcag gaatacaaag tctccagctg tgaacagaga ctcatcagtg     300
aaatagagta caggctagaa aggtctcctg tggatgaatc aggtgatgaa gttcagtatg     360
gagatgtgcc tgtggaaaat ggaatggcac cattctttga gatgaagctg aaacattaca     420
agatctttga gggaatgcca gtaactttca catgtagagt ggctggaaat ccaaagccaa     480
agatctattg gtttaaagat gggaagcaga tctctccaaa gagtgatcac tacaccattc     540
aaagagatct cgatgggacc tgctccctcc ataccacagc ctccacccta gatgatgatg     600
ggaattatac aattatggct gcaaaccctc agggccgcat cagttgtact ggacggctaa     660
tggtacaggc tgtcaaccaa agaggtcgaa gtccccggtc tccctcaggc catcctcatg     720
tcagaangnc tcgttctaga tcaagggaca gtggagacga aaatgaccca attcaggagc     780
gattcttcag acctcacttc ttgcaggctc ctggagatct gactggtcaa gaaggaaact     840
ctgcagatgg actgcaaagt cagtgggnta ccaccccaga tcta                      884
```

<210> SEQ ID NO 98
<211> LENGTH: 886
<212> TYPE: DNA
<213> ORGANISM: Homo sapiens
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (731)..(731)
<223> OTHER INFORMATION: n is a, c, g, or t
<220> FEATURE:
<221> NAME/KEY: misc_feature
<222> LOCATION: (740)..(740)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (809)..(809)
<223> OTHER INFORMATION: n is a, c, g, or t
<220> FEATURE:
<221> NAME/KEY: misc_feature
<222> LOCATION: (844)..(844)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t
<220> FEATURE:
<221> NAME/KEY: misc_feature
<222> LOCATION: (857)..(857)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (878)..(878)
<223> OTHER INFORMATION: n is a, c, g, or t

<400> SEQUENCE: 98

```
cgagggaaa ttacaaatag tgaccaaacc aaagcagatt tggactcgtc tctagatata      60
aaaaaaaatc ctgttccatg tcagaaatat agtttacgga attcaagtaa tgttatgtta     120
gatgataaac aatgtaaaat aaaacaaata caactgttaa ctaaaaaaag tgagtgcagc     180
atattacttt ctaaacaaac ttcagatttt ctgcaagtct gtaatgatac tttagagaaa     240
tctgaactaa ctgttccctg tgatatagta atcgaccacc atgtttcata tgctgctttt    300
agtgctaatt caaaactact tctgaagaac tcagataaaa atgtccatag tatgtctatg    360
ttggtgaaac ctaactcaag ccctggggga aaaactatgt gtaaaaatat gagtgatatg    420
caaaacagtc aatttaataa ctgtttggga tacttagaaa acactaatgt gaacatttcc    480
catcttcatc ttaacaatga gaatagtcat gcttcacaag ccaaagatgt gaaaactgct    540
gttcacatga aaacttgcac agaaacagag ttttccaata aaaagaatca gattgatgag    600
aatcaggtaa ctgaagccac aaaaaatgac ctcttccttt tgtgagcat taatgaaaga    660
cagcatacat tgtttaaata atacagagga aaacnggaat cattaaatga cattgtttcc    720
aggaaaaatg ntcagtgaan gacagctgga ggaatcacat tcatttcaca tagagcctct    780
ggagatttag taacagancg ggaaggncna cctttgatct ttcacttcag ataaaaaact    840
gagnaaactc cngtatnatg atttttcaga cccggncntg ggcaag                  886
```

<210> SEQ ID NO 99
<211> LENGTH: 851
<212> TYPE: DNA
<213> ORGANISM: Homo sapiens

<400> SEQUENCE: 99

```
cacgagggtc gagaggccgg catcactgga gtggtggcgc agctgtttcc tccggatatc     60
catcaaatat tgagaagaaa gaatatcagg agcaaagtgt tctaagttgc tgctcagaac    120
gtaaagatgc gaaccccaaa tcagtggttt gttcattctt catgcaagag caatgcacta    180
aaggagagaa gcaagctgtg gtgatcagtg actttggtga aagctaagaa ggttcaaaca    240
aatttgcaaa tgatatacaa cttctaagca ttccatattg gaagaagaga tttctacaca    300
tgaaaaaaat gcctttgttt agtaaatcac acaaaaatcc agcagaaatt gtgaaaatcc    360
tgaaagacaa tttggccatt ttggaaaagc aagacaaaaa gacagacaag gcttcagaag    420
aagtgtctaa atcactgcaa gcaatgaaag aaattctgtg tggtacaaac gagaaagaac    480
ccccaacaga agcagtggct cagctagcac aagaactcta cagcagtggc ctgctagtga    540
cactgatagc tgacctgcag ctgatagact ttgagggaaa aaaagatgtg acccagatat    600
ttaacaacat cttgagaaga cagataggca ctcggagtcc tactgtggag tatattagtg    660
ctcatcctca tatcctgttt atgctcctca aggatatga agcccacag attgccttac     720
gttgtgggga ttatgctgag agaatgtatt cgacatgaac cccttgccaa aatcatcctc    780
ttttctaatc aattcagaga tttctttagg tacgtggagt tgtccacatt tgatattgct    840
tcaaatgcct t                                                          851
```

<210> SEQ ID NO 100
<211> LENGTH: 639
<212> TYPE: DNA
<213> ORGANISM: Homo sapiens

<400> SEQUENCE: 100

| | | | | | | |
|---|---|---|---|---|---|---|
| cgaggggatg | acagtgtttt | cattgcagtt | aaagaaattg | gtcgtgatct | gtacaggggc | 60 |
| ttgcctacag | aggaaaggat | ccagaaacta | gagttcatgt | tggataagct | acagaatgaa | 120 |
| attgatcagg | agttggaaca | caataattcc | cttgttagag | aagaaaaaga | gacaactgat | 180 |
| acaaggaaaa | aatcacttct | ttctgctgcc | ttagctaaat | caggtgaaag | gctacaagct | 240 |
| ctaacacttc | ttatgattca | ctacagagca | ggcattgaag | atatagaaac | tttagaaagt | 300 |
| ctgtctttag | accagcactc | caaaaaaata | agcaagtaca | cagatgatac | agaagaagac | 360 |
| cttgataatg | aaataagcca | actaatagac | tctcagccat | tcagcagcat | atcagatgac | 420 |
| ttatttggcc | catccgagtc | tgtgtagcag | acaggtctat | ttaaactttc | aaatgaacag | 480 |
| ggtaaagttg | catctaaagt | accacagata | caaccatgtt | taaatcctcg | tatgcactct | 540 |
| ggcctgcttc | tccagttact | tgcttgtgta | agaacaaaaa | tgagaaaggt | tgttttccag | 600 |
| taaaaacatg | accagcttac | taaaaaaaaa | aaaaaaaa | | | 639 |

<210> SEQ ID NO 101
<211> LENGTH: 907
<212> TYPE: DNA
<213> ORGANISM: Homo sapiens
<220> FEATURE:
<221> NAME/KEY: misc_feature
<222> LOCATION: (797)..(797)
<223> OTHER INFORMATION: n is a, c, g, or t

<400> SEQUENCE: 101

| | | | | | | |
|---|---|---|---|---|---|---|
| cgagggtcat | gtgccaaact | gctcagcaag | gaagaggaag | caggtgttaa | ggaattagca | 60 |
| aagcaggtga | agagtttgcc | agtggtaaat | tacaacctcc | tcaagtatat | ttgcagattc | 120 |
| ttggatgaag | tacagtccta | ctcgggagtt | aacaaaatga | gtgtgcagaa | cttggcaacg | 180 |
| gtctttggtc | ctaatatcct | gcgccccaaa | gtggaagatc | ctttgactat | catggagggc | 240 |
| actgtggtgg | tccagcagtt | gatgtcagtg | atgattagca | aacatgattg | cctctttccc | 300 |
| aaagatgcag | aactacaaag | caagccccaa | gatggagtga | gcaacaacaa | tgaaattcag | 360 |
| aagaaagcca | ccatggggca | gttacagaac | aaggagaaca | ataacaccaa | ggacagccct | 420 |
| agtaggcagt | gctcctggga | caagtctgag | tcaccccaga | gaagcagcat | gaacaatgga | 480 |
| tcccccacag | ctctatcagg | cagcaaaacc | aacagcccaa | gaacagtgt | tcacaagcta | 540 |
| gatgtgtcta | gaagcccccc | tctcatggtc | aaaaagaacc | cagcctttaa | taagggtagt | 600 |
| gggatagtta | ccaatgggtc | cttcagcagc | agtaatgcag | aagtcttga | gaaaacccaa | 660 |
| accaccccca | atgggagcct | acaggccaga | aggagctctt | cactgaaggt | atctggtacc | 720 |
| aaaatgggca | cgcacagtgt | acagaatgga | acggtgcgca | tgggcatttt | gaacagcgac | 780 |
| acactcggga | acccacnaat | gttcgaacat | gagctggctg | ccaatggcta | tgtgacctga | 840 |
| gggatacaag | cagaagacag | ctggagagta | ggcacacaca | gatgtcccct | tgatatgtca | 900 |
| tcacagt | | | | | | 907 |

<210> SEQ ID NO 102
<211> LENGTH: 931
<212> TYPE: DNA
<213> ORGANISM: Homo sapiens

```
<220> FEATURE:
<221> NAME/KEY: misc_feature
<222> LOCATION: (881)..(881)
<223> OTHER INFORMATION: n is a, c, g, or t

<400> SEQUENCE: 102
cgagggcaca acaaggcggc gccgccgcag atcccggaca cccggcggga gctggcggag      60
ctcgtgaagc ggaagcagga gctggcggaa acattggcaa atttggagcg acagatctat     120
gcttttgagg aagctacct ggaagacact cagatgtatg gcaatattat tcgtggctgg      180
gatcggtatc tgaccaacca aaaaaactcc aatagcaaaa atgatcgaag gaaccggaag     240
tttaaggaag ctgagcggct cttcagtaaa tcctcggtta cctcagcagc tgcagtaagt     300
gcattggcag gagttcagga ccagctcatt gaaagagggg agccaggaag tgggacggaa     360
agtgacactt ctccagactt ccacaatcag gaaaatgagc ccagccagga ggaccctgag     420
gatctggatg gatctgtgca gggagtgaaa cctcagaagg ctgcttcttc tacttcctca     480
gggagtcacc acagcagcca taaaaagcga aagaataaaa accggcacag gattgatctg     540
aagttaaaca aaaaccacg agctgactat tagaagacac attagtgcag aagcttccag      600
gctgtagagc cctgcttccc ttctctgacc tcacaaagat aaacatcctt cacctgagtt     660
cgtggccatc cacctctgct ctcccagacc cagtgcctgt gactttgagt agtttgttct     720
aaatgtggtg acaaacaagt catttctgta agacattggg tcttacttta tgtcattttt     780
agtaacagaa ctgcaggaag atcaagacat gttgtaatcc cggcaagttg ctactgtgcg     840
ttctcccttc ttagatgatt gtctccccaa actggctggc ncagcttctc tgtgatacct     900
tcagaatgtt ctctggtttg tttatgctga a                                    931

<210> SEQ ID NO 103
<211> LENGTH: 737
<212> TYPE: DNA
<213> ORGANISM: Homo sapiens
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (646)..(646)
<223> OTHER INFORMATION: n is a, c, g, or t
<220> FEATURE:
<221> NAME/KEY: misc_feature
<222> LOCATION: (689)..(689)
<223> OTHER INFORMATION: n is a, c, g, or t

<400> SEQUENCE: 103
ggaagaacag catgctaaca catctgccaa ttatgatgtg gagctacttc atcacaaaga      60
tgcacatgta gatttcctga aaagtggtga ttcgcatcta ggtggcggca gtcgagaagg     120
ctcgtttaaa gaaacaataa cattaaagtg gtgtacacca aggacaaata acattgaatt     180
acactattgt actggagctt atcggatttc acctgtagat gtaaatagta gaccttcctc     240
ctgccttact aattttcttc taaatggtcg ttctgttta ttggaacaac cacgaaagtc      300
aggttctaaa gtcattagtc atatgcttag tagccatgga ggagagattt ttttgcacgt     360
ccttagcagt tctcgatcca ttctagaaga tccaccttca attagtgaag gatgtggagg     420
aagagttaca gactaccggg attacagatt ttggtgaatt tatgagggaa aacagattaa     480
ctccttttct agaccccaga tataaaatcg atggaagtct tgaggtccct ttgggaacga     540
gcaaaagatc agttagaaaa acatacccgt tactggccta tgatcatttc acaaaccacc     600 attttttaaca tgcaagcggt agttccatta gccagngtta ttgtgnaaaa aatctctgac     660
```
agaagagaat gtgttaaact gtcaaaaanc atatacaact tagttgatat ggaaagaaaa      720
atgatcctct acctatt                                                    737

<210> SEQ ID NO 104
<211> LENGTH: 770
<212> TYPE: DNA
<213> ORGANISM: Homo sapiens
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (640)..(641)
<223> OTHER INFORMATION: n is a, c, g, or t

<400> SEQUENCE: 104
cgaggactac ttgtacctac aagacctgct actcgccaag ggctgattgg gagaataatg      60
gaatctgaaa atatggattc tgaaaatatg aagacagaaa atatggaatc tcaaaatgta     120
gactttgaga gtgtttcttc ngttacagct ctggaagccc tctctaagct acttaatcct     180
gaagaagagg atgattctga ctatggacag acaaatggtt tatctactat tggagccatg     240
ggtcctggga atattggacc accccaaata gaagagctca agtcatccc tgaaaccagc      300 gaggaaaata tgaggacat ctggaattca gaagagattc cagaaggagc agaatatgat      360
gatatgtggg atgttagaga aatcccagag tatgagatta tattcagaca gcaggtggga     420
actgaagata tattttagg gttgtcaaaa aaggactcct caacaggttg ttgcagtgaa      480
ctagtggcta aaattaaatt gccaaataca aaccttctg atattcaaat tgatatccag      540
ggaaacaatc cttgaccttc gtactcctca gaagaagctg ttgataactc ttcctgagct     600
ggtggaatgt accagtgcca aagcattcta tatcccagan nactgaaact cttgaaatca     660
ctatgactat gaaagagag ttagatattg ctaatttctt ctgaaactgc atgaaaaga      720 taaaaagtag taaaatggca ttggtaacaa ttaaaaaact ttgaaaaaag               770

<210> SEQ ID NO 105
<211> LENGTH: 920
<212> TYPE: DNA
<213> ORGANISM: Homo sapiens
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (750)..(750)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (826)..(827)
<223> OTHER INFORMATION: n is a, c, g, or t
<220> FEATURE:
<221> NAME/KEY: misc_feature
<222> LOCATION: (849)..(849)
<223> OTHER INFORMATION: n is a, c, g, or t
<220> FEATURE:
<221> NAME/KEY: misc_feature
<222> LOCATION: (870)..(870)
<223> OTHER INFORMATION: n is a, c, g, or t

```
<220> FEATURE:
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (882)..(882)
<223> OTHER INFORMATION: n is a, c, g, or t
<220> FEATURE:
<221> NAME/KEY: misc_feature
<222> LOCATION: (889)..(889)
<223> OTHER INFORMATION: n is a, c, g, or t
<220> FEATURE:
<221> NAME/KEY: misc_feature
<222> LOCATION: (909)..(909)
<223> OTHER INFORMATION: n is a, c, g, or t

<400> SEQUENCE: 105
gaggctttac gcgcgtgccc ttcacccact ggttcttctc cttcgtggaa gacccgctga      60
tcgacttcga ggtgcgctcc cagtttgaag ggcggcccat gccccagctc acctccatca     120
tcgtcaacca gctcaagaag atcatcaagc gcaagcacac cctaccgaat tacaagatca     180
ggtttaagcc gttttttcca taccagacct tgcaaggatt tgaagaagat gaagagcata     240
tccatataca acaatgggca cttactgaag gccgtcttaa agttacgttg ttagaatgta     300
gcaggttact catttttgga tcctatgaca gagaggcaaa tgttcattgc acacttgagt     360
taagcagtag tgtttgggaa gaaaaacaga ggagttctat taagacggtt gaattaataa     420
aaggaaattt acaaagtgtt ggacttacac ttcgtcttgt ccagtcaact gatgggtatg     480
ctgggcacgt catcattgaa actgtggctc caaactcgcc tgctgcaatt gcagatcttc     540
agcggggaga tcgacttatc gccattggga ggtgtgaaaa tcacatcaac actgcaagtg     600
ttgaagctta tcaagcaggc tggtgaccga gtcctggtgt actatgaaag gcctgttggc     660
cagagtaatc aaggtgcagt gctgcangat aactttggcc agttggaaga aaacttttg     720 tcaagctcat gccaatcggg ttatgaagan gaaactgccg ggttgacagt aaatactgaa     780
aagtaaagag ctgggattct gaatttngan aacttggcaa gtgganntcc agagcccaaa     840
atgagttcna agatgaggca caatcattan gtcntagtcc cnaacgggnt ccaacaacac     900
ttttctatna aacccttgg                                                  920

<210> SEQ ID NO 106
<211> LENGTH: 938
<212> TYPE: DNA
<213> ORGANISM: Homo sapiens
<220> FEATURE:
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (860)..(860)
<223> OTHER INFORMATION: n is a, c, g, or t
<220> FEATURE:
<221> NAME/KEY: misc_feature
<222> LOCATION: (865)..(865)
<223> OTHER INFORMATION: n is a, c, g, or t
<220> FEATURE:
<221> NAME/KEY: misc_feature
<222> LOCATION: (867)..(867)
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t
```

```
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (882)..(882)
<223> OTHER INFORMATION: n is a, c, g, or t
<220> FEATURE:
<221> NAME/KEY: misc_feature
<222> LOCATION: (908)..(908)
<223> OTHER INFORMATION: n is a, c, g, or t

<400> SEQUENCE: 106
ctgcagaggc gcctcatgga aaccaacctg tctaagctcc gaagcggtcc ccgtgtccct      60
tgggcctcta agacgaacaa actcaatcag gctaagtctg aggggctaaa gaagtctgag     120
gaggatgaca tgattttggt ttcttgccag tgtgctggaa aggatgtgaa agccttggtt     180
gacacaggct gcctatataa tctcatctct ttggcctgtg tggacagatt gggactcaag     240
gagcatgtca atcccacaa gcatgaagga gaaaagcttt ctctaccccg gcatctcaaa     300
gtagtgggcc agattgagca cctagtgatc acactgggct ccctccgcct ggactgccca     360
gcagctgtgg ttgatgacaa tgagaaaaac ttgtcccttg gtctacagac tctccgatct     420
ctgaagtgca tcataaactt ggataagcac cggctgatca tggggaagac agacaaggaa     480 gaaatcccctt ttgtggagac agtctctttg aatgaagaca cacttcaga agcataacta     540 cagcctgcag catgtctgca cgtgtgcatg catacacacc gggttgacag attgagaaaa     600
ctgggtttga accaaatgcc gtagtgactt gctgtggacc aagtccttcc atctaataga     660
agctccaggg gctccttncc attcagacct ctctagacta tagtctatgc ttagagatct     720
tgtctggnta tggccattgt tttttactac tttgatcact taacttatag acctttttttg     780 acactgccag tctcactggg ggctatttct ctgctccttc cagaatttgc ttttattagt     840
caagtatagg gctgccaggn tctgngnccc atananatat gngcttcttt cctaagctaa     900
tggataanaa caggacctga cttttaaaaa aaaaaaaa                              938

<210> SEQ ID NO 107
<211> LENGTH: 949
<212> TYPE: DNA
<213> ORGANISM: Homo sapiens
<220> FEATURE:
<221> NAME/KEY: misc_feature
<222> LOCATION: (705)..(705)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (818)..(818)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (844)..(844)
<223> OTHER INFORMATION: n is a, c, g, or t
<220> FEATURE:
<221> NAME/KEY: misc_feature
<222> LOCATION: (865)..(865)
<223> OTHER INFORMATION: n is a, c, g, or t
<220> FEATURE:
<221> NAME/KEY: misc_feature
<222> LOCATION: (875)..(875)
<223> OTHER INFORMATION: n is a, c, g, or t
```

```
<220> FEATURE:
<221> NAME/KEY: misc_feature
<222> LOCATION: (893)..(893)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (908)..(908)
<223> OTHER INFORMATION: n is a, c, g, or t
<220> FEATURE:
<221> NAME/KEY: misc_feature
<222> LOCATION: (910)..(910)
<223> OTHER INFORMATION: n is a, c, g, or t
<220> FEATURE:
<221> NAME/KEY: misc_feature
<222> LOCATION: (918)..(918)
<223> OTHER INFORMATION: n is a, c, g, or t

<400> SEQUENCE: 107
cacgagggtg gtgtctgtca gacacacaca ggccgccagt gacttcacac acacctcatg      60
tgagaaccat gccttttta gtgtgtccta tttcatacct gtacacactt cctcgttttg     120
taatgagatt tacttacacc caaacagatc ctgaaagaaa gcttcaagtt ttctcagatg     180
atggatatgt tttcactgta ttcataact gacggatgta aggtgcacgt ttcctgatgt     240
gacgcactgt attccagctg gtgatcaagt ctggaacag ccgtaacagg tcaaccttgt      300
ggagccatcg cgagttagag ggtgaaagat ggcagaaaaa aaagtcttgt gtgtgagtgt     360
gttttttgag tttgcatcaa tcttaatgtc tcttcataat acttttataa tacattaagc     420
ctcttgtcta catatttgga gagaatatga ctttactagc agagaaatac aatatatctt     480
gtctactgga ctgtaaaata tatgtatgaa ataaaattag ttccatttgg tcttctagta     540
tattaaagtg ctatctgacg ttgttatcct gttttttgcaa aaaaaaaaaa aaaaaagtta     600
actacagacc attgtttcta ataagcagag agatctattt tagtagtaaa ctgaaggttt     660
agttgtgagc ttcagatttt gtgaactcca gatgttgtgc ggggnttttt tttttttttt     720
aagaccacca ctaaaaaatg ccaggaatat gtacctggga actgnagggg agctttcagt     780
attggaaaaa gattgttcta tacggacctt tttgctgntt atccgggatg naaaagcct      840 tccnaaacct atgggaaaaa aaagngagca ctgantctcc cctgttcctt cgnggaccct     900
tttggnangn aaactggnct gttttttaaaa tgggactaaa aaaaaaaa                 949

<210> SEQ ID NO 108
<211> LENGTH: 784
<212> TYPE: DNA
<213> ORGANISM: Homo sapiens

<400> SEQUENCE: 108
agaaggcttt ggcttctgat agtcatggac tcactaggct gctgaggaag atcaataata      60
cctactggaa tcagtcatga gaagtcaagc atggaaattg tgaattgtgt gtgtggccag     120
accagtacct ccaagtgttc agaagatgtg tgaccagaca aaacacagta aatgctgccc     180
agcaaaaggc aatcaatgct gcccaccaca gcagaaccag tgctgccagt caaaaggcaa     240
tcaatgctgc ccaccaaaac agaaccagtg ctgccagcca aaggcagtc aatgctgccc      300 accaaaacac aatcactgct gccagccaaa acccccatgc tgcattcagg ccaggtgctg     360
tggtttggag accaagcctg aagtctcacc ccttaacatg gagtctgagc ccaactcacc     420
gcaaactcag gacaagggct gtcaaaccca gcagcagccc catagcccac aaaatgagtc     480
caggccaagc aaatgagagc agaagaagtc aaacaaagaa gaagtccctg gggccatgcc     540
```

```
tttcactttg tagggtgggg gattactgag agtcaggcta gacctgtgtt tagagaagca    600
gttttcacag tgactaccat ttccacccaa tgagaggctc ctatttccca tcatagctcc    660
ctaccctagg gaggcctcca tctggaaatg ggaggatgaa gaggctagaa tcatctttcc    720
tagtgatcct gacatttaga cagcacagaa ataaagagca ataaaaagaa aaaaaaaaa     780 aaaa                                                                 784
```

<210> SEQ ID NO 109
<211> LENGTH: 294
<212> TYPE: PRT
<213> ORGANISM: Homo sapiens
<220> FEATURE:
<221> NAME/KEY: misc_feature
<222> LOCATION: (242)..(243)
<223> OTHER INFORMATION: Xaa can be any naturally occurring amino acid
<220> FEATURE:
<221> NAME/KEY: misc_feature
<222> LOCATION: (289)..(289)
<223> OTHER INFORMATION: Xaa can be any naturally occurring amino acid

<400> SEQUENCE: 109

```
Arg Gly Lys Gly Val Thr Pro Ala Gly Phe Pro Lys Lys Ala Ser Arg
1               5                   10                  15

Thr Ala Arg Ile Ala Ser Asp Glu Glu Ile Gln Gly Thr Lys Asp Ala
            20                  25                  30

Val Ile Gln Asp Leu Glu Arg Lys Leu Arg Phe Lys Glu Asp Leu Leu
        35                  40                  45

Asn Asn Gly Gln Pro Arg Leu Thr Tyr Glu Glu Arg Met Ala Arg Arg
    50                  55                  60

Leu Leu Gly Ala Asp Ser Ala Thr Val Phe Asn Ile Gln Glu Pro Glu
65                  70                  75                  80

Glu Glu Thr Ala Asn Gln Glu Tyr Lys Val Ser Ser Cys Glu Gln Arg
                85                  90                  95

Leu Ile Ser Glu Ile Glu Tyr Arg Leu Glu Arg Ser Pro Val Asp Glu
            100                 105                 110

Ser Gly Asp Glu Val Gln Tyr Gly Asp Val Pro Val Glu Asn Gly Met
        115                 120                 125

Ala Pro Phe Phe Glu Met Lys Leu Lys His Tyr Lys Ile Phe Glu Gly
    130                 135                 140

Met Pro Val Thr Phe Thr Cys Arg Val Ala Gly Asn Pro Lys Pro Lys
145                 150                 155                 160

Ile Tyr Trp Phe Lys Asp Gly Lys Gln Ile Ser Pro Lys Ser Asp His
                165                 170                 175

Tyr Thr Ile Gln Arg Asp Leu Asp Gly Thr Cys Ser Leu His Thr Thr
            180                 185                 190

Ala Ser Thr Leu Asp Asp Gly Asn Tyr Thr Ile Met Ala Ala Asn
        195                 200                 205

Pro Gln Gly Arg Ile Ser Cys Thr Gly Arg Leu Met Val Gln Ala Val
    210                 215                 220

Asn Gln Arg Gly Arg Ser Pro Arg Ser Pro Ser Gly His Pro His Val
225                 230                 235                 240

Arg Xaa Xaa Arg Ser Arg Ser Arg Asp Ser Gly Asp Glu Asn Asp Pro
                245                 250                 255

Ile Gln Glu Arg Phe Phe Arg Pro His Phe Leu Gln Ala Pro Gly Asp
            260                 265                 270

Leu Thr Gly Gln Glu Gly Asn Ser Ala Asp Gly Leu Gln Ser Gln Trp
        275                 280                 285
```

```
Xaa Thr Thr Pro Asp Leu
    290

<210> SEQ ID NO 110
<211> LENGTH: 226
<212> TYPE: PRT
<213> ORGANISM: Homo sapiens

<400> SEQUENCE: 110

Arg Gly Glu Ile Thr Asn Ser Asp Gln Thr Lys Ala Asp Leu Asp Ser
1               5                   10                  15

Ser Leu Asp Ile Lys Lys Asn Pro Val Pro Cys Gln Lys Tyr Ser Leu
            20                  25                  30

Arg Asn Ser Ser Asn Val Met Leu Asp Asp Lys Gln Cys Lys Ile Lys
        35                  40                  45

Gln Ile Gln Leu Leu Thr Lys Lys Ser Glu Cys Ser Ile Leu Leu Ser
    50                  55                  60

Lys Gln Thr Ser Asp Phe Leu Gln Val Cys Asn Asp Thr Leu Glu Lys
65                  70                  75                  80

Ser Glu Leu Thr Val Pro Cys Asp Ile Val Ile Asp His His Val Ser
                85                  90                  95

Tyr Ala Ala Phe Ser Ala Asn Ser Lys Leu Leu Leu Lys Asn Ser Asp
            100                 105                 110

Lys Asn Val His Ser Met Ser Met Leu Val Lys Pro Asn Ser Ser Pro
        115                 120                 125

Gly Gly Lys Thr Met Cys Lys Asn Met Ser Asp Met Gln Asn Ser Gln
    130                 135                 140

Phe Asn Asn Cys Leu Gly Tyr Leu Glu Asn Thr Asn Val Asn Ile Ser
145                 150                 155                 160

His Leu His Leu Asn Asn Glu Asn Ser His Ala Ser Gln Ala Lys Asp
                165                 170                 175

Val Lys Thr Ala Val His Met Lys Thr Cys Thr Glu Thr Glu Phe Ser
            180                 185                 190

Asn Lys Lys Asn Gln Ile Asp Glu Asn Gln Val Thr Glu Ala Thr Lys
        195                 200                 205

Asn Asp Leu Phe Leu Phe Val Ser Ile Asn Glu Arg Gln His Thr Leu
    210                 215                 220

Phe Lys
225

<210> SEQ ID NO 111
<211> LENGTH: 74
<212> TYPE: PRT
<213> ORGANISM: Homo sapiens

<400> SEQUENCE: 111

Arg Gly Ser Arg Gly Arg His His Trp Ser Gly Gly Ala Ala Val Ser
1               5                   10                  15

Ser Gly Tyr Pro Ser Asn Ile Glu Lys Lys Glu Tyr Gln Gln Ser
            20                  25                  30

Val Leu Ser Cys Cys Ser Glu Arg Lys Asp Ala Asn Pro Lys Ser Val
        35                  40                  45

Val Cys Ser Phe Phe Met Gln Glu Gln Cys Thr Lys Gly Glu Lys Gln
    50                  55                  60

Ala Val Val Ile Ser Asp Phe Gly Glu Ser
65                  70
```

```
<210> SEQ ID NO 112
<211> LENGTH: 148
<212> TYPE: PRT
<213> ORGANISM: Homo sapiens

<400> SEQUENCE: 112

Arg Gly Asp Asp Ser Val Phe Ile Ala Val Lys Glu Ile Gly Arg Asp
1               5                   10                  15

Leu Tyr Arg Gly Leu Pro Thr Glu Glu Arg Ile Gln Lys Leu Glu Phe
            20                  25                  30

Met Leu Asp Lys Leu Gln Asn Glu Ile Asp Gln Glu Leu Glu His Asn
        35                  40                  45

Asn Ser Leu Val Arg Glu Glu Lys Glu Thr Thr Asp Thr Arg Lys Lys
50                  55                  60

Ser Leu Leu Ser Ala Ala Leu Ala Lys Ser Gly Glu Arg Leu Gln Ala
65                  70                  75                  80

Leu Thr Leu Leu Met Ile His Tyr Arg Ala Gly Ile Glu Asp Ile Glu
                85                  90                  95

Thr Leu Glu Ser Leu Ser Leu Asp Gln His Ser Lys Lys Ile Ser Lys
            100                 105                 110

Tyr Thr Asp Asp Thr Glu Glu Asp Leu Asp Asn Glu Ile Ser Gln Leu
        115                 120                 125

Ile Asp Ser Gln Pro Phe Ser Ser Ile Ser Asp Leu Phe Gly Pro
    130                 135                 140

Ser Glu Ser Val
145

<210> SEQ ID NO 113
<211> LENGTH: 279
<212> TYPE: PRT
<213> ORGANISM: Homo sapiens
<220> FEATURE:
<221> NAME/KEY: misc_feature
<222> LOCATION: (266)..(266)
<223> OTHER INFORMATION: Xaa can be any naturally occurring amino acid

<400> SEQUENCE: 113

Arg Gly Ser Cys Ala Lys Leu Leu Ser Lys Glu Glu Ala Gly Val
1               5                   10                  15

Lys Glu Leu Ala Lys Gln Val Lys Ser Leu Pro Val Val Asn Tyr Asn
            20                  25                  30

Leu Leu Lys Tyr Ile Cys Arg Phe Leu Asp Glu Val Gln Ser Tyr Ser
        35                  40                  45

Gly Val Asn Lys Met Ser Val Gln Asn Leu Ala Thr Val Phe Gly Pro
50                  55                  60

Asn Ile Leu Arg Pro Lys Val Glu Asp Pro Leu Thr Ile Met Glu Gly
65                  70                  75                  80

Thr Val Val Val Gln Gln Leu Met Ser Val Met Ile Ser Lys His Asp
                85                  90                  95

Cys Leu Phe Pro Lys Asp Ala Glu Leu Gln Ser Lys Pro Gln Asp Gly
            100                 105                 110

Val Ser Asn Asn Asn Glu Ile Gln Lys Lys Ala Thr Met Gly Gln Leu
        115                 120                 125

Gln Asn Lys Glu Asn Asn Asn Thr Lys Asp Ser Pro Ser Arg Gln Cys
    130                 135                 140

Ser Trp Asp Lys Ser Glu Ser Pro Gln Arg Ser Ser Met Asn Asn Gly
145                 150                 155                 160
```

```
Ser Pro Thr Ala Leu Ser Gly Ser Lys Thr Asn Ser Pro Lys Asn Ser
            165                 170                 175

Val His Lys Leu Asp Val Ser Arg Ser Pro Pro Leu Met Val Lys Lys
            180                 185                 190

Asn Pro Ala Phe Asn Lys Gly Ser Gly Ile Val Thr Asn Gly Ser Phe
            195                 200                 205

Ser Ser Ser Asn Ala Glu Gly Leu Glu Lys Thr Gln Thr Thr Pro Asn
            210                 215                 220

Gly Ser Leu Gln Ala Arg Arg Ser Ser Ser Leu Lys Val Ser Gly Thr
225                 230                 235                 240

Lys Met Gly Thr His Ser Val Gln Asn Gly Thr Val Arg Met Gly Ile
            245                 250                 255

Leu Asn Ser Asp Thr Leu Gly Asn Pro Xaa Met Phe Glu His Glu Leu
            260                 265                 270

Ala Ala Asn Gly Tyr Val Thr
            275

<210> SEQ ID NO 114
<211> LENGTH: 190
<212> TYPE: PRT
<213> ORGANISM: Homo sapiens

<400> SEQUENCE: 114

Arg Gly His Asn Lys Ala Ala Pro Pro Gln Ile Pro Asp Thr Arg Arg
1               5                   10                  15

Glu Leu Ala Glu Leu Val Lys Arg Lys Gln Glu Leu Ala Glu Thr Leu
            20                  25                  30

Ala Asn Leu Glu Arg Gln Ile Tyr Ala Phe Glu Gly Ser Tyr Leu Glu
            35                  40                  45

Asp Thr Gln Met Tyr Gly Asn Ile Ile Arg Gly Trp Asp Arg Tyr Leu
        50                  55                  60

Thr Asn Gln Lys Asn Ser Asn Ser Lys Asn Asp Arg Arg Asn Arg Lys
65                  70                  75                  80

Phe Lys Glu Ala Glu Arg Leu Phe Ser Lys Ser Ser Val Thr Ser Ala
                85                  90                  95

Ala Ala Val Ser Ala Leu Ala Gly Val Gln Asp Gln Leu Ile Glu Lys
            100                 105                 110

Arg Glu Pro Gly Ser Gly Thr Glu Ser Asp Thr Ser Pro Asp Phe His
            115                 120                 125

Asn Gln Glu Asn Glu Pro Ser Gln Glu Asp Pro Glu Asp Leu Asp Gly
        130                 135                 140

Ser Val Gln Gly Val Lys Pro Gln Lys Ala Ala Ser Ser Thr Ser Ser
145                 150                 155                 160

Gly Ser His His Ser Ser His Lys Lys Arg Lys Asn Lys Asn Arg His
                165                 170                 175

Arg Ile Asp Leu Lys Leu Asn Lys Lys Pro Arg Ala Asp Tyr
            180                 185                 190

<210> SEQ ID NO 115
<211> LENGTH: 151
<212> TYPE: PRT
<213> ORGANISM: Homo sapiens

<400> SEQUENCE: 115

Glu Glu Gln His Ala Asn Thr Ser Ala Asn Tyr Asp Val Glu Leu Leu
1               5                   10                  15

His His Lys Asp Ala His Val Asp Phe Leu Lys Ser Gly Asp Ser His
```

```
                    20                  25                  30
Leu Gly Gly Gly Ser Arg Glu Gly Ser Phe Lys Glu Thr Ile Thr Leu
                35                  40                  45
Lys Trp Cys Thr Pro Arg Thr Asn Asn Ile Glu Leu His Tyr Cys Thr
 50                  55                  60
Gly Ala Tyr Arg Ile Ser Pro Val Asp Val Asn Ser Arg Pro Ser Ser
 65                  70                  75                  80
Cys Leu Thr Asn Phe Leu Leu Asn Gly Arg Ser Val Leu Leu Glu Gln
                85                  90                  95
Pro Arg Lys Ser Gly Ser Lys Val Ile Ser His Met Leu Ser Ser His
                100                 105                 110
Gly Gly Glu Ile Phe Leu His Val Leu Ser Ser Arg Ser Ile Leu
                115                 120                 125
Glu Asp Pro Pro Ser Ile Ser Glu Gly Cys Gly Arg Val Thr Asp
                130                 135                 140
Tyr Arg Asp Tyr Arg Phe Trp
145                 150

<210> SEQ ID NO 116
<211> LENGTH: 184
<212> TYPE: PRT
<213> ORGANISM: Homo sapiens

<400> SEQUENCE: 116

Arg Gly Leu Leu Val Pro Thr Arg Pro Ala Thr Arg Gln Gly Leu Ile
 1               5                  10                  15
Gly Arg Ile Met Glu Ser Glu Asn Met Asp Ser Glu Asn Met Lys Thr
                20                  25                  30
Glu Asn Met Glu Ser Gln Asn Val Asp Phe Glu Ser Val Ser Ser Val
                35                  40                  45
Thr Ala Leu Glu Ala Leu Ser Lys Leu Leu Asn Pro Glu Glu Glu Asp
 50                  55                  60
Asp Ser Asp Tyr Gly Gln Thr Asn Gly Leu Ser Thr Ile Gly Ala Met
 65                  70                  75                  80
Gly Pro Gly Asn Ile Gly Pro Pro Gln Ile Glu Glu Leu Lys Val Ile
                85                  90                  95
Pro Glu Thr Ser Glu Glu Asn Asn Glu Asp Ile Trp Asn Ser Glu Glu
                100                 105                 110
Ile Pro Glu Gly Ala Glu Tyr Asp Asp Met Trp Asp Val Arg Glu Ile
                115                 120                 125
Pro Glu Tyr Glu Ile Ile Phe Arg Gln Gln Val Gly Thr Glu Asp Ile
                130                 135                 140
Phe Leu Gly Leu Ser Lys Lys Asp Ser Ser Thr Gly Cys Cys Ser Glu
145                 150                 155                 160
Leu Val Ala Lys Ile Lys Leu Pro Asn Thr Asn Pro Ser Asp Ile Gln
                165                 170                 175
Ile Asp Ile Gln Gly Asn Asn Pro
                180

<210> SEQ ID NO 117
<211> LENGTH: 207
<212> TYPE: PRT
<213> ORGANISM: Homo sapiens

<400> SEQUENCE: 117

Gly Phe Thr Arg Val Pro Phe Thr His Trp Phe Phe Ser Phe Val Glu
 1               5                  10                  15
```

```
Asp Pro Leu Ile Asp Phe Glu Val Arg Ser Gln Phe Glu Gly Arg Pro
            20                  25                  30

Met Pro Gln Leu Thr Ser Ile Ile Val Asn Gln Leu Lys Lys Ile Ile
            35                  40                  45

Lys Arg Lys His Thr Leu Pro Asn Tyr Lys Ile Arg Phe Lys Pro Phe
 50                  55                  60

Phe Pro Tyr Gln Thr Leu Gln Gly Phe Glu Glu Asp Glu Glu His Ile
 65                  70                  75                  80

His Ile Gln Gln Trp Ala Leu Thr Gly Arg Leu Lys Val Thr Leu
                 85                  90                  95

Leu Glu Cys Ser Arg Leu Leu Ile Phe Gly Ser Tyr Asp Arg Glu Ala
                100                 105                 110

Asn Val His Cys Thr Leu Glu Leu Ser Ser Val Trp Glu Glu Lys
                115                 120                 125

Gln Arg Ser Ser Ile Lys Thr Val Glu Leu Ile Lys Gly Asn Leu Gln
    130                 135                 140

Ser Val Gly Leu Thr Leu Arg Leu Val Gln Ser Thr Asp Gly Tyr Ala
145                 150                 155                 160

Gly His Val Ile Ile Glu Thr Val Ala Pro Asn Ser Pro Ala Ala Ile
                165                 170                 175

Ala Asp Leu Gln Arg Gly Asp Arg Leu Ile Ala Ile Gly Arg Cys Glu
            180                 185                 190

Asn His Ile Asn Thr Ala Ser Val Glu Ala Tyr Gln Ala Gly Trp
            195                 200                 205

<210> SEQ ID NO 118
<211> LENGTH: 178
<212> TYPE: PRT
<213> ORGANISM: Homo sapiens

<400> SEQUENCE: 118

Leu Gln Arg Arg Leu Met Glu Thr Asn Leu Ser Lys Leu Arg Ser Gly
1               5                   10                  15

Pro Arg Val Pro Trp Ala Ser Lys Thr Asn Lys Leu Asn Gln Ala Lys
            20                  25                  30

Ser Glu Gly Leu Lys Lys Ser Glu Glu Asp Met Ile Leu Val Ser
            35                  40                  45

Cys Gln Cys Ala Gly Lys Asp Val Lys Ala Leu Val Asp Thr Gly Cys
 50                  55                  60

Leu Tyr Asn Leu Ile Ser Leu Ala Cys Val Asp Arg Leu Gly Leu Lys
 65                  70                  75                  80

Glu His Val Lys Ser His Lys His Glu Gly Glu Lys Leu Ser Leu Pro
                 85                  90                  95

Arg His Leu Lys Val Val Gly Gln Ile Glu His Leu Val Ile Thr Leu
                100                 105                 110

Gly Ser Leu Arg Leu Asp Cys Pro Ala Ala Val Val Asp Asp Asn Glu
            115                 120                 125

Lys Asn Leu Ser Leu Gly Leu Gln Thr Leu Arg Ser Leu Lys Cys Ile
    130                 135                 140

Ile Asn Leu Asp Lys His Arg Leu Ile Met Gly Lys Thr Asp Lys Glu
145                 150                 155                 160

Glu Ile Pro Phe Val Glu Thr Val Ser Leu Asn Glu Asp Asn Thr Ser
                165                 170                 175

Glu Ala
```

<210> SEQ ID NO 119
<211> LENGTH: 69
<212> TYPE: PRT
<213> ORGANISM: Homo sapiens

<400> SEQUENCE: 119

Arg Gly Trp Cys Leu Ser Asp Thr His Arg Pro Val Thr Ser His
1               5                   10                  15

Thr Pro His Val Arg Thr Met Pro Phe Leu Val Cys Pro Ile Ser Tyr
            20                  25                  30

Leu Tyr Thr Leu Pro Arg Phe Val Met Arg Phe Thr Tyr Thr Gln Thr
        35                  40                  45

Asp Pro Glu Arg Lys Leu Gln Val Phe Ser Asp Gly Tyr Val Phe
    50                  55                  60

Thr Val Phe Asn Asn
65

<210> SEQ ID NO 120
<211> LENGTH: 116
<212> TYPE: PRT
<213> ORGANISM: Homo sapiens

<400> SEQUENCE: 120

Met Cys Asp Gln Thr Lys His Ser Lys Cys Cys Pro Ala Lys Gly Asn
1               5                   10                  15

Gln Cys Cys Pro Pro Gln Gln Asn Gln Cys Cys Gln Ser Lys Gly Asn
            20                  25                  30

Gln Cys Cys Pro Pro Lys Gln Asn Gln Cys Cys Gln Pro Lys Gly Ser
        35                  40                  45

Gln Cys Cys Pro Pro Lys His Asn His Cys Cys Gln Lys Pro
    50                  55                  60

Cys Cys Ile Gln Ala Arg Cys Cys Gly Leu Glu Thr Lys Pro Glu Val
65                  70                  75                  80

Ser Pro Leu Asn Met Glu Ser Glu Pro Asn Ser Pro Gln Thr Gln Asp
                85                  90                  95

Lys Gly Cys Gln Thr Gln Gln Pro His Ser Pro Gln Asn Glu Ser
            100                 105                 110

Arg Pro Ser Lys
        115

<210> SEQ ID NO 121
<211> LENGTH: 372
<212> TYPE: DNA
<213> ORGANISM: Homo sapiens

<400> SEQUENCE: 121
atgcgggtca gcaaacccct tgggatgctc atgctctcca tttggatcct gctgttcgtg      60
tgctactacc tgtcctacta cctgtgctcc gggtcctcat attttgtgct tgcaaatgga     120
catatcctgc caacagtga aaatgctcat ggccaatctc tggaagaaga ttccgcattg     180
gaagctttgc tgaattttt ctttccaaca acttgcaatc tgagggaaaa tcaggtggca     240
aagccttgta atgagctgca agatcttagt gagagtgaat gtttgagaca caaatgctgt     300
ttttcatcat cggggaccac gagcttcaaa tgttttgctc catttagaga tgtgcctaaa     360
cagatgatgc aa                                                         372

<210> SEQ ID NO 122
<211> LENGTH: 124

```
<212> TYPE: PRT
<213> ORGANISM: Homo sapiens

<400> SEQUENCE: 122

Met Arg Val Ser Lys Pro Phe Gly Met Leu Met Leu Ser Ile Trp Ile
1               5                   10                  15

Leu Leu Phe Val Cys Tyr Tyr Leu Ser Tyr Tyr Leu Cys Ser Gly Ser
                20                  25                  30

Ser Tyr Phe Val Leu Ala Asn Gly His Ile Leu Pro Asn Ser Glu Asn
            35                  40                  45

Ala His Gly Gln Ser Leu Glu Glu Asp Ser Ala Leu Glu Ala Leu Leu
        50                  55                  60

Asn Phe Phe Pro Thr Thr Cys Asn Leu Arg Glu Asn Gln Val Ala
65                  70                  75                  80

Lys Pro Cys Asn Glu Leu Gln Asp Leu Ser Glu Ser Glu Cys Leu Arg
                85                  90                  95

His Lys Cys Cys Phe Ser Ser Ser Gly Thr Thr Ser Phe Lys Cys Phe
                100                 105                 110

Ala Pro Phe Arg Asp Val Pro Lys Gln Met Met Gln
            115                 120

<210> SEQ ID NO 123
<211> LENGTH: 129
<212> TYPE: DNA
<213> ORGANISM: Homo sapiens

<400> SEQUENCE: 123
acttgcaatc tgagggaaaa tcaggtggca aagccttgta atgagctgca agatcttagt      60
gagagtgaat gtttgagaca caaatgctgt ttttcatcat cggggaccac gagcttcaaa     120
tgttttgct                                                              129

<210> SEQ ID NO 124
<211> LENGTH: 43
<212> TYPE: PRT
<213> ORGANISM: Homo sapiens

<400> SEQUENCE: 124

Thr Cys Asn Leu Arg Glu Asn Gln Val Ala Lys Pro Cys Asn Glu Leu
1               5                   10                  15

Gln Asp Leu Ser Glu Ser Glu Cys Leu Arg His Lys Cys Cys Phe Ser
                20                  25                  30

Ser Ser Gly Thr Thr Ser Phe Lys Cys Phe Ala
            35                  40

<210> SEQ ID NO 125
<211> LENGTH: 30
<212> TYPE: DNA
<213> ORGANISM: Homo sapiens

<400> SEQUENCE: 125
aagaaacaaa gaaggaagcg aaagaggaag                                        30

<210> SEQ ID NO 126
<211> LENGTH: 10
<212> TYPE: PRT
<213> ORGANISM: Homo sapiens

<400> SEQUENCE: 126

Lys Lys Gln Arg Arg Lys Arg Lys Arg Lys
1               5                   10
```

<210> SEQ ID NO 127
<211> LENGTH: 75
<212> TYPE: DNA
<213> ORGANISM: Homo sapiens

<400> SEQUENCE: 127
atgcgggtca gcaaacccttt tgggatgctc atgctctcca tttggatcct gctgttcgtg    60
tgctactacc tgtcc    75

<210> SEQ ID NO 128
<211> LENGTH: 25
<212> TYPE: PRT
<213> ORGANISM: Homo sapiens

<400> SEQUENCE: 128

Met Arg Val Ser Lys Pro Phe Gly Met Leu Met Leu Ser Ile Trp Ile
1               5                   10                  15

Leu Leu Phe Val Cys Tyr Tyr Leu Ser
            20                  25

<210> SEQ ID NO 129
<211> LENGTH: 69
<212> TYPE: DNA
<213> ORGANISM: Homo sapiens

<400> SEQUENCE: 129
atgtttgggc ttggtgcgat cagccttatc ctggtatgtc tgcccattta ttgccgctct    60
cttttctgg    69

<210> SEQ ID NO 130
<211> LENGTH: 23
<212> TYPE: PRT
<213> ORGANISM: Homo sapiens

<400> SEQUENCE: 130

Met Phe Gly Leu Gly Ala Ile Ser Leu Ile Leu Val Cys Leu Pro Ile
1               5                   10                  15

Tyr Cys Arg Ser Leu Phe Trp
            20

<210> SEQ ID NO 131
<211> LENGTH: 582
<212> TYPE: DNA
<213> ORGANISM: Homo sapiens

<400> SEQUENCE: 131
atgcgggtca gcaaacccttt tgggatgctc atgctctcca tttggatcct gctgttcgtg    60
tgctactacc tgtcctacta cctgtgctcc gggtcctcat attttgtgct tgcaaatgga   120
catatcctgc ccaacagtga aaatgctcat ggccaatctc tggaagaaga ttccgcattg   180
gaagctttgc tgaattttt ctttccaaca acttgcaatc tgagggaaaa tcaggtggca   240
aagccttgta atgagctgca agatcttagt gagagtgaat gtttgagaca caatgctgt   300 ttttcatcat cggggaccac gagcttcaaa tgttttgctc catttagaga tgtgcctaaa   360
cagatgatgc aaaatgtttgg gcttggtgcg atcagcctta tcctggtatg tctgcccatt   420
tattgccgct ctcttttctg gaggagcgaa ccggccgatg atttacaaag gcaggacaac   480
agagttgtaa cgggtttgaa gaaacaaaga aggaagcgaa agaggaagtc tgaaatgtta   540
cagaaagcag caagaggacg tgaggaacat ggtgacgagc tc    582

<210> SEQ ID NO 132
<211> LENGTH: 193
<212> TYPE: PRT
<213> ORGANISM: Homo sapiens

<400> SEQUENCE: 132

Met Arg Val Ser Lys Pro Phe Gly Met Leu Met Leu Ser Ile Trp Ile
1               5                   10                  15

Leu Leu Phe Val Cys Tyr Tyr Leu Ser Tyr Tyr Leu Cys Ser Gly Ser
                20                  25                  30

Ser Tyr Phe Val Leu Ala Asn Gly His Ile Leu Pro Asn Ser Glu Asn
            35                  40                  45

Ala His Gly Gln Ser Leu Glu Glu Asp Ser Ala Leu Glu Ala Leu Leu
        50                  55                  60

Asn Phe Phe Phe Pro Thr Thr Cys Asn Leu Arg Glu Asn Gln Val Ala
65                  70                  75                  80

Lys Pro Cys Asn Glu Leu Gln Asp Leu Ser Glu Ser Cys Leu Arg
                85                  90                  95

His Lys Cys Cys Phe Ser Ser Ser Gly Thr Thr Ser Lys Cys Phe
            100                 105                 110

Ala Pro Phe Arg Asp Val Pro Lys Gln Met Met Gln Met Phe Gly Leu
        115                 120                 125

Gly Ala Ile Ser Leu Ile Leu Val Cys Leu Pro Ile Tyr Cys Arg Ser
    130                 135                 140

Leu Phe Trp Arg Ser Glu Pro Ala Asp Asp Leu Gln Arg Gln Asp Asn
145                 150                 155                 160

Arg Val Val Thr Gly Leu Lys Lys Gln Arg Arg Lys Arg Lys Arg Lys
                165                 170                 175

Ser Glu Met Leu Gln Lys Ala Ala Arg Gly Arg Glu Glu His Gly Asp
            180                 185                 190

Glu

<210> SEQ ID NO 133
<211> LENGTH: 717
<212> TYPE: DNA
<213> ORGANISM: Mus musculus

<400> SEQUENCE: 133
atgccttcgg atcgaaggcc aagtcagaga aggaatagat ctaagagccg tgattatcgt      60
ggtgcacggt caaaggtaac aagagctgat acgaggaaca gagacgatac tcttgccctc     120
agtatgtatc aggggcctcc gagtgccgac caggggaaca acatggcgga tgccctcgg     180 tttggcttct ggacttcagt aagccaatgt ctgcaatact tgtgggccag gaggcacttg     240
ggcctgcttc tacttttatt ctggacgctg gtgatcctgt tccgtcctgt gaacactgcg     300
aaattgccca ttcttgctga agctgcagaa cttgaacccc ctttgggaaa tatgttggac     360
ttttctcttc caacagcctg catcataagg acaaccagg tggtggtggc atgtaataac      420
cagccgtatc ttagcgagag tgaatgttta aaatccaagt gctgttcttc aacatctggg     480
actataatca aatgctatgc cccagtaagg acaagccta cacaggtgct acgggtgttt      540
ggccttgctg cgatcagcat tctagtcctg ggatttctgc tatgtgctg ctgctccatg      600 tgctggagga ggaagaggat gaacaggatg ttgaaggttt tgaagaaaca gaaatcaaaa     660
gggaagaagc ctaaaggaag gaaggcgtca gaagagagag ctttactgtc ccattga        717

```
<210> SEQ ID NO 134
<211> LENGTH: 238
<212> TYPE: PRT
<213> ORGANISM: Mus musculus

<400> SEQUENCE: 134

Met Pro Ser Asp Arg Arg Pro Ser Gln Arg Arg Asn Arg Ser Lys Ser
1               5                   10                  15

Arg Asp Tyr Arg Gly Ala Arg Ser Lys Val Thr Arg Ala Asp Thr Arg
            20                  25                  30

Asn Arg Asp Asp Thr Leu Ala Leu Ser Met Tyr Gln Gly Pro Pro Ser
        35                  40                  45

Ala Asp Gln Gly Asn Asn Met Ala Asp Ala Pro Arg Phe Gly Phe Trp
    50                  55                  60

Thr Ser Val Ser Gln Cys Leu Gln Tyr Leu Trp Ala Arg Arg His Leu
65                  70                  75                  80

Gly Leu Leu Leu Leu Phe Trp Thr Leu Val Ile Leu Phe Arg Pro
                85                  90                  95

Val Asn Thr Ala Lys Leu Pro Ile Leu Ala Glu Ala Ala Glu Leu Glu
            100                 105                 110

Pro Pro Leu Gly Asn Met Leu Asp Phe Phe Pro Thr Ala Cys Ile
            115                 120                 125

Ile Arg Asp Asn Gln Val Val Val Ala Cys Asn Asn Gln Pro Tyr Leu
    130                 135                 140

Ser Glu Ser Glu Cys Leu Lys Ser Lys Cys Cys Ser Ser Thr Ser Gly
145                 150                 155                 160

Thr Ile Ile Lys Cys Tyr Ala Pro Val Arg Asp Lys Pro Thr Gln Val
                165                 170                 175

Leu Arg Val Phe Gly Leu Ala Ala Ile Ser Ile Leu Val Leu Gly Phe
            180                 185                 190

Leu Pro Met Cys Cys Cys Ser Met Cys Trp Arg Arg Lys Arg Met Asn
            195                 200                 205

Arg Met Leu Lys Val Leu Lys Lys Gln Lys Ser Lys Gly Lys Lys Pro
    210                 215                 220

Lys Gly Arg Lys Ala Ser Glu Glu Arg Ala Leu Leu Ser His
225                 230                 235

<210> SEQ ID NO 135
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 135
cccggagcac gtcgaggtct ac                                                22

<210> SEQ ID NO 136
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 136
ggtgaggggc ccaggaagc                                                    19

<210> SEQ ID NO 137
<211> LENGTH: 21
<212> TYPE: DNA
```

```
<213> ORGANISM: Artificial Sequence
<220> FEATURE:
<223> OTHER INFORMATION: Synthetic Oligonucleotide

<400> SEQUENCE: 137
cacaatgtat cctgttgaaa g                                              21

<210> SEQ ID NO 138
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 138
gagatgatac attcttccag                                                20

<210> SEQ ID NO 139
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 139
cttccgccaa ctcctcctac c                                              21

<210> SEQ ID NO 140
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 140
gatgcccgtg tcttgtcctt                                                20

<210> SEQ ID NO 141
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 141
cactaggctg ctgaggaaga t                                              21

<210> SEQ ID NO 142
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 142
gttttggtgg gcagcattga g                                              21

<210> SEQ ID NO 143
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 143
ggaccacccc aaatagaa                                                  18
```

<210> SEQ ID NO 144
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 144
ccaccagctc aggaaga                                                  17

<210> SEQ ID NO 145
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 145
tctgatggag cggtgggatg c                                             21

<210> SEQ ID NO 146
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 146
gtgtgcctcg gcttctttct tc                                            22

<210> SEQ ID NO 147
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 147
tggtgcgatc agccttatcc                                               20

<210> SEQ ID NO 148
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 148
cggttcgctc ctccagaa                                                 18

<210> SEQ ID NO 149
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 149
tgtctgccca tttattgccg ctctct                                        26

<210> SEQ ID NO 150
<211> LENGTH: 795
<212> TYPE: DNA
<213> ORGANISM: Artificial Sequence
<220> FEATURE:
<223> OTHER INFORMATION: Synthetic Oligonucleotide

<400> SEQUENCE: 150

```
catatgtctt cacataggag gaaagcgaag gggaggaata ggagaagtca ccgtgccatg      60
cgtgtggctc acttagagct ggcaacttat gagttggcgg caactgagtc gaatcccgag     120
agcagccatc ctggatacga ggccgccatg gctgacaggc tcagccagg atggcgggaa      180
tctctaaaga tgcgggtcag caaacccttt gggatgctca tgctctccat ttggatcctg     240
ctgttcgtgt gctactacct gtcctactac ctgtgctccg ggtcctcata ttttgtgctt     300
gcaaatggac atatcctgcc aacagtgaa atgctcatg ccaatctct ggaagaagat        360
tccgcattgg aagctttgct gaattttttc tttccaacaa cttgcaatct gagggaaaat     420
caggtggcaa agccttgtaa tgagctgcaa gatcttagtg agagtgaatg tttgagacac     480
aaatgctgtt tttcatcatc ggggaccacg agcttcaaat gttttgctcc atttagagat     540
gtgcctaaac agatgatgca aatgtttggg cttggtgcga tcagccttat cctggtatgt     600
ctgcccattt attgccgctc tcttttctgg aggagcgaac cggccgatga tttacaaagg     660
caggacaaca gagttgtaac gggtttgaag aaacaaagaa ggaagcgaaa gaggaagtct     720
gaaatgttac agaaagcagc aagaggacgt gaggaacatg gtgacgagct cgagcaccac     780
caccaccacc actga                                                     795
```

<210> SEQ ID NO 151
<211> LENGTH: 263
<212> TYPE: PRT
<213> ORGANISM: Artificial Sequence
<220> FEATURE:
<223> OTHER INFORMATION: Synthetic Polypeptide

<400> SEQUENCE: 151

```
Met Ser Ser His Arg Arg Lys Ala Lys Gly Arg Asn Arg Arg Ser His
1               5                   10                  15

Arg Ala Met Arg Val Ala His Leu Glu Leu Ala Thr Tyr Glu Leu Ala
                20                  25                  30

Ala Thr Glu Ser Asn Pro Glu Ser Ser His Pro Gly Tyr Glu Ala Ala
            35                  40                  45

Met Ala Asp Arg Pro Gln Pro Gly Trp Arg Glu Ser Leu Lys Met Arg
        50                  55                  60

Val Ser Lys Pro Phe Gly Met Leu Met Leu Ser Ile Trp Ile Leu Leu
65                  70                  75                  80

Phe Val Cys Tyr Tyr Leu Ser Tyr Tyr Leu Cys Ser Gly Ser Ser Tyr
                85                  90                  95

Phe Val Leu Ala Asn Gly His Ile Leu Pro Asn Ser Glu Asn Ala His
            100                 105                 110

Gly Gln Ser Leu Glu Glu Asp Ser Ala Leu Glu Ala Leu Leu Asn Phe
        115                 120                 125

Phe Phe Pro Thr Thr Cys Asn Leu Arg Glu Asn Gln Val Ala Lys Pro
    130                 135                 140

Cys Asn Glu Leu Gln Asp Leu Ser Glu Ser Cys Leu Arg His Lys
145                 150                 155                 160

Cys Cys Phe Ser Ser Ser Gly Thr Thr Ser Phe Lys Cys Phe Ala Pro
                165                 170                 175

Phe Arg Asp Val Pro Lys Gln Met Met Gln Met Phe Gly Leu Gly Ala
            180                 185                 190

Ile Ser Leu Ile Leu Val Cys Leu Pro Ile Tyr Cys Arg Ser Leu Phe
        195                 200                 205

Trp Arg Ser Glu Pro Ala Asp Asp Leu Gln Arg Gln Asp Asn Arg Val
```

```
               210                 215                 220
Val Thr Gly Leu Lys Lys Gln Arg Arg Lys Arg Lys Ser Glu
225                 230                 235                 240

Met Leu Gln Lys Ala Ala Arg Gly Arg Glu Glu His Gly Asp Glu Leu
                245                 250                 255

Glu His His His His His His
            260

<210> SEQ ID NO 152
<211> LENGTH: 609
<212> TYPE: DNA
<213> ORGANISM: Artificial Sequence
<220> FEATURE:
<223> OTHER INFORMATION: Synthetic Oligonucleotide

<400> SEQUENCE: 152
catatgcggg tcagcaaacc ctttgggatg ctcatgctct ccatttggat cctgctgttc      60
gtgtgctact acctgtccta ctacctgtgc tccgggtcct catattttgt gcttgcaaat     120
ggacatatcc tgcccaacag tgaaaatgct catggccaat ctctggaaga agattccgca     180
ttggaagctt tgctgaattt tttctttcca caaacttgca atctgaggga aaatcaggtg     240
gcaaagcctt gtaatgagct gcaagatctt agtgagagtg aatgtttgag acacaaatgc     300 tgttttcat catcggggac cacgagcttc aaatgttttg ctccatttag agatgtgcct     360
aaacagatga tgcaaatgtt tgggcttggt gcgatcagcc ttatcctggt atgtctgccc     420
atttattgcc gctctctttt ctggaggagc gaaccggccg atgatttaca aaggcaggac     480
aacagagttg taacgggttt gaagaaacaa agaaggaagc gaaagaggaa gtctgaaatg     540
ttacagaaag cagcaagagg acgtgaggaa catggtgacg agctcgagca ccaccaccac     600
caccactga                                                             609

<210> SEQ ID NO 153
<211> LENGTH: 201
<212> TYPE: PRT
<213> ORGANISM: Artificial Sequence
<220> FEATURE:
<223> OTHER INFORMATION: Synthetic Polypeptide

<400> SEQUENCE: 153

Met Arg Val Ser Lys Pro Phe Gly Met Leu Met Leu Ser Ile Trp Ile
1               5                   10                  15

Leu Leu Phe Val Cys Tyr Tyr Leu Ser Tyr Tyr Leu Cys Ser Gly Ser
                20                  25                  30

Ser Tyr Phe Val Leu Ala Asn Gly His Ile Leu Pro Asn Ser Glu Asn
            35                  40                  45

Ala His Gly Gln Ser Leu Glu Glu Asp Ser Ala Leu Glu Ala Leu Leu
        50                  55                  60

Asn Phe Phe Phe Pro Thr Thr Cys Asn Leu Arg Glu Asn Gln Val Ala
65                  70                  75                  80

Lys Pro Cys Asn Glu Leu Gln Asp Leu Ser Glu Ser Glu Cys Leu Arg
                85                  90                  95

His Lys Cys Cys Phe Ser Ser Ser Gly Thr Thr Ser Phe Lys Cys Phe
            100                 105                 110

Ala Pro Phe Arg Asp Val Pro Lys Gln Met Met Gln Met Phe Gly Leu
        115                 120                 125

Gly Ala Ile Ser Leu Ile Leu Val Cys Leu Pro Ile Tyr Cys Arg Ser
    130                 135                 140
```

```
Leu Phe Trp Arg Ser Glu Pro Ala Asp Asp Leu Gln Arg Gln Asp Asn
145                 150                 155                 160

Arg Val Val Thr Gly Leu Lys Lys Gln Arg Lys Arg Lys Arg Lys
            165                 170                 175

Ser Glu Met Leu Gln Lys Ala Ala Arg Gly Arg Glu Glu His Gly Asp
        180                 185                 190

Glu Leu Glu His His His His His His
        195                 200
```

```
<210> SEQ ID NO 154
<211> LENGTH: 405
<212> TYPE: DNA
<213> ORGANISM: Artificial Sequence
<220> FEATURE:
<223> OTHER INFORMATION: Synthetic Oligonucleotide

<400> SEQUENCE: 154
catatgcggg tcagcaaacc ctttgggatg ctcatgctct ccatttggat cctgctgttc     60
gtgtgctact acctgtccta ctacctgtgc tccgggtcct catattttgt gcttgcaaat    120
ggacatatcc tgcccaacag tgaaaatgct catggccaat ctctggaaga agattccgca    180
ttggaagctt tgctgaattt tttctttcca acaacttgca atctgaggga aaatcaggtg    240
gcaaagcctt gtaatgagct gcaagatctt agtgagagtg aatgtttgag acacaaatgc    300 tgttttcat catcggggac cacgagcttc aaatgttttg ctccatttag agatgtgcct    360
aaacagatga tgcaaatgct cgagcaccac caccaccacc actga                    405
```

```
<210> SEQ ID NO 155
<211> LENGTH: 133
<212> TYPE: PRT
<213> ORGANISM: Artificial Sequence
<220> FEATURE:
<223> OTHER INFORMATION: Synthetic Polypeptide

<400> SEQUENCE: 155

Met Arg Val Ser Lys Pro Phe Gly Met Leu Met Leu Ser Ile Trp Ile
1               5                   10                  15

Leu Leu Phe Val Cys Tyr Tyr Leu Ser Tyr Tyr Leu Cys Ser Gly Ser
            20                  25                  30

Ser Tyr Phe Val Leu Ala Asn Gly His Ile Leu Pro Asn Ser Glu Asn
        35                  40                  45

Ala His Gly Gln Ser Leu Glu Glu Asp Ser Ala Leu Glu Ala Leu Leu
    50                  55                  60

Asn Phe Phe Phe Pro Thr Thr Cys Asn Leu Arg Glu Asn Gln Val Ala
65                  70                  75                  80

Lys Pro Cys Asn Glu Leu Gln Asp Leu Ser Glu Ser Glu Cys Leu Arg
                85                  90                  95

His Lys Cys Cys Phe Ser Ser Ser Gly Thr Thr Ser Phe Lys Cys Phe
            100                 105                 110

Ala Pro Phe Arg Asp Val Pro Lys Gln Met Met Gln Met Leu Glu His
        115                 120                 125

His His His His His
    130
```

```
<210> SEQ ID NO 156
<211> LENGTH: 38
<212> TYPE: DNA
<213> ORGANISM: Artificial Sequence
<220> FEATURE:
<223> OTHER INFORMATION: Synthetic Oligonucleotide
```

```
<400> SEQUENCE: 156
cacacacaca tatgtcttca cataggagga aagcgaag                                    38

<210> SEQ ID NO 157
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 157
cacacactcg agctcgtcac catgttcctc acgtc                                       35

<210> SEQ ID NO 158
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 158
cacacacaca tatgcgggtc agcaaaccct ttggga                                      36

<210> SEQ ID NO 159
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 159
cacacactcg agctcgtcac catgttcctc acgtc                                       35

<210> SEQ ID NO 160
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 160
cacacacaca tatgcgggtc agcaaaccct ttggga                                      36

<210> SEQ ID NO 161
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 161
cacacactcg agcatttgca tcatctgttt aggc                                        34

<210> SEQ ID NO 162
<211> LENGTH: 936
<212> TYPE: DNA
<213> ORGANISM: Artificial Sequence
<220> FEATURE:
<223> OTHER INFORMATION: Synthetic Oligonucleotide

<400> SEQUENCE: 162
gaattccttc tgggccacgg actgccggac cgttgggctg tgaggcagcg tctcagcgag            60
gcggcacccg gagccatgtc ttcacatagg aggaaagcga aggggaggaa taggagaagt           120
caccgtgcca tgcgtgtggc tcacttagag ctggcaactt atgagttggc ggcaactgag           180
```

```
tcgaatcccg agagcagcca tcctggatac gaggccgcca tggctgacag gcctcagcca      240
ggatggcggg aatctctaaa gatgcgggtc agcaaaccct ttgggatgct catgctctcc      300
atttggatcc tgctgttcgt gtgctactac ctgtcctact acctgtgctc cgggtcctca      360
tattttgtgc ttgcaaatgg acatatcctg cccaacagtg aaaatgctca tggccaatct      420
ctggaagaag attccgcatt ggaagctttg ctgaattttt tctttccaac aacttgcaat      480
ctgagggaaa atcaggtggc aaagccttgt aatgagctgc aagatcttag tgagagtgaa      540
tgtttgagac acaaatgctg tttttcatca tcggggacca cgagcttcaa atgttttgct      600
ccatttagag atgtgcctaa acagatgatg caaatgtttg ggcttggtgc gatcagcctt      660
atcctggtat gtctgcccat ttattgccgc tctcttttct ggaggagcga accggccgat      720
gatttacaaa ggcaggacaa cagagttgta acgggtttga gaaacaaag aaggaagcga      780 aagaggaagt ctgaaatgtt acagaaagca gcaagaggac gtgaggaaca tggtgacgag      840
ctcgagtcta gagggccctt cgaaggtaag cctatcccta accctctcct cggtctcgat      900
tctacgcgta ccggtcatca tcaccatcac cattga                                936
```

<210> SEQ ID NO 163
<211> LENGTH: 311
<212> TYPE: PRT
<213> ORGANISM: Artificial Sequence
<220> FEATURE:
<223> OTHER INFORMATION: Synthetic Polypeptide

<400> SEQUENCE: 163

```
Glu Phe Leu Leu Gly His Gly Leu Pro Asp Arg Trp Ala Val Arg Gln
  1               5                  10                  15

Arg Leu Ser Glu Ala Ala Pro Gly Ala Met Ser Ser His Arg Arg Lys
             20                  25                  30

Ala Lys Gly Arg Asn Arg Arg Ser His Arg Ala Met Arg Val Ala His
         35                  40                  45

Leu Glu Leu Ala Thr Tyr Glu Leu Ala Ala Thr Glu Ser Asn Pro Glu
     50                  55                  60

Ser Ser His Pro Gly Tyr Glu Ala Ala Met Ala Asp Arg Pro Gln Pro
 65                  70                  75                  80

Gly Trp Arg Glu Ser Leu Lys Met Arg Val Ser Lys Pro Phe Gly Met
                 85                  90                  95

Leu Met Leu Ser Ile Trp Ile Leu Leu Phe Val Cys Tyr Tyr Leu Ser
            100                 105                 110

Tyr Tyr Leu Cys Ser Gly Ser Ser Tyr Phe Val Leu Ala Asn Gly His
        115                 120                 125

Ile Leu Pro Asn Ser Glu Asn Ala His Gly Gln Ser Leu Glu Glu Asp
    130                 135                 140

Ser Ala Leu Glu Ala Leu Leu Asn Phe Phe Phe Pro Thr Thr Cys Asn
145                 150                 155                 160

Leu Arg Glu Asn Gln Val Ala Lys Pro Cys Asn Glu Leu Gln Asp Leu
                165                 170                 175

Ser Glu Ser Glu Cys Leu Arg His Lys Cys Cys Phe Ser Ser Ser Gly
            180                 185                 190

Thr Thr Ser Phe Lys Cys Phe Ala Pro Phe Arg Asp Val Pro Lys Gln
        195                 200                 205

Met Met Gln Met Phe Gly Leu Gly Ala Ile Ser Leu Ile Leu Val Cys
    210                 215                 220

Leu Pro Ile Tyr Cys Arg Ser Leu Phe Trp Arg Ser Glu Pro Ala Asp
```

```
                225                 230                 235                 240
        Asp Leu Gln Arg Gln Asp Asn Arg Val Val Thr Gly Leu Lys Lys Gln
                        245                 250                 255

Arg Arg Lys Arg Lys Arg Lys Ser Glu Met Leu Gln Lys Ala Ala Arg
                    260                 265                 270

Gly Arg Glu Glu His Gly Asp Glu Leu Glu Ser Arg Gly Pro Phe Glu
                275                 280                 285

Gly Lys Pro Ile Pro Asn Pro Leu Leu Gly Leu Asp Ser Thr Arg Thr
                    290                 295                 300

Gly His His His His His His
        305                 310

<210> SEQ ID NO 164
<211> LENGTH: 67
<212> TYPE: DNA
<213> ORGANISM: Artificial Sequence
<220> FEATURE:
<223> OTHER INFORMATION: Synthetic Oligonucleotide

<400> SEQUENCE: 164
gggaattcat gtcttcacat aggaggaaag cgcacacact cgagctcgtc accatgttcc      60
tcacgtc                                                                67

<210> SEQ ID NO 165
<211> LENGTH: 73
<212> TYPE: DNA
<213> ORGANISM: Artificial Sequence
<220> FEATURE:
<223> OTHER INFORMATION: Synthetic Oligonucleotide

<400> SEQUENCE: 165
cacacacaca tatgtcttca cataggagga aagcgaagca cactcgag ctcgtcacca       60 tgttcctcac gtc                                                        73

<210> SEQ ID NO 166
<211> LENGTH: 74
<212> TYPE: DNA
<213> ORGANISM: Artificial Sequence
<220> FEATURE:
<223> OTHER INFORMATION: Synthetic Oligonucleotide

<400> SEQUENCE: 166
cacacacaca tatgcgggtc agcaaaccct tgggacaca cacacatatg tcttcacata      60
ggaggaaagc gaag                                                       74

<210> SEQ ID NO 167
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 167
tactcccctg ccctcaacaa gctcaggcgg ctcataggg                            39
```